United States Patent
Kajaste-Rudnitski et al.

(10) Patent No.: US 12,059,478 B2
(45) Date of Patent: Aug. 13, 2024

(54) GENE THERAPY

(71) Applicants: Ospedale San Raffaele S.r.l., Milan (IT); Fondazione Telethon ETS, Rome (IT)

(72) Inventors: Anna Christina Kajaste-Rudnitski, Milan (IT); Francesco Piras, Milan (IT)

(73) Assignees: Ospedale San Raffaele S.r.l., Milan (IT); Fondazione Telethon ETS, Rome (IT)

(*) Notice: Subject to any disclaimer, the term of this patent is extended or adjusted under 35 U.S.C. 154(b) by 809 days.

(21) Appl. No.: 16/302,120

(22) PCT Filed: May 19, 2017

(86) PCT No.: PCT/EP2017/062197
§ 371 (c)(1),
(2) Date: May 6, 2019

(87) PCT Pub. No.: WO2017/198868
PCT Pub. Date: Nov. 23, 2017

(65) Prior Publication Data
US 2019/0175764 A1     Jun. 13, 2019

(30) Foreign Application Priority Data
May 20, 2016 (GB) .................... 1608944

(51) Int. Cl.
*A61K 48/00* (2006.01)
*A61P 7/06* (2006.01)
(Continued)

(52) U.S. Cl.
CPC ...... *A61K 48/0058* (2013.01); *A61K 48/0008* (2013.01); *A61K 48/0066* (2013.01);
(Continued)

(58) Field of Classification Search
None
See application file for complete search history.

(56) References Cited

U.S. PATENT DOCUMENTS

| 4,797,368 A | 1/1989 | Carter et al. |
| 5,139,941 A | 8/1992 | Muzyczka et al. |

(Continued)

FOREIGN PATENT DOCUMENTS

| JP | 2006-521813 A | 9/2006 |
| WO | WO-98/005635 A1 | 2/1998 |

(Continued)

OTHER PUBLICATIONS

Miciak et al., Long story short: p53 mediates innate immunity (BBA, 2016, 1865:220-227) (Year: 2016).*

(Continued)

*Primary Examiner* — Arthur S Leonard
(74) *Attorney, Agent, or Firm* — MARSHALL, GERSTEIN & BORUN LLP

(57) ABSTRACT

An inhibitor of p53 activation for use in haematopoietic stem and/or progenitor cell gene therapy, preferably wherein the inhibitor is an inhibitor of p53 phosphorylation, more preferably an inhibitor of p53 Serine 15 phosphorylation.

28 Claims, 39 Drawing Sheets

Specification includes a Sequence Listing.

(51) Int. Cl.
  A61P 43/00    (2006.01)
  C07K 14/47    (2006.01)
  C12N 15/00    (2006.01)
  C12N 15/86    (2006.01)

(52) U.S. Cl.
  CPC ............ *A61K 48/0091* (2013.01); *A61P 7/06* (2018.01); *A61P 43/00* (2018.01); *C07K 14/4746* (2013.01); *C12N 15/86* (2013.01); *C12N 2750/14132* (2013.01); *C12N 2750/14141* (2013.01)

(56) References Cited

U.S. PATENT DOCUMENTS

| | | | |
|---|---|---|---|
| 11,001,809 B2* | 5/2021 | Kim .................... | C12N 15/113 |
| 2005/0054103 A1 | 3/2005 | Peled et al. | |
| 2012/0076762 A1* | 3/2012 | Kawamura ............ | A61P 43/00 435/366 |
| 2014/0369967 A1 | 12/2014 | Gao et al. | |
| 2015/0010502 A1* | 1/2015 | Smith .................. | C12N 15/113 424/85.4 |
| 2018/0071330 A1* | 3/2018 | D'Andrea .......... | A61K 31/7088 |
| 2019/0127762 A1* | 5/2019 | Church ............... | C12N 15/907 |

FOREIGN PATENT DOCUMENTS

| | | | | |
|---|---|---|---|---|
| WO | WO-98/007859 A2 | 2/1998 | | |
| WO | WO-98/09985 A2 | 3/1998 | | |
| WO | WO-98/017815 A1 | 4/1998 | | |
| WO | WO-01/66699 A2 | 9/2001 | | |
| WO | WO-2004/031144 A2 | 4/2004 | | |
| WO | WO-2006/006171 A2 | 1/2006 | | |
| WO | WO-2011/016588 A1 | 2/2011 | | |
| WO | WO-2015057976 A1 * | 4/2015 | ............. | A61K 35/28 |

OTHER PUBLICATIONS

Mittelman et al., Generation of p53 Suppressor Peptide From the Fragment of p53 Protein (Somat Cell Mol Genet, 1999, 25:115-1128) (Year: 1999).*
Kamada et al. Cancer-associated p53 Tetramerization Domain Mutants (JBC, 2011, 286:252-258) (Year: 2011).*
Giorgetti et al. (Cell Stem Cell, 2009, 5:353-357) (Year: 2009).*
Philippe et al. (PNAS, 2006, 103:17684-17689) (Year: 2006).*
Shaulian et al. (MCB, 1992, 12:5581-5592). (Year: 1992).*
European Patent Application No. 17727135.0, Communication Pursuant to Article 94(3) EPC, dated Sep. 16, 2019.
Watts et al., Hematopoietic stem cell expansion and gene therapy, Cytotherapy, 13(10):1164-71 (Nov. 2011).
"Retroviral Taxonomy, Protein Structures, Sequences, and Genetic Maps", pp. 757-763 In: Coffin et al. (eds.), Retroviruses, Cold Spring Harbor Laboratory Press (1997).
Aiuti et al., Gene therapy for immunodeficiency due to adenosine deaminase deficiency, N. Engl. J. Med., 360(5):447-58 (Jan. 2009).
Aiuti et al., Lentiviral hematopoietic stem cell gene therapy in patients with Wiskott-Aldrich syndrome, Science, 341(6148):1233151 (Aug. 2013).
Amendola et al., Coordinate dual-gene transgenesis by lentiviral vectors carrying synthetic bidirectional promoters, Nat. Biotechnol., 23(1):108-16 (Jan. 2005).
Biasco et al., In Vivo Tracking of Human Hematopoiesis Reveals Patterns of Clonal Dynamics during Early and Steady-State Reconstitution Phases, Cell Stem Cell, 19(1):107-19 (Jul. 2016).
Biffi et al., Lentiviral hematopoietic stem cell gene therapy benefits metachromatic leukodystrophy, Science, 341(6148):1233158 (Aug. 2013).
Boztug et al., Stem-cell gene therapy for the Wiskott-Aldrich syndrome, N. Engl. J. Med., 363(20):1918-27 (Nov. 2010).
Brady et al., Distinct p53 transcriptional programs dictate acute DNA-damage responses and tumor suppression, Cell, 145(4):571-83 (May 2011).
Bushman et al., Genome-wide analysis of retroviral DNA integration, Nat. Rev. Microbiol., 3(11):848-58 (Nov. 2005).
Cabezas-Wallscheid et al., Identification of regulatory networks in HSCs and their immediate progeny via integrated proteome, transcriptome, and DNA methylome analysis, Cell Stem Cell, 15(4):507-22 (Oct. 2014).
Carter et al., HIV-1 infects multipotent progenitor cells causing cell death and establishing latent cellular reservoirs, Nat. Med., 16(4):446-51 (Apr. 2010).
Cartier et al., Gene therapy of x-linked adrenoleukodystrophy using hematopoietic stem cells and a lentiviral vector, Bull. Acad. Natl. Med., 194(2):255-64 (Feb. 2010). *French with English Abstract.*
Cartier et al., Hematopoietic stem cell gene therapy with a lentiviral vector in X-linked adrenoleukodystrophy, Science, 326(5954):818-23 (Nov. 2009).
Chang et al., The genetic engineering of hematopoietic stem cells: the rise of lentiviral vectors, the conundrum of the ltr, and the promise of lineage-restricted vectors, Mol. Ther., 15(3):445-56 (Mar. 2007).
Cooper et al., HIV-1 causes CD4 cell death through DNA-dependent protein kinase during viral integration, Nature, 498(7454):376-9 (Jun. 2013).
Craigie et al., HIV DNA integration, Cold Spring Harb. Perspect. Med., 2(7):a006890 (Jul. 2012).
Doulatov et al., Hematopoiesis: a human perspective, Cell Stem Cell, 10(2):120-36 (Feb. 2012).
Elbashir et al., Functional anatomy of siRNAs for mediating efficient RNAi in *Drosophila melanogaster* embryo lysate, EMBO J., 20(23):6877-88 (Dec. 2001).
Espinosa et al., Transcriptional regulation by p53 through intrinsic DNA/chromatin binding and site-directed cofactor recruitment, Mol. Cell, 8(1):57-69 (Jul. 2001).
Follenzi et al., Gene transfer by lentiviral vectors is limited by nuclear translocation and rescued by HIV-1 pol sequences, Nat. Genet., 25(2):217-22 (Jun. 2000).
Follenzi et al., HIV-based vectors. Preparation and use, Methods Mol Med, vol. 69, p. 259-274 (2002).
Gao et al., Cyclic GMP-AMP synthase is an innate immune sensor of HIV and other retroviruses, Science, 341(6148):903-6 (Aug. 2013).
Geest et al., MAPK signaling pathways in the regulation of hematopoiesis, J. Leukoc. Biol., 86(2):237-50 (Aug. 2009).
Genovese et al., Targeted genome editing in human repopulating haematopoietic stem cells, Nature, 510(7504):235-40 (Jun. 2014).
Gentner et al., Identification of hematopoietic stem cell-specific miRNAs enables gene therapy of globoid cell leukodystrophy, Sci. Transl. Med., 2(58):58ra84 (2010).
Hacien-Bey-Abina et al., Efficacy of gene therapy for X-linked severe combined immunodeficiency, N. Engl. J. Med., 363(4):355-64 (Jul. 2010).
Hastie et al., Assay of protein kinases using radiolabeled ATP: a protocol, Nat. Protoc., 1(2):968-71 (2006).
Hickson et al., Identification and characterization of a novel and specific inhibitor of the ataxia-telangiectasia mutated kinase ATM, Cancer Res., 64(24):9152-9 (Dec. 2004).
Hu et al., ELDA: extreme limiting dilution analysis for comparing depleted and enriched populations in stem cell and other assays, J. Immunol. Methods, 347(102):70-8 (Aug. 2009).
Hutvágner et al., A cellular function for the RNA-interference enzyme Dicer in the maturation of the let-7 small temporal RNA, Science, 293(5531):834-8 (Aug. 2001).
Härtlova et al., DNA damage primes the type I interferon system via the cytosolic DNA sensor STING to promote anti-microbial innate immunity, Immunity, 42(2):332-43 (Feb. 2015).
International Application No. PCT/EP2017/062197, International Preliminary Report on Patentability, dated Nov. 20, 2018.
International Application No. PCT/EP2017/062197, International Search Report and Written Opinion, dated Aug. 2, 2017.
Jackson et al., The DNA-damage response in human biology and disease, Nature, 461(7267):1071-8 (Oct. 2009).

(56) References Cited

OTHER PUBLICATIONS

Josefsson et al., Hematopoietic precursor cells isolated from patients on long-term suppressive HIV therapy did not contain HIV-1 DNA, J. Infect. Dis., 206(1):28-34 (Jul. 2012).
Kajaste-Rudnitski et al., Cellular innate immunity and restriction of viral infection: implications for lentiviral gene therapy in human hematopoietic cells, Hum Gene Ther., 26(4):201-9 (Apr. 2015).
Kajaste-Rudnitski et al., The 2',5'-oligoadenylate synthetase 1b is a potent inhibitor of West Nile virus replication inside infected cells, J. Biol. Chem., 281(8):4624-37 (Feb. 2006).
Kandalla et al., M-CSF improves protection against bacterial and fungal infections after hematopoietic stem/progenitor cell transplantation, J. Exp. med., 213(11):2269-79 (Oct. 2016).
Kang et al., Functional interaction of H2AX, NBS1, and p53 in ATM-dependent DNA damage responses and tumor suppression, Mol. Cell Biol., 25(2):661-70 (Jan. 2005).
Kawase et al., PH domain-only protein PHLDA3 is a p53-regulated repressor of Akt, Cell, 136(3):535-50 (Feb. 2009).
Kruse et al., SnapShot: p53 posttranslational modifications, Cell, 133(5):930-30.e1 (May 2008).
Lane et al., Stem cells and DNA damage: persist or perish?, Cell, 142(3):360-2 (Aug. 2010).
Lau et al., Suppression of HIV-1 infection by a small molecule inhibitor of the ATM kinase, Nat. Cell Biol., 7(5):493-500 (May 2005).
Leavitt et al., Human immunodeficiency virus type 1 integrase mutants retain in vitro integrase activity yet fail to integrate viral DNA efficiently during infection, J. Virol., 70(2):721-8 (Feb. 1996).
Lechman et al., Attenuation of miR-126 activity expands HSC in vivo without exhaustion, Cell Stem Cell, 11(6):799-811 (2012).
Lee et al., ATM activation by DNA double-strand breaks through the Mre11-Rad50-Nbs1 complex, Science, 308(5721):551-4 (Apr. 2005).
Lee et al., Zinc-finger antiviral protein mediates retinoic acid inducible gene I-like receptor-independent antiviral response to murine leukemia virus, Proc. Natl. Acad. Sci. USA, 110(30):12379-84 (Jul. 2013).
Lewis et al., Human immunodeficiency virus infection of cells arrested in the cell cycle, EMBO J., 11(8):3053-8 (Aug. 1992).
Lewis et al., Passage through mitosis is required for oncoretroviruses but not for the human immunodeficiency virus, J. Virol., 68(1):510-6 (Jan. 1994).
Liu et al., Arginine methyltransferase PRMT5 is essential for sustaining normal adult hematopoiesis, J. Clin. Invest., 125(9):3532-44 (Sep. 2015).
Liu et al., p53 regulates hematopoietic stem cell quiescence, Cell Stem Cell, 4(1):37-48 (Jan. 2009).
Liu et al., The p53 tumor suppressor protein is a critical regulator of hematopoietic stem cell behavior, Cell Cycle, 8(19):3120-4 (Oct. 2009).
Lombardo et al., Site-specific integration and tailoring of cassette design for sustainable gene transfer, Nat Methods, vol. 8 pp. 861-869 (2011).
Lombardo et al., Gene editing in human stem cells using zinc finger nucleases and integrase-defective lentiviral vector delivery, Nat. Biotechnol., 25(11):1298-306 (Nov. 2007).
Marechal et al., DNA damage sensing by the ATM and ATR kinases, Cold Spring Harb. Perspect. Biol., 5(9) (Sep. 2013).
Merten et al., Large-scale manufacture and characterization of a lentiviral vector produced for clinical ex vivo gene therapy application, Hum. Gene Ther., 22(3):343-56 (Mar. 2011).
Milyavsky et al., A distinctive DNA damage response in human hematopoietic stem cells reveals an apoptosis-independent role for p53 in self-renewal, Cell Stem Cell, 7(2):186-97 (Aug. 2010).
Mingozzi et al., Therapeutic in vivo gene transfer for genetic disease using AAV: progress and challenges, Nat. Rev. Genet., 12(5):341-5 (May 2011).
Mohrin et al., Hematopoietic stem cell quiescence promotes error-prone DNA repair and mutagenesis, Cell Stem Cell, 7(2):174-85 (Aug. 2010).
Montini et al., Hematopoietic stem cell gene transfer in a tumor-prone mouse model uncovers low genotoxicity of lentiviral vector integration, Nat. Biotechnol., 24(6):687-96 (Jun. 2006).
Naldini et al., Efficient transfer, integration, and sustained long-term expression of the transgene in adult rat brains injected with a lentiviral vector, Proc. Natl. Acad. Sci. USA, 93(12):11382-8 (Oct. 1996).
Naldini et al., Gene therapy returns to centre stage, Nature, 526(7573):351-60 (Oct. 2015).
Naldini et al., In vivo gene delivery and stable transduction of nondividing cells by a lentiviral vector, Science, 272(5259):263-7 (Apr. 1996).
Nightingale et al., Transient gene expression by nonintegrating lentiviral vectors, Mol Ther, vol. 13, pp. 1121-1132 (2006).
Nonnenmacher et al., Intracellular transport of recombinant adeno-associated virus vectors, Gene Ther., 19(6):649-58 (Jun. 2012).
Notta et al., Distinct routes of lineage development reshape the human blood hierarchy across ontogeny, Science, 351(6269):aab2116 (Jan. 2016).
Nucera et al., miRNA-126 Orchestrates an Oncogenic Program in B Cell Precursor Acute Lymphoblastic Leukemia, Cancer Cell, 29(6):905-21 (Jun. 2016).
Ossovskaya et al., Use of genetic suppressor elements to dissect distinct biological effects of separate p53 domains, Proc. Natl. Acad. Sci. USA, 93(19):10309-14 (Sep. 1996).
Petrillo et al., Cyclosporin a and rapamycin relieve distinct lentiviral restriction blocks in hematopoietic stem and progenitor cells, Mol. Ther., 23(2):352-62 (Feb. 2015).
Piras et al., Lentiviral vectors escape innate sensing but trigger p53 in human hematopoietic stem and progenitor cells, EMBO Mol. Med., 9(9):1198-211 (Sep. 2017).
Ralph et al., Silencing mutant SOD1 using RNAi protects against neurodegeneration and extends survival in an ALS model, Nat. Med., 1194):429-33 (Apr. 2005).
Riley et al., Transcriptional control of human p53-regulated genes, Nat. Rev. Mol. Cell Biol., 9(5):402-12 (May 2008).
Roers et al., Recognition of Endogenous Nucleic Acids by the Innate Immune System, Immunity, 44(4):739-54 (Apr. 2016).
Roos et al., DNA damage and the balance between survival and death in cancer biology, Nat. Rev. Cancer, 1691):20-33 (Jan. 2016).
Sambrook et al., Molecular Cloning: a Laboratory Manual, Cold Harbor Laboratory, 2nd edition (1989).
Santoni de Sio et al., Lentiviral vector gene transfer is limited by the proteasome at postentry steps in various types of stem cells, Stem Cells, 26(8):2142-52 (Aug. 2008).
Sauter et al., HIV replication: a game of hide and sense, Cur.. Opin. HIV AIDS, 11(2):173-81 (Mar. 2016).
Sellers et al., No impact of lentiviral transduction on hematopoietic stem/progenitor cell telomere length or gene expression in the rhesus macaque model, Mol. Ther., 22(1):52-8 (Jan. 2014).
Sessa et al., Lentiviral haemopoietic stem-cell gene therapy in early-onset metachromatic leukodystrophy: an ad-hoc analysis of a non-randomised, open-label, phase 1/2 trial, Lancet, 388(10043):476-87 (Jul. 2016).
Shiotani et al., Single-stranded DNA orchestrates an ATM-to-ATR switch at DNA breaks, Mol. Cell, 33(5):547-58 (Mar. 2009).
Stark et al., How cells respond to interferons, Annu. Rev. Biochem., 67:227-64 (1998).
Tomblyn et al., Guidelines for preventing infectious complications among hematopoietic cell transplantation recipients: a global perspective, Biol. Blood Marrow Transplant, 15(10):1143-238 (Oct. 2009).
Towers et al., Interactions between HIV-1 and the cell-autonomous innate immune system, Cell Host Microbe, 16(1):10-18 (Jul. 2014).
Walter et al., Exit from dormancy provokes DNA-damage-induced attrition in haematopoietic stem cells, Nature, 520(7548):549-52 (Apr. 2015).
Wang et al., Homology-driven genome editing in hematopoietic stem and progenitor cells using ZFN mRNA and AAV6 donors, Nat. Biotechnol., 33(12):1256-63 (Dec. 2015).
Wu et al., Molecular linkage between the kinase ATM and NF-kappaB signaling in response to genotoxic stimuli, Science, 311(5764):1141-6 (Feb. 2006).

(56) References Cited

OTHER PUBLICATIONS

Wu et al., VentX trans-activates p53 and p16ink4a to regulate cellular senescence, J. Biol. Chem., 286(14):12693-701 (Apr. 2011).
Yang et al., Trex1 exonuclease degrades ssDNA to prevent chronic checkpoint activation and autoimmune disease, Cell, 131(5):873-86 (Nov. 2007).
Yu et al., DNA-damage-induced type I interferon promotes senescence and inhibits stem cell function, Cell Rep., 11(5):785-97 (May 2015).
Zennou et al., HIV-1 genome nuclear import is mediated by a central DNA flap, Cell, 101(2):173-85 (Apr. 2000).
Zonari et al., Efficient Ex Vivo Engineering and Expansion of Highly Purified Human Hematopoietic Stem and Progenitor Cell Populations for Gene Therapy, Stem Cell Reports, 8(4):977-90 (Apr. 2017).
Ausubel et al. (eds.), Short Protocols in Molecular Biology, Third Edition, John Wiley & Sons, Inc. (1995).
Chen et al., Enrichr: interactive and collaborative HTML5 gene list enrichment analysis tool, BMC Bioinformatics, 14:128 (2013).
Gait (ed.), Oligonucleotide Synthesis: A Practical Approach, Oxford, England: IRL Press Limited (1984).
Lilley et al. (eds.), DNA Structures, Part A, Synthesis and Physical Analysis of DNA, vol. 211 in Methods in Enzymology, San Diego, California: Academic Press, Inc. (1992).
Mátrai et al., Hepatocyte-targeted expression by integrase-defective lentiviral vectors induces antigen-specific tolerance in mice with low genotoxic risk, Hepatology, 53(5):1696-707 (May 2011).
Naka et al., Regulation of reactive oxygen species and genomic stability in hematopoietic stem cells, Antioxid. Redox Signal., 10(11):1883-94 (Nov. 2008).
Naldini, Ex vivo gene transfer and correction for cell-based therapies, Nat. Rev. Genet., 12(5):301-15 (May 2011).
NCBI Reference Sequence: NP_001175.2, Serine/threonine-protein kinase ATR isoform 1 [*Homo sapiens*] (Apr. 23, 2019).
Polak et al. (eds.), In Situ Hybridization: Principles and Practice, New York: Oxford University Press (1990).
Roe et al., DNA Isolation and Sequencing: Essential Techniques, Chichester, West Sussex: John Wiley & Sons (1996).
Roos et al., DNA damage-induced cell death: from specific DNA lesions to the DNA damage response and apoptosis, Cancer Lett., 332(2):237-48 (May 2013).
Sanli et al., AMP-activated protein kinase (AMPK) beyond metabolism: a novel genomic stress sensor participating in the DNA damage response pathway, Cancer Biol. Ther., 15(2):156-69 (Feb. 2014).
Shiloh et al., The ATM protein kinase: regulating the cellular response to genotoxic stress, and more, Nat. Rev. Mol. Cell Biol., 14(4):197-210 (Apr. 2013).
Smyth, Linear Models and Empirical Bayes Methods for Assessing Differential Expression in Microarray Experiments, Statistical Applications in Genetics and Molecular Biology 3 (2004), No. 1, Article 3.
Weber et al., ATM and ATR as therapeutic targets in cancer, Pharmacol. Ther., 149:124-38 (May 2015).
Zhang et al., Silencing p21(Waf1/Cip1/Sdi1) expression increases gene transduction efficiency in primitive human hematopoietic cells, Gene Ther., 12(19):1444-52 (Oct. 2005).
Barber, Host defense, viruses and apoptosis, Cell Death and Differentiation, 8:113-126 (2001).
Piras et al., Insight into how lentiviral transduction modulates the human hematopoietic stem cell transcriptome, Human Gene Therapy, 26(10):A103 abstract p. 261 (2015), Oct. 20.
Li et al., DNA mismatch repair and the DNA damage response, DNA Repair, 38: 94-101 (2016).
NCBI Reference Sequence: NM_000051.3, *Homo sapiens* ATM serine/threonine kinase (ATM), mRNA (Oct. 6, 2016).
NCBI Reference Sequence: NM_000537.3, *Homo sapiens* renin (REN), mRNA (Oct. 6, 2016).
NCBI Reference Sequence: NM_001184.3, *Homo sapiens* ATR serine/threonine kinase (ATR), mRNA (Sep. 15, 2016).
NCBI Reference Sequence: NP_000042.3, Serine-protein kinase ATM isoform a [*Homo sapiens*] (Oct. 6, 2016).
Verhalen et al., Viral DNA Replication-Dependent DNA Damage Response Activation during BK Polyomavirus Infection, Journal of Virology, vol. 89(9): 5032-5039 (May 2015).
Molchadsky et al., p53 is balancing development, differentiation and de-differentiation to assure cancer prevention, Carcinogenesis, 31(9): 1501-1508 (Sep. 2010).

* cited by examiner

B

KEGG 2016        Bar Graph   Table   Grid   Network   Clustergram 

Click on the bars to sort. Now sorted by p-value ranking.

SVG PNG JPG

| p53 signaling pathway_Homo sapiens_hsa04115 | $1.031 \times 10^{-12}$ |

Cytokine-cytokine receptor interaction_Homo sapiens_hsa04060

Apoptosis_Homo sapiens_hsa04210

FoxO signaling pathway_Homo sapiens_hsa04068

Hepatitis B_Homo sapiens_hsa05161

Bladder cancer_Homo sapiens_hsa05219

Osteoclast differentiation_Homo sapiens_hsa04380

Longevity regulating pathway-mammal_Homo sapiens_hsa04211

Epstein-Barr virus infection_Homo sapiens_hsa05169

Non-alcoholic fatty liver disease (NAFLD)_Homo sapiens_hsa04932

KEGG 2016        Bar Graph   Table   Grid   Network   Clustergram 

Click on the bars to sort. Now sorted by p-value ranking.

SVG PNG JPG

| p53 signaling pathway_Homo sapiens_hsa04115 | $4.394 \times 10^{-3}$ |

ECM-receptor interaction_Homo sapiens_hsa04512

Chemokine signaling pathway_Homo sapiens_hsa04062

ABC transporters_Homo sapiens_hsa02010

Staphylococcus aureus infection_Homo sapiens_hsa05150

Vascular smooth muscle contraction_Homo sapiens_hsa04270

Transcriptional misregulation in cancer_Homo sapiens_hsa05202

Cytokine-cytokine receptor interaction_Homo sapiens_hsa04060 cAMP signaling pathway_Homo sapiens_hsa04024

Complement and coagulation cascades_Homo sapiens_hsa04610

FIG. 1 (Continued)

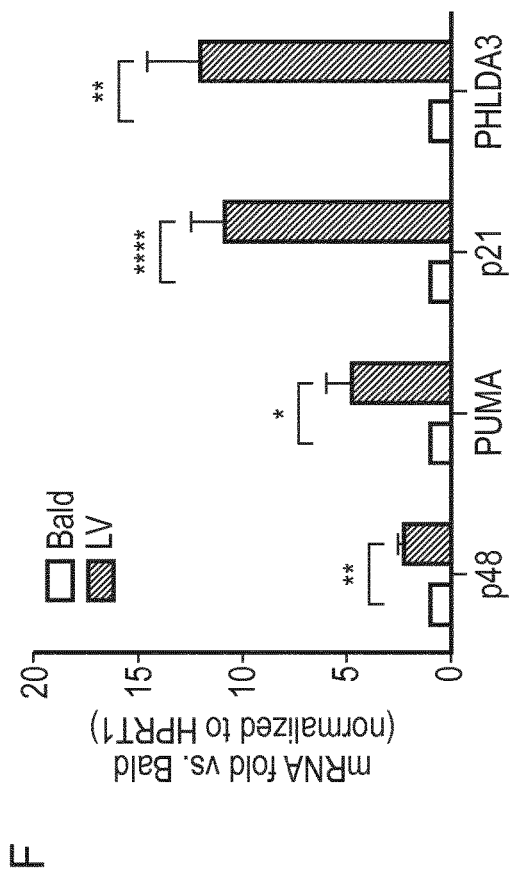
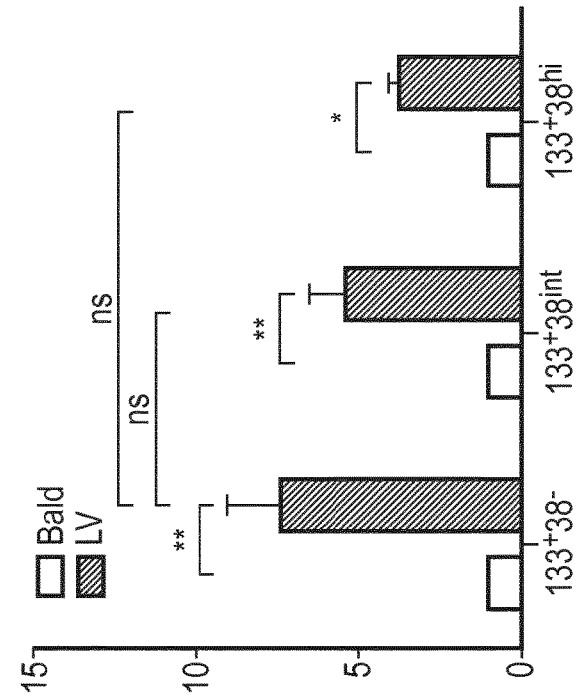
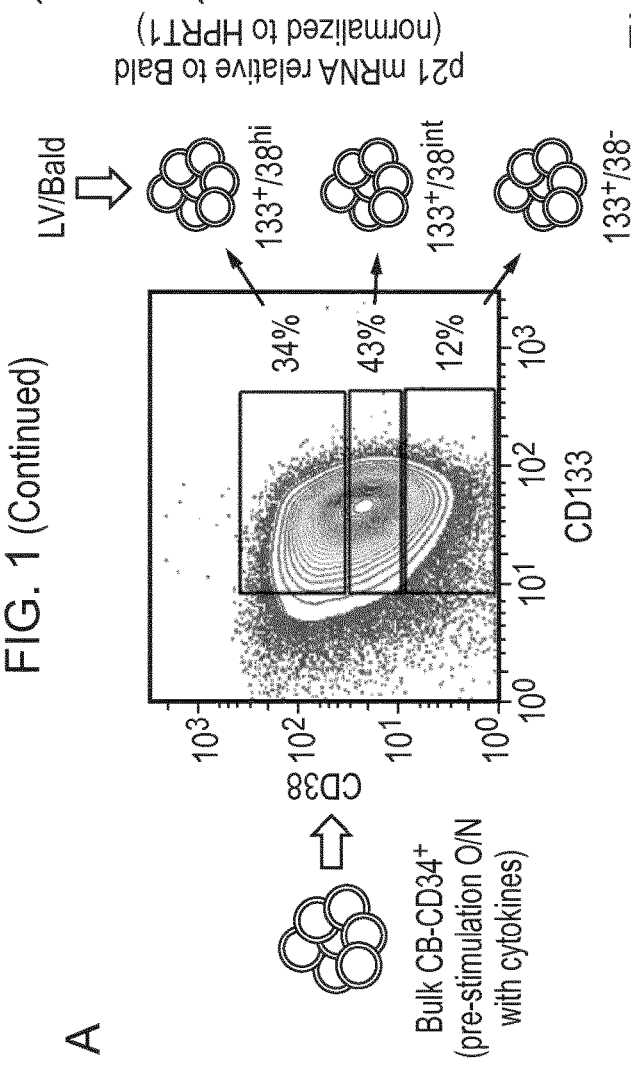
FIG. 1 (Continued)
FIG. 2

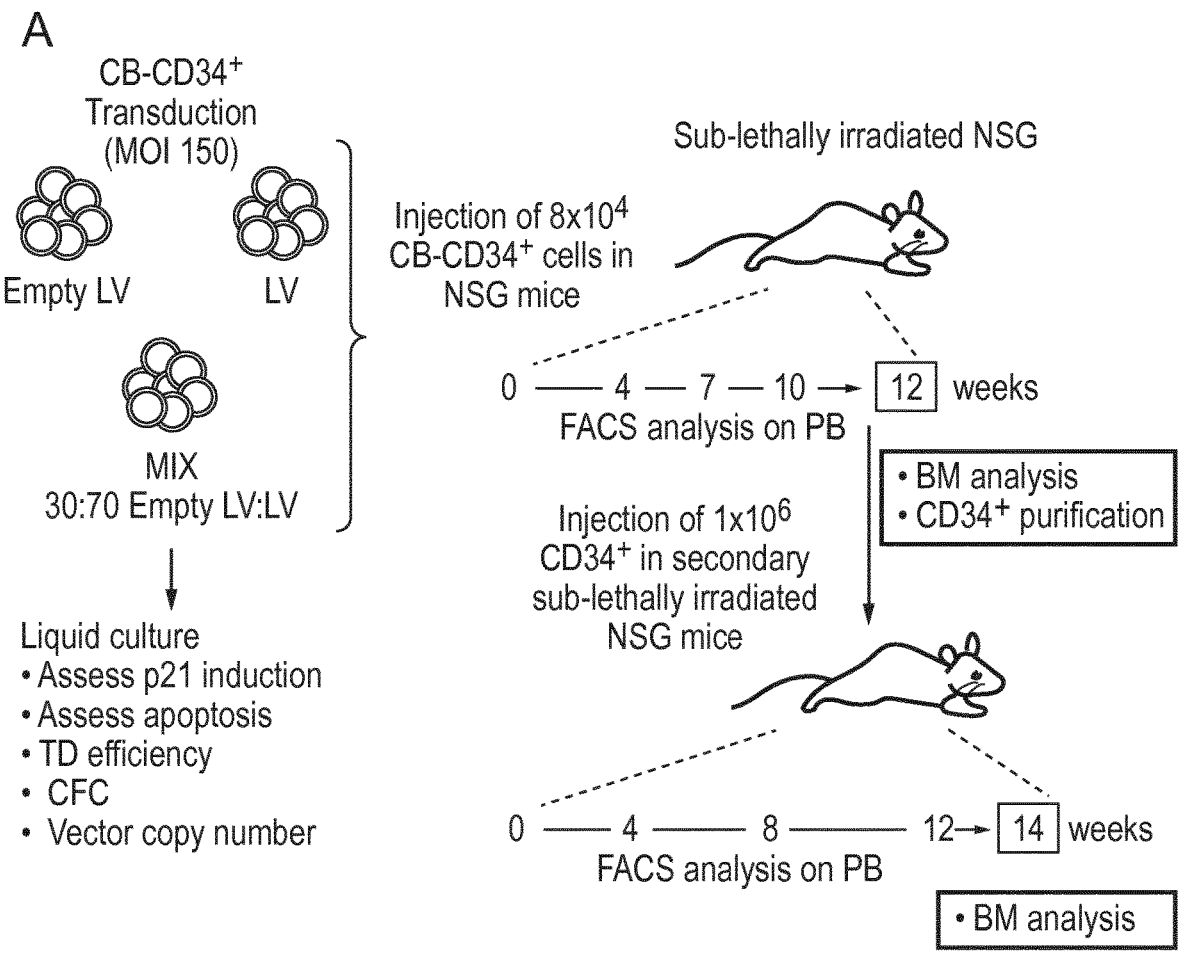
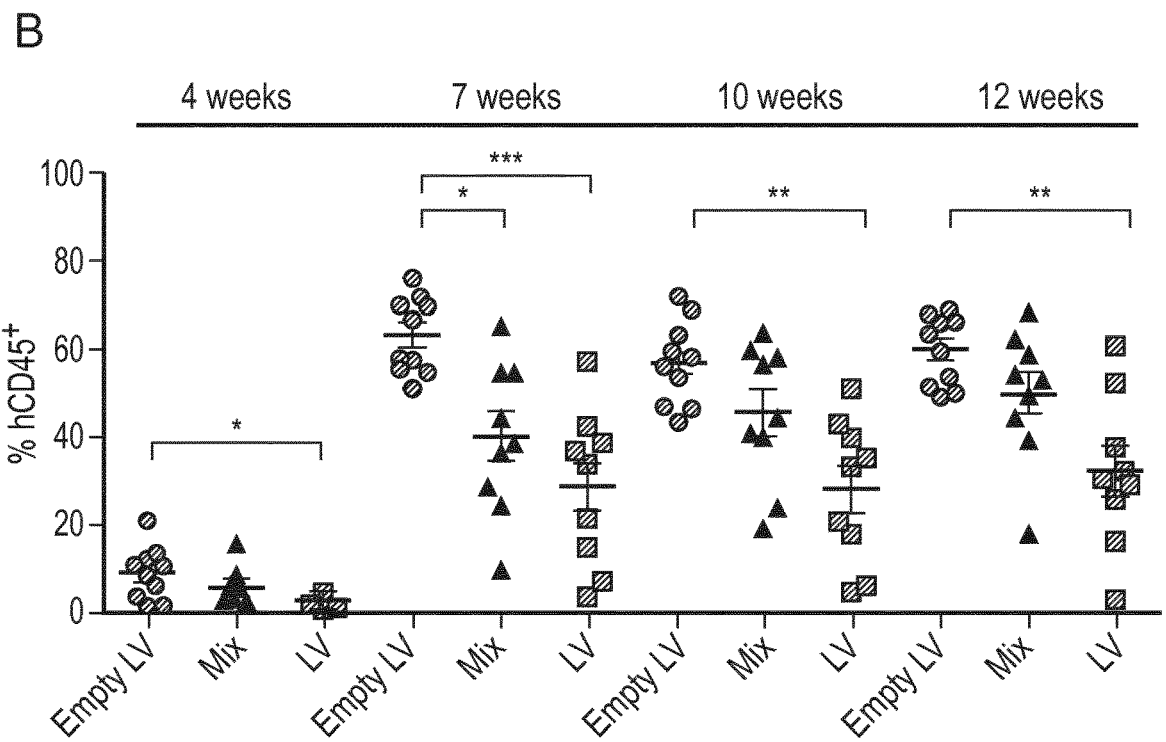
FIG. 5

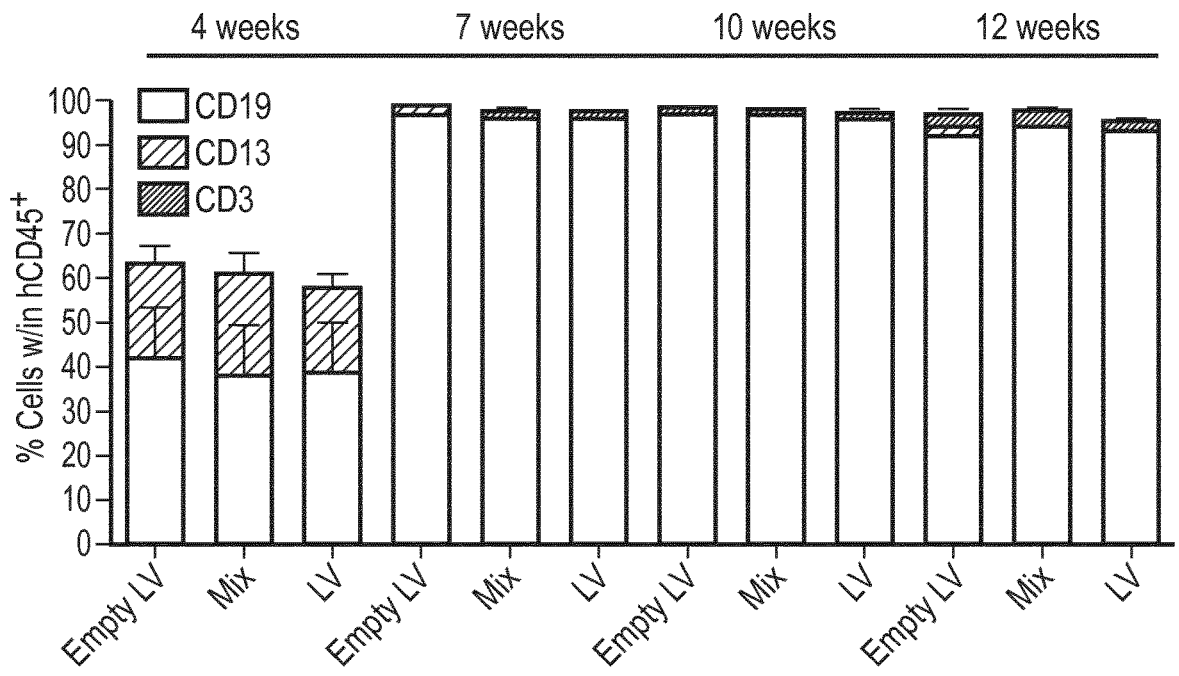
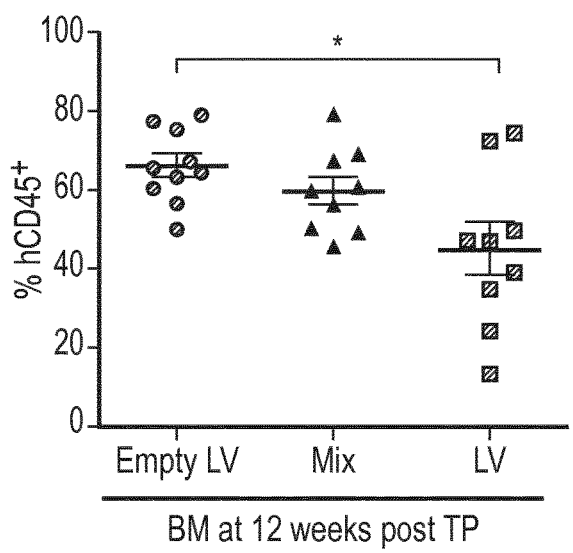
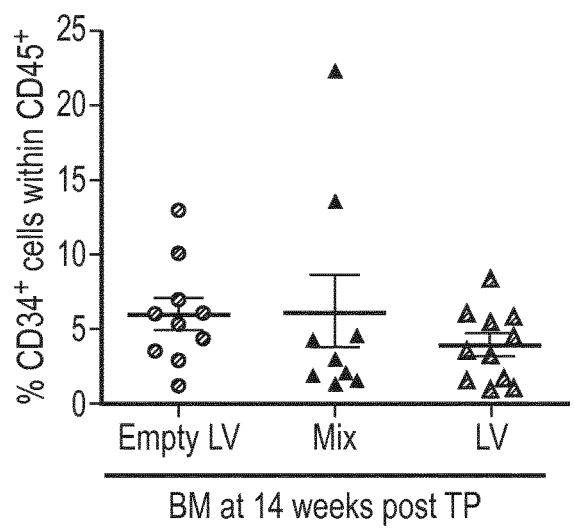
FIG. 5 (Continued)

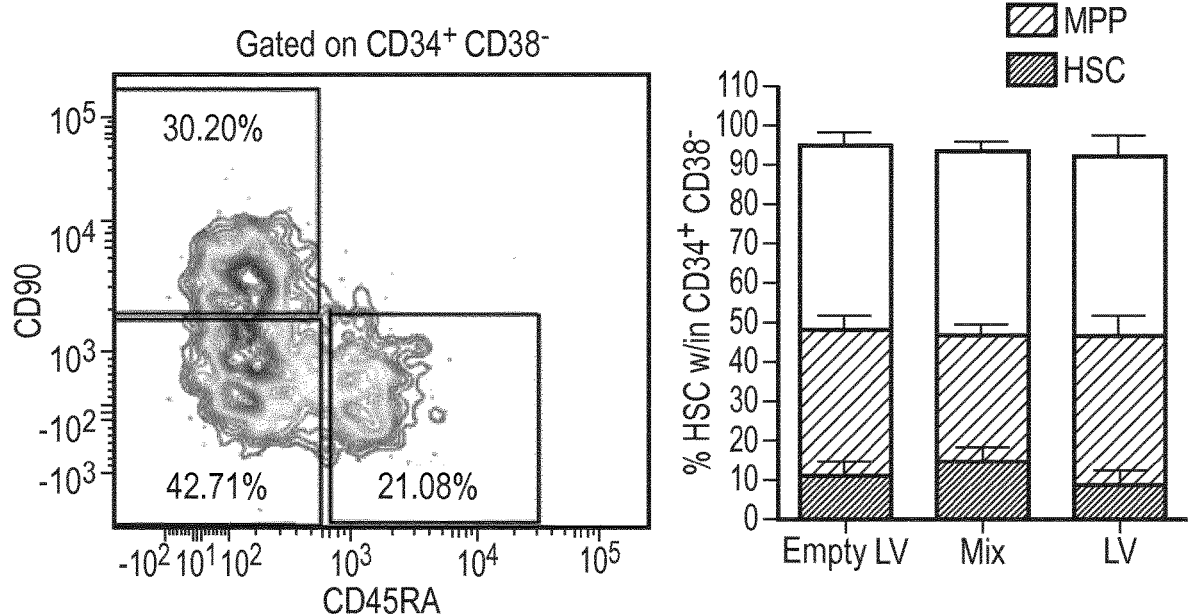
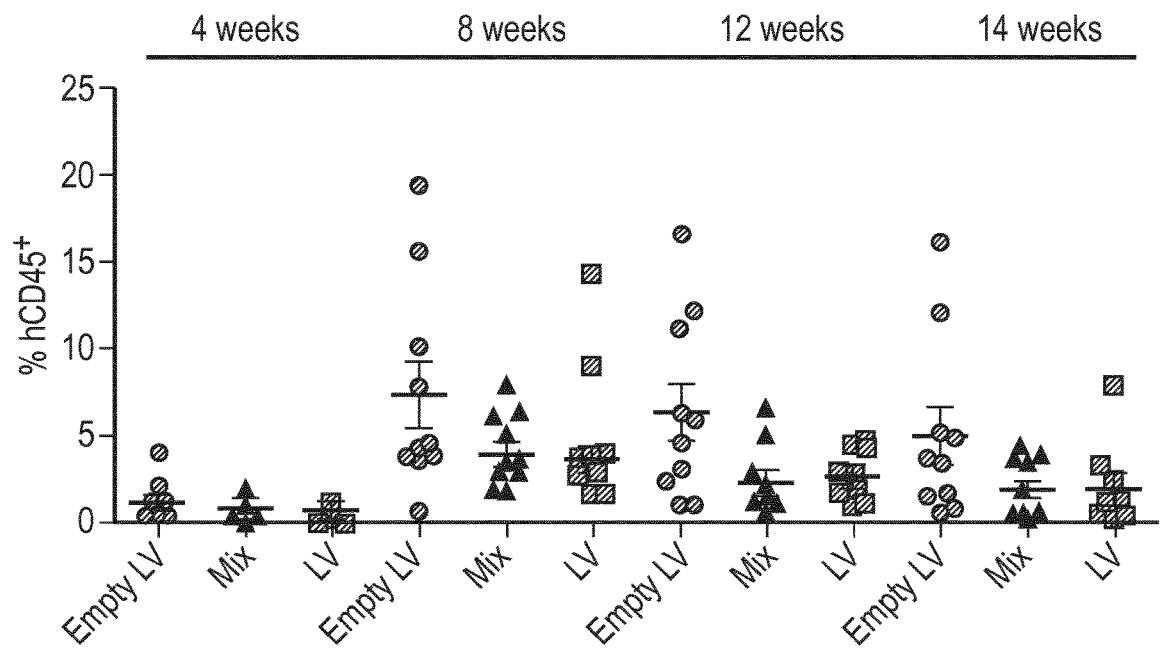
FIG. 5 (Continued)

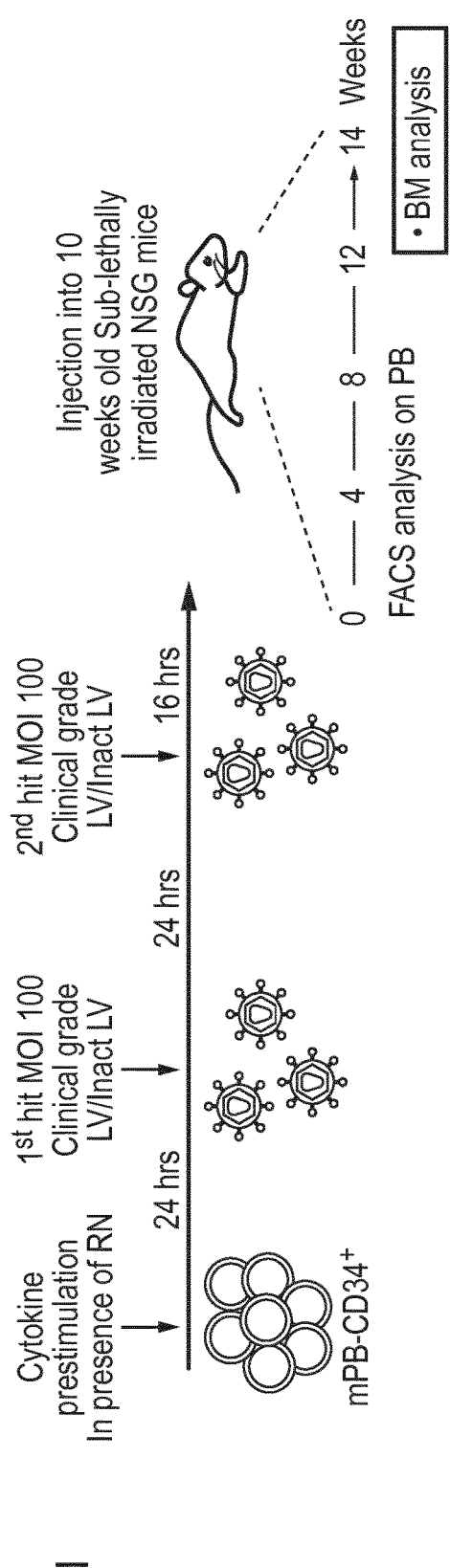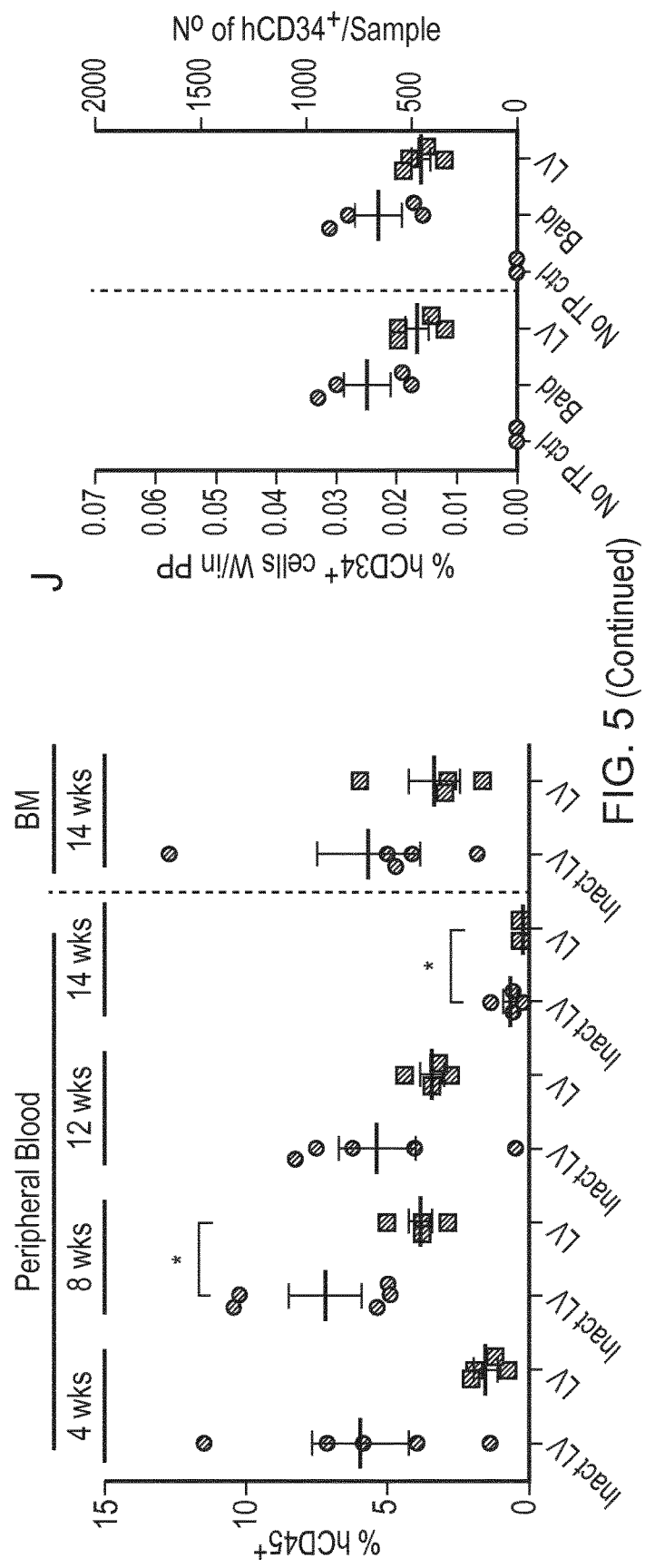
FIG. 5 (Continued)

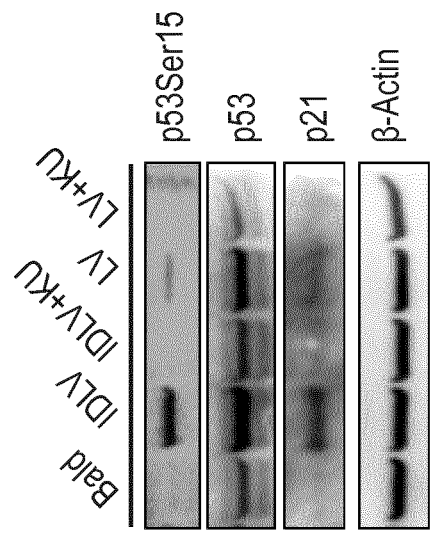
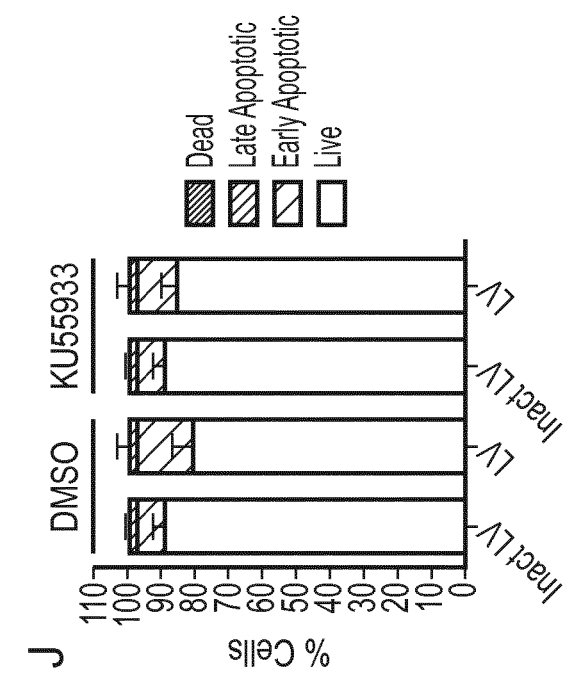
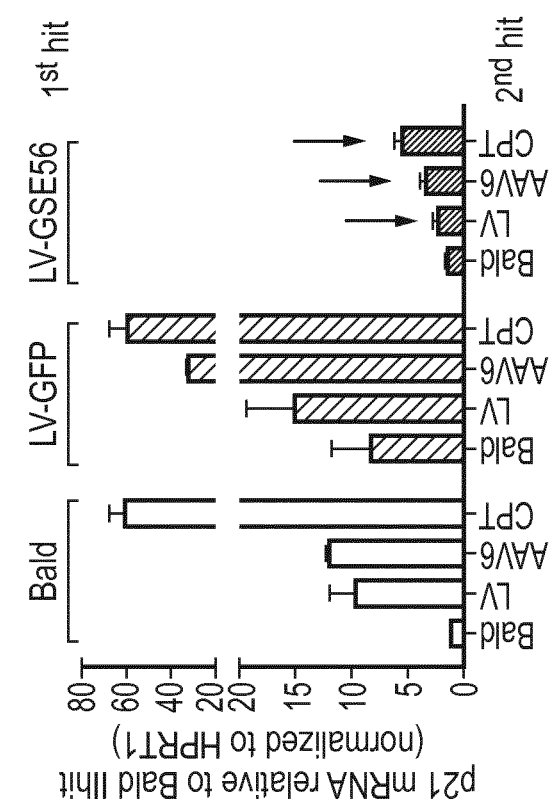
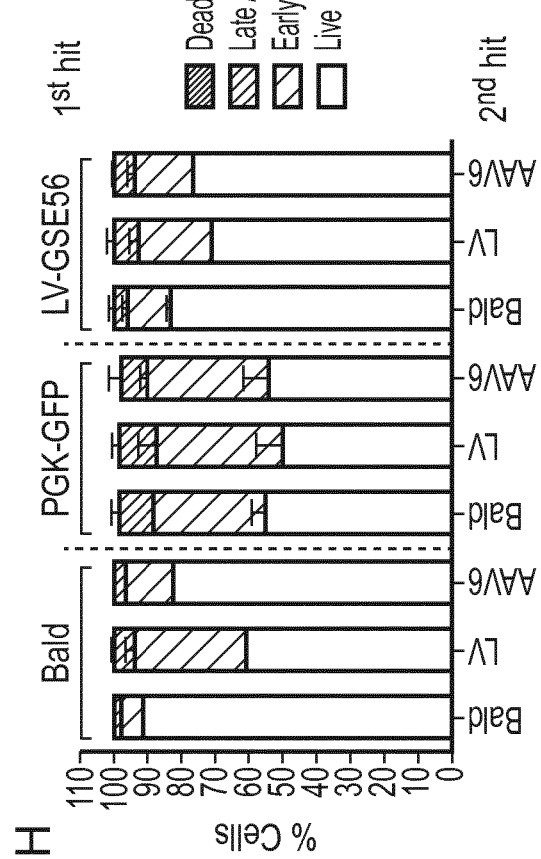
FIG. 6 (Continued)

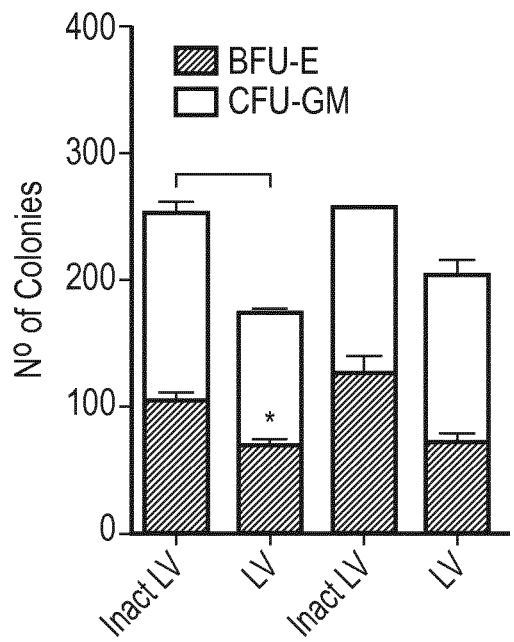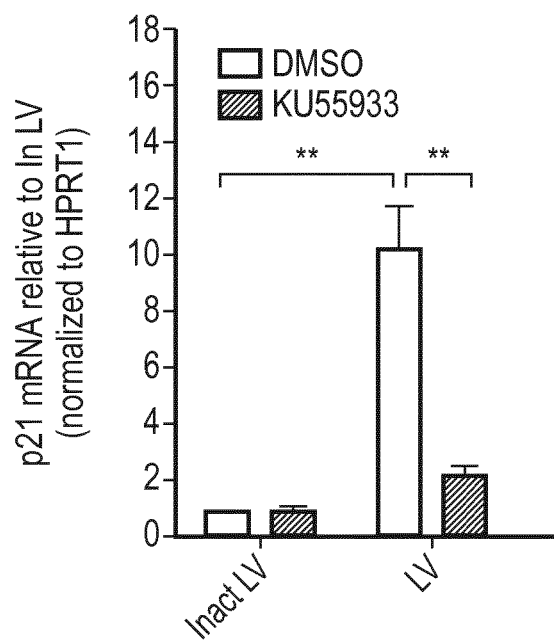
FIG. 6 (Continued)

B

WikiPathways 2015        Bar Graph   Table   Grid   Network ✿

Click the bars to sort. Now sorted by combined score.

SVG PNG JPG

MAPK Signaling Pathway(Homo sapiens)
MAPK Signaling Pathway(Mus musculus)
Glutathione and one carbon metabolism(Mus musculus)
RANKL/RANK Signaling Pathway(Homo sapiens)
Cell Cycle(Homo sapiens)
ATM Signaling Pathway(Homo sapiens)
Regulation of toll-like receptor signaling pathway(Homo sapiens)
DNA Damage Response(Homo sapiens)
TGF Beta Signaling Pathway(Mus musculus)
Structural Pathway of Interleukin 1 (IL-1)(Homo sapiens)

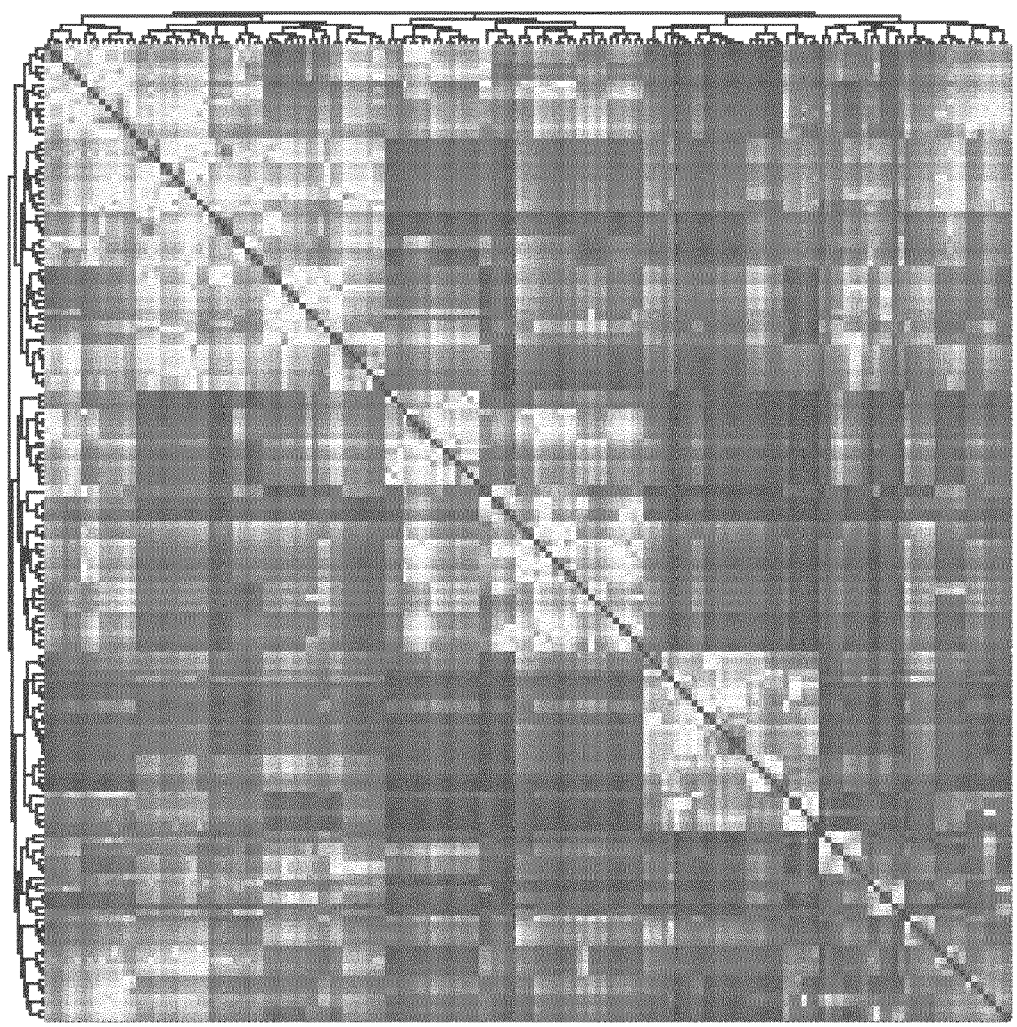

WikiPathways 2016   Bar Graph   Table   Grid   Network   Clustergram   

Click the bars to sort. Now sorted by p-value ranking.

SVG PNG JPG

| Type II interferon signaling (IFNG)_Homo sapiens_WP619 |
| Type II interferon signaling (IFNG)_Mus musculus_WP1253 |
| Fatty Acid Omega Oxidation_Mus musculus_WP33 |
| Type III interferon signaling_Homo sapiens_WP2113 |
| Non-homologous end joining_Mus musculus_WP1242 |
| Thyroxine (Thyroid Hormone) Production_Homo sapiens_WP1981 |
| NLR Proteins_Homo sapiens_WP288 |
| Heme Biosynthesis_Homo sapiens_WP561 |
| Heme Biosynthesis_Mus musculus_WP18 |
| Non-homologous end joining_Homo sapiens_WP438 |

FIG. 8

A 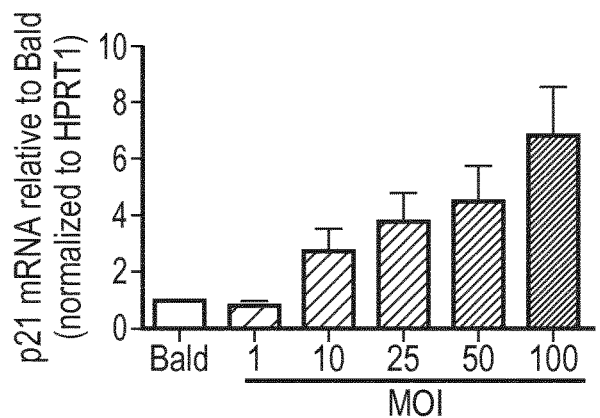 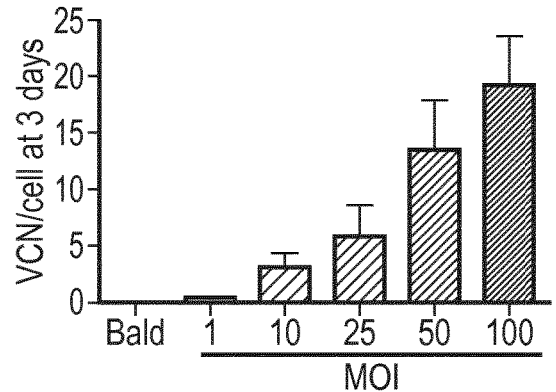
B 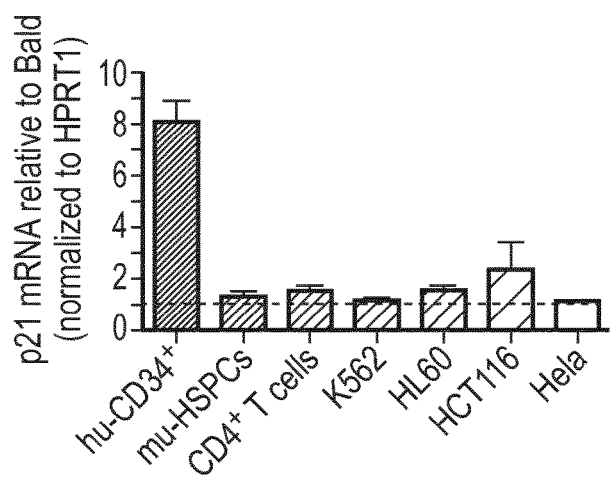 C 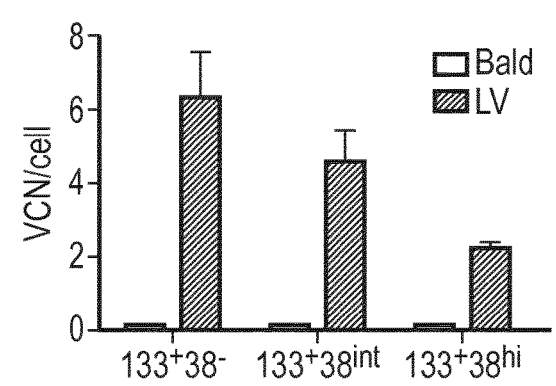
D 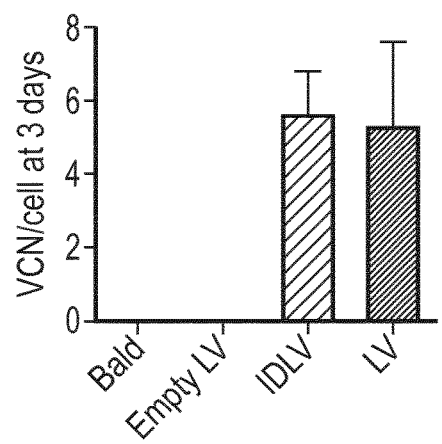 E 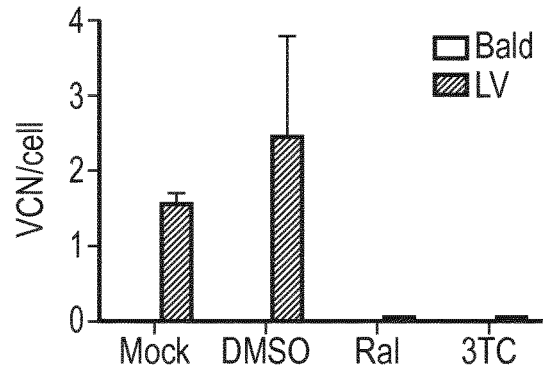
FIG. 11

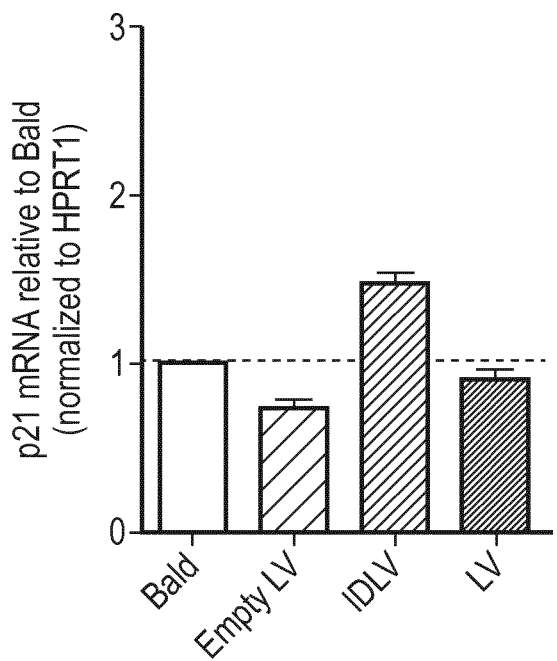
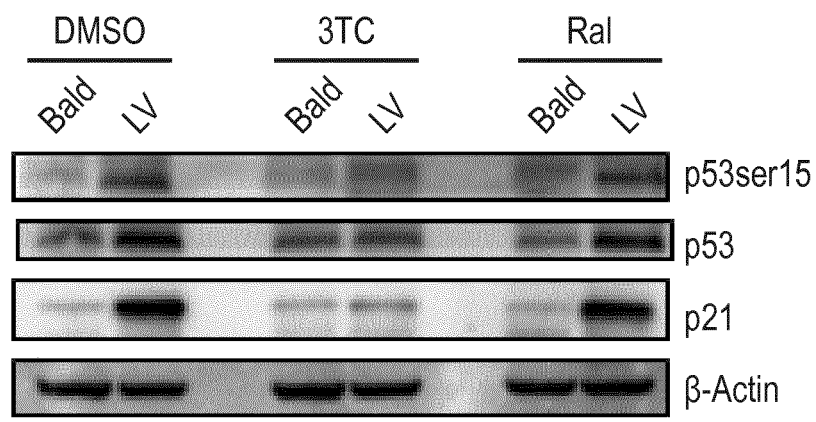
FIG. 11 (Continued)

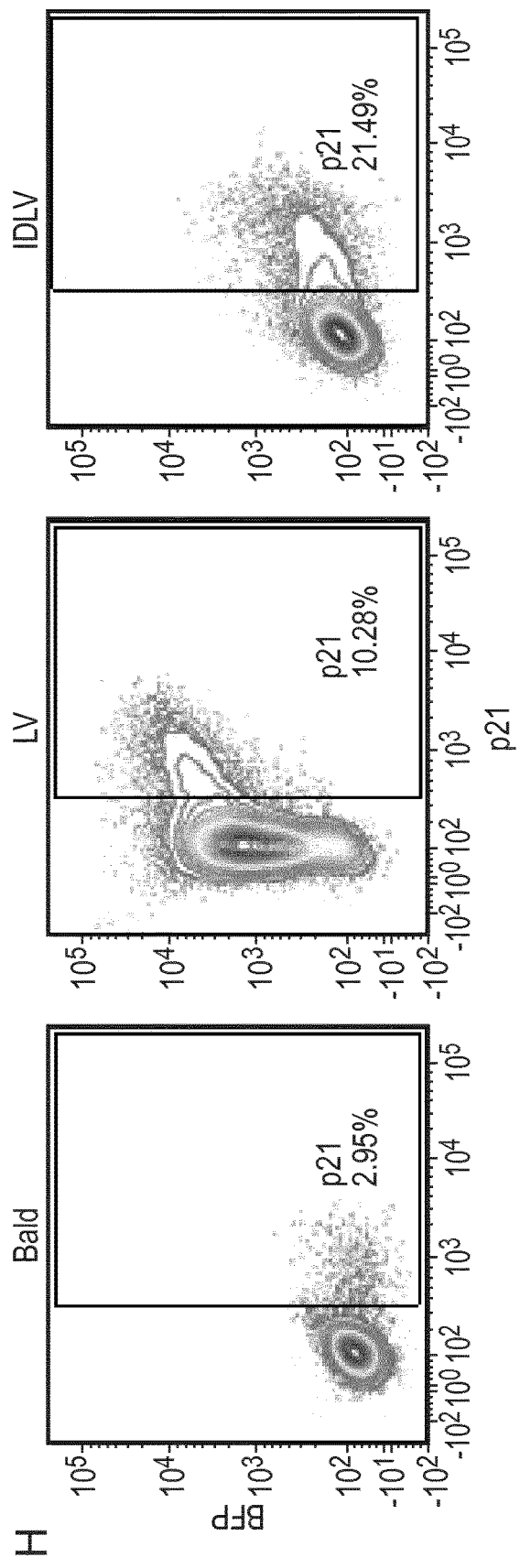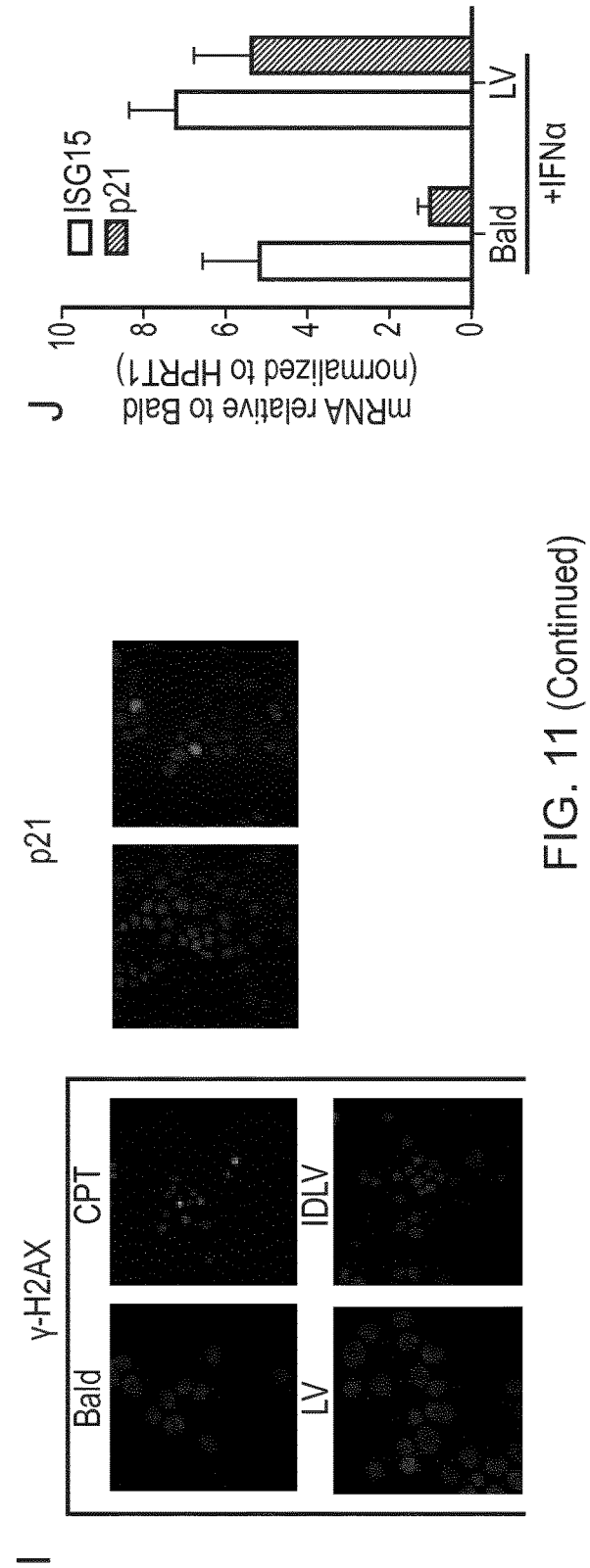
FIG. 11 (Continued)

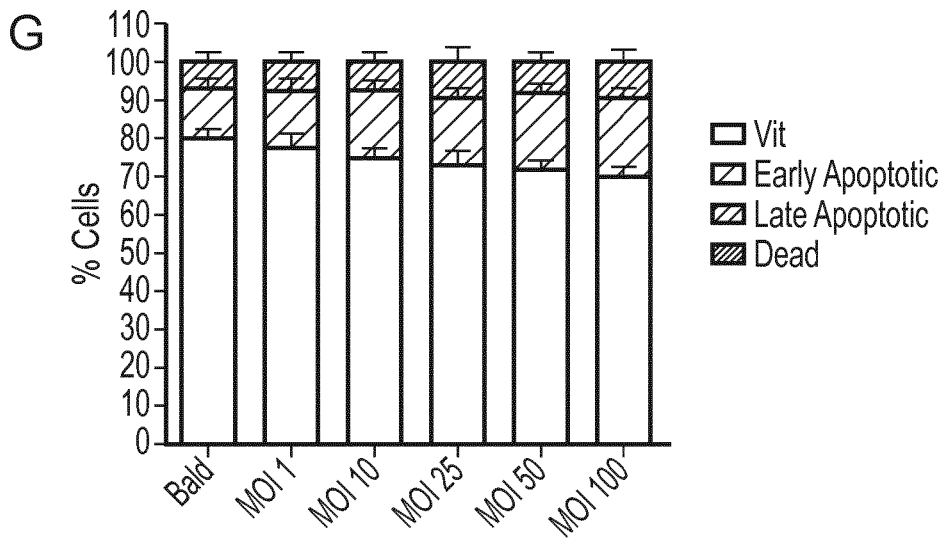
FIG. 13 (Continued)
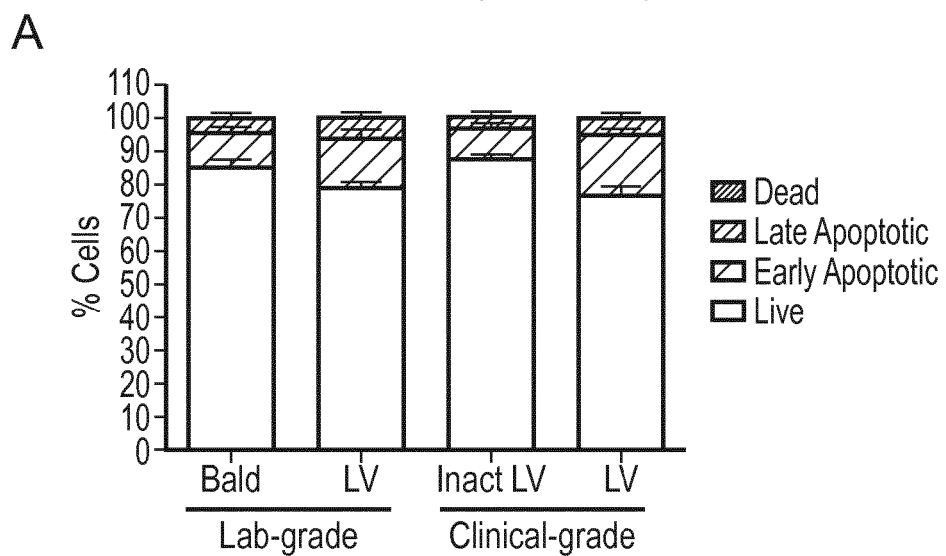
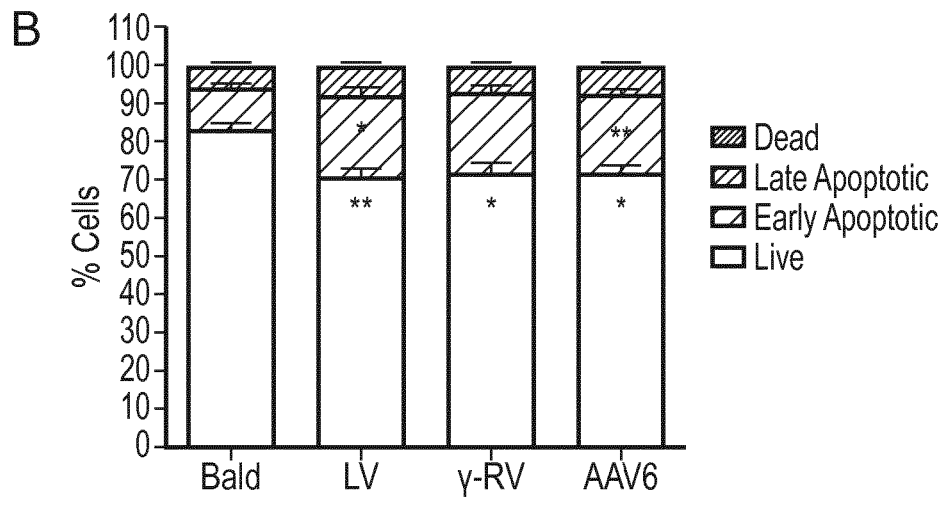
FIG. 14

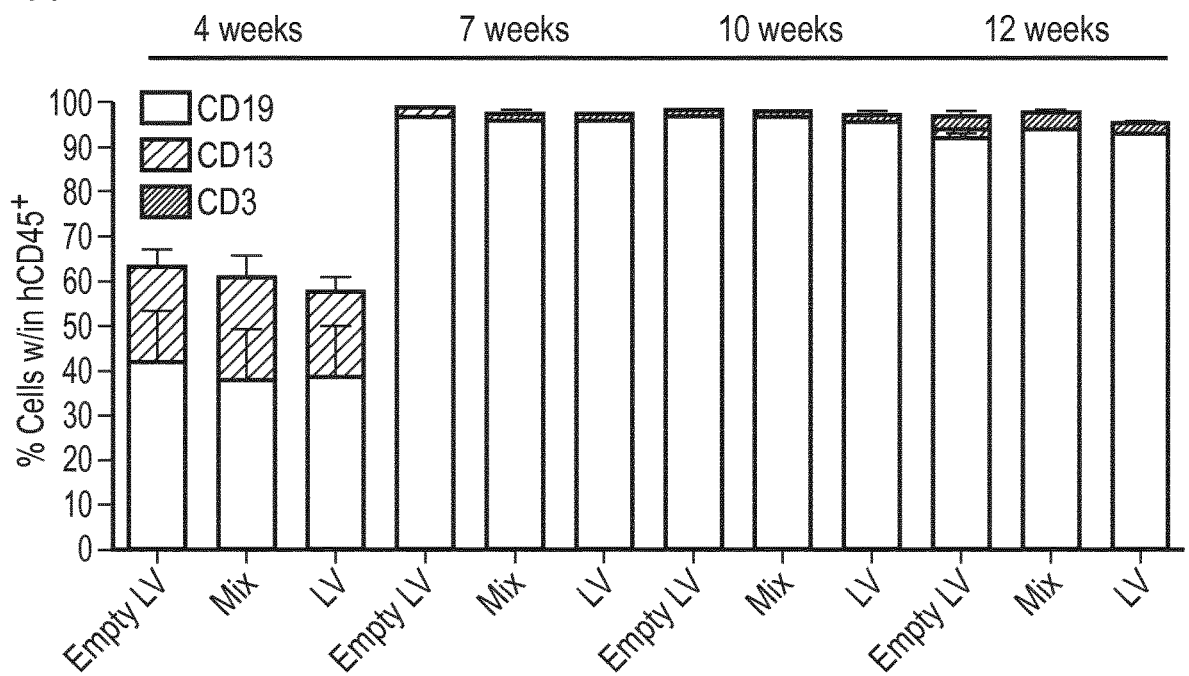
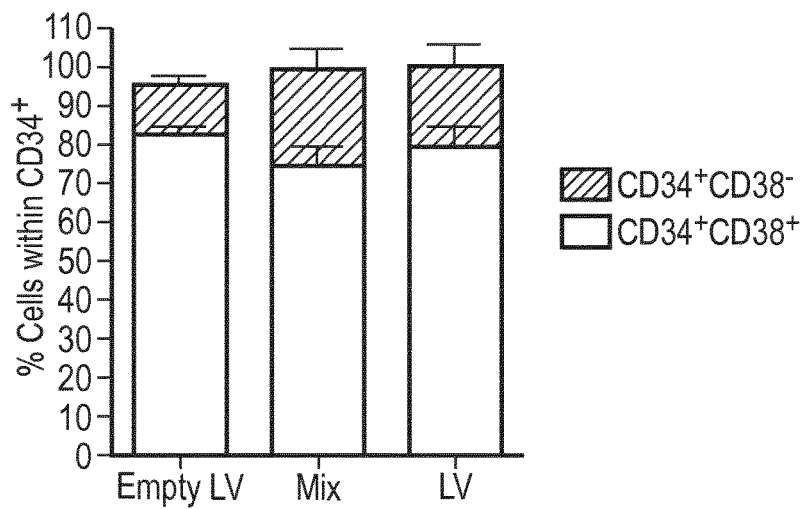
FIG. 15 (Continued)

SEQUENCE LISTING

```
<160> NUMBER OF SEQ ID NOS: 20

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125
```

```
Ala Leu Asn Lys Met Phe Cys Gln Leu Ala Lys Thr Cys Pro Val Gln
            130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 2
<211> LENGTH: 3056
<212> TYPE: PRT
<213> ORGANISM: Homo sapiens

<400> SEQUENCE: 2

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
    50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
```

-continued

```
                100                 105                 110
Pro Arg Leu Lys Cys Gln Glu Leu Leu Asn Tyr Ile Met Asp Thr Val
            115                 120                 125
Lys Asp Ser Ser Asn Gly Ala Ile Tyr Gly Ala Asp Cys Ser Asn Ile
            130                 135                 140
Leu Leu Lys Asp Ile Leu Ser Val Arg Lys Tyr Trp Cys Glu Ile Ser
145                 150                 155                 160
Gln Gln Gln Trp Leu Glu Leu Phe Ser Val Tyr Phe Arg Leu Tyr Leu
                165                 170                 175
Lys Pro Ser Gln Asp Val His Arg Val Leu Val Ala Arg Ile Ile His
            180                 185                 190
Ala Val Thr Lys Gly Cys Cys Ser Gln Thr Asp Gly Leu Asn Ser Lys
            195                 200                 205
Phe Leu Asp Phe Phe Ser Lys Ala Ile Gln Cys Ala Arg Gln Glu Lys
            210                 215                 220
Ser Ser Ser Gly Leu Asn His Ile Leu Ala Ala Leu Thr Ile Phe Leu
225                 230                 235                 240
Lys Thr Leu Ala Val Asn Phe Arg Ile Arg Val Cys Glu Leu Gly Asp
            245                 250                 255
Glu Ile Leu Pro Thr Leu Leu Tyr Ile Trp Thr Gln His Arg Leu Asn
            260                 265                 270
Asp Ser Leu Lys Glu Val Ile Ile Glu Leu Phe Gln Leu Gln Ile Tyr
            275                 280                 285
Ile His His Pro Lys Gly Ala Lys Thr Gln Glu Lys Gly Ala Tyr Glu
            290                 295                 300
Ser Thr Lys Trp Arg Ser Ile Leu Tyr Asn Leu Tyr Asp Leu Leu Val
305                 310                 315                 320
Asn Glu Ile Ser His Ile Gly Ser Arg Gly Lys Tyr Ser Ser Gly Phe
                325                 330                 335
Arg Asn Ile Ala Val Lys Glu Asn Leu Ile Glu Leu Met Ala Asp Ile
            340                 345                 350
Cys His Gln Val Phe Asn Glu Asp Thr Arg Ser Leu Glu Ile Ser Gln
            355                 360                 365
Ser Tyr Thr Thr Thr Gln Arg Glu Ser Ser Asp Tyr Ser Val Pro Cys
            370                 375                 380
Lys Arg Lys Lys Ile Glu Leu Gly Trp Glu Val Ile Lys Asp His Leu
385                 390                 395                 400
Gln Lys Ser Gln Asn Asp Phe Asp Leu Val Pro Trp Leu Gln Ile Ala
            405                 410                 415
Thr Gln Leu Ile Ser Lys Tyr Pro Ala Ser Leu Pro Asn Cys Glu Leu
            420                 425                 430
Ser Pro Leu Leu Met Ile Leu Ser Gln Leu Leu Pro Gln Gln Arg His
            435                 440                 445
Gly Glu Arg Thr Pro Tyr Val Leu Arg Cys Leu Thr Glu Val Ala Leu
            450                 455                 460
Cys Gln Asp Lys Arg Ser Asn Leu Glu Ser Ser Gln Lys Ser Asp Leu
465                 470                 475                 480
Leu Lys Leu Trp Asn Lys Ile Trp Cys Ile Thr Phe Arg Gly Ile Ser
                485                 490                 495
Ser Glu Gln Ile Gln Ala Glu Asn Phe Gly Leu Leu Gly Ala Ile Ile
            500                 505                 510
Gln Gly Ser Leu Val Glu Val Asp Arg Glu Phe Trp Lys Leu Phe Thr
            515                 520                 525
```

```
Gly Ser Ala Cys Arg Pro Ser Cys Pro Ala Val Cys Cys Leu Thr Leu
        530                 535                 540

Ala Leu Thr Thr Ser Ile Val Pro Gly Thr Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
            580                 585                 590

Thr Glu Val Pro Pro Ile Leu His Ser Asn Phe Pro His Leu Val Leu
        595                 600                 605

Glu Lys Ile Leu Val Ser Leu Thr Met Lys Asn Cys Lys Ala Ala Met
610                 615                 620

Asn Phe Phe Gln Ser Val Pro Glu Cys Glu His His Gln Lys Asp Lys
625                 630                 635                 640

Glu Glu Leu Ser Phe Ser Glu Val Glu Glu Leu Phe Leu Gln Thr Thr
                645                 650                 655

Phe Asp Lys Met Asp Phe Leu Thr Ile Val Arg Glu Cys Gly Ile Glu
            660                 665                 670

Lys His Gln Ser Ser Ile Gly Phe Ser Val His Gln Asn Leu Lys Glu
        675                 680                 685

Ser Leu Asp Arg Cys Leu Leu Gly Leu Ser Glu Gln Leu Leu Asn Asn
690                 695                 700

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Lys Ser Leu
            740                 745                 750

Met Gln Cys Ala Gly Glu Ser Ile Thr Leu Phe Lys Asn Lys Thr Asn
        755                 760                 765

Glu Glu Phe Arg Ile Gly Ser Leu Arg Asn Met Met Gln Leu Cys Thr
770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
            820                 825                 830

Gly Glu Val Glu Ser Met Glu Asp Thr Asn Gly Asn Leu Met Glu
        835                 840                 845

Val Glu Asp Gln Ser Ser Met Asn Leu Phe Asn Asp Tyr Pro Asp Ser
850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
                885                 890                 895

Phe Leu Asp Met Leu Lys Phe Leu Cys Leu Cys Val Thr Thr Ala Gln
            900                 905                 910

Thr Asn Thr Val Ser Phe Arg Ala Ala Asp Ile Arg Arg Lys Leu Leu
        915                 920                 925

Met Leu Ile Asp Ser Ser Thr Leu Glu Pro Thr Lys Ser Leu His Leu
930                 935                 940
```

```
His Met Tyr Leu Met Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
                980                 985                 990

His Val Leu His Val Val Lys Asn Leu Gly Gln Ser Asn Met Asp Ser
            995                 1000                1005

Glu Asn Thr Arg Asp Ala Gln Gly Gln Phe Leu Thr Val Ile Gly
    1010                1015                1020

Ala Phe Trp His Leu Thr Lys Glu Arg Lys Tyr Ile Phe Ser Val
    1025                1030                1035

Arg Met Ala Leu Val Asn Cys Leu Lys Thr Leu Leu Glu Ala Asp
    1040                1045                1050

Pro Tyr Ser Lys Trp Ala Ile Leu Asn Val Met Gly Lys Asp Phe
    1055                1060                1065

Pro Val Asn Glu Val Phe Thr Gln Phe Leu Ala Asp Asn His His
    1070                1075                1080

Gln Val Arg Met Leu Ala Ala Glu Ser Ile Asn Arg Leu Phe Gln
    1085                1090                1095

Asp Thr Lys Gly Asp Ser Ser Arg Leu Leu Lys Ala Leu Pro Leu
    1100                1105                1110

Lys Leu Gln Gln Thr Ala Phe Glu Asn Ala Tyr Leu Lys Ala Gln
    1115                1120                1125

Glu Gly Met Arg Glu Met Ser His Ser Ala Glu Asn Pro Glu Thr
    1130                1135                1140

Leu Asp Glu Ile Tyr Asn Arg Lys Ser Val Leu Leu Thr Leu Ile
    1145                1150                1155

Ala Val Val Leu Ser Cys Ser Pro Ile Cys Glu Lys Gln Ala Leu
    1160                1165                1170

Phe Ala Leu Cys Lys Ser Val Lys Glu Asn Gly Leu Glu Pro His
    1175                1180                1185

Leu Val Lys Lys Val Leu Glu Lys Val Ser Glu Thr Phe Gly Tyr
    1190                1195                1200

Arg Arg Leu Glu Asp Phe Met Ala Ser His Leu Asp Tyr Leu Val
    1205                1210                1215

Leu Glu Trp Leu Asn Leu Gln Asp Thr Glu Tyr Asn Leu Ser Ser
    1220                1225                1230

Phe Pro Phe Ile Leu Leu Asn Tyr Thr Asn Ile Glu Asp Phe Tyr
    1235                1240                1245

Arg Ser Cys Tyr Lys Val Leu Ile Pro His Leu Val Ile Arg Ser
    1250                1255                1260

His Phe Asp Glu Val Lys Ser Ile Ala Asn Gln Ile Gln Glu Asp
    1265                1270                1275

Trp Lys Ser Leu Leu Thr Asp Cys Phe Pro Lys Ile Leu Val Asn
    1280                1285                1290

Ile Leu Pro Tyr Phe Ala Tyr Glu Gly Thr Arg Asp Ser Gly Met
    1295                1300                1305

Ala Gln Gln Arg Glu Thr Ala Thr Lys Val Tyr Asp Met Leu Lys
    1310                1315                1320

Ser Glu Asn Leu Leu Gly Lys Gln Ile Asp His Leu Phe Ile Ser
    1325                1330                1335

Asn Leu Pro Glu Ile Val Val Glu Leu Leu Met Thr Leu His Glu
```

-continued

```
            1340                1345                1350

Pro Ala Asn Ser Ser Ala Ser Gln Ser Thr Asp Leu Cys Asp Phe
        1355                1360                1365

Ser Gly Asp Leu Asp Pro Ala Pro Asn Pro Pro His Phe Pro Ser
        1370                1375                1380

His Val Ile Lys Ala Thr Phe Ala Tyr Ile Ser Asn Cys His Lys
        1385                1390                1395

Thr Lys Leu Lys Ser Ile Leu Glu Ile Leu Ser Lys Ser Pro Asp
        1400                1405                1410

Ser Tyr Gln Lys Ile Leu Leu Ala Ile Cys Glu Gln Ala Ala Glu
        1415                1420                1425

Thr Asn Asn Val Tyr Lys Lys His Arg Ile Leu Lys Ile Tyr His
        1430                1435                1440

Leu Phe Val Ser Leu Leu Leu Lys Asp Ile Lys Ser Gly Leu Gly
        1445                1450                1455

Gly Ala Trp Ala Phe Val Leu Arg Asp Val Ile Tyr Thr Leu Ile
        1460                1465                1470

His Tyr Ile Asn Gln Arg Pro Ser Cys Ile Met Asp Val Ser Leu
        1475                1480                1485

Arg Ser Phe Ser Leu Cys Cys Asp Leu Leu Ser Gln Val Cys Gln
        1490                1495                1500

Thr Ala Val Thr Tyr Cys Lys Asp Ala Leu Glu Asn His Leu His
        1505                1510                1515

Val Ile Val Gly Thr Leu Ile Pro Leu Val Tyr Glu Gln Val Glu
        1520                1525                1530

Val Gln Lys Gln Val Leu Asp Leu Leu Lys Tyr Leu Val Ile Asp
        1535                1540                1545

Asn Lys Asp Asn Glu Asn Leu Tyr Ile Thr Ile Lys Leu Leu Asp
        1550                1555                1560

Pro Phe Pro Asp His Val Val Phe Lys Asp Leu Arg Ile Thr Gln
        1565                1570                1575

Gln Lys Ile Lys Tyr Ser Arg Gly Pro Phe Ser Leu Leu Glu Glu
        1580                1585                1590

Ile Asn His Phe Leu Ser Val Ser Val Tyr Asp Ala Leu Pro Leu
        1595                1600                1605

Thr Arg Leu Glu Gly Leu Lys Asp Leu Arg Arg Gln Leu Glu Leu
        1610                1615                1620

His Lys Asp Gln Met Val Asp Ile Met Arg Ala Ser Gln Asp Asn
        1625                1630                1635

Pro Gln Asp Gly Ile Met Val Lys Leu Val Val Asn Leu Leu Gln
        1640                1645                1650

Leu Ser Lys Met Ala Ile Asn His Thr Gly Glu Lys Glu Val Leu
        1655                1660                1665

Glu Ala Val Gly Ser Cys Leu Gly Glu Val Gly Pro Ile Asp Phe
        1670                1675                1680

Ser Thr Ile Ala Ile Gln His Ser Lys Asp Ala Ser Tyr Thr Lys
        1685                1690                1695

Ala Leu Lys Leu Phe Glu Asp Lys Glu Leu Gln Trp Thr Phe Ile
        1700                1705                1710

Met Leu Thr Tyr Leu Asn Asn Thr Leu Val Glu Asp Cys Val Lys
        1715                1720                1725

Val Arg Ser Ala Ala Val Thr Cys Leu Lys Asn Ile Leu Ala Thr
        1730                1735                1740
```

```
Lys Thr Gly His Ser Phe Trp Glu Ile Tyr Lys Met Thr Thr Asp
1745                1750                1755

Pro Met Leu Ala Tyr Leu Gln Pro Phe Arg Thr Ser Arg Lys Lys
    1760                1765                1770

Phe Leu Glu Val Pro Arg Phe Asp Lys Glu Asn Pro Phe Glu Gly
    1775                1780                1785

Leu Asp Asp Ile Asn Leu Trp Ile Pro Leu Ser Glu Asn His Asp
    1790                1795                1800

Ile Trp Ile Lys Thr Leu Thr Cys Ala Phe Leu Asp Ser Gly Gly
    1805                1810                1815

Thr Lys Cys Glu Ile Leu Gln Leu Leu Lys Pro Met Cys Glu Val
    1820                1825                1830

Lys Thr Asp Phe Cys Gln Thr Val Leu Pro Tyr Leu Ile His Asp
    1835                1840                1845

Ile Leu Leu Gln Asp Thr Asn Glu Ser Trp Arg Asn Leu Leu Ser
    1850                1855                1860

Thr His Val Gln Gly Phe Phe Thr Ser Cys Leu Arg His Phe Ser
    1865                1870                1875

Gln Thr Ser Arg Ser Thr Thr Pro Ala Asn Leu Asp Ser Glu Ser
    1880                1885                1890

Glu His Phe Phe Arg Cys Cys Leu Asp Lys Lys Ser Gln Arg Thr
    1895                1900                1905

Met Leu Ala Val Val Asp Tyr Met Arg Arg Gln Lys Arg Pro Ser
    1910                1915                1920

Ser Gly Thr Ile Phe Asn Asp Ala Phe Trp Leu Asp Leu Asn Tyr
    1925                1930                1935

Leu Glu Val Ala Lys Val Ala Gln Ser Cys Ala Ala His Phe Thr
    1940                1945                1950

Ala Leu Leu Tyr Ala Glu Ile Tyr Ala Asp Lys Lys Ser Met Asp
    1955                1960                1965

Asp Gln Glu Lys Arg Ser Leu Ala Phe Glu Glu Gly Ser Gln Ser
    1970                1975                1980

Thr Thr Ile Ser Ser Leu Ser Glu Lys Ser Lys Glu Glu Thr Gly
    1985                1990                1995

Ile Ser Leu Gln Asp Leu Leu Leu Glu Ile Tyr Arg Ser Ile Gly
    2000                2005                2010

Glu Pro Asp Ser Leu Tyr Gly Cys Gly Gly Gly Lys Met Leu Gln
    2015                2020                2025

Pro Ile Thr Arg Leu Arg Thr Tyr Glu His Glu Ala Met Trp Gly
    2030                2035                2040

Lys Ala Leu Val Thr Tyr Asp Leu Glu Thr Ala Ile Pro Ser Ser
    2045                2050                2055

Thr Arg Gln Ala Gly Ile Ile Gln Ala Leu Gln Asn Leu Gly Leu
    2060                2065                2070

Cys His Ile Leu Ser Val Tyr Leu Lys Gly Leu Asp Tyr Glu Asn
    2075                2080                2085

Lys Asp Trp Cys Pro Glu Leu Glu Glu Leu His Tyr Gln Ala Ala
    2090                2095                2100

Trp Arg Asn Met Gln Trp Asp His Cys Thr Ser Val Ser Lys Glu
    2105                2110                2115

Val Glu Gly Thr Ser Tyr His Glu Ser Leu Tyr Asn Ala Leu Gln
    2120                2125                2130
```

```
Ser Leu Arg Asp Arg Glu Phe Ser Thr Phe Tyr Glu Ser Leu Lys
    2135                2140                2145

Tyr Ala Arg Val Lys Glu Val Glu Glu Met Cys Lys Arg Ser Leu
    2150                2155                2160

Glu Ser Val Tyr Ser Leu Tyr Pro Thr Leu Ser Arg Leu Gln Ala
    2165                2170                2175

Ile Gly Glu Leu Glu Ser Ile Gly Glu Leu Phe Ser Arg Ser Val
    2180                2185                2190

Thr His Arg Gln Leu Ser Glu Val Tyr Ile Lys Trp Gln Lys His
    2195                2200                2205

Ser Gln Leu Leu Lys Asp Ser Asp Phe Ser Phe Gln Glu Pro Ile
    2210                2215                2220

Met Ala Leu Arg Thr Val Ile Leu Glu Ile Leu Met Glu Lys Glu
    2225                2230                2235

Met Asp Asn Ser Gln Arg Glu Cys Ile Lys Asp Ile Leu Thr Lys
    2240                2245                2250

His Leu Val Glu Leu Ser Ile Leu Ala Arg Thr Phe Lys Asn Thr
    2255                2260                2265

Gln Leu Pro Glu Arg Ala Ile Phe Gln Ile Lys Gln Tyr Asn Ser
    2270                2275                2280

Val Ser Cys Gly Val Ser Glu Trp Gln Leu Glu Glu Ala Gln Val
    2285                2290                2295

Phe Trp Ala Lys Lys Glu Gln Ser Leu Ala Leu Ser Ile Leu Lys
    2300                2305                2310

Gln Met Ile Lys Lys Leu Asp Ala Ser Cys Ala Ala Asn Asn Pro
    2315                2320                2325

Ser Leu Lys Leu Thr Tyr Thr Glu Cys Leu Arg Val Cys Gly Asn
    2330                2335                2340

Trp Leu Ala Glu Thr Cys Leu Glu Asn Pro Ala Val Ile Met Gln
    2345                2350                2355

Thr Tyr Leu Glu Lys Ala Val Glu Val Ala Gly Asn Tyr Asp Gly
    2360                2365                2370

Glu Ser Ser Asp Glu Leu Arg Asn Gly Lys Met Lys Ala Phe Leu
    2375                2380                2385

Ser Leu Ala Arg Phe Ser Asp Thr Gln Tyr Gln Arg Ile Glu Asn
    2390                2395                2400

Tyr Met Lys Ser Ser Glu Phe Glu Asn Lys Gln Ala Leu Leu Lys
    2405                2410                2415

Arg Ala Lys Glu Glu Val Gly Leu Leu Arg Glu His Lys Ile Gln
    2420                2425                2430

Thr Asn Arg Tyr Thr Val Lys Val Gln Arg Glu Leu Glu Leu Asp
    2435                2440                2445

Glu Leu Ala Leu Arg Ala Leu Lys Glu Asp Arg Lys Arg Phe Leu
    2450                2455                2460

Cys Lys Ala Val Glu Asn Tyr Ile Asn Cys Leu Leu Ser Gly Glu
    2465                2470                2475

Glu His Asp Met Trp Val Phe Arg Leu Cys Ser Leu Trp Leu Glu
    2480                2485                2490

Asn Ser Gly Val Ser Glu Val Asn Gly Met Met Lys Arg Asp Gly
    2495                2500                2505

Met Lys Ile Pro Thr Tyr Lys Phe Leu Pro Leu Met Tyr Gln Leu
    2510                2515                2520

Ala Ala Arg Met Gly Thr Lys Met Met Gly Gly Leu Gly Phe His
```

```
            2525                2530                2535

Glu Val Leu Asn Asn Leu Ile Ser Arg Ile Ser Met Asp His Pro
    2540                2545                2550

His His Thr Leu Phe Ile Ile Leu Ala Leu Ala Asn Ala Asn Arg
    2555                2560                2565

Asp Glu Phe Leu Thr Lys Pro Glu Val Ala Arg Arg Ser Arg Ile
    2570                2575                2580

Thr Lys Asn Val Pro Lys Gln Ser Ser Gln Leu Asp Glu Asp Arg
    2585                2590                2595

Thr Glu Ala Ala Asn Arg Ile Ile Cys Thr Ile Arg Ser Arg Arg
    2600                2605                2610

Pro Gln Met Val Arg Ser Val Glu Ala Leu Cys Asp Ala Tyr Ile
    2615                2620                2625

Ile Leu Ala Asn Leu Asp Ala Thr Gln Trp Lys Thr Gln Arg Lys
    2630                2635                2640

Gly Ile Asn Ile Pro Ala Asp Gln Pro Ile Thr Lys Leu Lys Asn
    2645                2650                2655

Leu Glu Asp Val Val Val Pro Thr Met Glu Ile Lys Val Asp His
    2660                2665                2670

Thr Gly Glu Tyr Gly Asn Leu Val Thr Ile Gln Ser Phe Lys Ala
    2675                2680                2685

Glu Phe Arg Leu Ala Gly Gly Val Asn Leu Pro Lys Ile Ile Asp
    2690                2695                2700

Cys Val Gly Ser Asp Gly Lys Glu Arg Arg Gln Leu Val Lys Gly
    2705                2710                2715

Arg Asp Asp Leu Arg Gln Asp Ala Val Met Gln Gln Val Phe Gln
    2720                2725                2730

Met Cys Asn Thr Leu Leu Gln Arg Asn Thr Glu Thr Arg Lys Arg
    2735                2740                2745

Lys Leu Thr Ile Cys Thr Tyr Lys Val Val Pro Leu Ser Gln Arg
    2750                2755                2760

Ser Gly Val Leu Glu Trp Cys Thr Gly Thr Val Pro Ile Gly Glu
    2765                2770                2775

Phe Leu Val Asn Asn Glu Asp Gly Ala His Lys Arg Tyr Arg Pro
    2780                2785                2790

Asn Asp Phe Ser Ala Phe Gln Cys Gln Lys Lys Met Met Glu Val
    2795                2800                2805

Gln Lys Lys Ser Phe Glu Glu Lys Tyr Glu Val Phe Met Asp Val
    2810                2815                2820

Cys Gln Asn Phe Gln Pro Val Phe Arg Tyr Phe Cys Met Glu Lys
    2825                2830                2835

Phe Leu Asp Pro Ala Ile Trp Phe Glu Lys Arg Leu Ala Tyr Thr
    2840                2845                2850

Arg Ser Val Ala Thr Ser Ser Ile Val Gly Tyr Ile Leu Gly Leu
    2855                2860                2865

Gly Asp Arg His Val Gln Asn Ile Leu Ile Asn Glu Gln Ser Ala
    2870                2875                2880

Glu Leu Val His Ile Asp Leu Gly Val Ala Phe Glu Gln Gly Lys
    2885                2890                2895

Ile Leu Pro Thr Pro Glu Thr Val Pro Phe Arg Leu Thr Arg Asp
    2900                2905                2910

Ile Val Asp Gly Met Gly Ile Thr Gly Val Glu Gly Val Phe Arg
    2915                2920                2925
```

| | | | | | | | | | | | |
|---|---|---|---|---|---|---|---|---|---|---|---|
|Arg|Cys|Cys|Glu|Lys|Thr|Met|Glu|Val|Met|Arg|Asn|Ser|Gln|Glu|
| |2930| | | |2935| | | |2940| | | | | |

Arg Cys Cys Glu Lys Thr Met Glu Val Met Arg Asn Ser Gln Glu
    2930                2935                2940

Thr Leu Leu Thr Ile Val Glu Val Leu Leu Tyr Asp Pro Leu Phe
    2945                2950                2955

Asp Trp Thr Met Asn Pro Leu Lys Ala Leu Tyr Leu Gln Gln Arg
    2960                2965                2970

Pro Glu Asp Glu Thr Glu Leu His Pro Thr Leu Asn Ala Asp Asp
    2975                2980                2985

Gln Glu Cys Lys Arg Asn Leu Ser Asp Ile Asp Gln Ser Phe Asn
    2990                2995                3000

Lys Val Ala Glu Arg Val Leu Met Arg Leu Gln Glu Lys Leu Lys
    3005                3010                3015

Gly Val Glu Glu Gly Thr Val Leu Ser Val Gly Gly Gln Val Asn
    3020                3025                3030

Leu Leu Ile Gln Gln Ala Ile Asp Pro Lys Asn Leu Ser Arg Leu
    3035                3040                3045

Phe Pro Gly Trp Lys Ala Trp Val
    3050                3055

<210> SEQ ID NO 3
<211> LENGTH: 9171
<212> TYPE: DNA
<213> ORGANISM: Homo sapiens

<400> SEQUENCE: 3

```
atgagtctag tacttaatga tctgcttatc tgctgccgtc aactagaaca tgatagagct     60
acagaacgaa agaaagaagt tgagaaattt aagcgcctga ttcgagatcc tgaaacaatt    120
aaacatctag atcggcattc agattccaaa caaggaaaat atttgaattg ggatgctgtt    180
tttagatttt tacagaaata tattcagaaa gaaacagaat gtctgagaat agcaaaacca    240
aatgtatcag cctcaacaca agcctccagg cagaaaaaga tgcaggaaat cagtagtttg    300
gtcaaatact tcatcaaatg tgcaaacaga gagcaccta ggctaaaatg tcaagaactc    360
ttaaattata tcatggatac agtgaaagat tcatctaatg tgctatttta cggagctgat    420
tgtagcaaca tactactcaa agacattctt tctgtgagaa atactggtg tgaaatatct    480
cagcaacagt ggttagaatt gttctctgtg tacttcaggc tctatctgaa accttcacaa    540
gatgttcata gagttttagt ggctagaata attcatgctg ttaccaaagg atgctgttct    600
cagactgacg gattaaattc caaatttttg gacttttttt ccaaggctat tcagtgtgcg    660
agacaagaaa agagctcttc aggtctaaat catatcttag cagctcttac tatcttcctc    720
aagactttgg ctgtcaactt tcgaattcga gtgtgtgaat taggagatga aattcttccc    780
actttgcttt atatttggac tcaacatagg cttaatgatt ctttaaaaga agtcattatt    840
gaattatttc aactgcaaat ttatatccat catccgaaag gagccaaaac ccaagaaaaa    900
ggtgcttatg aatcaacaaa atggagaagt attttataca acttatatga tctgctagtg    960
aatgagataa gtcatatagg aagtagagga agtattcttt caggattcg taatatgtcc   1020
gtcaaagaaa atttgattga attgatggca gatatctgtc accaggtttt taatgaagat   1080
accagatcct tggagatttc tcaatcttac actactacac aaagagaatc tagtgattac   1140
agtgtccctt gcaaaaggaa gaaaatagaa ctaggctggg aagtaataaa agatcacctt   1200
cagaagtcac agaatgattt tgatcttgtg ccttggctac agattgcaac ccaattaata   1260
tcaaagtatc ctgcaagttt acctaactgt gagctgtctc cattactgat gatactatct   1320
```

-continued

```
cagcttctac cccaacagcg acatggggaa cgtacaccat atgtgttacg atgccttacg   1380
gaagttgcat tgtgtcaaga caagaggtca aacctagaaa gctcacaaaa gtcagattta   1440
ttaaaactct ggaataaaat ttggtgtatt acctttcgtg gtataagttc tgagcaaata   1500
caagctgaaa actttggctt acttggagcc ataattcagg gtagtttagt tgaggttgac   1560
agagaattct ggaagttatt tactgggtca gcctgcagac cttcatgtcc tgcagtatgc   1620
tgtttgactt tggcactgac caccagtata gttccaggaa cggtaaaaat gggaatagag   1680
caaaatatgt gtgaagtaaa tagaagcttt tcttaaagg aatcaataat gaaatggctc   1740
ttattctatc agttagaggg tgacttagaa aatagcacag aagtgcctcc aattcttcac   1800
agtaattttc ctcatcttgt actggagaaa attcttgtga gtctcactat gaaaaactgt   1860
aaagctgcaa tgaattttt ccaaagcgtg ccagaatgtg aacaccacca aaaagataaa   1920
gaagaacttt cattctcaga agtagaagaa ctatttcttc agacaacttt tgacaagatg   1980
gactttttaa ccattgtgag agaatgtggt atagaaaagc accagtccag tattggcttc   2040
tctgtccacc agaatctcaa ggaatcactg gatcgctgtc ttctgggatt atcagaacag   2100
cttctgaata attactcatc tgagattaca aattcagaaa ctcttgtccg gtgttcacgt   2160
cttttggtgg gtgtccttgg ctgctactgt tacatgggtg taatagctga agaggaagca   2220
tataagtcag aattattcca gaaagccaag tctctaatgc aatgtgcagg agaaagtatc   2280
actctgttta aaataagac aaatgaggaa ttcagaattg gttccttgag aaatatgatg   2340
cagctatgta cacgttgctt gagcaactgt accaagaaga gtccaaataa gattgcatct   2400 ggcttttcc tgcgattgtt aacatcaaag ctaatgaatg acattgcaga tatttgtaaa   2460
agtttagcat ccttcatcaa aaagccattt gaccgtggag aagtagaatc aatggaagat   2520
gatactaatg gaaatctaat ggaggtggag gatcagtcat ccatgaatct atttaacgat   2580
taccctgata gtagtgttag tgatgcaaac gaacctggag agagccaaag taccataggt   2640
gccattaatc ctttagctga agaatatctg tcaaagcaag atctacttt ctagacatg   2700 ctcaagttct tgtgtttgtg tgtaactact gctcagacca atactgtgtc ctttagggca   2760
gctgatattc ggaggaaatt gttaatgtta attgattcta gcacgctaga acctaccaaa   2820
tccctccacc tgcatatgta tctaatgctt ttaaaggagc ttcctggaga agagtacccc   2880
ttgccaatgg aagatgttct tgaacttctg aaaccactat ccaatgtgtg ttctttgtat   2940
cgtcgtgacc aagatgtttg taaaactatt ttaaaccatg tccttcatgt agtgaaaaac   3000
ctaggtcaaa gcaatatgga ctctgagaac acaaggggat ctcaaggaca gtttcttaca   3060
gtaattggag cattttggca tctaacaaag gagaggaaat atatattctc tgtaagaatg   3120
gccctagtaa attgccttaa aactttgctt gaggctgatc cttattcaaa atgggccatt   3180
cttaatgtaa tgggaaaaga ctttcctgta aatgaagtat ttacacaatt tcttgctgac   3240
aatcatcacc aagttcgcat gttggctgca gagtcaatca atagattgtt ccaggacacg   3300
aagggagatt cttccaggtt actgaaagca cttcctttga gcttcagca aacagctttt   3360 gaaaatgcat acttgaaagc tcaggaagga atgagagaaa tgtcccatag tgctgagaac   3420
cctgaaactt ggatgaaat ttataataga aaatctgttt tactgacgtt gatagctgtg   3480
gttttatcct gtagccctat ctgcgaaaaa caggctttgt ttgccctgtg taaatctgtg   3540
aaagagaatg gattagaacc tcaccttgtg aaaaaggttt tagagaaagt ttctgaaact   3600
tttggatata gacgtttaga agactttatg gcatctcatt tagattatct ggttttggaa   3660
```

```
tggctaaatc ttcaagatac tgaatacaac ttatcttctt ttcctttat  tttattaaac   3720
tacacaaata ttgaggattt ctatagatct tgttataagg ttttgattcc acatctggtg   3780
attagaagtc attttgatga ggtgaagtcc attgctaatc agattcaaga ggactggaaa   3840
agtcttctaa cagactgctt tccaaagatt cttgtaaata ttcttcctta ttttgcctat   3900
gagggtacca gagacagtgg gatggcacag caaagagaga ctgctaccaa ggtctatgat   3960
atgcttaaaa gtgaaaactt attgggaaaa cagattgatc acttattcat tagtaattta   4020
ccagagattg tggtggagtt attgatgacg ttacatgagc cagcaaattc tagtgccagt   4080
cagagcactg acctctgtga cttttcaggg gatttggatc ctgctcctaa tccacctcat   4140
tttccatcgc atgtgattaa agcaacattt gcctatatca gcaattgtca taaaaccaag   4200
ttaaaaagca ttttagaaat tcttttccaaa agccctgatt cctatcagaa aattcttctt   4260
gccatatgtg agcaagcagc tgaaacaaat aatgtttata agaagcacag aattcttaaa   4320
atatatcacc tgtttgttag tttattactg aaagatataa aaagtggctt aggaggagct   4380
tgggcctttg ttcttcgaga cgttatttat actttgattc actatatcaa ccaaaggcct   4440
tcttgtatca tggatgtgtc attacgtagc ttctcccttt gttgtgactt attaagtcag   4500
gtttgccaga cagccgtgac ttactgtaag gatgctctag aaaaccatct tcatgttatt   4560
gttggtacac ttatacccct tgtgtatgag caggtggagg ttcagaaaca ggtattggac   4620
ttgttgaaat acttagtgat agataacaag gataatgaaa acctctatat cacgattaag   4680
cttttagatc cttttcctga ccatgttgtt tttaaggatt tgcgtattac tcagcaaaaa   4740
atcaaataca gtagaggacc cttttcactc ttggaggaaa ttaaccattt tctctcagta   4800
agtgtttatg atgcacttcc attgacaaga cttgaaggac taaaggatct tcgaagacaa   4860
ctggaactac ataaagatca gatggtggac attatgagag cttctcagga taatccgcaa   4920
gatgggatta tggtgaaact agttgtcaat ttgttgcagt tatccaagat ggcaataaac   4980
cacactggta aaaagaagt  tctagaggct gttggaagct gcttgggaga gtgggtcct   5040
atagatttct ctaccatagc tatacaacat agtaaagatg catcttatac caaggccctt   5100
aagttatttg aagataaaga acttcagtgg accttcataa tgctgaccta cctgaataac   5160
acactggtag aagattgtgt caaagttcga tcagcagctg ttacctgttt gaaaaacatt   5220
ttagccacaa agactggaca tagtttctgg gagatttata agatgacaac agatccaatg   5280
ctggcctatc tacagccttt tagaacatca agaaaaaagt ttttagaagt acccagattt   5340
gacaaagaaa accctttga  aggcctggat gatataaatc tgtggattcc tctaagtgaa   5400
aatcatgaca tttggataaa gacactgact tgtgcttttt tggacagtgg aggcacaaaa   5460
tgtgaaattc ttcaattatt aaagccaatg tgtgaagtga aaactgactt ttgtcagact   5520
gtacttccat acttgattca tgatattta  ctccaagata caaatgaatc atggagaaat   5580
ctgctttcta cacatgttca gggatttttc accagctgtc ttcgacactt ctcgcaaacg   5640
agccgatcca caaccccctgc aaacttggat tcagagtcag agcactttt  ccgatgctgt   5700
ttggataaaa aatcacaaag aacaatgctt gctgttgtgg actacatgag aagacaaaag   5760
agaccttctt caggaacaat ttttaatgat gctttctggc tggatttaaa ttatctagaa   5820
gttgccaagg tagctcagtc ttgtgctgct cactttacag ctttactcta tgcagaaatc   5880
tatgcagata agaaaagtat ggatgatcaa gagaaaagaa gtcttgcatt tgaagaagga   5940
agccagagta caactatttc tagcttgagt gaaaaaagta aagaagaaac tggaataagt   6000
ttacaggatc ttctcttaga aatctacaga agtataggg  agccagatag tttgtatggc   6060
```

```
tgtggtggag ggaagatgtt acaacccatt actagactac gaacatatga acacgaagca   6120
atgtggggca aagccctagt aacatatgac ctcgaaacag caatcccctc atcaacacgc   6180
caggcaggaa tcattcaggc cttgcagaat ttgggactct gccatattct ttccgtctat   6240
ttaaaaggat tggattatga aaataaagac tggtgtcctg aactagaaga acttcattac   6300
caagcagcat ggaggaatat gcagtgggac cattgcactt ccgtcagcaa agaagtagaa   6360
ggaaccagtt accatgaatc attgtacaat gctctacaat ctctaagaga cagagaattc   6420
tctacatttt atgaaagtct caaatatgcc agagtaaaag aagtggaaga gatgtgtaag   6480
cgcagccttg agtctgtgta ttcgctctat cccacactta gcaggttgca ggccattgga   6540
gagctggaaa gcattgggga gcttttctca agatcagtca cacatagaca actctctgaa   6600
gtatatatta agtggcagaa acactcccag cttctcaagg acagtgattt tagttttcag   6660
gagcctatca tggctctacg cacagtcatt ttggagatcc tgatggaaaa ggaaatggac   6720
aactcacaaa gagaatgtat taaggacatt ctcaccaaac accttgtaga actctctata   6780
ctggccagaa cttttcaagaa cactcagctc cctgaaaggg caatatttca aattaaacag   6840
tacaattcag ttagctgtgg agtctctgag tggcagctgg aagaagcaca agtattctgg   6900
gcaaaaaagg agcagagtct tgccctgagt attctcaagc aaatgatcaa gaagttggat   6960
gccagctgtg cagcgaacaa tcccagccta aaacttacat acacagaatg tctgagggtt   7020
tgtggcaact ggttagcaga aacgtgctta gaaaatcctg cggtcatcat gcagacctat   7080
ctagaaaagg cagtagaagt tgctggaaat tatgatggag aaagtagtga tgagctaaga   7140
aatggaaaaa tgaaggcatt tctctcatta gcccggtttt cagatactca ataccaaaga   7200
attgaaaact acatgaaatc atcggaattt gaaaacaagc aagctctcct gaaaagagcc   7260
aaagaggaag taggtctcct tagggaacat aaaattcaga caaacagata cacagtaaag   7320
gttcagcgag agctggagtt ggatgaatta gccctgcgtg cactgaaaga ggatcgtaaa   7380
cgcttcttat gtaaagcagt tgaaaattat atcaactgct tattaagtgg agaagaacat   7440
gatatgtggg tattccgact tgttccctc tggcttgaaa attctggagt ttctgaagtc   7500
aatggcatga tgaagagaga cggaatgaag attccaacat ataaattttt gcctcttatg   7560
taccaattgg ctgctagaat ggggaccaag atgatgggag gcctaggatt tcatgaagtc   7620
ctcaataatc taatctctag aatttcaatg gatcacccc atcacacttt gtttattata   7680
ctggccttag caaatgcaaa cagagatgaa tttctgacta aaccagaggt agccagaaga   7740
agcagaataa ctaaaaatgt gcctaaacaa agctctcagc ttgatgagga tcgaacagag   7800
gctgcaaata gaataatatg tactatcaga agtaggagac ctcagatggt cagaagtgtt   7860
gaggcacttt gtgatgctta tattatatta gcaaacttag atgccactca gtggaagact   7920
cagagaaaag gcataaatat tccagcagac cagccaatta ctaaacttaa gaatttagaa   7980
gatgttgttg tccctactat ggaaattaag gtggaccaca caggagaata tggaaatctg   8040
gtgactatac agtcatttaa agcagaattt cgcttagcag gaggtgtaaa tttaccaaaa   8100
ataatagatt gtgtaggttc cgatggcaag gagaggagac agcttgttaa gggccgtgat   8160
gacctgagac aagatgctgt catgcaacag gtcttccaga tgtgtaatac attactgcag   8220
agaaacacgg aaactaggaa gaggaaatta actatctgta cttataaggt ggttcccctc   8280
tctcagcgaa gtggtgttct tgaatggtgc acaggaactg tccccattgg tgaatttctt   8340
gttaacaatg aagatggtgc tcataaaaga tacaggccaa atgatttcag tgcctttcag   8400
```

| | |
|---|---|
| tgccaaaaga aaatgatgga ggtgcaaaaa aagtcttttg aagagaaata tgaagtcttc | 8460 |
| atggatgttt gccaaaattt tcaaccagtt ttccgttact tctgcatgga aaaattcttg | 8520 |
| gatccagcta tttggtttga aagcgattg gcttatacgc gcagtgtagc tacttcttct | 8580 |
| attgttggtt acatacttgg acttggtgat agacatgtac agaatatctt gataaatgag | 8640 |
| cagtcagcag aacttgtaca tatagatcta ggtgttgctt ttgaacaggg caaaatcctt | 8700 |
| cctactcctg agacagttcc ttttagactc accagagata ttgtggatgg catgggcatt | 8760 |
| acgggtgttg aaggtgtctt cagaagatgc tgtgagaaaa ccatggaagt gatgagaaac | 8820 |
| tctcaggaaa ctctgttaac cattgtagag gtccttctat atgatccact ctttgactgg | 8880 |
| accatgaatc ctttgaaagc tttgtattta cagcagaggc cggaagatga aactgagctt | 8940 |
| caccctactc tgaatgcaga tgaccaagaa tgcaaacgaa atctcagtga tattgaccag | 9000 |
| agtttcaaca aagtagctga acgtgtctta atgagactac aagagaaact gaaaggagtg | 9060 |
| gaagaaggca ctgtgctcag tgttggtgga caagtgaatt tgctcataca gcaggccata | 9120 |
| gaccccaaaa atctcagccg acttttccca ggatggaaag cttgggtgtg a | 9171 |

```
<210> SEQ ID NO 4
<211> LENGTH: 2644
<212> TYPE: PRT
<213> ORGANISM: Homo sapiens

<400> SEQUENCE: 4

Met Gly Glu His Gly Leu Glu Leu Ala Ser Met Ile Pro Ala Leu Arg
1               5                   10                  15

Glu Leu Gly Ser Ala Thr Pro Glu Glu Tyr Asn Thr Val Val Gln Lys
            20                  25                  30

Pro Arg Gln Ile Leu Cys Gln Phe Ile Asp Arg Ile Leu Thr Asp Val
        35                  40                  45

Asn Val Val Ala Val Glu Leu Val Lys Lys Thr Asp Ser Gln Pro Thr
    50                  55                  60

Ser Val Met Leu Leu Asp Phe Ile Gln His Ile Met Lys Ser Ser Pro
65                  70                  75                  80

Leu Met Phe Val Asn Val Ser Gly Ser His Glu Ala Lys Gly Ser Cys
                85                  90                  95

Ile Glu Phe Ser Asn Trp Ile Ile Thr Arg Leu Leu Arg Ile Ala Ala
            100                 105                 110

Thr Pro Ser Cys His Leu Leu His Lys Lys Ile Cys Glu Val Ile Cys
        115                 120                 125

Ser Leu Leu Phe Leu Phe Lys Ser Lys Ser Pro Ala Ile Phe Gly Val
    130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Val Met Ser
                165                 170                 175

Arg Phe Leu Ser Gln Leu Asp Glu His Met Gly Tyr Leu Gln Ser Ala
            180                 185                 190

Pro Leu Gln Leu Met Ser Met Gln Asn Leu Glu Phe Ile Glu Val Thr
        195                 200                 205

Leu Leu Met Val Leu Thr Arg Ile Ile Ala Ile Val Phe Phe Arg Arg
    210                 215                 220

Gln Glu Leu Leu Leu Trp Gln Ile Gly Cys Val Leu Leu Glu Tyr Gly
225                 230                 235                 240
```

```
Ser Pro Lys Ile Lys Ser Leu Ala Ile Ser Phe Leu Thr Glu Leu Phe
            245                 250                 255

Gln Leu Gly Gly Leu Pro Ala Gln Pro Ala Ser Thr Phe Phe Ser Ser
        260                 265                 270

Phe Leu Glu Leu Leu Lys His Leu Val Glu Met Asp Thr Asp Gln Leu
    275                 280                 285

Lys Leu Tyr Glu Glu Pro Leu Ser Lys Leu Ile Lys Thr Leu Phe Pro
290                 295                 300

Phe Glu Ala Glu Ala Tyr Arg Asn Ile Glu Pro Val Tyr Leu Asn Met
305                 310                 315                 320

Leu Leu Glu Lys Leu Cys Val Met Phe Glu Asp Gly Val Leu Met Arg
                325                 330                 335

Leu Lys Ser Asp Leu Leu Lys Ala Ala Leu Cys His Leu Leu Gln Tyr
            340                 345                 350

Phe Leu Lys Phe Val Pro Ala Gly Tyr Glu Ser Ala Leu Gln Val Arg
        355                 360                 365

Lys Val Tyr Val Arg Asn Ile Cys Lys Ala Leu Leu Asp Val Leu Gly
    370                 375                 380

Ile Glu Val Asp Ala Glu Tyr Leu Leu Gly Pro Leu Tyr Ala Ala Leu
385                 390                 395                 400

Lys Met Glu Ser Met Glu Ile Ile Glu Glu Ile Gln Cys Gln Thr Gln
                405                 410                 415

Gln Glu Asn Leu Ser Ser Asn Ser Asp Gly Ile Ser Pro Lys Arg Arg
            420                 425                 430

Arg Leu Ser Ser Ser Leu Asn Pro Ser Lys Arg Ala Pro Lys Gln Thr
        435                 440                 445

Glu Glu Ile Lys His Val Asp Met Asn Gln Lys Ser Ile Leu Trp Ser
    450                 455                 460

Ala Leu Lys Gln Lys Ala Glu Ser Leu Gln Ile Ser Leu Glu Tyr Ser
465                 470                 475                 480

Gly Leu Lys Asn Pro Val Ile Glu Met Leu Glu Gly Ile Ala Val Val
                485                 490                 495

Leu Gln Leu Thr Ala Leu Cys Thr Val His Cys Ser His Gln Asn Met
            500                 505                 510

Asn Cys Arg Thr Phe Lys Asp Cys Gln His Lys Ser Lys Lys Lys Pro
        515                 520                 525

Ser Val Val Ile Thr Trp Met Ser Leu Asp Phe Tyr Thr Lys Val Leu
    530                 535                 540

Lys Ser Cys Arg Ser Leu Leu Glu Ser Val Gln Lys Leu Asp Leu Glu
545                 550                 555                 560

Ala Thr Ile Asp Lys Val Val Lys Ile Tyr Asp Ala Leu Ile Tyr Met
                565                 570                 575

Gln Val Asn Ser Ser Phe Glu Asp His Ile Leu Glu Asp Leu Cys Gly
            580                 585                 590

Met Leu Ser Leu Pro Trp Ile Tyr Ser His Ser Asp Asp Gly Cys Leu
        595                 600                 605

Lys Leu Thr Thr Phe Ala Ala Asn Leu Leu Thr Leu Ser Cys Arg Ile
    610                 615                 620

Ser Asp Ser Tyr Ser Pro Gln Ala Gln Ser Arg Cys Val Phe Leu Leu
625                 630                 635                 640

Thr Leu Phe Pro Arg Arg Ile Phe Leu Glu Trp Arg Thr Ala Val Tyr
                645                 650                 655

Asn Trp Ala Leu Gln Ser Ser His Glu Val Ile Arg Ala Ser Cys Val
```

-continued

```
                660                 665                 670
    Ser Gly Phe Phe Ile Leu Leu Gln Gln Gln Asn Ser Cys Asn Arg Val
                675                 680                 685
    Pro Lys Ile Leu Ile Asp Lys Val Lys Asp Ser Asp Ile Val Lys
    690                 695                 700
    Lys Glu Phe Ala Ser Ile Leu Gly Gln Leu Val Cys Thr Leu His Gly
    705                 710                 715                 720
    Met Phe Tyr Leu Thr Ser Ser Leu Thr Glu Pro Phe Ser Glu His Gly
                725                 730                 735
    His Val Asp Leu Phe Cys Arg Asn Leu Lys Ala Thr Ser Gln His Glu
                740                 745                 750
    Cys Ser Ser Ser Gln Leu Lys Ala Ser Val Cys Lys Pro Phe Leu Phe
                755                 760                 765
    Leu Leu Lys Lys Lys Ile Pro Ser Pro Val Lys Leu Ala Phe Ile Asp
                770                 775                 780
    Asn Leu His His Leu Cys Lys His Leu Asp Phe Arg Glu Asp Glu Thr
    785                 790                 795                 800
    Asp Val Lys Ala Val Leu Gly Thr Leu Leu Asn Leu Met Glu Asp Pro
                805                 810                 815
    Asp Lys Asp Val Arg Val Ala Phe Ser Gly Asn Ile Lys His Ile Leu
                820                 825                 830
    Glu Ser Leu Asp Ser Asp Gly Phe Ile Lys Glu Leu Phe Val Leu
                835                 840                 845
    Arg Met Lys Glu Ala Tyr Thr His Ala Gln Ile Ser Arg Asn Asn Glu
    850                 855                 860
    Leu Lys Asp Thr Leu Ile Leu Thr Thr Gly Asp Ile Gly Arg Ala Ala
    865                 870                 875                 880
    Lys Gly Asp Leu Val Pro Phe Ala Leu Leu His Leu Leu His Cys Leu
                885                 890                 895
    Leu Ser Lys Ser Ala Ser Val Ser Gly Ala Ala Tyr Thr Glu Ile Arg
                900                 905                 910
    Ala Leu Val Ala Ala Lys Ser Val Lys Leu Gln Ser Phe Phe Ser Gln
                915                 920                 925
    Tyr Lys Lys Pro Ile Cys Gln Phe Leu Val Glu Ser Leu His Ser Ser
                930                 935                 940
    Gln Met Thr Ala Leu Pro Asn Thr Pro Cys Gln Asn Ala Asp Val Arg
    945                 950                 955                 960
    Lys Gln Asp Val Ala His Gln Arg Glu Met Ala Leu Asn Thr Leu Ser
                965                 970                 975
    Glu Ile Ala Asn Val Phe Asp Phe Pro Asp Leu Asn Arg Phe Leu Thr
                980                 985                 990
    Arg Thr Leu Gln Val Leu Leu Pro  Asp Leu Ala Ala Lys  Ala Ser Pro
                995                 1000                1005
    Ala Ala  Ser Ala Leu Ile Arg  Thr Leu Gly Lys Gln  Leu Asn Val
                1010                1015                1020
    Asn Arg  Arg Glu Ile Leu Ile  Asn Asn Phe Lys Tyr  Ile Phe Ser
                1025                1030                1035
    His Leu  Val Cys Ser Cys Ser  Lys Asp Glu Leu Glu  Arg Ala Leu
                1040                1045                1050
    His Tyr  Leu Lys Asn Glu Thr  Glu Ile Glu Leu Gly  Ser Leu Leu
                1055                1060                1065
    Arg Gln  Asp Phe Gln Gly Leu  His Asn Glu Leu Leu  Leu Arg Ile
                1070                1075                1080
```

Gly Glu His Tyr Gln Gln Val Phe Asn Gly Leu Ser Ile Leu Ala
1085                1090                1095

Ser Phe Ala Ser Ser Asp Asp Pro Tyr Gln Gly Pro Arg Asp Ile
1100                1105                1110

Ile Ser Pro Glu Leu Met Ala Asp Tyr Leu Gln Pro Lys Leu Leu
1115                1120                1125

Gly Ile Leu Ala Phe Phe Asn Met Gln Leu Leu Ser Ser Ser Val
1130                1135                1140

Gly Ile Glu Asp Lys Lys Met Ala Leu Asn Ser Leu Met Ser Leu
1145                1150                1155

Met Lys Leu Met Gly Pro Lys His Val Ser Ser Val Arg Val Lys
1160                1165                1170

Met Met Thr Thr Leu Arg Thr Gly Leu Arg Phe Lys Asp Asp Phe
1175                1180                1185

Pro Glu Leu Cys Cys Arg Ala Trp Asp Cys Phe Val Arg Cys Leu
1190                1195                1200

Asp His Ala Cys Leu Gly Ser Leu Leu Ser His Val Ile Val Ala
1205                1210                1215

Leu Leu Pro Leu Ile His Ile Gln Pro Lys Glu Thr Ala Ala Ile
1220                1225                1230

Phe His Tyr Leu Ile Ile Glu Asn Arg Asp Ala Val Gln Asp Phe
1235                1240                1245

Leu His Glu Ile Tyr Phe Leu Pro Asp His Pro Glu Leu Lys Lys
1250                1255                1260

Ile Lys Ala Val Leu Gln Glu Tyr Arg Lys Glu Thr Ser Glu Ser
1265                1270                1275

Thr Asp Leu Gln Thr Thr Leu Gln Leu Ser Met Lys Ala Ile Gln
1280                1285                1290

His Glu Asn Val Asp Val Arg Ile His Ala Leu Thr Ser Leu Lys
1295                1300                1305

Glu Thr Leu Tyr Lys Asn Gln Glu Lys Leu Ile Lys Tyr Ala Thr
1310                1315                1320

Asp Ser Glu Thr Val Glu Pro Ile Ile Ser Gln Leu Val Thr Val
1325                1330                1335

Leu Leu Lys Gly Cys Gln Asp Ala Asn Ser Gln Ala Arg Leu Leu
1340                1345                1350

Cys Gly Glu Cys Leu Gly Glu Leu Gly Ala Ile Asp Pro Gly Arg
1355                1360                1365

Leu Asp Phe Ser Thr Thr Glu Thr Gln Gly Lys Asp Phe Thr Phe
1370                1375                1380

Val Thr Gly Val Glu Asp Ser Ser Phe Ala Tyr Gly Leu Leu Met
1385                1390                1395

Glu Leu Thr Arg Ala Tyr Leu Ala Tyr Ala Asp Asn Ser Arg Ala
1400                1405                1410

Gln Asp Ser Ala Ala Tyr Ala Ile Gln Glu Leu Leu Ser Ile Tyr
1415                1420                1425

Asp Cys Arg Glu Met Glu Thr Asn Gly Pro Gly His Gln Leu Trp
1430                1435                1440

Arg Arg Phe Pro Glu His Val Arg Glu Ile Leu Glu Pro His Leu
1445                1450                1455

Asn Thr Arg Tyr Lys Ser Ser Gln Lys Ser Thr Asp Trp Ser Gly
1460                1465                1470

```
Val Lys Lys Pro Ile Tyr Leu Ser Lys Leu Gly Ser Asn Phe Ala
1475                1480                1485

Glu Trp Ser Ala Ser Trp Ala Gly Tyr Leu Ile Thr Lys Val Arg
1490                1495                1500

His Asp Leu Ala Ser Lys Ile Phe Thr Cys Cys Ser Ile Met Met
1505                1510                1515

Lys His Asp Phe Lys Val Thr Ile Tyr Leu Leu Pro His Ile Leu
1520                1525                1530

Val Tyr Val Leu Leu Gly Cys Asn Gln Glu Asp Gln Gln Glu Val
1535                1540                1545

Tyr Ala Glu Ile Met Ala Val Leu Lys His Asp Gln His Thr
1550                1555                1560

Ile Asn Thr Gln Asp Ile Ala Ser Asp Leu Cys Gln Leu Ser Thr
1565                1570                1575

Gln Thr Val Phe Ser Met Leu Asp His Leu Thr Gln Trp Ala Arg
1580                1585                1590

His Lys Phe Gln Ala Leu Lys Ala Glu Lys Cys Pro His Ser Lys
1595                1600                1605

Ser Asn Arg Asn Lys Val Asp Ser Met Val Ser Thr Val Asp Tyr
1610                1615                1620

Glu Asp Tyr Gln Ser Val Thr Arg Phe Leu Asp Leu Ile Pro Gln
1625                1630                1635

Asp Thr Leu Ala Val Ala Ser Phe Arg Ser Lys Ala Tyr Thr Arg
1640                1645                1650

Ala Val Met His Phe Glu Ser Phe Ile Thr Glu Lys Lys Gln Asn
1655                1660                1665

Ile Gln Glu His Leu Gly Phe Leu Gln Lys Leu Tyr Ala Ala Met
1670                1675                1680

His Glu Pro Asp Gly Val Ala Gly Val Ser Ala Ile Arg Lys Ala
1685                1690                1695

Glu Pro Ser Leu Lys Glu Gln Ile Leu Glu His Glu Ser Leu Gly
1700                1705                1710

Leu Leu Arg Asp Ala Thr Ala Cys Tyr Asp Arg Ala Ile Gln Leu
1715                1720                1725

Glu Pro Asp Gln Ile Ile His Tyr His Gly Val Val Lys Ser Met
1730                1735                1740

Leu Gly Leu Gly Gln Leu Ser Thr Val Ile Thr Gln Val Asn Gly
1745                1750                1755

Val His Ala Asn Arg Ser Glu Trp Thr Asp Glu Leu Asn Thr Tyr
1760                1765                1770

Arg Val Glu Ala Ala Trp Lys Leu Ser Gln Trp Asp Leu Val Glu
1775                1780                1785

Asn Tyr Leu Ala Ala Asp Gly Lys Ser Thr Thr Trp Ser Val Arg
1790                1795                1800

Leu Gly Gln Leu Leu Leu Ser Ala Lys Lys Arg Asp Ile Thr Ala
1805                1810                1815

Phe Tyr Asp Ser Leu Lys Leu Val Arg Ala Glu Gln Ile Val Pro
1820                1825                1830

Leu Ser Ala Ala Ser Phe Glu Arg Gly Ser Tyr Gln Arg Gly Tyr
1835                1840                1845

Glu Tyr Ile Val Arg Leu His Met Leu Cys Glu Leu Glu His Ser
1850                1855                1860

Ile Lys Pro Leu Phe Gln His Ser Pro Gly Asp Ser Ser Gln Glu
```

```
                 1865                1870                1875

Asp Ser Leu Asn Trp Val Ala Arg Leu Glu Met Thr Gln Asn Ser
            1880                1885                1890

Tyr Arg Ala Lys Glu Pro Ile Leu Ala Leu Arg Arg Ala Leu Leu
            1895                1900                1905

Ser Leu Asn Lys Arg Pro Asp Tyr Asn Glu Met Val Gly Glu Cys
            1910                1915                1920

Trp Leu Gln Ser Ala Arg Val Ala Arg Lys Ala Gly His His Gln
            1925                1930                1935

Thr Ala Tyr Asn Ala Leu Leu Asn Ala Gly Glu Ser Arg Leu Ala
            1940                1945                1950

Glu Leu Tyr Val Glu Arg Ala Lys Trp Leu Trp Ser Lys Gly Asp
            1955                1960                1965

Val His Gln Ala Leu Ile Val Leu Gln Lys Gly Val Glu Leu Cys
            1970                1975                1980

Phe Pro Glu Asn Glu Thr Pro Pro Glu Gly Lys Asn Met Leu Ile
            1985                1990                1995

His Gly Arg Ala Met Leu Leu Val Gly Arg Phe Met Glu Glu Thr
            2000                2005                2010

Ala Asn Phe Glu Ser Asn Ala Ile Met Lys Lys Tyr Lys Asp Val
            2015                2020                2025

Thr Ala Cys Leu Pro Glu Trp Glu Asp Gly His Phe Tyr Leu Ala
            2030                2035                2040

Lys Tyr Tyr Asp Lys Leu Met Pro Met Val Thr Asp Asn Lys Met
            2045                2050                2055

Glu Lys Gln Gly Asp Leu Ile Arg Tyr Ile Val Leu His Phe Gly
            2060                2065                2070

Arg Ser Leu Gln Tyr Gly Asn Gln Phe Ile Tyr Gln Ser Met Pro
            2075                2080                2085

Arg Met Leu Thr Leu Trp Leu Asp Tyr Gly Thr Lys Ala Tyr Glu
            2090                2095                2100

Trp Glu Lys Ala Gly Arg Ser Asp Arg Val Gln Met Arg Asn Asp
            2105                2110                2115

Leu Gly Lys Ile Asn Lys Val Ile Thr Glu His Thr Asn Tyr Leu
            2120                2125                2130

Ala Pro Tyr Gln Phe Leu Thr Ala Phe Ser Gln Leu Ile Ser Arg
            2135                2140                2145

Ile Cys His Ser His Asp Glu Val Phe Val Val Leu Met Glu Ile
            2150                2155                2160

Ile Ala Lys Val Phe Leu Ala Tyr Pro Gln Gln Ala Met Trp Met
            2165                2170                2175

Met Thr Ala Val Ser Lys Ser Ser Tyr Pro Met Arg Val Asn Arg
            2180                2185                2190

Cys Lys Glu Ile Leu Asn Lys Ala Ile His Met Lys Lys Ser Leu
            2195                2200                2205

Glu Lys Phe Val Gly Asp Ala Thr Arg Leu Thr Asp Lys Leu Leu
            2210                2215                2220

Glu Leu Cys Asn Lys Pro Val Asp Gly Ser Ser Ser Thr Leu Ser
            2225                2230                2235

Met Ser Thr His Phe Lys Met Leu Lys Lys Leu Val Glu Glu Ala
            2240                2245                2250

Thr Phe Ser Glu Ile Leu Ile Pro Leu Gln Ser Val Met Ile Pro
            2255                2260                2265
```

```
Thr Leu Pro Ser Ile Leu Gly Thr His Ala Asn His Ala Ser His
    2270            2275            2280

Glu Pro Phe Pro Gly His Trp Ala Tyr Ile Ala Gly Phe Asp Asp
    2285            2290            2295

Met Val Glu Ile Leu Ala Ser Leu Gln Lys Pro Lys Lys Ile Ser
    2300            2305            2310

Leu Lys Gly Ser Asp Gly Lys Phe Tyr Ile Met Met Cys Lys Pro
    2315            2320            2325

Lys Asp Asp Leu Arg Lys Asp Cys Arg Leu Met Glu Phe Asn Ser
    2330            2335            2340

Leu Ile Asn Lys Cys Leu Arg Lys Asp Ala Glu Ser Arg Arg Arg
    2345            2350            2355

Glu Leu His Ile Arg Thr Tyr Ala Val Ile Pro Leu Asn Asp Glu
    2360            2365            2370

Cys Gly Ile Ile Glu Trp Val Asn Asn Thr Ala Gly Leu Arg Pro
    2375            2380            2385

Ile Leu Thr Lys Leu Tyr Lys Glu Lys Gly Val Tyr Met Thr Gly
    2390            2395            2400

Lys Glu Leu Arg Gln Cys Met Leu Pro Lys Ser Ala Ala Leu Ser
    2405            2410            2415

Glu Lys Leu Lys Val Phe Arg Glu Phe Leu Leu Pro Arg His Pro
    2420            2425            2430

Pro Ile Phe His Glu Trp Phe Leu Arg Thr Phe Pro Asp Pro Thr
    2435            2440            2445

Ser Trp Tyr Ser Ser Arg Ser Ala Tyr Cys Arg Ser Thr Ala Val
    2450            2455            2460

Met Ser Met Val Gly Tyr Ile Leu Gly Leu Gly Asp Arg His Gly
    2465            2470            2475

Glu Asn Ile Leu Phe Asp Ser Leu Thr Gly Glu Cys Val His Val
    2480            2485            2490

Asp Phe Asn Cys Leu Phe Asn Lys Gly Glu Thr Phe Glu Val Pro
    2495            2500            2505

Glu Ile Val Pro Phe Arg Leu Thr His Asn Met Val Asn Gly Met
    2510            2515            2520

Gly Pro Met Gly Thr Glu Gly Leu Phe Arg Arg Ala Cys Glu Val
    2525            2530            2535

Thr Met Arg Leu Met Arg Asp Gln Arg Glu Pro Leu Met Ser Val
    2540            2545            2550

Leu Lys Thr Phe Leu His Asp Pro Leu Val Glu Trp Ser Lys Pro
    2555            2560            2565

Val Lys Gly His Ser Lys Ala Pro Leu Asn Glu Thr Gly Glu Val
    2570            2575            2580

Val Asn Glu Lys Ala Lys Thr His Val Leu Asp Ile Glu Gln Arg
    2585            2590            2595

Leu Gln Gly Val Ile Lys Thr Arg Asn Arg Val Thr Gly Leu Pro
    2600            2605            2610

Leu Ser Ile Glu Gly His Val His Tyr Leu Ile Gln Glu Ala Thr
    2615            2620            2625

Asp Glu Asn Leu Leu Cys Gln Met Tyr Leu Gly Trp Thr Pro Tyr
    2630            2635            2640

Met
```

-continued

```
<210> SEQ ID NO 5
<211> LENGTH: 7935
<212> TYPE: DNA
<213> ORGANISM: Homo sapiens

<400> SEQUENCE: 5
atgggggaac atggcctgga gctggcttcc atgatccccg ccctgcggga gctgggcagt      60
gccacaccag aggaatataa tacagttgta cagaagccaa gacaaattct gtgtcaattc     120
attgaccgga tacttacaga tgtaaatgtt gttgctgtag aacttgtaaa gaaaactgac     180
tctcagccaa cctccgtgat gttgcttgat tcatccagc atatcatgaa atcctcccca      240
cttatgtttg taaatgtgag tggaagccat gaggccaaag gcagttgtat tgaattcagt     300
aattggatca taacgagact tctgcggatt gcagcaactc cctcctgtca tttgttacac     360
aagaaaatct gtgaagtcat ctgttcatta ttatttcttt ttaaaagcaa gagtcctgct     420
atttttgggg tactcacaaa agaattatta caacttttg aagacttggt ttacctccat      480
agaagaaatg tgatgggtca tgctgtggaa tggccagtgg tcatgagccg atttttaagt     540
caattagatg aacacatggg atatttacaa tcagctcctt gcagttgat gagtatgcaa      600 aatttagaat ttattgaagt cactttatta atggttctta ctcgtattat tgcaattgtg     660 tttttagaa ggcaagaact cttactttgg cagataggtt gtgttctgct agagtatggt      720
agtccaaaaa ttaaatccct agcaattagc ttttaacag aacttttca gcttggagga      780 ctaccagcac aaccagctag cactttttc agctcatttt tggaattatt aaaacacctt     840
gtagaaatgg atactgacca attgaaactc tatgaagagc cattatcaaa gctgataaag     900
acactatttc cctttgaagc agaagcttat agaaatattg aacctgtcta tttaaatatg     960 ctgctgaaa actctgtgt catgtttgaa gacggtgtgc tcatgcggct taagtctgat     1020
ttgctaaaag cagctttgtg ccatttactg cagtatttcc ttaaatttgt gccagctggg    1080
tatgaatctg ctttacaagt caggaaggtc tatgtgagaa atatttgtaa agctctttg     1140 gatgtgcttg gaattgaggt agatgcagag tacttgttgg gcccacttta tgcagctttg    1200
aaaatggaaa gtatggaaat cattgaggag attcaatgcc aaactcaaca ggaaaacctc    1260
agcagtaata gtgatggaat tcacccaaa aggcgtcgtc tcagctcgtc tctaaaccct    1320
tctaaaagag caccaaaaca gactgaggaa attaaacatg tggacatgaa ccaaaagagc    1380
atattatgga gtgcactgaa acagaaagct gaatcccttc agatttccct tgaatacagt    1440
ggcctaaaga atcctgttat tgagatgtta gaaggaattg ctgttgtctt caactgact    1500 gctctgtgta ctgttcattg ttctcatcaa aacatgaact gccgtacttt caaggactgt    1560
caacataaat ccaagaagaa accttctgta gtgataactt ggatgtcatt ggatttttac    1620
acaaaagtgc ttaagagctg tagaagtttg ttagaatctg ttcagaaact ggacctggag    1680
gcaaccattg ataaggtggt gaaaattat gatgctttga tttatatgca agtaaacagt    1740
tcatttgaag atcatatcct ggaagattta tgtggtatgc ctcacttcc atggatttat    1800 tcccattctg atgatggctg tttaaagttg accacatttg ccgctaatct tctaacatta    1860
agctgtagga tttcagatag ctattccacca caggcacaat cacgatgtgt gtttcttctg    1920
actctgtttc caagaagaat attccttgag tggagaacag cagtttacaa ctgggccctg    1980
cagagctccc atgaagtaat ccgggctagt tgtgttagtg atttttat cttattgcag    2040 cagcagaatt cttgtaacag agttcccaag attcttatag ataaagtcaa agatgattct    2100
gacattgtca agaaagaatt tgcttctata cttggtcaac ttgtctgtac tcttcacggc    2160
```

```
atgttttatc tgacaagttc tttaacagaa cctttctctg aacacggaca tgtggacctc    2220
ttctgtagga acttgaaagc cacttctcaa catgaatgtt catcttctca actaaaagct    2280
tctgtctgca agccattcct tttcctactg aaaaaaaaaa tacctagtcc agtaaaactt    2340
gctttcatag ataatctaca tcatctttgt aagcatcttg attttagaga agatgaaaca    2400
gatgtaaaag cagttcttgg aactttatta aatttaatgg aagatccaga caaagatgtt    2460
agagtggctt ttagtggaaa tatcaagcac atattggaat ccttggactc tgaagatgga    2520
tttataaagg agcttttttgt cttaagaatg aaggaagcat atacacatgc ccaaatatca    2580
agaaataatg agctgaagga taccttgatt cttacaacag gggatattgg aagggccgca    2640
aaaggagatt tggtaccatt tgcactctta cacttattgc attgtttgtt atccaagtca    2700
gcatctgtct ctggagcagc atacacagaa attagagctc tggttgcagc taaaagtgtt    2760
aaactgcaaa gttttttcag ccagtataag aaacccatct gtcagttttt ggtagaatcc    2820
cttcactcta gtcagatgac agcacttccg aatactccat gccagaatgc tgacgtgcga    2880
aaacaagatg tggctcacca gagagaaatg gctttaaata cgttgtctga aattgccaac    2940
gttttcgact ttcctgatct taatcgtttt cttactagga cattacaagt tctactacct    3000
gatcttgctg ccaaagcaag ccctgcagct tctgctctca ttcgaacttt aggaaaacaa    3060
ttaaatgtca atcgtagaga gattttaata aacaacttca aatatatttt ttctcatttg    3120
gtctgttctt gttccaaaga tgaattagaa cgtgcccttc attatctgaa gaatgaaaca    3180
gaaattgaac tggggagcct gttgagacaa gatttccaag gattgcataa tgaattattg    3240
ctgcgtattg gagaacacta tcaacaggtt tttaatggtt tgtcaatact tgcctcattt    3300
gcatccagtg atgatccata tcagggcccg agagatatca tatcacctga actgatggct    3360
gattatttac aacccaaatt gttgggcatt ttggcttttt ttaacatgca gttactgagc    3420
tctagtgttg gcattgaaga taagaaaatg gccttgaaca gtttgatgtc tttgatgaag    3480
ttaatgggac ccaaacatgt cagttctgtg agggtgaaga tgatgaccac actgagaact    3540
ggccttcgat tcaaggatga tttttcctgaa ttgtgttgca gagcttggga ctgctttgtt    3600
cgctgcctgg atcatgcttg tctgggctcc cttctcagtc atgtaatagt agctttgtta    3660
cctcttatac acatccagcc taaagaaact gcagctatct tccactacct cataattgaa    3720
aacagggatg ctgtgcaaga ttttcttcat gaaatatatt ttttacctga tcatccagaa    3780
ttaaaaaaga taaaagccgt tctccaggaa tacagaaagg agacctctga gagcactgat    3840
cttcagacaa ctcttcagct ctctatgaag gccattcaac atgaaaatgt cgatgttcgt    3900
attcatgctc ttacaagctt gaaggaaacc ttgtataaaa atcaggaaaa actgataaag    3960
tatgcaacag acagtgaaac agtagaacct attatctcac agttggtgac agtgcttttg    4020
aaaggttgcc aagatgcaaa ctctcaagct cggttgctct gtggggaatg tttaggggaa    4080
ttgggggcga tagatccagg tcgattagat ttctcaacaa ctgaaactca aggaaaagat    4140
tttacatttg tgactggagt agaagattca agctttgcct atggattatt gatggagcta    4200
acaagagctt accttgcgta tgctgataat agccgagctc aagattcagc tgcctatgcc    4260
attcaggagt tgctttctat ttatgactgt agagagatgg agaccaacgg cccaggtcac    4320
caattgtgga ggagatttcc tgagcatgtt cgggaaatac tagaacctca tctaaatacc    4380
agatacaaga gttctcagaa gtcaaccgat tggtctggag taaagaagcc aatttactta    4440
agtaaattgg gtagtaactt tgcagaatgg tcagcatctt gggcaggtta tcttattaca    4500
aaggttcgac atgatcttgc cagtaaaatt ttcacctgct gtagcattat gatgaagcat    4560
```

-continued

```
gatttcaaag tgaccatcta tcttcttcca catattctgg tgtatgtctt actgggttgt      4620
aatcaagaag atcagcagga ggtttatgca gaaattatgg cagttctaaa gcatgacgat      4680
cagcatacca taaatatccca agacattgca tctgatctgt gtcaactcag tacacagact    4740
gtgttctcca tgcttgacca tctcacacag tgggcaaggc acaaatttca ggcactgaaa     4800
gctgagaaat gtccacacag caaatcaaac agaaataagg tagactcaat ggtatctact    4860
gtggattatg aagactatca gagtgtaacc cgttttctag acctcatacc ccaggatact    4920
ctggcagtag cttcctttcg ctccaaagca tacacgag ctgtaatgca ctttgaatca     4980
tttattacag aaaagaagca aaatattcag gaacatcttg gatttttaca gaaattgtat    5040
gctgctatgc atgaacctga tggagtggcc ggagtcagtg caattagaaa ggcagaacca    5100
tctctaaaag aacagatcct tgaacatgaa agccttggct tgctgaggga tgccactgct    5160
tgttatgaca gggctattca gctagaacca gaccagatca ttcattatca tggtgtagta    5220
aagtccatgt taggtcttgg tcagctgtct actgttatca ctcaggtgaa tggagtgcat    5280
gctaacaggt ccgagtggac agatgaatta acacgtaca gagtggaagc agcttggaaa    5340
ttgtcacagt gggatttggt ggaaaactat ttggcagcag atggaaaatc tacaacatgg    5400
agtgtcagac tgggacagct attattatca gccaaaaaaa gagatatcac agcttttttat   5460 gactcactga aactagtgag agcagaacaa attgtacctc tttcagctgc aagctttgaa    5520
agaggctcct accaacgagg atatgaatat attgtgagat tgcacatgtt atgtgagttg    5580
gagcatagca tcaaaccact tttccagcat tctccaggtg acagttctca agaagattct    5640
ctaaactggg tagctcgact agaaatgacc cagaattcct acagagccaa ggagcctatc    5700
ctggctctcc ggagggcttt actaagcctc aacaaaagac cagattacaa tgaaatggtt    5760
ggagaatgct ggctgcagag tgccagggta gctagaaagg ctggtcacca ccagacagcc    5820
tacaatgctc tccttaatgc aggggaatca cgactcgctg aactgtacgt ggaaagggca    5880
aagtggctct ggtccaaggg tgatgttcac caggcactaa ttgttcttca aaaaggtgtt    5940
gaattatgtt ttcctgaaaa tgaaacccca cctgagggta agaacatgtt aatccatggt    6000
cgagctatgc tactagtggg ccgatttatg gaagaaacag ctaactttga aagcaatgca    6060
attatgaaaa aatataagga tgtgaccgcg tgcctgccag aatgggagga tgggcatttt    6120
taccttgcca agtactatga caaattgatg cccatggtca cagacaacaa aatggaaaag    6180
caaggtgatc tcatccggta tatagttctt cattttggca gatctctaca atatggaaat    6240
cagttcatat atcagtcaat gccacgaatg ttaactctat ggcttgatta tggtacaaag    6300
gcatatgaat gggaaaaagc tggccgctcc gatcgtgtac aaatgaggaa tgatttgggt    6360
aaaataaaca aggttatcac agagcataca aactatttag ctccatatca atttttgact    6420 gcttttcac aattgatctc tcgaatttgt cattctcacg atgaagtttt tgttgtcttg    6480
atggaaataa tagccaaagt atttctagcc tatcctcaac aagcaatgtg atgatgaca    6540 gctgtgtcaa agtcatctta tcccatgcgt gtgaacagat gcaaggaaat cctcaataaa    6600
gctattcata tgaaaaaatc cttagagaag tttgttggag atgcaactcg cctaacagat    6660
aagcttctag aattgtgcaa taaccggtt gatggaagta gttccacatt aagcatgagc    6720 actcattta aaatgcttaa aaagctggta gaagaagcaa catttagtga aatcctcatt    6780
cctctacaat cagtcatgat acctacactt ccatcaattc tgggtaccca tgctaaccat    6840
gctagccatg aaccatttcc tggacattgg gcctatattg cagggtttga tgatatggtg    6900
```

-continued

| | |
|---|---|
| gaaattcttg cttctcttca gaaaccaaag aagatttctt taaaaggctc agatggaaag | 6960 |
| ttctacatca tgatgtgtaa gccaaaagat gacctgagaa aggattgtag actaatggaa | 7020 |
| ttcaattcct tgattaataa gtgcttaaga aaagatgcag agtctcgtag aagagaactt | 7080 |
| catattcgaa catatgcagt tattccacta aatgatgaat gtgggattat tgaatgggtg | 7140 |
| aacaacactg ctggtttgag acctattctg accaaactat ataaagaaaa gggagtgtat | 7200 |
| atgacaggaa aagaacttcg ccagtgtatg ctaccaaagt cagcagcttt atctgaaaaa | 7260 |
| ctcaaagtat tccgagaatt tctcctgccc aggcatcctc ctattttca tgagtggttt | 7320 |
| ctgagaacat tccctgatcc tacatcatgg tacagtagta gatcagctta ctgccgttcc | 7380 |
| actgcagtaa tgtcaatggt tggttatatt ctggggcttg agaccgtca tggtgaaaat | 7440 |
| attctctttg attctttgac tggtgaatgc gtacatgtag atttcaattg tcttttcaat | 7500 |
| aagggagaaa cctttgaagt tccagaaatt gtgccatttc gcctgactca taatatggtt | 7560 |
| aatggaatgg gtcctatggg aacagagggt cttttcgaa gagcatgtga agttacaatg | 7620 |
| aggctgatgc gtgatcagcg agagccttta atgagtgtct taaagacttt tctacatgat | 7680 |
| cctcttgtgg aatggagtaa accagtgaaa gggcattcca aagcgccact gaatgaaact | 7740 |
| ggagaagttg tcaatgaaaa ggccaagacc catgttcttg acattgagca gcgactacaa | 7800 |
| ggtgtaatca agactcgaaa tagagtgaca ggactgccgt tatctattga aggacatgtg | 7860 |
| cattaccta tacaggaagc tactgatgaa aacttactat gccagatgta tcttggttgg | 7920 |
| actccatata tgtga | 7935 |

<210> SEQ ID NO 6
<211> LENGTH: 94
<212> TYPE: PRT
<213> ORGANISM: Homo sapiens

<400> SEQUENCE: 6

Cys Pro Gly Arg Asp Arg Arg Thr Glu Glu Asn Phe Arg Lys Lys
1               5                   10                  15

Glu Glu His Cys Pro Glu Leu Pro Pro Gly Ser Ala Lys Arg Ala Leu
            20                  25                  30

Pro Thr Ser Thr Ser Ser Ser Pro Gln Gln Lys Lys Lys Pro Leu Asp
        35                  40                  45

Gly Glu Tyr Phe Thr Leu Lys Ile Arg Gly Arg Glu Arg Phe Glu Met
    50                  55                  60

Phe Arg Glu Leu Asn Glu Ala Leu Glu Leu Lys Asp Ala Arg Ala Ala
65                  70                  75                  80

Glu Glu Ser Gly Asp Ser Arg Ala His Ser Ser Tyr Pro Lys
            85                  90

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
cgagctcaat aaaagagccc ac                                        22

<210> SEQ ID NO 8
<211> LENGTH: 20
<212> TYPE: DNA
<213> ORGANISM: Artificial Sequence

```
<220> FEATURE:
<223> OTHER INFORMATION: Primer

<400> SEQUENCE: 8
gagtcctgcg tcggagagag                                               20

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
tactgacgct ctcgcacc                                                 18

<210> SEQ ID NO 10
<211> LENGTH: 17
<212> TYPE: DNA
<213> ORGANISM: Artificial Sequence
<220> FEATURE:
<223> OTHER INFORMATION: Primer

<400> SEQUENCE: 10
tctcgacgca ggactcg                                                  17

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
atctctctcc ttccttctag cctc                                          24

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
tcactcccaa cgaagacaag atc                                           23

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gagtcctgcg tcgagagag                                                19

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
cgagctcaat aaaagagccc ac                                            22
```

```
<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
acagataggt tgctggccag                                              20

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
ggcacacgtg gcttttcg                                                18

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ggtgaacctc gtaagtttat gcaa                                         24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
tcaggacgtc gagtggacac ggtg                                         24

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
cagtgtggaa aatctctagc agtac                                        25

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
gccgtgcgcg cttcagcaag c                                            21
```

GENE THERAPY

CROSS-REFERENCE TO RELATED APPLICATIONS

This application is a U.S. National Phase of International Application No. PCT/EP2017/062197, filed May 19, 2017, which claims priority benefit of Application No. 1608944.3, filed on May 20, 2016, in the United Kingdom.

INCORPORATION BY REFERENCE OF MATERIALS SUBMITTED ELECTRONICALLY

This application contains, as a separate part of the disclosure, a Sequence Listing in computer readable form (Filename: 53682_Seqlisting.txt; Size: 79,729 bytes; Created: Nov. 13, 2018), which is incorporated by reference in its entirety.

FIELD OF THE INVENTION

The present invention relates to the genetic modification of haematopoietic stem and progenitor cells. In particular, the invention relates to the use of agents for increasing the survival and engraftment of haematopoietic stem and progenitor cells transduced with viral vectors.

BACKGROUND TO THE INVENTION

The haematopoietic system is a complex hierarchy of cells of different mature cell lineages. These include cells of the immune system that offer protection from pathogens, cells that carry oxygen through the body and cells involved in wound healing. All these mature cells are derived from a pool of haematopoietic stem cells (HSCs) that are capable of self-renewal and differentiation into any blood cell lineage. HSCs have the ability to replenish the entire haematopoietic system.

Haematopoietic cell transplantation (HCT) is a curative therapy for several inherited and acquired disorders. However, allogeneic HCT is limited by the poor availability of matched donors, the mortality associated with the allogeneic procedure which is mostly related to graft-versus-host disease (GvHD), and infectious complications provoked by the profound and long-lasting state of immune dysfunction.

Gene therapy approaches based on the transplantation of genetically modified autologous HSCs offer potentially improved safety and efficacy over allogeneic HCT. They are particularly relevant for patients lacking a matched donor.

The concept of stem cell gene therapy is based on the genetic modification of a relatively small number of stem cells. These persist long-term in the body by undergoing self-renewal, and generate large numbers of genetically "corrected" progeny. This can ensure a continuous supply of corrected cells for the rest of the patient's lifetime. HSCs are particularly attractive targets for gene therapy since their genetic modification will be passed to all blood cell lineages as they differentiate. Furthermore, HSCs can be easily and safely obtained, for example from bone marrow, mobilised peripheral blood and umbilical cord blood.

Efficient long-term gene modification of HSCs and their progeny benefits from technology which permits stable integration of the corrective DNA into the genome, without affecting HSC function. Accordingly, the use of integrating recombinant viral systems such as γ-retroviruses, lentiviruses and spumaviruses has dominated this field (Chang, A. H. et al. (2007) Mol. Ther. 15: 445-56). Therapeutic benefits have already been achieved in γ-retrovirus-based clinical trials for Adenosine Deaminase Severe Combined Immunodeficiency (ADA-SCID; Aiuti, A. et al. (2009) N. Engl. J. Med. 360: 447-58), X-linked Severe Combined Immunodeficiency (SCID-X1; Hacein-Bey-Abina, S. et al. (2010) N. Engl. J. Med. 363: 355-64) and Wiskott-Aldrich syndrome (WAS; Bortug, K. et al. (2010) N. Engl. J. Med. 363: 1918-27). In addition, lentiviruses have been employed as delivery vehicles in the treatment of X-linked adrenoleukodystrophy (ALD; Cartier, N. et al. (2009) Science 326: 818-23) and beta-thalassemia (Cartier, N. et al. (2010) Bull. Acad. Natl. Med. 194: 255-264; discussion 264-258), and recently for metachromatic leukodystrophy (MLD; Biffi, A. et al. (2013) Science 341: 1233158) and WAS (Aiuti, A. et al. (2013) Science 341: 1233151).

In addition to the use of retro- and lentiviral-based vectors, vectors derived from other viruses, such as adenoviruses and adeno-associated viruses (AAV), may also be utilised for the modification of haematopoietic stem and progenitor cells.

Although substantial progress has been made in this area, difficulties remain with the methods employed for the genetic modification of haematopoietic stem and progenitor cells. In particular, the multiple hits of high vector doses required and prolonged ex vivo transduction times associated with existing methods give rise to problems with survival of the transduced haematopoietic stem and progenitor cells during culture and potentially impact their biological properties. Furthermore, improvements in the engraftment of transduced cells will greatly benefit clinical applications.

SUMMARY OF THE INVENTION

The inventors have surprisingly found that, instead of triggering canonical innate immune pathways, transduction with lentiviral vectors (LVs) triggers ataxia telangiectasia mutated (ATM)-dependent DNA damage responses in human haematopoietic stem and progenitor cells. The inventors observed that this induction requires synthesis and nuclear import of the vector DNA, but is independent of genomic integration. Similarly, non-integrating adeno-associated viral (AAV) DNA was observed to induce p53 signalling, while gamma-retroviral transduction was found to trigger type I IFN responses through cytosolic RNA sensing.

In addition, the inventors found that LV-mediated signalling led to a delay in haematopoietic stem and progenitor cell proliferation, G0 arrest and slightly increased apoptosis in culture. These acute responses led to reduced engraftment of transduced cells in vivo at limiting cell doses, although no long-term consequences or competitive disadvantage were detected.

Following from these findings, the inventors demonstrated that inhibition of ATM prevented p53 activation and partially rescued in vitro apoptosis as well as in vivo engraftment of haematopoietic stem and progenitor cells.

While not wishing to be bound by theory, the inventors' findings suggest that the inhibition of p53 activation, for example by inhibition of phosphorylation of p53 (e.g. at Serine 15), in particular by inhibiting kinases that catalyse that phosphorylation (e.g. ATM kinase, and ataxia telangiectasia and Rad3-related protein (ATR)) will improve methods for haematopoietic stem and progenitor cell-based gene therapy.

Accordingly, in one aspect the invention provides an inhibitor of p53 activation for use in haematopoietic stem and/or progenitor cell gene therapy.

In one embodiment, the inhibitor is an inhibitor of p53 phosphorylation. In another embodiment, the inhibitor is an inhibitor of p53 Serine 15 phosphorylation.

The haematopoietic stem and/or progenitor cell gene therapy may be, for example, treatment of a disease selected from the group consisting of mucopolysaccharidosis type I (MPS-1), chronic granulomatous disorder (CGD), Fanconi anaemia (FA), sickle cell disease, Pyruvate kinase deficiency (PKD), Leukocyte adhesion deficiency (LAD), metachromatic leukodystrophy (MLD), globoid cell leukodystrophy (GLD), $GM_2$ gangliosidosis, thalassemia and cancer.

In another aspect, the invention provides an inhibitor of p53 activation for use in reducing or preventing neutropenia associated with haematopoietic stem and/or progenitor cell transplantation.

In another aspect, the invention provides an inhibitor of p53 activation for use in increasing survival and/or engraftment of haematopoietic stem and/or progenitor cells.

In another aspect, the invention provides the use of an inhibitor of p53 activation in a method of culturing an isolated population of haematopoietic stem and/or progenitor cells. In one embodiment, the inhibitor increases survival and/or engraftment of the haematopoietic stem and/or progenitor cells.

In another aspect, the invention provides the use of an inhibitor of p53 activation in a method of transducing an isolated population of haematopoietic stem and/or progenitor cells with a viral vector. In one embodiment, the inhibitor increases survival and/or engraftment of the haematopoietic stem and/or progenitor cells.

In another aspect, the invention provides the use of an inhibitor of p53 activation for increasing cell survival in an isolated population of haematopoietic stem and/or progenitor cells.

In one embodiment, the inhibitor is an inhibitor of p53 phosphorylation. In another embodiment, the inhibitor is an inhibitor of p53 Serine 15 phosphorylation.

In a preferred embodiment, the inhibitor is an ataxia telangiectasia mutated (ATM) kinase inhibitor. In another embodiment, the inhibitor is an ataxia telangiectasia and Rad3-related protein (ATR) inhibitor.

In one embodiment, the inhibitor is a p53 dominant negative peptide. In one embodiment, the inhibitor is GSE56.

In one embodiment, at least 1%, 2%, 3%, 4%, 5%, 6%, 7%, 8%, 9%, 10%, 15%, 20%, 25%, 30%, 40%, 50% or 75%, preferably at least 10%, more cells survive in culture for a period of time (e.g. about 6 or 12 hours, or 1, 2, 3, 4, 5, 6, 7 or more days, preferably about 2 days) when the cells have been exposed to the inhibitor than in its absence. Preferably, the period of time begins with transduction of the cells with a viral vector.

In one embodiment, the inhibitor substantially prevents or reduces apoptosis in the haematopoietic stem and/or progenitor cells, in particular during in vitro culture.

In one embodiment, at least 1%, 2%, 3%, 4%, 5%, 6%, 7%, 8%, 9%, 10%, 15%, 20%, 25%, 30%, 40%, 50% or 75%, preferably at least 25%, fewer cells become apoptotic following culture for a period of time (e.g. about 6 or 12 hours, or 1, 2, 3, 4, 5, 6, 7 or more days, preferably about 2 days) when the cells have been exposed to the inhibitor than in its absence. Preferably, the period of time begins with the transduction of the cells with a viral vector.

In one embodiment, at least 1%, 2%, 3%, 4%, 5%, 6%, 7%, 8%, 9%, 10%, 15%, 20%, 25%, 30%, 40%, 50% or 75%, preferably at least 10%, more transplanted haematopoietic stem and/or progenitor cells and/or their descendant cells (e.g. graft-derived cells) engraft in a host subject when the cells have been exposed to the inhibitor than in its absence.

In a preferred embodiment, the haematopoietic stem and/or progenitor cells are human haematopoietic stem and/or progenitor cells.

In one embodiment, the cells are haematopoietic stem cells. In one embodiment, the cells are haematopoietic progenitor cells. In one embodiment, the cells are short-term re-populating cells. In one embodiment, the cells are long-term re-populating cells.

In one embodiment, the haematopoietic stem and/or progenitor cells are CD34+ cells. In one embodiment, the haematopoietic stem and/or progenitor cells are CD34+ CD38− cells. In one embodiment, the haematopoietic stem and/or progenitor cells are CD34+CD38+ cells.

In one embodiment, the population of haematopoietic stem and/or progenitor cells comprises, is enriched in or substantially consists of CD34+ cells. The population of cells may be further enriched for a particular sub-population of cells, for example CD34+CD38− cells.

In one embodiment, the population of haematopoietic stem and/or progenitor cells comprises, is enriched in or substantially consists of CD34+CD38− cells. In one embodiment, the population of haematopoietic stem and/or progenitor cells comprises, is enriched in or substantially consists of CD34+CD38+ cells.

In one embodiment, the haematopoietic stem and/or progenitor cells are transduced by a viral vector. For example, the survival and/or engraftment is increased in haematopoietic stem and/or progenitor cells transduced by a viral vector.

In another aspect, the invention provides a method of culturing a population of haematopoietic stem and/or progenitor cells comprising the step of contacting the population of cells with an inhibitor of p53 activation.

In another aspect, the invention provides a method of transducing a population of haematopoietic stem and/or progenitor cells with a viral vector comprising the steps:
 (a) contacting the population of cells with an inhibitor of p53 activation; and
 (b) transducing the population of cells with the viral vector.

In one embodiment, the inhibitor is an inhibitor of p53 phosphorylation. In another embodiment, the inhibitor is an inhibitor of p53 Serine 15 phosphorylation.

In a preferred embodiment, the inhibitor is an ataxia telangiectasia mutated (ATM) kinase inhibitor. In another embodiment, the inhibitor is an ataxia telangiectasia and Rad3-related protein (ATR) inhibitor.

In one embodiment, the inhibitor is a p53 dominant negative peptide. In one embodiment, the inhibitor is GSE56.

The haematopoietic stem and/or progenitor cells may be, for example, contacted with the inhibitor, and/or transduced with the viral vector in vitro or as part of an ex vivo procedure. Thus, in one embodiment of the method of transducing a population of haematopoietic stem and/or progenitor cells, steps (a) and (b) are carried out ex vivo or in vitro.

Preferably, the inhibition is transient (transient inhibition of p53 signalling during the ex vivo transduction improved engraftment by about 25%, giving rise to comparable levels of human CD45+ cells detected in the peripheral blood between transduced and control virus-exposed cells).

In one embodiment, the inhibitor is a transient inhibitor (e.g. has an inhibitory action lasting less than about 1, 2, 3, 4, 5, 6, 7 or 14 days), such as a reversible inhibitor.

Preferably, the cells are exposed to the inhibitor for about 1-48 or 1-24 hours, preferably 1-24 hours. The cells may be, for example, exposed to the inhibitor at the same time as the viral vector or before the viral vector.

In a preferred embodiment, the haematopoietic stem and/or progenitor cells are human haematopoietic stem and/or progenitor cells.

In one embodiment, the cells are haematopoietic stem cells. In one embodiment, the cells are haematopoietic progenitor cells. In one embodiment, the cells are short-term re-populating cells. In one embodiment, the cells are long-term re-populating cells.

In one embodiment, the haematopoietic stem and/or progenitor cells are CD34+ cells. In one embodiment, the haematopoietic stem and/or progenitor cells are CD34+CD38− cells. In one embodiment, the haematopoietic stem and/or progenitor cells are CD34+CD38+ cells.

In one embodiment, the population of haematopoietic stem and/or progenitor cells comprises, is enriched in or substantially consists of CD34+ cells. The population of cells may be further enriched for a particular sub-population of cells, for example CD34+CD38− cells.

In one embodiment, the population of haematopoietic stem and/or progenitor cells comprises, is enriched in or substantially consists of CD34+CD38− cells. In one embodiment, the population of haematopoietic stem and/or progenitor cells comprises, is enriched in or substantially consists of CD34+CD38+ cells.

In one embodiment, the inhibitor is KU-55933 or a derivative thereof; KU-60019, BEZ235, wortmannin, CP-466722, Torin 2, CGK 733, KU-559403, AZD6738 or derivatives thereof; or an siRNA, shRNA, miRNA or antisense DNA/RNA. Preferably, the inhibitor is KU-55933 or a derivative thereof.

In one embodiment, the inhibitor (e.g. KU-55933 or derivative thereof) is added to the haematopoietic stem and/or progenitor cells (e.g. in an in vitro or ex vivo culture) at a concentration of about 1-50, 1-40, 1-30, 1-20 or 1-15 μM, preferably about 1-15 μM. In another embodiment, the inhibitor (e.g. KU-55933 or derivative thereof) is added to the haematopoietic stem and/or progenitor cells at a concentration of about 5-50, 5-40, 5-30, 5-20 or 5-15 μM, preferably about 5-15 μM.

In one embodiment, the inhibitor (e.g. KU-55933 or derivative thereof) is added to the haematopoietic stem and/or progenitor cells (e.g. in an in vitro or ex vivo culture) at a concentration of about 1, 2, 3, 4, 5, 6, 7, 8, 9, 10, 11, 12, 13, 14, 15, 20, 25, 30, 35, 40, 45 or 50 μM, preferably about 10 μM.

In one embodiment, the haematopoietic stem and/or progenitor cells (e.g. the population of cells in step (a) of the method of transducing a population of haematopoietic stem and/or progenitor cells of the invention) are contacted with the inhibitor about 30 minutes to about 4 hours; about 30 minutes to about 3 hours; or about 30 minutes to about 2 hours before transducing the population of cells with the viral vector. In another embodiment, the haematopoietic stem and/or progenitor cells are contacted with the inhibitor about 1-4 hours; 1-3 hours; or 1-2 hours before transducing the population of cells with the viral vector.

In one embodiment, the haematopoietic stem and/or progenitor cells (e.g. the population of cells in step (a) of the method of transducing a population of haematopoietic stem and/or progenitor cells of the invention) are contacted with the inhibitor about 30 minutes, 1 hour, 1.5 hours, 2 hours, 2.5 hours, 3 hours, 3.5 hours or 4 hours, preferably about 2 hours, before transducing the population of cells with the viral vector.

In one embodiment, the viral vector is a lentiviral or adeno-associated viral (AAV) vector. The lentiviral vector may be, for example, a vector derived from HIV-1, HIV-2, EIAV, SIV or FIV. Preferably, the lentiviral vector is a vector derived from HIV-1. The AAV vector may be, for example, a vector comprising an AAV serotype 1, 2, 3, 4, 5, 6, 7, 8, 9, 10, or 11 capsid (when the vector is in the form of a viral vector particle) and/or genome. Preferably, the AAV vector is a vector comprising an AAV serotype 6 capsid and/or genome.

In one embodiment, the population of haematopoietic stem and/or progenitor cells is obtained from mobilised peripheral blood, bone marrow or umbilical cord blood.

In one embodiment, the method of transducing a population of haematopoietic stem and/or progenitor cells includes a further step of enriching the population for haematopoietic stem and/or progenitor cells.

In another aspect, the invention provides a method of gene therapy comprising the steps:
  (a) transducing a population of haematopoietic stem and/or progenitor cells according to the method of the invention; and
  (b) administering the transduced cells to a subject.

The method of gene therapy may be, for example, a method of treatment of a disease selected from the group consisting of mucopolysaccharidosis type I (MPS-1), chronic granulomatous disorder (CGD), Fanconi anaemia (FA), sickle cell disease, Pyruvate kinase deficiency (PKD), Leukocyte adhesion deficiency (LAD), metachromatic leukodystrophy (MLD), globoid cell leukodystrophy (GLD), $GM_2$ gangliosidosis, thalassemia and cancer.

In one embodiment, the subject is a mammalian subject, preferably a human subject.

In one embodiment, the transduced cells are administered to a subject as part of an autologous stem cell transplant procedure or an allogeneic stem cell transplant procedure.

In another aspect, the invention provides a population of haematopoietic stem and/or progenitor cells prepared according to the method of the invention.

In another aspect, the invention provides a pharmaceutical composition comprising the population of haematopoietic stem and/or progenitor cells of the invention.

In another aspect, the invention provides the population of haematopoietic stem and/or progenitor cells of the invention for use in therapy.

In one embodiment, the population of haematopoietic stem and/or progenitor cells of the invention are administered to a subject as part of an autologous stem cell transplant procedure or an allogeneic stem cell transplant procedure.

In another aspect the invention provides the use of an inhibitor of p53 activation for the manufacture of a medicament for haematopoietic stem and/or progenitor cell gene therapy.

In another aspect the invention provides the use of an inhibitor of p53 activation for the manufacture of a medicament for increasing survival and/or engraftment of haematopoietic stem and/or progenitor cells.

In another aspect, the invention provides a method of increasing survival and/or engraftment of haematopoietic stem and/or progenitor cells comprising the steps:
  (a) contacting a population of haematopoietic stem and/or progenitor cells with an inhibitor of p53 activation; and
  (b) transducing the population of cells with a viral vector.

In another aspect, the invention provides an inhibitor of p53 activation for use in a method of transducing a population of haematopoietic stem and/or progenitor cells with a viral vector.

The inhibitor may be as disclosed herein.

In another aspect, the invention provides a method of screening for an agent capable of increasing survival and/or engraftment of haematopoietic stem and/or progenitor cells comprising the steps:
(a) contacting a population of haematopoietic stem and/or progenitor cells with a candidate agent;
(b) transducing the population of cells with a viral vector; and optionally
(c) administering the transduced cells to a subject, Cell survival and/or engraftment may be subsequently analysed using a method as disclosed herein. Preferably, the candidate agent has been identified as an inhibitor of p53 activation, in particular p53 phosphorylation, for example Serine 15 phosphorylation (e.g. preferably an ATM kinase inhibitor or ATR inhibitor) using a kinase activity assay, for example as disclosed herein.

DESCRIPTION OF THE DRAWINGS

FIG. 8. Heat map of clustered biological terms highlighted by differentially expressed genes in the untreated sample respect to the Poly(I:C) (A) The heat map represents semantic similarity among gene ontology (GO) Biological Process (BP) terms. Rows and columns show the list of enriched GO BP terms derived from term enrichment analysis of the differentially expressed genes over time between the untreated and Poly(I:C) conditions. The colours represent the semantic distances calculated using GOSemSim Bioconductor package. Yellow-red clusters identify groups of terms sharing semantic similarity about biological processes.

FIG. 11. Characterisation of LV-induced p53 signalling. (A) (Left Panel) p21 mRNA levels 48 hours post-transduction or (Right Panel) Vector Copy number (VCN) 3 days after transduction were measured in CB-CD34+ exposed to increasing MOI of 100 PGK-GFP SIN LV (LV) or p24 equivalent of Bald as control. P21 mRNA was normalised to HPRT1. Results are shown respect to Bald set to value 1, (mean±SEM) of three independent experiments. (B) p21 mRNA levels 48 hours post-transduction in different human and murine cell lines or primary cells exposed to PGK-GFP SIN LV or p24 equivalent of Bald as control. p21 mRNA was measured 48 hours after the transduction and normalised to HPRT1 for human cells or Hprt for Murine cells. Results are shown respect to Bald for each cell type set to value 1 (Red threshold). (C) VCN per cell were performed 14 days after exposure of sorted CB-CD34+ to PGK-GFP SIN LV (LV), at MOI 100 or p24 equivalents of Env-less (Bald) as indicated. Values are mean±SEM of 4 independent experiments. (D) Copy number per cell of total viral DNA three days after the transduction of human CB-CD34+ exposed to an MOI of 100 PGK-GFP SIN LV (LV), integrase-defective LV (IDLV), p24 equivalent genome-less (Empty LV) or Env-less (Bald). Results are shown as mean±SEM. (E) Vector copy number results of CB-CD34+ transduced with an MOI of 100 of PGK-GFP SIN LV (LV), or Env-less (Bald) as control. Transductions were performed in presence of the integrase inhibitor Raltegravir (Ral), or the Reverse transcriptase inhibitor Lamivudine (3TC). As control cells were transduced in DMSO or kept untreated (Mock). VCN was performed on the integrated LV genome 14 days after transduction, values are mean±SEM of 4 independent experiments. (F) p21 mRNA levels in CB-CD34+ cells 5 days after transduction with an MOI 100 of LV, IDLV or p24 equivalent of Bald or Empty LV as controls. (G) Western blot (WB) for p53 and p21 of CB-CD34+ transduced with an MOI of 100 of PGK-GFP SIN LV (LV), or Env-less (Bald) as control. Transductions were performed in presence of the integrase inhibitor Raltegravir (Ral), or the Reverse transcriptase inhibitor Lamivudine (3TC). As control cells were transduced in DMSO or kept untreated (Mock). WB was performed 48 hours after transduction. (H) Representative FACS plot of CB-CD34+ cells 48 hours after the transduction with PGK-BFP LV, IDLV, or Bald as control and stained with anti-p21 antibody. (I) Immunofluorescence of CB-CD34+ cells stained for γH2AX (Left Panel), 12 hours after the transduction with the indicated vector or camptothecin (CPT) exposure, and for p21 (Right Panel) 48 hours after the transduction with PGK-mCHERRY LV, IDLV, a p21 overexpressing LV (p21 OE) or Bald as a control. (J) ISG15 and p21 mRNA levels in CB-CD34+ cells exposed to 1000 U/mL of human IFNα for 24 hours and transduced for 48 hours either with an MOI 100 of a PGK-GFP LV or p24 equivalent of Bald as a control.

FIG. 14. In vitro impact of clinical-grade LV and other vectors. (A-B) Annexin staining for apoptotic cells was performed two days after transduction of Human CB-CD34+ exposed to an MOI of 100 PGK-GFP SIN LV (LV), MOI of 100 clinical grade LV (Clinical LV), MOI 10000 of AAV6 and MOI 100 OF PGK-GFP SINRV (RV) or to p24 equivalent of Env-less (Bald) or inactivated Clinical LV as controls (Inactivated Clinical LV). Mean±SEM of 2 (A) or n (B) independent experiments. Statistic evaluation was performed by Kruskal-Wallis test (* p≤0.05; ** p≤0.01).

DETAILED DESCRIPTION OF THE INVENTION

Figure 1:
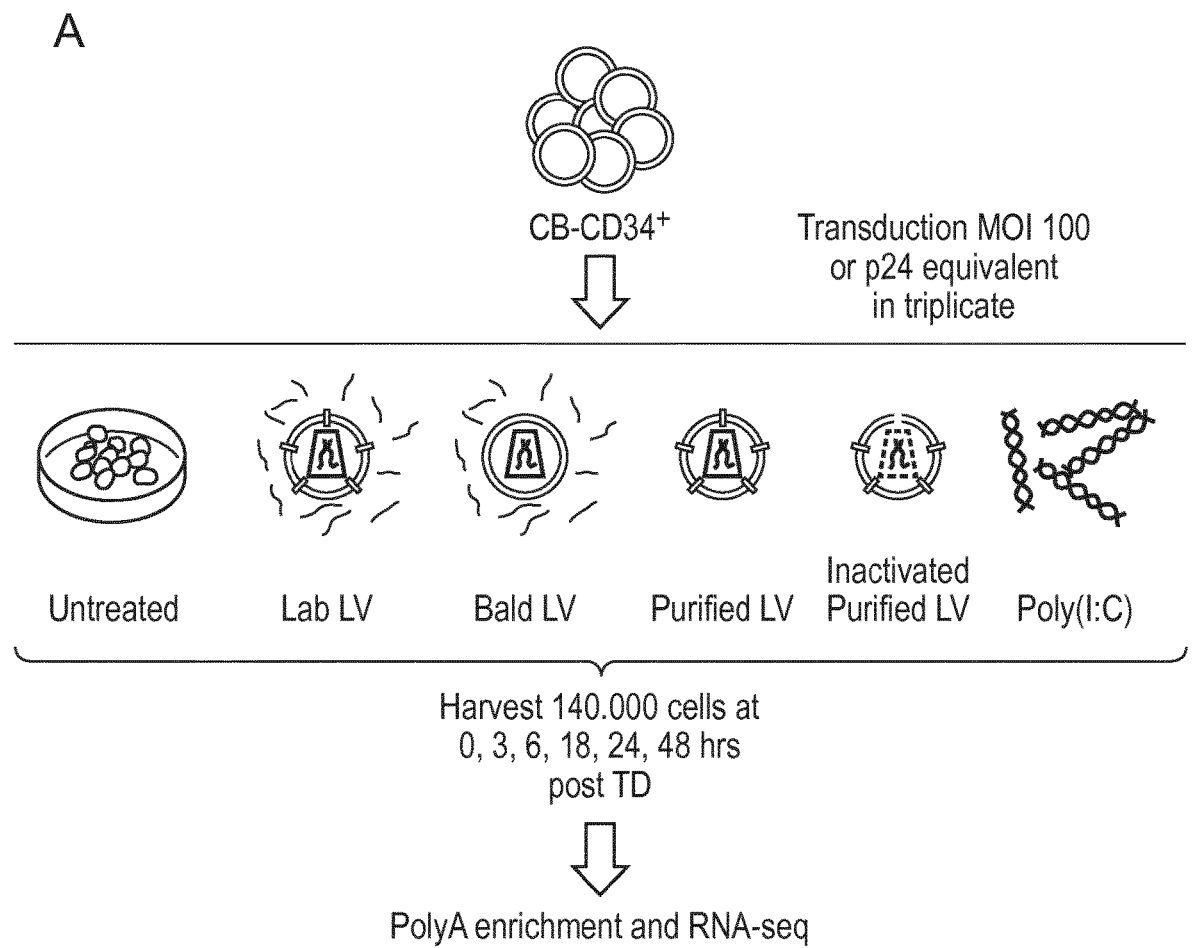
FIG. 1. Lentiviral transduction induces p53 and DDR transcriptional signalling in human HSPC. (A) Scheme of the RNA-Seq experiment. After 16 hours of cytokine pre-stimulation on human cord-blood (CB)-derived CD34+ cells were exposed to Lab-grade (Lab LV) or purified (Purified LV) LV at a multiplicity of infection (MOI) of 100, kept in culture untreated or exposed to p24 equivalent of non-transducing Env-less (Bald LV), heat inactivated purified LV or Poly(I:C). RNA was extracted at different times post-transduction and processed. Bar chart of the pathway enrichment analysis perform on the significant (nom p-value ≤0.05) differentially expressed genes over time retrieved from the comparison between (B) Bald LV and the Lab LV or (C) Inactivated purified LV and the Purified LV conditions. The length of the bar represents the significance (p-value Ranking) of that specific pathway. In addition, the brighter the colour, the more significant that term is. (D) Heat map showing the profile over time of the most significantly (nom p-value 0.01) differentially expressed genes between Lab LV and Bald LV conditions. Genes are clustered upon the semantic distances and represented over time for each separated condition. (E) Genes differentially expressed in the Lab LV condition respect to the Bald LV are highlighted by the red star in the KEGG p53 signalling pathway. (F) Gene expression levels of different p53-induced genes (p48, PUMA, p21, PHLDA3) in CB-CD34+ cells transduced with PGK-GFP SIN LV at MOI 100 (LV) or exposed to p24 equivalent of Env-less (Bald) vector as control were measured 48 hours after the transduction. Expression levels were normalised to HPRT1 and shown respect to Bald set to value of 1. Results are the mean±SEM of four independent experiments, p-values are for One sample t-test (* p≤05;  p≤0.01; ** p≤0001).
Figure 1:
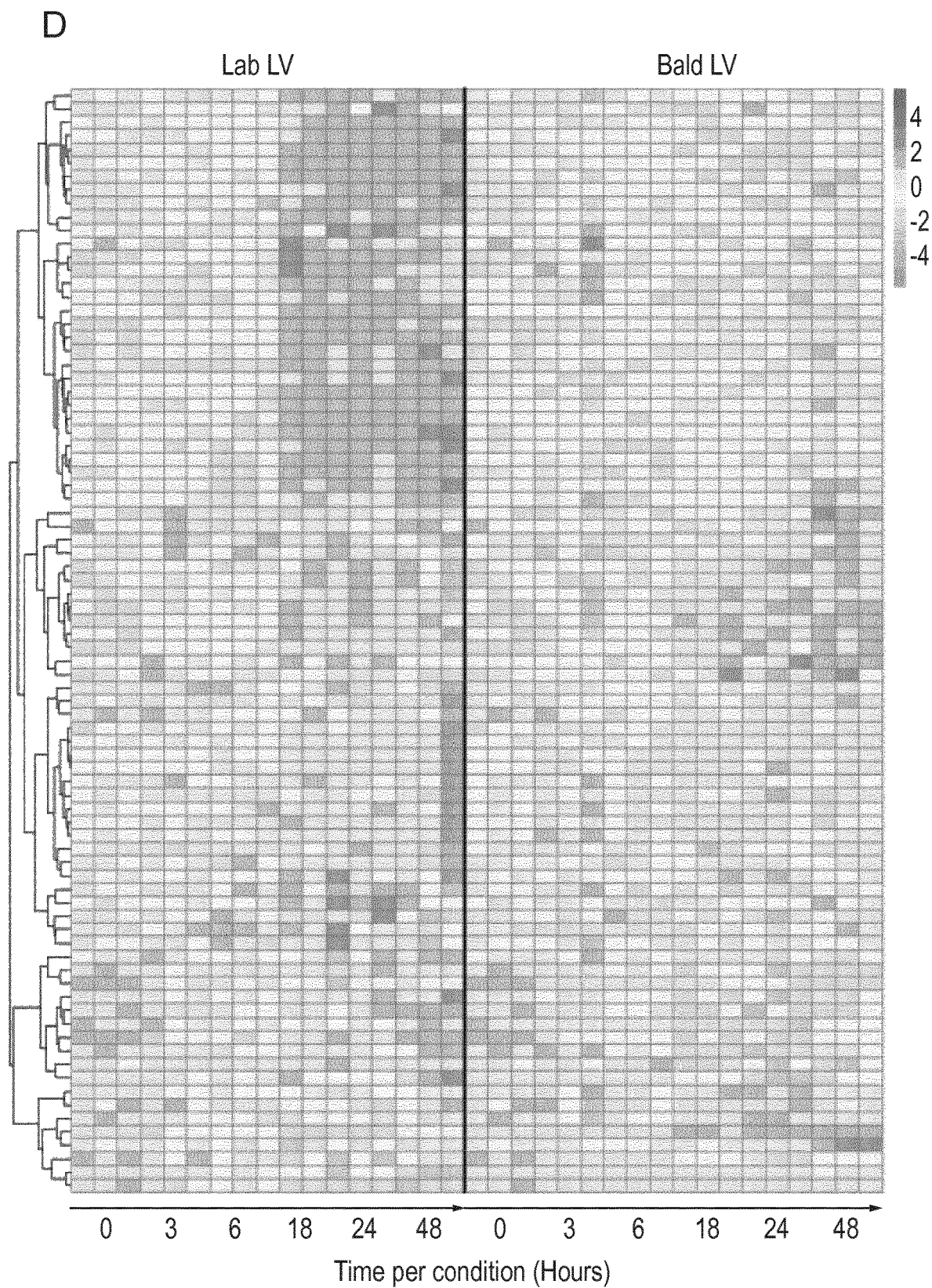
Figure 1:
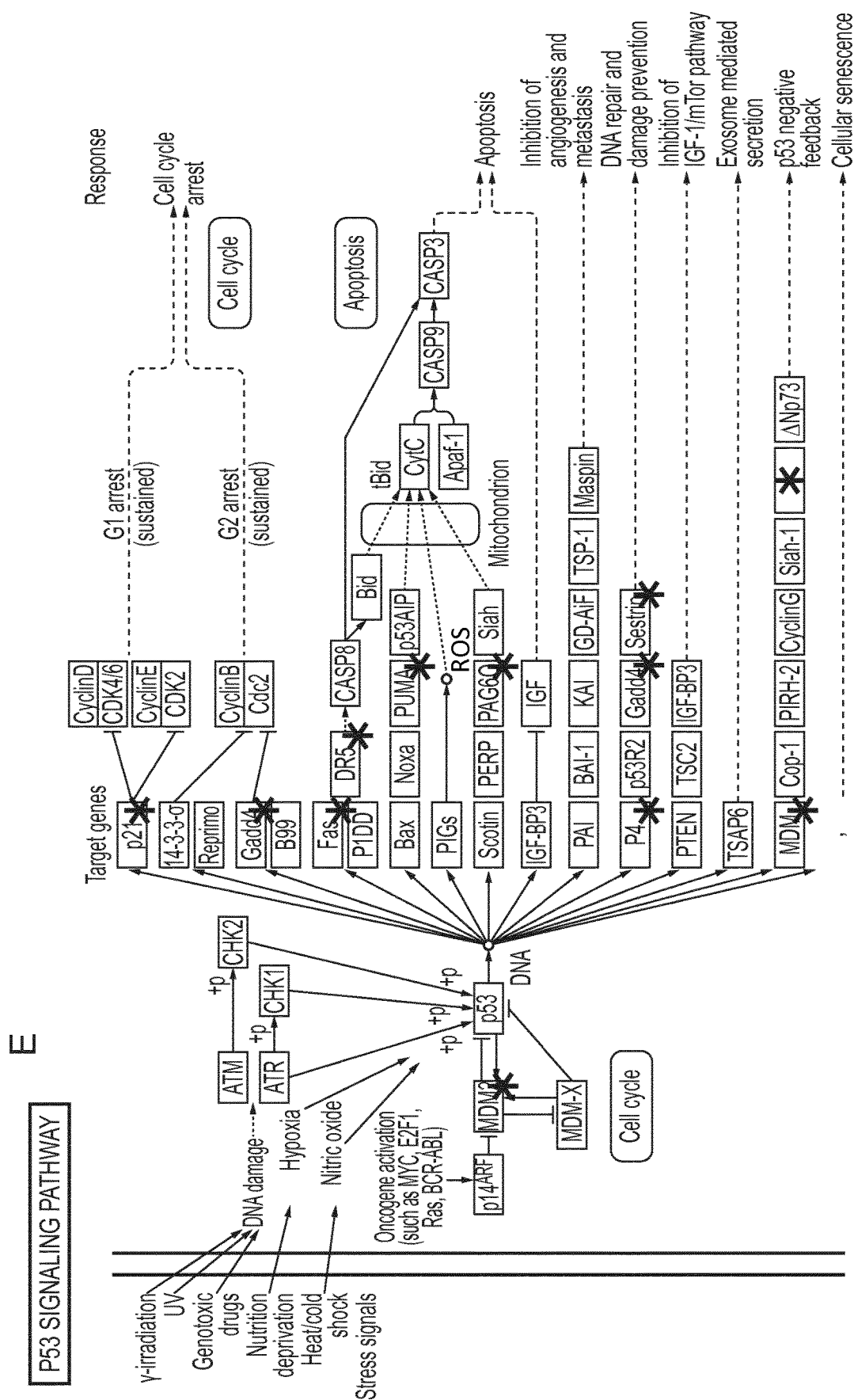

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

Cell Survival and Engraftment

The term "survival" refers to the ability of the haematopoietic stem and/or progenitor cells to remain alive (e.g. not die or become apoptotic) during in vitro or ex vivo culture. Haematopoietic stem and/or progenitor cells may, for example, undergo increased apoptosis following transduction with a viral vector during cell culture; thus, the surviving cells may have avoided apoptosis and/or cell death.

Cell survival may be readily analysed by the skilled person. For example, the numbers of live, dead and/or apoptotic cells in a cell culture may be quantified at the beginning of culture and/or following culture for a period of time (e.g. about 6 or 12 hours, or 1, 2, 3, 4, 5, 6, 7 or more days; preferably, the period of time begins with the transduction of the cells with a viral vector). The effect of an agent, such as an inhibitor of the invention, on cell survival may be assessed by comparing the numbers and/or percentages of live, dead and/or apoptotic cells at the beginning and/or end of the culture period between experiments carried out in the presence and absence of the agent, but under otherwise substantially identical conditions.

Cell numbers and/or percentages in certain states (e.g. live, dead or apoptotic cells) may be quantified using any of a number of methods known in the art, including use of haemocytometers, automated cell counters, flow cytometers and fluorescence activated cell sorting machines. These techniques may enable distinguishing between live, dead and/or apoptotic cells. In addition or in the alternative, apoptotic cells may be detected using readily available apoptosis assays (e.g. assays based on the detection of phosphatidylserine (PS) on the cell membrane surface, such as through use of Annexin V, which binds to exposed PS; apoptotic cells may be quantified through use of fluorescently-labelled Annexin V), which may be used to complement other techniques.

The term "engraftment" refers to the ability of the haematopoietic stem and/or progenitor cells to populate and survive in a subject following their transplantation, i.e. in the short and/or long term after transplantation. For example, engraftment may refer to the number and/or percentages of haematopoietic cells descended from the transplanted haematopoietic stem and/or progenitor cells (e.g. graft-derived cells) that are detected about 1 day to 24 weeks, 1 day to 10 weeks, or 1-30 days or 10-30 days after transplantation. In the xenograft model of human haematopoietic stem and/or progenitor cell engraftment and repopulation, engraftment may be evaluated in the peripheral blood as the percentage of cells deriving from the human xenograft (e.g. positive for the CD45 surface marker), for example. In one embodiment, engraftment is assessed at about 1, 2, 3, 4, 5, 6, 7, 8, 9, 10, 15, 20, 25 or 30 days after transplantation. In another embodiment, engraftment is assessed at about 4, 5, 6, 7, 8, 9, 10, 11, 12, 13, 14, 15, 16, 17, 18, 19, 20, 21, 22, 23 or 24 weeks after transplantation. In another embodiment, engraftment is assessed at about 16-24 weeks, preferably 20 weeks, after transplantation.

Engraftment may be readily analysed by the skilled person. For example, the transplanted haematopoietic stem and/or progenitor cells may be engineered to comprise a marker (e.g. a reporter protein, such as a fluorescent protein), which can be used to quantify the graft-derived cells. Samples for analysis may be extracted from relevant tissues and analysed ex vivo (e.g. using flow cytometry).

p53 Activation

The term "p53 activation" refers to an increase in the activity of p53, for example through a post-translational modification of the p53 protein. Example post-translational modifications include phosphorylation, acetylation and methylation, and are described in Kruse, J. P. et al. (2008) SnapShot: p53 Posttranslational Modifications Cell 133: 930-931. In the context of the invention, the p53 activation preferably results from phosphorylation of p53, particularly preferably at amino acid Serine 15.

Methods for analysing such post-translational modifications are known in the art (example methods for analysing kinase activity are disclosed herein, further methods include, for example, mass spectrometry- and antibody recognition-based methods).

An example amino acid sequence of p53, which may be used to provide an amino acid numbering convention, is:

```
MEEPQSDPSVEPPLSQETFSDLWKLLPENNVLSPLPSQAMDDLMLSPDDI

EQWFTEDPGPDEAPRMPEAAPPVAPAPAAPTPAAPAPAPSWPLSSSVPSQ

KTYQGSYGFRLGFLHSGTAKSVTCTYSPALNKMFCQLAKTCPVQLWVDST
```
-continued
```
PPPGTRVRAMAIYKQSQHMTEVVRRCPHHERCSDSDGLAPPQHLIRVEGN

LRVEYLDDRNTFRHSVVVPYEPPEVGSDCTTIHYNYMCNSSCMGGMNRRP

ILTIITLEDSSGNLLGRNSFEVRVCACPGRDRRTEEENLRKKGEPHHELP

PGSTKRALPNNTSSSPQPKKKPLDGEYFTLQIRGRERFEMFRELNEALEL

KDAQAGKEPGGSRAHSSHLKSKKGQSTSRHKKLMFKTEGPDSD
(SEQ ID NO: 1; NCBI Accession No. 000537.3)
```

Ataxia Telangiectasia Mutated (ATM) Kinase

Ataxia telangiectasia mutated (ATM) kinase (also known as "ataxia telangiectasia mutated") is a serine/threonine kinase which is recruited to and activated by double-strand DNA breaks. ATM kinase is known to phosphorylate a number of proteins (including p53, CHK2, BRCA1, NBS1 and H2AX) that initiate activation of the DNA damage checkpoint, leading to cell cycle arrest, DNA repair or apoptosis.

In one embodiment, the ATM kinase is human ATM kinase.

In one embodiment, the amino acid sequence of ATM kinase is the sequence deposited under NCBI Accession No. NP_000042.3.

An example amino acid sequence of the ATM kinase is:

```
                                                    (SEQ ID NO: 2)
MSLVLNDLLICCRQLEHDRATERKKEVEKFKRLIRDPETIKHLDRHSDSKQGKYLNWDAVFRFLQKYIQKET

ECLRIAKPNVSASTQASRQKKMQEISSLVKYFIKCANRRAPRLKCQELLNYIMDTVKDSSNGAIYGADCSNI

LLKDILSVRKYWCEISQQQWLELFSVYFRLYLKPSQDVHRVLVARIIHAVTKGCCSQTDGLNSKFLDFFSKA

IQCARQEKSSSGLNHILAALTIFLKTLAVNFRIRVCELGDEILPTLLYIWTQHRLNDSLKEVIIELFQLQIY

IHHPKGAKTQEKGAYESTKWRSILYNLYDLLVNEISHIGSRGKYSSGFRNIAVKENLIELMADICHQVFNED

TRSLEISQSYTTTQRESSDYSVPCKRKKIELGWEVIKDHLQKSQNDFDLVPWLQIATQLISKYPASLPNCEL

SPLLMILSQLLPQQRHGERTPYVLRCLTEVALCQDKRSNLESSQKSDLLKLWNKIWCITFRGISSEQIQAEN

FGLLGAIIQGSLVEVDREFWKLFTGSACRPSCPAVCCLTLALTTSIVPGTVKMGIEQNMCEVNRSFSLKESI

MKWLLFYQLEGDLENSTEVPPILHSNFPHLVLEKILVSLTMKNCKAAMNFFQSVPECEHHQKDKEELSFSEV

EELFLQTTFDKMDFLTIVRECGIEKHQSSIGFSVHQNLKESLDRCLLGLSEQLLNNYSSEITNSETLVRCSR

LLVGVLGCYCYMGVIAEEEAYKSELFQKAKSLMQCAGESITLFKNKTNEEFRIGSLRNMMQLCTRCLSNCTK

KSPNKIASGFFLRLLTSKLMNDIADICKSLASFIKKPFDRGEVESMEDDTNGNLMEVEDQSSMNLFNDYPDS

SVSDANEPGESQSTIGAINPLAEEYLSKQDLLFLDMLKFLCLCVTTAQTNTVSFRAADIRRKLLMLIDSSTL

EPTKSLHLHMYLMLLKELPGEEYPLPMEDVLELLKPLSNVCSLYRRDQDVCKTILNHVLHVVKNLGQSNMDS

ENTRDAQGQFLTVIGAFWHLTKERKYIFSVRMALVNCLKTLLEADPYSKWAILNVMGKDFPVNEVFTQFLAD

NHHQVRMLAAESINRLFQDTKGDSSRLLKALPLKLQQTAFENAYLKAQEGMREMSHSAENPETLDEIYNRKS

VLLTLIAVVLSCSPICEKQALFALCKSVKENGLEPHLVKKVLEKVSETFGYRRLEDFMASHLDYLVLEWLNL

QDTEYNLSSFPFILLNYTNIEDFYRSCYKVLIPHLVIRSHFDEVKSIANQIQEDWKSLLTDCFPKILVNILP

YFAYEGTRDSGMAQQRETATKVYDMLKSENLLGKQIDHLFISNLPEIVVELLMTLHEPANSSASQSTDLCDF

SGDLDPAPNPPHFPSHVIKATFAYISNCHKTKLKSILEILSKSPDSYQKILLAICEQAAETNNVYKKHRILK

IYHLFVSLLLKDIKSGLGGAWAFVLRDVIYTLIHYINQRPSCIMDVSLRSFSLCCDLLSQVCQTAVTYCKDA

LENHLHVIVGTLIPLVYEQVEVQKQVLDLLKYLVIDNKDNENLYITIKLLDPFPDHVVFKDLRITQQKIKYS

RGPFSLLEEINHFLSVSVYDALPLTRLEGLKDLRRQLELHKDQMVDIMRASQDNPQDGIMVKLVVNLLQLSK

MAINHTGEKEVLEAVGSCLGEVGPIDFSTIAIQHSKDASYTKALKLFEDKELQWTFIMLTYLNNTLVEDCVK
```

-continued
```
VRSAAVTCLKNILATKTGHSFWEIYKMTTDPMLAYLQPFRTSRKKFLEVPRFDKENPFEGLDDINLWIPLSE

NHDIWIKTLTCAFLDSGGTKCEILQLLKPMCEVKTDFCQTVLPYLIHDILLQDTNESWRNLLSTHVQGFFTS

CLRHFSQTSRSTTPANLDSESEHFFRCCLDKKSQRTMLAVVDYMRRQKRPSSGTIFNDAFWLDLNYLEVAKV

AQSCAAHFTALLYAEIYADKKSMDDQEKRSLAFEEGSQSTTISSLSEKSKEETGISLQDLLLEIYRSIGEPD

SLYGCGGGKMLQPITRLRTYEHEAMWGKALVTYDLETAIPSSTRQAGIIQALQNLGLCHILSVYLKGLDYEN

KDWCPELEELHYQAAWRNMQWDHCTSVSKEVEGTSYHESLYNALQSLRDREFSTFYESLKYARVKEVEEMCK

RSLESVYSLYPTLSRLQAIGELESIGELFSRSVTHRQLSEVYIKWQKHSQLLKDSDFSFQEPIMALRTVILE

ILMEKEMDNSQRECIKDILTKHLVELSILARTFKNTQLPERAIFQIKQYNSVSCGVSEWQLEEAQVFWAKKE

QSLALSILKQMIKKLDASCAANNPSLKLTYTECLRVCGNWLAETCLENPAVIMQTYLEKAVEVAGNYDGESS

DELRNGKMKAFLSLARFSDTQYQRIENYMKSSEFENKQALLKRAKEEVGLLREHKIQTNRYTVKVQRELELD

ELALRALKEDRKRFLCKAVENYINCLLSGEEHDMWVFRLCSLWLENSGVSEVNGMMKRDGMKIPTYKFLPLM

YQLAARMGTKMMGGLGFHEVLNNLISRISMDHPHHTLFIILALANANRDEFLTKPEVARRSRITKNVPKQSS

QLDEDRTEAANRIICTIRSRRPQMVRSVEALCDAYIILANLDATQWKTQRKGINIPADQPITKLKNLEDVVV

PTMEIKVDHTGEYGNLVTIQSFKAEFRLAGGVNLPKIIDCVGSDGKERRQLVKGRDDLRQDAVMQQVFQMCN

TLLQRNTETRKRKLTICTYKVVPLSQRSGVLEWCTGTVPIGEFLVNNEDGAHKRYRPNDFSAFQCQKKMMEV

QKKSFEEKYEVFMDVCQNFQPVFRYFCMEKFLDPAIWFEKRLAYTRSVATSSIVGYILGLGDRHVQNILINE

QSAELVHIDLGVAFEQGKILPTPETVPFRLTRDIVDGMGITGVEGVFRRCCEKTMEVMRNSQETLLTIVEVL

LYDPLFDWTMNPLKALYLQQRPEDETELHPTLNADDQECKRNLSDIDQSFNKVAERVLMRLQEKLKGVEEGT

VLSVGGQVNLLIQQAIDPKNLSRLFPGWKAWV
```

An example nucleic acid sequence encoding the ATM kinase is:

```
ATGAGTCTAGTACTTAATGATCTGCTTATCTGCTGCCGTCAACTAGAACATGATAGAGCTACAGAACGAA

AGAAAGAAGTTGAGAAATTTAAGCGCCTGATTCGAGATCCTGAAACAATTAAACATCTAGATCGGCATTC

AGATTCCAAACAAGGAAATATTTGAATTGGGATGCTGTTTTTAGATTTTTACAGAAATATATTCAGAAA

GAAACAGAATGTCTGAGAATAGCAAAACCAAATGTATCAGCCTCAACACAAGCCTCCAGGCAGAAAAAGA

TGCAGGAAATCAGTAGTTTGGTCAAATACTTCATCAAATGTGCAAACAGAAGAGCACCTAGGCTAAAATG

TCAAGAACTCTTAAATTATATCATGGATACAGTGAAAGATTCATCTAATGGTGCTATTTACGGAGCTGAT

TGTAGCAACATACTACTCAAAGACATTCTTTCTGTGAGAAAATACTGGTGTGAAATATCTCAGCAACAGT

GGTTAGAATTGTTCTCTGTGTACTTCAGGCTCTATCTGAAACCTTCACAAGATGTTCATAGAGTTTTAGT

GGCTAGAATAATTCATGCTGTTACCAAAGGATGCTGTTCTCAGACTGACGGATTAAATTCCAAATTTTTG

GACTTTTTTCCAAGGCTATTCAGTGTGCGAGACAAGAAAAGAGCTCTTCAGGTCTAAATCATATCTTAG

CAGCTCTTACTATCTTCCTCAAGACTTTGGCTGTCAACTTTCGAATTCGAGTGTGTGAATTAGGAGATGA

AATTCTTCCCACTTTGCTTTATATTTGGACTCAACATAGGCTTAATGATTCTTTAAAAGAAGTCATTATT

GAATATTTCAACTGCAAATTTATATCCATCATCCGAAAGGAGCCAAAACCCAAGAAAAAGGTGCTTATG

AATCAACAAAATGGAGAAGTATTTTATACAACTTATATGATCTGCTAGTGAATGAGATAAGTCATATAGG

AAGTAGAGGAAAGTATTCTTCAGGATTTCGTAATATTGCCGTCAAAGAAAATTTGATTGAATTGATGGCA

GATATCTGTCACCAGGTTTTTAATGAAGATACCAGATCCTTGGAGATTTCTCAATCTTACACTACTACAC

AAAGAGAATCTAGTGATTACAGTGTCCCTTGCAAAAGGAAGAAAATAGAACTAGGCTGGGAAGTAATAAA

AGATCACCTTCAGAAGTCACAGAATGATTTTGATCTTGTGCCTTGGCTACAGATTGCAACCCAATTAATA

TCAAAGTATCCTGCAAGTTTACCTAACTGTGAGCTGTCTCCATTACTGATGATACTATCTCAGCTTCTAC
```

-continued

```
CCCAACAGCGACATGGGGAACGTACACCATATGTGTTACGATGCCTTACGGAAGTTGCATTGTGTCAAGA
CAAGAGGTCAAACCTAGAAAGCTCACAAAAGTCAGATTTATTAAAACTCTGGAATAAAATTTGGTGTATT
ACCTTTCGTGGTATAAGTTCTGAGCAAATACAAGCTGAAAACTTTGGCTTACTTGGAGCCATAATTCAGG
GTAGTTTAGTTGAGGTTGACAGAGAATTCTGGAAGTTATTTACTGGGTCAGCCTGCAGACCTTCATGTCC
TGCAGTATGCTGTTTGACTTTGGCACTGACCACCAGTATAGTTCCAGGAACGGTAAAAATGGGAATAGAG
CAAAATATGTGTGAAGTAAATAGAAGCTTTTCTTTAAAGGAATCAATAATGAAATGGCTCTTATTCTATC
AGTTAGAGGGTGACTTAGAAAATAGCACAGAAGTGCCTCCAATTCTTCACAGTAATTTTCCTCATCTTGT
ACTGGAGAAAATTCTTGTGAGTCTCACTATGAAAAACTGTAAAGCTGCAATGAATTTTTTCCAAAGCGTG
CCAGAATGTGAACACCACCAAAAAGATAAAGAAGAACTTTCATTCTCAGAAGTAGAAGAACTATTTCTTC
AGACAACTTTTGACAAGATGGACTTTTTAACCATTGTGAGAGAATGTGGTATAGAAAAGCACCAGTCCAG
TATTGGCTTCTCTGTCCACCAGAATCTCAAGGAATCACTGGATCGCTGTCTTCTGGGATTATCAGAACAG
CTTCTGAATAATTACTCATCTGAGATTACAAATTCAGAAACTCTTGTCCGGTGTTCACGTCTTTTGGTGG
GTGTCCTTGGCTGCTACTGTTACATGGGTGTAATAGCTGAAGAGGAAGCATATAAGTCAGAATTATTCCA
GAAAGCCAAGTCTCTAATGCAATGTGCAGGAGAAAGTATCACTCTGTTTAAAAATAAGCAAATGAGGAA
TTCAGAATTGGTTCCTTGAGAAATATGATGCAGCTATGTACACGTTGCTTGAGCAACTGTACCAAGAAGA
GTCCAAATAAGATTGCATCTGGCTTTTTCCTGCGATTGTTAACATCAAAGCTAATGAATGACATTGCAGA
TATTTGTAAAAGTTTAGCATCCTTCATCAAAAAGCCATTTGACCGTGGAGAAGTAGAATCAATGGAAGAT
GATACTAATGGAAATCTAATGGAGGTGGAGGATCAGTCATCCATGAATCTATTTAACGATTACCCTGATA
GTAGTGTTAGTGATGCAAACGAACCTGGAGAGAGCCAAAGTACCATAGGTGCCATTAATCCTTTAGCTGA
AGAATATCTGTCAAAGCAAGATCTACTTTTCTTAGACATGCTCAAGTTCTTGTGTTTGTGTGTAACTACT
GCTCAGACCAATACTGTGTCCTTTAGGGCAGCTGATATTCGGAGGAAATTGTTAATGTTAATTGATTCTA
GCACGCTAGAACCTACCAAATCCCTCCACCTGCATATGTATCTAATGCTTTTAAAGGAGCTTCCTGGAGA
AGAGTACCCCTTGCCAATGGAAGATGTTCTTGAACTTCTGAAACCACTATCCAATGTGTGTTCTTTGTAT
CGTCGTGACCAAGATGTTTGTAAAACTATTTTAAACCATGTCCTTCATGTAGTGAAAAACCTAGGTCAAA
GCAATATGGACTCTGAGAACACAAGGGATGCTCAAGGACAGTTTCTTACAGTAATTGGAGCATTTTGGCA
TCTAACAAAGGAGAGGAAATATATATTCTCTGTAAGAATGGCCCTAGTAAATTGCCTTAAAACTTTGCTT
GAGGCTGATCCTTATTCAAAATGGGCCATTCTTAATGTAATGGGAAAAGACTTTCCTGTAAATGAAGTAT
TTACACAATTTCTTGCTGACAATCATCACCAAGTTCGCATGTTGGCTGCAGAGTCAATCAATAGATTGTT
CCAGGACACGAAGGGAGATTCTTCCAGGTTACTGAAAGCACTTCCTTTGAAGCTTCAGCAAACAGCTTTT
GAAAATGCATACTTGAAAGCTCAGGAAGGAATGAGAGAAATGTCCCATAGTGCTGAGAACCCTGAAACTT
TGGATGAAATTTATAATAGAAAATCTGTTTTACTGACGTTGATAGCTGTGGTTTTATCCTGTAGCCCTAT
CTGCGAAAAACAGGCTTTGTTTGCCCTGTGTAAATCTGTGAAAGAGAATGGATTAGAACCTCACCTTGTG
AAAAGGTTTTAGAGAAAGTTTCTGAAACTTTTGGATATAGACGTTTAGAAGACTTTATGGCATCTCATT
TAGATTATCTGGTTTTGGAATGGCTAAATCTTCAAGATACTGAATACAACTTATCTTCTTTTCCTTTTAT
TTTATTAAACTACACAAATATTGAGGATTTCTATAGATCTTGTTATAAGGTTTTGATTCCACATCTGGTG
ATTAGAAGTCATTTTGATGAGGTGAAGTCCATTGCTAATCAGATTCAAGAGGACTGGAAAAGTCTTCTAA
CAGACTGCTTTCCAAAGATTCTTGTAAATATTCTTCCTTATTTTGCCTATGAGGGTACCAGAGACAGTGG
GATGGCACAGCAAAGAGAGACTGCTACCAAGGTCTATGATATGCTTAAAAGTGAAAACTTATTGGGAAAA
CAGATTGATCACTTATTCATTAGTAATTTACCAGAGATTGTGGTGGAGTTATTGATGACGTTACATGAGC
CAGCAAATTCTAGTGCCAGTCAGAGCACTGACCTCTGTGACTTTTCAGGGGATTTGGATCCTGCTCCTAA
```

-continued

```
TCCACCTCATTTTCCATCGCATGTGATTAAAGCAACATTTGCCTATATCAGCAATTGTCATAAAACCAAG

TTAAAAAGCATTTTAGAAATTCTTTCCAAAAGCCCTGATTCCTATCAGAAAATTCTTCTTGCCATATGTG

AGCAAGCAGCTGAAACAAATAATGTTTATAAGAAGCACAGAATTCTTAAAATATATCACCTGTTTGTTAG

TTTATTACTGAAAGATATAAAAAGTGGCTTAGGAGGAGCTTGGGCCTTTGTTCTTCGAGACGTTATTTAT

ACTTTGATTCACTATATCAACCAAAGGCCTTCTTGTATCATGGATGTGTCATTACGTAGCTTCTCCCTTT

GTTGTGACTTATTAAGTCAGGTTTGCCAGACAGCCGTGACTTACTGTAAGGATGCTCTAGAAAACCATCT

TCATGTTATTGTTGGTACACTTATACCCCTTGTGTATGAGCAGGTGGAGGTTCAGAAACAGGTATTGGAC

TTGTTGAAATACTTAGTGATAGATAACAAGGATAATGAAAACCTCTATATCACGATTAAGCTTTTAGATC

CTTTTCCTGACCATGTTGTTTTTAAGGATTTGCGTATTACTCAGCAAAAAATCAAATACAGTAGAGGACC

CTTTTCACTCTTGGAGGAAATTAACCATTTTCTCTCAGTAAGTGTTTATGATGCACTTCCATTGACAAGA

CTTGAAGGACTAAAGGATCTTCGAAGACAACTGGAACTACATAAAGATCAGATGGTGGACATTATGAGAG

CTTCTCAGGATAATCCGCAAGATGGGATTATGGTGAAACTAGTTGTCAATTTGTTGCAGTTATCCAAGAT

GGCAATAAACCACACTGGTGAAAAGAAGTTCTAGAGGCTGTTGGAAGCTGCTTGGGAGAAGTGGGTCCT

ATAGATTTCTCTACCATAGCTATACAACATAGTAAAGATGCATCTTATACCAAGGCCCTTAAGTTATTTG

AAGATAAAGAACTTCAGTGGACCTTCATAATGCTGACCTACCTGAATAACACACTGGTAGAAGATTGTGT

CAAAGTTCGATCAGCAGCTGTTACCTGTTTGAAAAACATTTTAGCCACAAAGACTGGACATAGTTTCTGG

GAGATTTATAAGATGACAACAGATCCAATGCTGGCCTATCTACAGCCTTTTAGAACATCAAGAAAAAGT

TTTTAGAAGTACCCAGATTTGACAAAGAAAACCCTTTTGAAGGCCTGGATGATATAAATCTGTGGATTCC

TCTAAGTGAAAATCATGACATTTGGATAAAGACACTGACTTGTGCTTTTTTGGACAGTGGAGGCACAAAA

TGTGAAATTCTTCAATTATTAAAGCCAATGTGTGAAGTGAAAACTGACTTTTGTCAGACTGTACTTCCAT

ACTTGATTCATGATATTTTACTCCAAGATACAAATGAATCATGGAGAAATCTGCTTTCTACACATGTTCA

GGGATTTTTCACCAGCTGTCTTCGACACTTCTCGCAAACGAGCCGATCCACAACCCCTGCAAACTTGGAT

TCAGAGTCAGAGCACTTTTTCCGATGCTGTTTGGATAAAAAATCACAAAGAACAATGCTTGCTGTTGTGG

ACTACATGAGAAGACAAAAGAGACCTTCTTCAGGAACAATTTTTAATGATGCTTTCTGGCTGGATTTAAA

TTATCTAGAAGTTGCCAAGGTAGCTCAGTCTTGTGCTGCTCACTTTACAGCTTTACTCTATGCAGAAATC

TATGCAGATAAGAAAAGTATGGATGATCAAGAGAAAAGAAGTCTTGCATTTGAAGAAGGAAGCCAGAGTA

CAACTATTTCTAGCTTGAGTGAAAAAAGTAAAGAAGAAACTGGAATAAGTTTACAGGATCTTCTCTTAGA

AATCTACAGAAGTATAGGGGAGCCAGATAGTTTGTATGGCTGTGGTGGAGGGAAGATGTTACAACCCATT

ACTAGACTACGAACATATGAACACGAAGCAATGTGGGGCAAAGCCCTAGTAACATATGACCTCGAAACAG

CAATCCCCTCATCAACACGCCAGGCAGGAATCATTCAGGCCTTGCAGAATTTGGGACTCTGCCATATTCT

TTCCGTCTATTTAAAAGGATTGGATTATGAAAATAAAGACTGGTGTCCTGAACTAGAAGAACTTCATTAC

CAAGCAGCATGGAGGAATATGCAGTGGGACCATTGCACTTCCGTCAGCAAAGAAGTAGAAGGAACCAGTT

ACCATGAATCATTGTACAATGCTCTACAATCTCTAAGAGACAGAGAATTCTCTACATTTTATGAAAGTCT

CAAATATGCCAGAGTAAAAGAAGTGGAAGAGATGTGTAAGCGCAGCCTTGAGTCTGTGTATTCGCTCTAT

CCCACACTTAGCAGGTTGCAGGCCATTGGAGAGCTGGAAAGCATTGGGGAGCTTTTCTCAAGATCAGTCA

CACATAGACAACTCTCTGAAGTATATATTAAGTGGCAGAAACACTCCCAGCTTCTCAAGGACAGTGATTT

TAGTTTTCAGGAGCCTATCATGGCTCTACGCACAGTCATTTTGGAGATCCTGATGGAAAAGGAAATGGAC

AACTCACAAAGAGAATGTATTAAGGACATTCTCACCAAACACCTTGTAGAACTCTCTATACTGGCCAGAA

CTTTCAAGAACACTCAGCTCCCTGAAAGGGCAATATTTCAAATTAAACAGTACAATTCAGTTAGCTGTGG

AGTCTCTGAGTGGCAGCTGGAAGAAGCACAAGTATTCTGGGCAAAAAAGGAGCAGAGTCTTGCCCTGAGT

ATTCTCAAGCAAATGATCAAGAAGTTGGATGCCAGCTGTGCAGCGAACAATCCCAGCCTAAAACTTACAT
```

-continued

```
ACACAGAATGTCTGAGGGTTTGTGGCAACTGGTTAGCAGAAACGTGCTTAGAAAATCCTGCGGTCATCAT

GCAGACCTATCTAGAAAAGGCAGTAGAAGTTGCTGGAAATTATGATGGAGAAAGTAGTGATGAGCTAAGA

AATGGAAAAATGAAGGCATTTCTCTCATTAGCCCGGTTTTCAGATACTCAATACCAAAGAATTGAAAACT

ACATGAAATCATCGGAATTTGAAAACAAGCAAGCTCTCCTGAAAAGAGCCAAAGAGGAAGTAGGTCTCCT

TAGGGAACATAAAATTCAGACAAACAGATACACAGTAAAGGTTCAGCGAGAGCTGGAGTTGGATGAATTA

GCCCTGCGTGCACTGAAAGAGGATCGTAAACGCTTCTTATGTAAAGCAGTTGAAAATTATATCAACTGCT

TATTAAGTGGAGAAGAACATGATATGTGGGTATTCCGACTTTGTTCCCTCTGGCTTGAAAATTCTGGAGT

TTCTGAAGTCAATGGCATGATGAAGAGAGACGGAATGAAGATTCCAACATATAAATTTTTGCCTCTTATG

TACCAATTGGCTGCTAGAATGGGGACCAAGATGATGGGAGGCCTAGGATTTCATGAAGTCCTCAATAATC

TAATCTCTAGAATTTCAATGGATCACCCCCATCACACTTTGTTTATTATACTGGCCTTAGCAAATGCAAA

CAGAGATGAATTTCTGACTAAACCAGAGGTAGCCAGAAGAAGCAGAATAACTAAAAATGTGCCTAAACAA

AGCTCTCAGCTTGATGAGGATCGAACAGAGGCTGCAAATAGAATAATATGTACTATCAGAAGTAGGAGAC

CTCAGATGGTCAGAAGTGTTGAGGCACTTTGTGATGCTTATATTATATTAGCAAACTTAGATGCCACTCA

GTGGAAGACTCAGAGAAAAGGCATAAATATTCCAGCAGACCAGCCAATTACTAAACTTAAGAATTTAGAA

GATGTTGTTGTCCCTACTATGGAAATTAAGGTGGACCACACAGGAGAATATGGAAATCTGGTGACTATAC

AGTCATTTAAAGCAGAATTTCGCTTAGCAGGAGGTGTAAATTTACCAAAAATAATAGATTGTGTAGGTTC

CGATGGCAAGGAGAGGAGACAGCTTGTTAAGGGCCGTGATGACCTGAGACAAGATGCTGTCATGCAACAG

GTCTTCCAGATGTGTAATACATTACTGCAGAGAAACACGGAAACTAGGAAGAGGAAATTAACTATCTGTA

CTTATAAGGTGGTTCCCCTCTCTCAGCGAAGTGGTGTTCTTGAATGGTGCACAGGAACTGTCCCCATTGG

TGAATTTCTTGTTAACAATGAAGATGGTGCTCATAAAAGATACAGGCCAAATGATTTCAGTGCCTTTCAG

TGCCAAAAGAAAATGATGGAGGTGCAAAAAAAGTCTTTTGAAGAGAAATATGAAGTCTTCATGGATGTTT

GCCAAAATTTTCAACCAGTTTTCCGTTACTTCTGCATGGAAAAATTCTTGGATCCAGCTATTTGGTTTGA

GAAGCGATTGGCTTATACGCGCAGTGTAGCTACTTCTTCTATTGTTGGTTACATACTTGGACTTGGTGAT

AGACATGTACAGAATATCTTGATAAATGAGCAGTCAGCAGAACTTGTACATATAGATCTAGGTGTTGCTT

TTGAACAGGGCAAAATCCTTCCTACTCCTGAGACAGTTCCTTTTAGACTCACCAGAGATATTGTGGATGG

CATGGGCATTACGGGTGTTGAAGGTGTCTTCAGAAGATGCTGTGAGAAAACCATGGAAGTGATGAGAAAC

TCTCAGGAAACTCTGTTAACCATTGTAGAGGTCCTTCTATATGATCCACTCTTTGACTGGACCATGAATC

CTTTGAAAGCTTTGTATTTACAGCAGAGGCCGGAAGATGAAACTGAGCTTCACCCTACTCTGAATGCAGA

TGACCAAGAATGCAAACGAAATCTCAGTGATATTGACCAGAGTTTCAACAAAGTAGCTGAACGTGTCTTA

ATGAGACTACAAGAGAAACTGAAAGGAGTGGAAGAAGGCACTGTGCTCAGTGTTGGTGGACAAGTGAATT

TGCTCATACAGCAGGCCATAGACCCCAAAAATCTCAGCCGACTTTTCCCAGGATGGAAAGCTTGGGTGTG

A (SEQ ID NO: 3; NCBI Accession No. NM_000051.3)
```

Ataxia Telangiectasia and Rad3-Related Protein (ATR)

Ataxia telangiectasia and Rad3-related protein (ATR), also known as serine/threonine-protein kinase ATR or FRAP-related protein 1 (FRP1), is a serine/threonine-specific kinase involved in DNA damage sensing. It may be involved in activating the DNA damage checkpoint, which leads to cell cycle arrest In one embodiment, the ATR is human ATR.

In one embodiment, the amino acid sequence of ATR is the sequence deposited under NCBI Accession No. NP_001175.2.

An example amino acid sequence of the ATR is:

(SEQ ID NO: 4)
MGEHGLELASMIPALRELGSATPEEYNTVVQKPRQILCQFIDRILTDVNVVAVELVKKTDSQPTSVMLLDFI

QHIMKSSPLMFVNVSGSHEAKGSCIEFSNWIITRLLRIAATPSCHLLHKKICEVICSLLFLEKSKSPAIFGV

-continued

LTKELLQLFEDLVYLHRRNVMGHAVEWPVVMSRFLSQLDEHMGYLQSAPLQLMSMQNLEFIEVTLLMVLTRI
IAIVFFRRQELLLWQIGCVLLEYGSPKIKSLAISFLTELFQLGGLPAQPASTFFSSFLELLKHLVEMDTDQL
KLYEEPLSKLIKTLFPFEAEAYRNIEPVYLNMLLEKLCVMFEDGVLMRLKSDLLKAALCHLLQYFLKFVPAG
YESALQVRKVYVRNICKALLDVLGIEVDAEYLLGPLYAALKMESMEIIEEIQCQTQQENLSSNSDGISPKRR
RLSSSLNPSKRAPKQTEEIKHVDMNQKSILWSALKQKAESLQISLEYSGLKNPVIEMLEGIAVVLQLTALCT
VHCSHQNMNCRTFKDCQHKSKKKPSVVITWMSLDFYTKVLKSCRSLLESVQKLDLEATIDKVVKIYDALIYM
QVNSSFEDHILEDLCGMLSLPWIYSHSDDGCLKLTTFAANLLTLSCRISDSYSPQAQSRCVFLLTLFPRRIF
LEWRTAVYNWALQSSHEVIRASCVSGFFILLQQQNSCNRVPKILIDKVKDDSDIVKKEFASILGQLVCTLHG
MFYLTSSLTEPFSEHGHVDLFCRNLKATSQHECSSSQLKASVCKPFLFLLKKKIPSPVKLAFIDNLHHLCKH
LDFREDETDVKAVLGTLLNLMEDPDKDVRVAFSGNIKHILESLDSEDGFIKELFVLRMKEAYTHAQISRNNE
LKDTLILTTGDIGRAAKGDLVPFALLHLLHCLLSKSASVSGAAYTEIRALVAAKSVKLQSFFSQYKKPICQF
LVESLHSSQMTALPNTPCQNADVRKQDVAHQREMALNTLSEIANVFDFPDLNRFLTRTLQVLLPDLAAKASP
AASALIRTLGKQLNVNRREILINNFKYIFSHLVCSCSKDELERALHYLKNETEIELGSLLRQDFQGLHNELL
LRIGEHYQQVFNGLSILASFASSDDPYQGPRDIISPELMADYLQPKLLGILAFFNMQLLSSSVGIEDKKMAL
NSLMSLMKLMGPKHVSSVRVKMMTTLRTGLRFKDDFPELCCRAWDCFVRCLDHACLGSLLSHVIVALLPLIH
IQPKETAAIFHYLIIENRDAVQDFLHEIYFLPDHPELKKIKAVLQEYRKETSESTDLQTTLQLSMKAIQHEN
VDVRIHALTSLKETLYKNQEKLIKYATDSETVEPIISQLVTVLLKGCQDANSQARLLCGECLGELGAIDPGR
LDFSTTETQGKDFTFVTGVEDSSFAYGLLMELTRAYLAYADNSRAQDSAAYAIQELLSIYDCREMETNGPGH
QLWRRFPEHVREILEPHLNTRYKSSQKSTDWSGVKKPIYLSKLGSNFAEWSASWAGYLITKVRHDLASKIFT
CCSIMMKHDFKVTIYLLPHILVYVLLGCNQEDQQEVYAEIMAVLKHDDQHTINTQDIASDLCQLSTQTVFSM
LDHLTQWARHKFQALKAEKCPHSKSNRNKVDSMVSTVDYEDYQSVTRFLDLIPQDTLAVASFRSKAYTRAVM
HFESFITEKKQNIQEHLGFLQKLYAAMHEPDGVAGVSAIRKAEPSLKEQILEHESLGLLRDATACYDRAIQL
EPDQIIHYHGVVKSMLGLGQLSTVITQVNGVHANRSEWTDELNTYRVEAAWKLSQWDLVENYLAADGKSTTW
SVRLGQLLLSAKKRDITAFYDSLKLVRAEQIVPLSAASFERGSYQRGYEYIVRLHMLCELEHSIKPLFQHSP
GDSSQEDSLNWVARLEMTQNSYRAKEPILALRRALLSLNKRPDYNEMVGECWLQSARVARKAGHHQTAYNAL
LNAGESRLAELYVERAKWLWSKGDVHQALIVLQKGVELCFPENETPPEGKNMLIHGRAMLLVGRFMEETANF
ESNAIMKKYKDVTACLPEWEDGHFYLAKYYDKLMPMVTDNKMEKQGDLIRYIVLHFGRSLQYGNQFIYQSMP
RMLTLWLDYGTKAYEWEKAGRSDRVQMRNDLGKINKVITEHTNYLAPYQFLTAFSQLISRICHSHDEVFVVL
MEIIAKVFLAYPQQAMWMMTAVSKSSYPMRVNRCKEILNKAIHMKKSLEKFVGDATRLTDKLLELCNKPVDG
SSSTLSMSTHFKMLKKLVEEATFSEILIPLQSVMIPTLPSILGTHANHASHEPFPGHWAYIAGFDDMVEILA
SLQKPKKISLKGSDGKFYIMMCKPKDDLRKDCRLMEFNSLINKCLRKDAESRRRELHIRTYAVIPLNDECGI
IEWVNNTAGLRPILTKLYKEKGVYMTGKELRQCMLPKSAALSEKLKVFREFLLPRHPPIFHEWFLRTFPDPT
SWYSSRSAYCRSTAVMSMVGYILGLGDRHGENILFDSLTGECVHVDFNCLFNKGETFEVPEIVPFRLTHNMV
NGMGPMGTEGLFRRACEVTMRLMRDQREPLMSVLKTFLHDPLVEWSKPVKGHSKAPLNETGEVVNEKAKTHV
LDIEQRLQGVIKTRNRVTGLPLSIEGHVHYLIQEATDENLLCQMYLGWTPYM

An example nucleic acid sequence encoding the ATR is:

ATGGGGGAACATGGCCTGGAGCTGGCTTCCATGATCCCCGCCCTGCGGGAGCTGGGCAGTGCCACACCAG
AGGAATATAATACAGTTGTACAGAAGCCAAGACAAATTCTGTGTCAATTCATTGACCGGATACTTACAGA
TGTAAATGTTGTTGCTGTAGAACTTGTAAAGAAAACTGACTCTCAGCCAACCTCCGTGATGTTGCTTGAT

-continued

```
TTCATCCAGCATATCATGAAATCCTCCCCACTTATGTTTGTAAATGTGAGTGGAAGCCATGAGGCCAAAG

GCAGTTGTATTGAATTCAGTAATTGGATCATAACGAGACTTCTGCGGATTGCAGCAACTCCCTCCTGTCA

TTTGTTACACAAGAAAATCTGTGAAGTCATCTGTTCATTATTATTTCTTTTTAAAAGCAAGAGTCCTGCT

ATTTTTGGGGTACTCACAAAAGAATTATTACAACTTTTTGAAGACTTGGTTTACCTCCATAGAAGAAATG

TGATGGGTCATGCTGTGGAATGGCCAGTGGTCATGAGCCGATTTTTAAGTCAATTAGATGAACACATGGG

ATATTTACAATCAGCTCCTTTGCAGTTGATGAGTATGCAAAATTTAGAATTTATTGAAGTCACTTTATTA

ATGGTTCTTACTCGTATTATTGCAATTGTGTTTTTTAGAAGGCAAGAACTCTTACTTTGGCAGATAGGTT

GTGTTCTGCTAGAGTATGGTAGTCCAAAAATTAAATCCCTAGCAATTAGCTTTTTAACAGAACTTTTTCA

GCTTGGAGGACTACCAGCACAACCAGCTAGCACTTTTTTCAGCTCATTTTTGGAATTATTAAAACACCTT

GTAGAAATGGATACTGACCAATTGAAACTCTATGAAGAGCCATTATCAAAGCTGATAAAGACACTATTTC

CCTTTGAAGCAGAAGCTTATAGAAATATTGAACCTGTCTATTTAAATATGCTGCTGGAAAAACTCTGTGT

CATGTTTGAAGACGGTGTGCTCATGCGGCTTAAGTCTGATTTGCTAAAAGCAGCTTTGTGCCATTTACTG

CAGTATTTCCTTAAATTTGTGCCAGCTGGGTATGAATCTGCTTTACAAGTCAGGAAGGTCTATGTGAGAA

ATATTTGTAAAGCTCTTTTGGATGTGCTTGGAATTGAGGTAGATGCAGAGTACTTGTTGGGCCCACTTTA

TGCAGCTTTGAAAATGGAAAGTATGGAAATCATTGAGGAGATTCAATGCCAAACTCAACAGGAAAACCTC

AGCAGTAATAGTGATGGAATATCACCCAAAAGGCGTCGTCTCAGCTCGTCTCTAAACCCTTCTAAAAGAG

CACCAAAACAGACTGAGGAAATTAAACATGTGGACATGAACCAAAAGAGCATATTATGGAGTGCACTGAA

ACAGAAAGCTGAATCCCTTCAGATTTCCCTTGAATACAGTGGCCTAAAGAATCCTGTTATTGAGATGTTA

GAAGGAATTGCTGTTGTCTTACAACTGACTGCTCTGTGTACTGTTCATTGTTCTCATCAAAACATGAACT

GCCGTACTTTCAAGGACTGTCAACATAAATCCAAGAAGAAACCTTCTGTAGTGATAACTTGGATGTCATT

GGATTTTTACACAAAAGTGCTTAAGAGCTGTAGAAGTTTGTTAGAATCTGTTCAGAAACTGGACCTGGAG

GCAACCATTGATAAGGTGGTGAAAATTTATGATGCTTTGATTTATATGCAAGTAAACAGTTCATTTGAAG

ATCATATCCTGGAAGATTTATGTGGTATGCTCTCACTTCCATGGATTTATTCCCATTCTGATGATGGCTG

TTTAAAGTTGACCACATTTGCCGCTAATCTTCTAACATTAAGCTGTAGGATTTCAGATAGCTATTCACCA

CAGGCACAATCACGATGTGTGTTTCTTCTGACTCTGTTTCCAAGAAGAATATTCCTTGAGTGGAGAACAG

CAGTTTACAACTGGGCCCTGCAGAGCTCCCATGAAGTAATCCGGGCTAGTTGTGTTAGTGGATTTTTTAT

CTTATTGCAGCAGCAGAATTCTTGTAACAGAGTTCCCAAGATTCTTATAGATAAAGTCAAAGATGATTCT

GACATTGTCAAGAAAGAATTTGCTTCTATACTTGGTCAACTTGTCTGTACTCTTCACGGCATGTTTTATC

TGACAAGTTCTTTAACAGAACCTTTCTCTGAACACGGACATGTGGACCTCTTCTGTAGGAACTTGAAAGC

CACTTCTCAACATGAATGTTCATCTTCTCAACTAAAAGCTTCTGTCTGCAAGCCATTCCTTTTCCTACTG

AAAAAAAAAATACCTAGTCCAGTAAAACTTGCTTTCATAGATAATCTACATCATCTTTGTAAGCATCTTG

ATTTTAGAGAAGATGAAACAGATGTAAAAGCAGTTCTTGGAACTTTATTAAATTTAATGGAAGATCCAGA

CAAAGATGTTAGAGTGGCTTTTAGTGGAAATATCAAGCACATATTGGAATCCTTGGACTCTGAAGATGGA

TTTATAAAGGAGCTTTTTGTCTTAAGAATGAAGGAAGCATATACACATGCCCAAATATCAAGAAATAATG

AGCTGAAGGATACCTTGATTCTTACAACAGGGGATATTGGAAGGGCCGCAAAAGGAGATTTGGTACCATT

TGCACTCTTACACTTATTGCATTGTTTGTTATCCAAGTCAGCATCTGTCTCTGGAGCAGCATACACAGAA

ATTAGAGCTCTGGTTGCAGCTAAAAGTGTTAAACTGCAAAGTTTTTTCAGCCAGTATAAGAAACCCATCT

GTCAGTTTTTGGTAGAATCCCTTCACTCTAGTCAGATGACAGCACTTCCGAATACTCCATGCCAGAATGC

TGACGTGCGAAAACAAGATGTGGCTCACCAGAGAGAAATGGCTTTAAATACGTTGTCTGAAATTGCCAAC

GTTTTCGACTTTCCTGATCTTAATCGTTTTCTTACTAGGACATTACAAGTTCTACTACCTGATCTTGCTG

CCAAAGCAAGCCCTGCAGCTTCTGCTCTCATTCGAACTTTAGGAAAACAATTAAATGTCAATCGTAGAGA
```

-continued

```
GATTTTAATAAACAACTTCAAATATATTTTTTCTCATTTGGTCTGTTCTTGTTCCAAAGATGAATTAGAA

CGTGCCCTTCATTATCTGAAGAATGAAACAGAAATTGAACTGGGGAGCCTGTTGAGACAAGATTTCCAAG

GATTGCATAATGAATTATTGCTGCGTATTGGAGAACACTATCAACAGGTTTTTAATGGTTTGTCAATACT

TGCCTCATTTGCATCCAGTGATGATCCATATCAGGGCCCGAGAGATATCATATCACCTGAACTGATGGCT

GATTATTTACAACCCAAATTGTTGGGCATTTTGGCTTTTTTTAACATGCAGTTACTGAGCTCTAGTGTTG

GCATTGAAGATAAGAAAATGGCCTTGAACAGTTTGATGTCTTTGATGAAGTTAATGGGACCCAAACATGT

CAGTTCTGTGAGGGTGAAGATGATGACCACACTGAGAACTGGCCTTCGATTCAAGGATGATTTTCCTGAA

TTGTGTTGCAGAGCTTGGGACTGCTTTGTTCGCTGCCTGGATCATGCTTGTCTGGGCTCCCTTCTCAGTC

ATGTAATAGTAGCTTTGTTACCTCTTATACACATCCAGCCTAAAGAAACTGCAGCTATCTTCCACTACCT

CATAATTGAAAACAGGGATGCTGTGCAAGATTTTCTTCATGAAATATATTTTTTACCTGATCATCCAGAA

TTAAAAAAGATAAAAGCCGTTCTCCAGGAATACAGAAAGGAGACCTCTGAGAGCACTGATCTTCAGACAA

CTCTTCAGCTCTCTATGAAGGCCATTCAACATGAAAATGTCGATGTTCGTATTCATGCTCTTACAAGCTT

GAAGGAAACCTTGTATAAAAATCAGGAAAAACTGATAAAGTATGCAACAGACAGTGAAACAGTAGAACCT

ATTATCTCACAGTTGGTGACAGTGCTTTTGAAAGGTTGCCAAGATGCAAACTCTCAAGCTCGGTTGCTCT

GTGGGGAATGTTTAGGGGAATTGGGGGCGATAGATCCAGGTCGATTAGATTTCTCAACAACTGAAACTCA

AGGAAAAGATTTTACATTTGTGACTGGAGTAGAAGATTCAAGCTTTGCCTATGGATTATTGATGGAGCTA

ACAAGAGCTTACCTTGCGTATGCTGATAATAGCCGAGCTCAAGATTCAGCTGCCTATGCCATTCAGGAGT

TGCTTTCTATTTATGACTGTAGAGAGATGGAGACCAACGGCCCAGGTCACCAATTGTGGAGGAGATTTCC

TGAGCATGTTCGGGAAATACTAGAACCTCATCTAAATACCAGATACAAGAGTTCTCAGAAGTCAACCGAT

TGGTCTGGAGTAAAGAAGCCAATTTACTTAAGTAAATTGGGTAGTAACTTTGCAGAATGGTCAGCATCTT

GGGCAGGTTATCTTATTACAAAGGTTCGACATGATCTTGCCAGTAAAATTTTCACCTGCTGTAGCATTAT

GATGAAGCATGATTTCAAAGTGACCATCTATCTTCTTCCACATATTCTGGTGTATGTCTTACTGGGTTGT

AATCAAGAAGATCAGCAGGAGGTTTATGCAGAAATTATGGCAGTTCTAAAGCATGACGATCAGCATACCA

TAAATACCCAAGACATTGCATCTGATCTGTGTCAACTCAGTACACAGACTGTGTTCTCCATGCTTGACCA

TCTCACACAGTGGGCAAGGCACAAATTTCAGGCACTGAAAGCTGAGAAATGTCCACACAGCAAATCAAAC

AGAAATAAGGTAGACTCAATGGTATCTACTGTGGATTATGAAGACTATCAGAGTGTAACCCGTTTTCTAG

ACCTCATACCCCAGGATACTCTGGCAGTAGCTTCCTTTCGCTCCAAAGCATACACACGAGCTGTAATGCA

CTTTGAATCATTTATTACAGAAAAGAAGCAAAATATTCAGGAACATCTTGGATTTTTACAGAAATTGTAT

GCTGCTATGCATGAACCTGATGGAGTGGCCGGAGTCAGTGCAATTAGAAAGGCAGAACCATCTCTAAAAG

AACAGATCCTTGAACATGAAAGCCTTGGCTTGCTGAGGGATGCCACTGCTTGTTATGACAGGGCTATTCA

GCTAGAACCAGACCAGATCATTCATTATCATGGTGTAGTAAAGTCCATGTTAGGTCTTGGTCAGCTGTCT

ACTGTTATCACTCAGGTGAATGGAGTGCATGCTAACAGGTCCGAGTGGACAGATGAATTAAACACGTACA

GAGTGGAAGCAGCTTGGAAATTGTCACAGTGGGATTTGGTGGAAAACTATTTGGCAGCAGATGGAAAATC

TACAACATGGAGTGTCAGACTGGGACAGCTATTATTATCAGCCAAAAAAGAGATATCACAGCTTTTTAT

GACTCACTGAAACTAGTGAGAGCAGAACAAATTGTACCTCTTTCAGCTGCAAGCTTTGAAAGAGGCTCCT

ACCAACGAGGATATGAATATATTGTGAGATTGCACATGTTATGTGAGTTGGAGCATAGCATCAAACCACT

TTTCCAGCATTCTCCAGGTGACAGTTCTCAAGAAGATTCTCTAAACTGGGTAGCTCGACTAGAAATGACC

CAGAATTCCTACAGAGCCAAGGAGCCTATCCTGGCTCTCCGGAGGGCTTTACTAAGCCTCAACAAAAGAC

CAGATTACAATGAAATGGTTGGAGAATGCTGGCTGCAGAGTGCCAGGGTAGCTAGAAAGGCTGGTCACCA

CCAGACAGCCTACAATGCTCTCCTTAATGCAGGGGAATCACGACTCGCTGAACTGTACGTGGAAAGGGCA
```

```
                             -continued
AAGTGGCTCTGGTCCAAGGGTGATGTTCACCAGGCACTAATTGTTCTTCAAAAAGGTGTTGAATTATGTT

TTCCTGAAAATGAAACCCCACCTGAGGGTAAGAACATGTTAATCCATGGTCGAGCTATGCTACTAGTGGG

CCGATTTATGGAAGAAACAGCTAACTTTGAAAGCAATGCAATTATGAAAAAATATAAGGATGTGACCGCG

TGCCTGCCAGAATGGGAGGATGGGCATTTTTACCTTGCCAAGTACTATGACAAATTGATGCCCATGGTCA

CAGACAACAAAATGGAAAAGCAAGGTGATCTCATCCGGTATATAGTTCTTCATTTTGGCAGATCTCTACA

ATATGGAAATCAGTTCATATATCAGTCAATGCCACGAATGTTAACTCTATGGCTTGATTATGGTACAAAG

GCATATGAATGGGAAAAAGCTGGCCGCTCCGATCGTGTACAAATGAGGAATGATTGGGTAAAATAAACA

AGGTTATCACAGAGCATACAAACTATTTAGCTCCATATCAATTTTTGACTGCTTTTTCACAATTGATCTC

TCGAATTTGTCATTCTCACGATGAAGTTTTTGTTGTCTTGATGGAAATAATAGCCAAAGTATTTCTAGCC

TATCCTCAACAAGCAATGTGGATGATGACAGCTGTGTCAAAGTCATCTTATCCCATGCGTGTGAACAGAT

GCAAGGAAATCCTCAATAAAGCTATTCATATGAAAAAATCCTTAGAGAAGTTTGTTGGAGATGCAACTCG

CCTAACAGATAAGCTTCTAGAATTGTGCAATAAACCGGTTGATGGAAGTAGTTCCACATTAAGCATGAGC

ACTCATTTTAAAATGCTTAAAAAGCTGGTAGAAGAAGCAACATTTAGTGAAATCCTCATTCCTCTACAAT

CAGTCATGATACCTACACTTCCATCAATTCTGGGTACCCATGCTAACCATGCTAGCCATGAACCATTTCC

TGGACATTGGGCCTATATTGCAGGGTTTGATGATATGGTGGAAATTCTTGCTTCTCTTCAGAAACCAAAG

AAGATTTCTTTAAAAGGCTCAGATGGAAAGTTCTACATCATGATGTGTAAGCCAAAAGATGACCTGAGAA

AGGATTGTAGACTAATGGAATTCAATTCCTTGATTAATAAGTGCTTAAGAAAAGATGCAGAGTCTCGTAG

AAGAGAACTTCATATTCGAACATATGCAGTTATTCCACTAAATGATGAATGTGGGATTATTGAATGGGTG

AACAACACTGCTGGTTTGAGACCTATTCTGACCAAACTATATAAAGAAAAGGGAGTGTATATGACAGGAA

AAGAACTTCGCCAGTGTATGCTACCAAAGTCAGCAGCTTTATCTGAAAAACTCAAAGTATTCCGAGAATT

TCTCCTGCCCAGGCATCCTCCTATTTTTCATGAGTGGTTTCTGAGAACATTCCCTGATCCTACATCATGG

TACAGTAGTAGATCAGCTTACTGCCGTTCCACTGCAGTAATGTCAATGGTTGGTTATATTCTGGGCTTG

GAGACCGTCATGGTGAAAATATTCTCTTTGATTCTTTGACTGGTGAATGCGTACATGTAGATTTCAATTG

TCTTTTCAATAAGGGAGAAACCTTTGAAGTTCCAGAAATTGTGCCATTTCGCCTGACTCATAATATGGTT

AATGGAATGGGTCCTATGGGAACAGAGGGTCTTTTTCGAAGAGCATGTGAAGTTACAATGAGGCTGATGC

GTGATCAGCGAGAGCCTTTAATGAGTGTCTTAAAGACTTTTCTACATGATCCTCTTGTGGAATGGAGTAA

ACCAGTGAAAGGGCATTCCAAAGCGCCACTGAATGAAACTGGAGAAGTTGTCAATGAAAAGGCCAAGACC

CATGTTCTTGACATTGAGCAGCGACTACAAGGTGTAATCAAGACTCGAAATAGAGTGACAGGACTGCCGT

TATCTATTGAAGGACATGTGCATTACCTTATACAGGAAGCTACTGATGAAAACTTACTATGCCAGATGTA

TCTTGGTTGGACTCCATATATGTGA
(SEQ ID NO: 5; NCBI Accession No. NM_001184.3)
```

Kinase Inhibitors

In one aspect the invention provides an ataxia telangiectasia mutated (ATM) kinase inhibitor or an ataxia telangiectasia and Rad3-related protein (ATR) inhibitor for use in haematopoietic stem and/or progenitor cell gene therapy.

The invention also provides methods for identifying agents that are capable of acting as ATM kinase or ATR inhibitors and agents that are identified by such methods.

The activity of ATM kinase and ATR may be analysed directly, for example by analysing the enzymatic activity of the ATM kinase or ATR in vitro.

The ability of a candidate agent to inhibit (e.g. reduce the activity) ATM kinase or ATR may be expressed in terms of an IC50 value, which is the concentration of an agent that is required to give rise to a 50% reduction in the activity of the kinase. Preferably, the inhibitors of the invention have an IC50 value for inhibition (e.g. of ATM kinase or ATR) of less than 100 µM, more preferably less than 10 µM, for example less than 1 µM, less than 100 nM or less than 10 nM (e.g. KU-55933 has an IC50 value of about 13 nM for ATM kinase).

A number of techniques are known in the art for measuring kinase activity. Preferably, the kinase activity assays are carried out on a kinase (e.g. ATM kinase or ATR) that has been isolated from a cell. The kinase may have been expressed using recombinant techniques, and preferably has been purified. For example, kinase activity may be determined by monitoring the incorporation of radiolabelled phosphate from [γ-$^{32}$P]-labelled ATP into a substrate. Such assay techniques are described in, for example, Hastie et al. (Hastie, C. J. et al. (2006) Nat. Protocols 1: 968-971).

Preferably, the inhibitors are of low toxicity for mammals, such as humans, and in particular are of low toxicity for haematopoietic stem and/or progenitor cells.

A candidate inhibitor may be further analysed for its ability to increase cell survival and/or engraftment using a method as disclosed herein.

Preferably, the inhibitor is a transient inhibitor (e.g. has an inhibitory action lasting less than about 1, 2, 3, 4, 5, 6, 7 or 14 days).

Preferably, the inhibitor is a pharmacological inhibitor.

KU-55933

In a preferred embodiment, the inhibitor is KU-55933 or a derivative thereof.

KU-55933 (CAS No. 587871-26-9) is a selective, competitive ATM kinase inhibitor having the following structure:

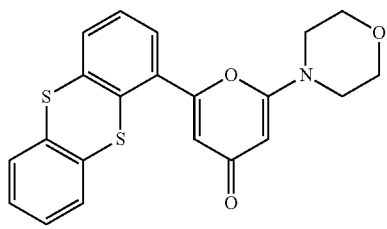 [SMILES: O=c1cc(-c2cccc3c2Sc2ccccc2S3)oc(N2CCOCC2)c1]

Solutions of KU-55933 for use in the invention may be prepared using routine methods known in the art, for example KU-55933 is known to be soluble in DMSO and ethanol.

The concentration at which KU-55933 or a derivative thereof is applied to a population of haematopoietic stem and/or progenitor cells may be adjusted for different vector systems to optimise cell survival (e.g. during in vitro or ex vivo culture) and/or engraftment.

The invention encompasses the use of KU-55933 and derivatives of KU-55933. The KU-55933 derivatives of the invention are those which increase the survival (e.g. during in vitro or ex vivo culture) and/or engraftment of haematopoietic stem and/or progenitor cells, in particular cells transduced by a viral vector.

KU-55933 derivatives of the invention may have been developed, for example, for increased solubility, increased stability and/or reduced toxicity.

KU-55933 derivatives of the invention are preferably of low toxicity for mammals, in particular humans. Preferably, KU-55933 derivatives of the invention are of low toxicity for haematopoietic stem and/or progenitor cells.

Suitable KU-55933 derivatives may be identified using methods known in the art for determining cell survival in culture and/or engraftment. Examples of such methods have been described above. The method employed is preferably one which is amenable to automation and/or high throughput screening of candidate KU-55933 derivatives. The candidate KU-55933 derivatives may form part of a library of KU-55933 derivatives.

Additional Inhibitors

Further kinase inhibitors that may be used in the invention include:

KU-60019, which is an improved analogue of KU-55933 and has an IC50 of 6.3 nM for ATM kinase in cell-free assays. KU-60019 has the structure:

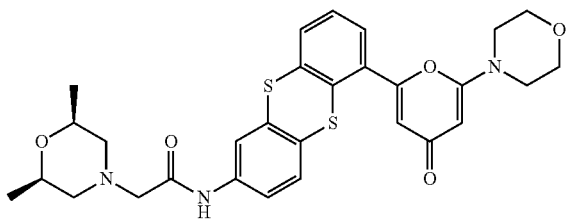 [SMILES: C[C@@H]1CN(CC(=O)Nc2ccc3c(c2)Sc2cccc(-c4cc(=O)cc(N5CCOCC5)o4)c2S3)C[C@H](C)O1]

BEZ235 (NVP-BEZ235, Dactolisib), which is a dual ATP-competitive PI3K and mTOR inhibitor for p110α/γ/δ/β and mTOR(p70S6K), and inhibits ATR with an IC50 of about 21 nM in 3T3TopBP1-ER cells. BEZ235 has the structure:

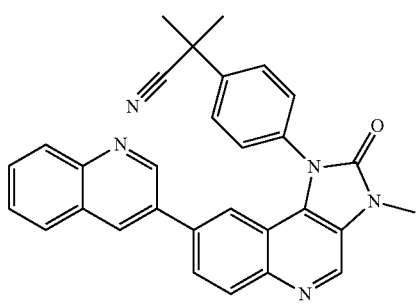 [SMILES: Cn1c(=O)n(-c2ccc(C(C)(C)C#N)cc2)c2c3cc(-c4cnc5ccccc5c4)ccc3ncc21]

Wortmannin, which has the structure:

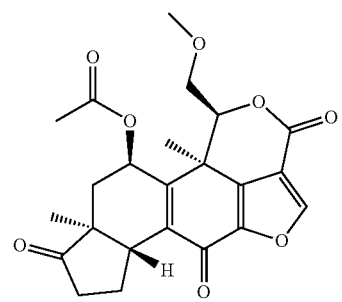 [SMILES: COC[C@H]1OC(=O)c2coc3c2[C@@]1(C)C1=C(C3=O)[C@@H]2CCC(=O)[C@@]2(C)C[C@H]1OC(C)=O]

CP-466722, which is a potent and reversible ATM kinase inhibitor, but does not affect ATR. CP-466722 has the structure:

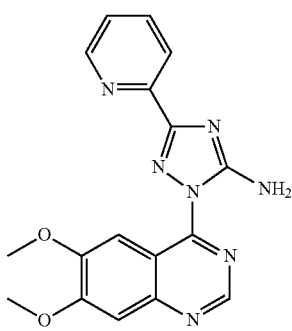 [SMILES: COc1cc2ncnc(-n3nc(-c4ccccn4)nc3N)c2cc1OC]

Torin 2, which ATM kinase and ATR with EC50 values of 28 nM and 35 nM, respectively. Torin 2 has the structure:

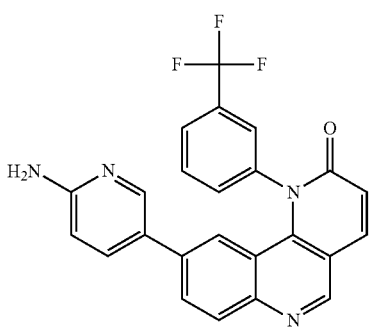 [SMILES: Nc1ccc(-c2ccc3ncc4ccc(=O)n(-c5cccc(C(F)(F)F)c5)c4c3c2)cn1]

CGK 733 (CAS No. 905973-89-9), which is a potent and selective inhibitor of ATM kinase and ATR with IC50 values of about 200 nM. CGK 733 has the structure:

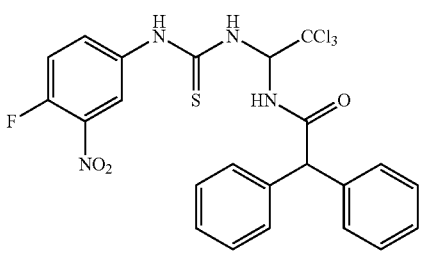

KU-559403 (Weber et al. (2015) Pharmacology & Therapeutics 149: 124-138). KU-559403 has the structure:

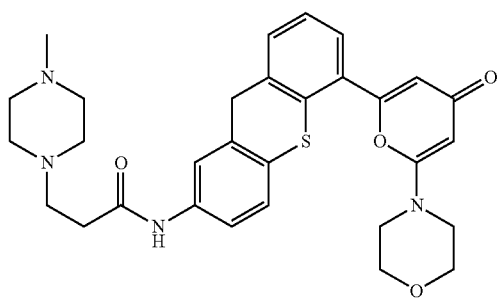 [SMILES: CN1CCN(CCC(=O)Nc2ccc3c(c2)Cc2cccc(-c4cc(=O)cc(N5CCOCC5)o4)c2S3)CC1]

AZD6738, which has the structure:

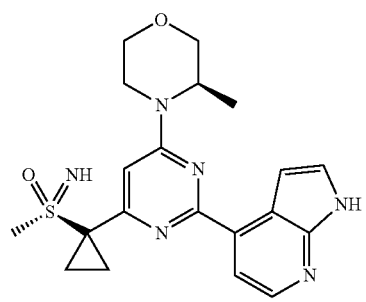 [SMILES: C[C@@H]1COCCN1c1cc(C2([S@](C)(=N)=O)CC2)nc(-c2ccnc3[nH]ccc23)n1]

Derivatives of these inhibitors, possessing characteristics as described for the KU-55933 derivatives, may also be used in the invention, and may be identified using analogous methods to those described for the KU-55933 derivatives.

siRNAs, shRNAs, miRNAs and Antisense DNAs/RNAs

Inhibition (e.g. of the kinase) may be achieved using post-transcriptional gene silencing (PTGS). Post-transcriptional gene silencing mediated by double-stranded RNA (dsRNA) is a conserved cellular defence mechanism for controlling the expression of foreign genes. It is thought that the random integration of elements such as transposons or viruses causes the expression of dsRNA which activates sequence-specific degradation of homologous single-stranded mRNA or viral genomic RNA. The silencing effect is known as RNA interference (RNAi) (Ralph et al. (2005) Nat. Medicine 11: 429-433). The mechanism of RNAi involves the processing of long dsRNAs into duplexes of about 21-25 nucleotide (nt) RNAs. These products are called small interfering or silencing RNAs (siRNAs) which are the sequence-specific mediators of mRNA degradation. In differentiated mammalian cells, dsRNA >30 bp has been found to activate the interferon response leading to shut-down of protein synthesis and non-specific mRNA degradation (Stark et al. (1998) Ann. Rev. Biochem. 67: 227-64). However, this response can be bypassed by using 21 nt siRNA duplexes (Elbashir et al. (2001) EMBO J. 20: 6877-88; Hutvagner et al. (2001) Science 293: 834-8) allowing gene function to be analysed in cultured mammalian cells.

shRNAs consist of short inverted RNA repeats separated by a small loop sequence. These are rapidly processed by the cellular machinery into 19-22 nt siRNAs, thereby suppressing the target gene expression.

Micro-RNAs (miRNAs) are small (22-25 nucleotides in length) noncoding RNAs that can effectively reduce the translation of target mRNAs by binding to their 3' untranslated region (UTR). Micro-RNAs are a very large group of small RNAs produced naturally in organisms, at least some of which regulate the expression of target genes. Founding members of the micro-RNA family are let-7 and lin-4. The let-7 gene encodes a small, highly conserved RNA species that regulates the expression of endogenous protein-coding genes during worm development. The active RNA species is transcribed initially as an ~70 nt precursor, which is post-transcriptionally processed into a mature ~21 nt form. Both let-7 and lin-4 are transcribed as hairpin RNA precursors which are processed to their mature forms by Dicer enzyme.

The antisense concept is to selectively bind short, possibly modified, DNA or RNA molecules to messenger RNA in cells and prevent the synthesis of the encoded protein.

Methods for the design of siRNAs, shRNAs, miRNAs and antisense DNAs/RNAs to modulate the expression of a target protein, and methods for the delivery of these agents to a cell of interest are well known in the art.

p53 Dominant Negative Peptide

The term "p53 dominant negative peptide", as used herein, may refer to a peptide which inhibits the function of wild-type p53 when present in the same cell, for example a p53 dominant negative peptide may reduce or prevent p53 signalling.

In one embodiment, the p53 dominant negative peptide comprises or consists of GSE56 (Ossovskaya V. S. et al. (1996) Proc Natl Acad Sci USA 93: 10309-10314).

GSE56 may have the amino acid sequence:

```
                                              (SEQ ID NO: 6)
CPGRDRRTEEENFRKKEEHCPELPPGSAKRALPTSTSSSPQQKKKPLDGE

YFTLKIRGRERFEMFRELNEALELKDARAAEESGDSRAHSSYPK
```

In one embodiment, the p53 dominant negative peptide is a variant of GSE56 comprising 1, 2, 3, 4, 5, 6, 7, 8, 9 or 10 amino acid substitutions, additions or deletions, while retaining the activity of GSE56, for example in reducing or preventing p53 signalling.

In one embodiment, the p53 dominant negative peptide comprises an amino acid sequence having at least 70%, 75%, 80%, 85%, 90%, 95%, 96%, 97%, 98% or 99% identity to SEQ ID NO: 6. Preferably, reference to a sequence which has a percent identity to any one of the SEQ ID NOs detailed herein refers to a sequence which has the stated percent identity over the entire length of the SEQ ID NO referred to.

The p53 dominant negative peptide, for example GSE56, may be expressed in a cell using a viral vector (e.g. a retroviral, lentiviral or AAV vector) comprising a nucleotide sequence encoding the peptide.

Haematopoietic Stem and Progenitor Cells

A stem cell is able to differentiate into many cell types. A cell that is able to differentiate into all cell types is known as totipotent. In mammals, only the zygote and early embryonic cells are totipotent. Stem cells are found in most, if not all, multicellular organisms. They are characterised by the ability to renew themselves through mitotic cell division and differentiate into a diverse range of specialised cell types. The two broad types of mammalian stem cells are embryonic stem cells that are isolated from the inner cell mass of blastocysts, and adult stem cells that are found in adult tissues. In a developing embryo, stem cells can differentiate into all of the specialised embryonic tissues. In adult organisms, stem cells and progenitor cells act as a repair system for the body, replenishing specialised cells, but also maintaining the normal turnover of regenerative organs, such as blood, skin or intestinal tissues.

Haematopoietic stem cells (HSCs) are multipotent stem cells that may be found, for example, in peripheral blood, bone marrow and umbilical cord blood. HSCs are capable of self-renewal and differentiation into any blood cell lineage. They are capable of recolonising the entire immune system, and the erythroid and myeloid lineages in all the haematopoietic tissues (such as bone marrow, spleen and thymus). They provide for life-long production of all lineages of haematopoietic cells.

Haematopoietic progenitor cells have the capacity to differentiate into a specific type of cell. In contrast to stem cells however, they are already far more specific: they are pushed to differentiate into their "target" cell. A difference between stem cells and progenitor cells is that stem cells can replicate indefinitely, whereas progenitor cells can only divide a limited number of times. Haematopoietic progenitor cells can be rigorously distinguished from HSCs only by functional in vivo assay (i.e. transplantation and demonstration of whether they can give rise to all blood lineages over prolonged time periods).

The haematopoietic stem and progenitor cells of the invention comprise the CD34 cell surface marker (denoted as CD34+).

Haematopoietic Stem and/or Progenitor Cell (HSPC) Sources

A population of haematopoietic stem and/or progenitor cells (HSPCs) may be obtained from a tissue sample.

For example, a population of haematopoietic stem and/or progenitor cells may be obtained from peripheral blood (e.g. adult and foetal peripheral blood), umbilical cord blood, bone marrow, liver or spleen. Preferably, these cells are obtained from peripheral blood or bone marrow. They may be obtained after mobilisation of the cells in vivo by means of growth factor treatment.

Mobilisation may be carried out using, for example, G-CSF, plerixaphor or combinations thereof. Other agents, such as NSAIDs and dipeptidyl peptidase inhibitors, may also be useful as mobilising agents.

With the availability of the stem cell growth factors GM-CSF and G-CSF, most haematopoietic stem cell transplantation procedures are now performed using stem cells collected from the peripheral blood, rather than from the bone marrow. Collecting peripheral blood stem cells provides a bigger graft, does not require that the donor be subjected to general anaesthesia to collect the graft, results in a shorter time to engraftment and may provide for a lower long-term relapse rate.

Bone marrow may be collected by standard aspiration methods (either steady-state or after mobilisation), or by using next-generation harvesting tools (e.g. Marrow Miner).

In addition, HSPCs may also be derived from induced pluripotent stem cells.

HSC Characteristics

HSCs are typically of low forward scatter and side scatter profile by flow cytometric procedures. Some are metabolically quiescent, as demonstrated by Rhodamine labelling which allows determination of mitochondrial activity. HSCs may comprise certain cell surface markers such as CD34, CD45, CD133, CD90 and CD49f. They may also be defined as cells lacking the expression of the CD38 and CD45RA cell surface markers. However, expression of some of these markers is dependent upon the developmental stage and tissue-specific context of the HSC. Some HSCs called "side population cells" exclude the Hoechst 33342 dye as detected by flow cytometry. Thus, HSCs have descriptive characteristics that allow for their identification and isolation.

Negative Markers

CD38 is the most established and useful single negative marker for human HSCs.

Human HSCs may also be negative for lineage markers such as CD2, CD3, CD14, CD16, CD19, CD20, CD24, CD36, CD56, CD66b, CD271 and CD45RA. However, these markers may need to be used in combination for HSC enrichment.

By "negative marker" it is to be understood that human HSCs lack the expression of these markers.

Positive Markers

CD34 and CD133 are the most useful positive markers for HSCs.

Some HSCs are also positive for lineage markers such as CD90, CD49f and CD93. However, these markers may need to be used in combination for HSC enrichment.

By "positive marker" it is to be understood that human HSCs express these markers.

Differentiated Cells

A differentiated cell is a cell which has become more specialised in comparison to a stem cell or progenitor cell. Differentiation occurs during the development of a multicellular organism as the organism changes from a single zygote to a complex system of tissues and cell types. Differentiation is also a common process in adults: adult stem cells divide and create fully-differentiated daughter cells during tissue repair and normal cell turnover. Differentiation dramatically changes a cell's size, shape, membrane potential, metabolic activity and responsiveness to signals. These changes are largely due to highly-controlled modifications in gene expression. In other words, a differentiated cell is a cell which has specific structures and performs certain functions due to a developmental process which involves the activation and deactivation of specific genes. Here, a differentiated cell includes differentiated cells of the haematopoietic lineage such as monocytes, macrophages, neutrophils, basophils, eosinophils, erythrocytes, megakaryocytes/platelets, dendritic cells, T-cells, B-cells and NK-cells. For example, differentiated cells of the haematopoietic lineage can be distinguished from stem cells and progenitor cells by detection of cell surface molecules which are not expressed or are expressed to a lesser degree on undifferentiated cells. Examples of suitable human lineage markers include CD33, CD13, CD14, CD15 (myeloid), CD19, CD20, CD22, CD79a (B), CD36, CD71, CD235a (erythroid), CD2, CD3, CD4, CD8 (T) and CD56 (NK).

Isolation and Enrichment of Populations of Cells

By "isolated population" of cells it is to be understood that the population of cells has been previously removed from the body. An isolated population of cells may be cultured and manipulated ex vivo or in vitro using standard techniques known in the art. An isolated population of cells may later be reintroduced into a subject. Said subject may be the same subject from which the cells were originally isolated or a different subject.

A population of cells may be purified selectively for cells that exhibit a specific phenotype or characteristic, and from other cells which do not exhibit that phenotype or characteristic, or exhibit it to a lesser degree. For example, a population of cells that expresses a specific marker (such as CD34) may be purified from a starting population of cells. Alternatively, or in addition, a population of cells that does not express another marker (such as CD38) may be purified.

By "enriching" a population of cells for a certain type of cells it is to be understood that the concentration of that type of cells is increased within the population. The concentration of other types of cells may be concomitantly reduced.

Purification or enrichment may result in the population of cells being substantially pure of other types of cell.

Purifying or enriching for a population of cells expressing a specific marker (e.g. CD34 or CD38) may be achieved by using an agent that binds to that marker, preferably substantially specifically to that marker.

An agent that binds to a cellular marker may be an antibody, for example an anti-CD34 or anti-CD38 antibody.

The term "antibody" refers to complete antibodies or antibody fragments capable of binding to a selected target, and including Fv, ScFv, F(ab') and F(ab')$_2$, monoclonal and polyclonal antibodies, engineered antibodies including chimeric, CDR-grafted and humanised antibodies, and artificially selected antibodies produced using phage display or alternative techniques.

In addition, alternatives to classical antibodies may also be used in the invention, for example "avibodies", "avimers", "anticalins", "nanobodies" and "DARPins".

The agents that bind to specific markers may be labelled so as to be identifiable using any of a number of techniques known in the art. The agent may be inherently labelled, or may be modified by conjugating a label thereto. By "conjugating" it is to be understood that the agent and label are operably linked. This means that the agent and label are linked together in a manner which enables both to carry out their function (e.g. binding to a marker, allowing fluorescent identification, or allowing separation when placed in a magnetic field) substantially unhindered. Suitable methods of conjugation are well known in the art and would be readily identifiable by the skilled person.

A label may allow, for example, the labelled agent and any cell to which it is bound to be purified from its environment (e.g. the agent may be labelled with a magnetic bead or an affinity tag, such as avidin), detected or both. Detectable markers suitable for use as a label include fluorophores (e.g. green, cherry, cyan and orange fluorescent proteins) and peptide tags (e.g. His tags, Myc tags, FLAG tags and HA tags).

A number of techniques for separating a population of cells expressing a specific marker are known in the art. These include magnetic bead-based separation technologies (e.g. closed-circuit magnetic bead-based separation), flow cytometry, fluorescence-activated cell sorting (FACS), affinity tag purification (e.g. using affinity columns or beads, such as biotin columns to separate avidin-labelled agents) and microscopy-based techniques.

It may also be possible to perform the separation using a combination of different techniques, such as a magnetic bead-based separation step followed by sorting of the resulting population of cells for one or more additional (positive or negative) markers by flow cytometry.

Clinical grade separation may be performed, for example, using the CliniMACS® system (Miltenyi). This is an example of a closed-circuit magnetic bead-based separation technology.

It is also envisaged that dye exclusion properties (e.g. side population or rhodamine labelling) or enzymatic activity (e.g. ALDH activity) may be used to enrich for HSCs.

Vectors

A vector is a tool that allows or facilitates the transfer of an entity from one environment to another. The vectors used to transduce haematopoietic stem and/or progenitor cells in the invention are viral vectors.

Preferably, the viral vector is in the form of a viral vector particle.

The viral vector may be, for example, a retroviral, lentiviral, adeno-associated viral (AAV) or adenoviral vector. Preferably, the viral vector is a lentiviral or AAV vector, more preferably a lentiviral vector. Preferably, the retroviral vector is not a γ-retroviral vector.

By "vector derived from" a certain type of virus, it is to be understood that the vector comprises at least one component part derivable from that type of virus.

Retro Viral and Lentiviral Vectors

A retroviral vector may be derived from or may be derivable from any suitable retrovirus. A large number of different retroviruses have been identified. Examples include murine leukaemia virus (MLV), human T-cell leukaemia virus (HTLV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), avian myelocytomatosis virus-29 (MC29) and avian erythroblastosis virus (AEV). A detailed list of retroviruses may be found in Coffin, J. M. et al. (1997) Retroviruses, Cold Spring Harbour Laboratory Press, 758-63.

Retroviruses may be broadly divided into two categories, "simple" and "complex". Retroviruses may be even further divided into seven groups. Five of these groups represent retroviruses with oncogenic potential. The remaining two groups are the lentiviruses and the spumaviruses. A review of these retroviruses is presented in Coffin, J. M. et al. (1997) Retroviruses, Cold Spring Harbour Laboratory Press, 758-63.

The basic structure of retrovirus and lentivirus genomes share many common features such as a 5' LTR and a 3' LTR. Between or within these are located a packaging signal to enable the genome to be packaged, a primer binding site, integration sites to enable integration into a host cell genome, and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration and transcription. LTRs also serve as enhancer-promoter sequences and can control the expression of the viral genes.

The LTRs themselves are identical sequences that can be divided into three elements: U3, R and U5. U3 is derived from the sequence unique to the 3' end of the RNA. R is derived from a sequence repeated at both ends of the RNA. U5 is derived from the sequence unique to the 5' end of the RNA. The sizes of the three elements can vary considerably among different retroviruses.

In a defective retroviral vector genome gag, pol and env may be absent or not functional.

In a typical retroviral vector, at least part of one or more protein coding regions essential for replication may be removed from the virus. This makes the viral vector replication-defective. Portions of the viral genome may also be replaced by a library encoding candidate modulating moieties operably linked to a regulatory control region and a reporter moiety in the vector genome in order to generate a vector comprising candidate modulating moieties which is capable of transducing a target host cell and/or integrating its genome into a host genome.

Lentivirus vectors are part of the larger group of retroviral vectors. A detailed list of lentiviruses may be found in Coffin, J. M. et al. (1997) Retroviruses, Cold Spring Harbour Laboratory Press, 758-63. In brief, lentiviruses can be divided into primate and non-primate groups. Examples of primate lentiviruses include but are not limited to human immunodeficiency virus (HIV), the causative agent of human acquired immunodeficiency syndrome (AIDS); and simian immunodeficiency virus (Sly). Examples of non-primate lentiviruses include the prototype "slow virus" visna/maedi virus (VMV), as well as the related caprine arthritis-encephalitis virus (CAEV), equine infectious anaemia virus (EIAV), and the more recently described feline immunodeficiency virus (FIV) and bovine immunodeficiency virus (BIV).

The lentivirus family differs from retroviruses in that lentiviruses have the capability to infect both dividing and non-dividing cells (Lewis, P et al. (1992) EMBO J. 11: 3053-8; Lewis, P. F. et al. (1994) J. Virol. 68: 510-6). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be a "primate" vector. The lentiviral vector may be a "non-primate" vector (i.e. derived from a virus which does not primarily infect primates, especially humans). Examples of non-primate lentiviruses may be any member of the family of lentiviridae which does not naturally infect a primate.

As examples of lentivirus-based vectors, HIV-1- and HIV-2-based vectors are described below.

The HIV-1 vector contains cis-acting elements that are also found in simple retroviruses. It has been shown that sequences that extend into the gag open reading frame are important for packaging of HIV-1. Therefore, HIV-1 vectors often contain the relevant portion of gag in which the translational initiation codon has been mutated. In addition, most HIV-1 vectors also contain a portion of the env gene that includes the RRE. Rev binds to RRE, which permits the transport of full-length or singly spliced mRNAs from the nucleus to the cytoplasm. In the absence of Rev and/or RRE, full-length HIV-1 RNAs accumulate in the nucleus. Alternatively, a constitutive transport element from certain simple retroviruses such as Mason-Pfizer monkey virus can be used to relieve the requirement for Rev and RRE. Efficient transcription from the HIV-1 LTR promoter requires the viral protein Tat.

Most HIV-2-based vectors are structurally very similar to HIV-1 vectors. Similar to HIV-1-based vectors, HIV-2 vectors also require RRE for efficient transport of the full-length or singly spliced viral RNAs.

In one system, the vector and helper constructs are from two different viruses, and the reduced nucleotide homology may decrease the probability of recombination. In addition to vectors based on the primate lentiviruses, vectors based on FIV have also been developed as an alternative to vectors derived from the pathogenic HIV-1 genome. The structures of these vectors are also similar to the HIV-1 based vectors.

Preferably, the viral vector used in the present invention has a minimal viral genome.

By "minimal viral genome" it is to be understood that the viral vector has been manipulated so as to remove the non-essential elements and to retain the essential elements in order to provide the required functionality to infect, transduce and deliver a nucleotide sequence of interest to a target host cell. Further details of this strategy can be found in WO 1998/017815.

Preferably, the plasmid vector used to produce the viral genome within a host cell/packaging cell will have sufficient lentiviral genetic information to allow packaging of an RNA genome, in the presence of packaging components, into a viral particle which is capable of infecting a target cell, but is incapable of independent replication to produce infectious viral particles within the final target cell. Preferably, the vector lacks a functional gag-pol and/or env gene and/or other genes essential for replication.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed viral sequence (i.e. the 5' U3 region), or they may be a heterologous promoter, such as another viral promoter (e.g. the CMV promoter).

The vectors may be self-inactivating (SIN) vectors in which the viral enhancer and promoter sequences have been deleted. SIN vectors can be generated and transduce non-dividing cells in vivo with an efficacy similar to that of wild-type vectors. The transcriptional inactivation of the long terminal repeat (LTR) in the SIN provirus should prevent mobilisation by replication-competent virus. This should also enable the regulated expression of genes from internal promoters by eliminating any cis-acting effects of the LTR.

The vectors may be integration-defective. Integration defective lentiviral vectors (IDLVs) can be produced, for example, either by packaging the vector with catalytically inactive integrase (such as an HIV integrase bearing the D64V mutation in the catalytic site; Naldini, L. et al. (1996) Science 272: 263-7; Naldini, L. et al. (1996) Proc. Natl.

Acad. Sci. USA 93: 11382-8; Leavitt, A. D. et al. (1996) J. Virol. 70: 721-8) or by modifying or deleting essential at sequences from the vector LTR (Nightingale, S. J. et al. (2006) Mol. Ther. 13: 1121-32), or by a combination of the above.

Adeno-Associated Viral (AAV) Vectors

Adeno-associated virus (AAV) is an attractive vector system for use in the invention as it has a high frequency of integration and it can infect non-dividing cells. This makes it useful for delivery of genes into mammalian cells in tissue culture.

AAV has a broad host range for infectivity. Details concerning the generation and use of AAV vectors are described in U.S. Pat. Nos. 5,139,941 and 4,797,368.

Recombinant AAV vectors have been used successfully for in vitro and in vivo transduction of marker genes and genes involved in human diseases.

Adenoviral Vectors

The adenovirus is a double-stranded, linear DNA virus that does not go through an RNA intermediate. There are over 50 different human serotypes of adenovirus divided into 6 subgroups based on the genetic sequence homology. The natural targets of adenovirus are the respiratory and gastrointestinal epithelia, generally giving rise to only mild symptoms. Serotypes 2 and 5 (with 95% sequence homology) are most commonly used in adenoviral vector systems and are normally associated with upper respiratory tract infections in the young.

Adenoviruses have been used as vectors for gene therapy and for expression of heterologous genes. The large (36 kb) genome can accommodate up to 8 kb of foreign insert DNA and is able to replicate efficiently in complementing cell lines to produce very high titres of up to $10^{12}$. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, they function episomally (independently from the host genome) as a linear genome in the host nucleus. Hence the use of recombinant adenovirus alleviates the problems associated with random integration into the host genome.

Nucleotide of Interest

The vector of the invention preferably comprises a nucleotide of interest (NOI).

Preferably the nucleotide of interest gives rise to a therapeutic effect.

Suitable NOIs include, but are not limited to, sequences encoding enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, anti-sense RNA, microRNA, shRNA, siRNA, ribozymes, miRNA target sequences, a transdomain negative mutant of a target protein, toxins, conditional toxins, antigens, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group). The NOIs may also encode pro-drug activating enzymes.

An example of a NOI is the beta-globin chain which may be used for gene therapy of thalassemia/sickle cell disease.

NOIs also include those useful for the treatment of other diseases requiring non-urgent/elective gene correction in the myeloid lineage such as: chronic granulomatous disease (CGD, e.g. the gp91phox transgene), leukocyte adhesion defects, other phagocyte disorders in patients without ongoing severe infections and inherited bone marrow failure syndromes (e.g. Fanconi anaemia), as well as primary immunodeficiencies (SCIDs).

NOIs also include those useful in the treatment of lysosomal storage disorders and immunodeficiencies.

Pharmaceutical Composition

The cells of the invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of cell therapy products is preferably performed in compliance with FACT-JACIE International Standards for cellular therapy.

Haematopoietic Stem and/or Progenitor Cell Transplantation

The invention provides a population of haematopoietic stem and/or progenitor cells prepared according to a method of the invention for use in therapy, for example for use in gene therapy.

The use may be as part of a haematopoietic stem and/or progenitor cell transplantation procedure.

Haematopoietic stem cell transplantation (HSCT) is the transplantation of blood stem cells derived from the bone marrow (in this case known as bone marrow transplantation) or blood. Stem cell transplantation is a medical procedure in the fields of haematology and oncology, most often performed for people with diseases of the blood or bone marrow, or certain types of cancer.

Many recipients of HSCTs are multiple myeloma or leukaemia patients who would not benefit from prolonged treatment with, or are already resistant to, chemotherapy. Candidates for HSCTs include paediatric cases where the patient has an inborn defect such as severe combined immunodeficiency or congenital neutropenia with defective stem cells, and also children or adults with aplastic anaemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumour and Hodgkin's disease. More recently non-myeloablative, or so-called "mini transplant", procedures have been developed that require smaller doses of preparative chemotherapy and radiation. This has allowed HSCT to be conducted in the elderly and other patients who would otherwise be considered too weak to withstand a conventional treatment regimen.

In one embodiment, a population of haematopoietic stem and/or progenitor cells prepared according to a method of the invention is administered as part of an autologous stem cell transplant procedure.

In another embodiment, a population of haematopoietic stem and/or progenitor cells prepared according to a method of the invention is administered as part of an allogeneic stem cell transplant procedure.

By "autologous stem cell transplant procedure" it is to be understood that the starting population of cells (which are then transduced according to a method of the invention) is obtained from the same subject as that to which the transduced cell population is administered. Autologous transplant procedures are advantageous as they avoid problems associated with immunological incompatibility and are available to subjects irrespective of the availability of a genetically matched donor.

By "allogeneic stem cell transplant procedure" it is to be understood that the starting population of cells (which are then transduced according to a method of the invention) is obtained from a different subject as that to which the transduced cell population is administered. Preferably, the donor will be genetically matched to the subject to which the cells are administered to minimise the risk of immunological incompatibility.

Suitable doses of transduced cell populations are such as to be therapeutically and/or prophylactically effective. The dose to be administered may depend on the subject and condition to be treated, and may be readily determined by a skilled person.

Haematopoietic progenitor cells provide short term engraftment. Accordingly, gene therapy by administering transduced haematopoietic progenitor cells would provide a non-permanent effect in the subject. For example, the effect may be limited to 1-6 months following administration of the transduced haematopoietic progenitor cells. An advantage of this approach would be better safety and tolerability, due to the self-limited nature of the therapeutic intervention.

Such haematopoietic progenitor cell gene therapy may be suited to treatment of acquired disorders, for example cancer, where time-limited expression of a (potentially toxic) anti-cancer nucleotide of interest may be sufficient to eradicate the disease.

The invention (e.g. the haematopoietic stem and/or progenitor cell gene therapy) may be, for example, useful in the treatment of a disease selected from the group consisting of mucopolysaccharidosis type I (MPS-1), chronic granulomatous disorder (CGD), Fanconi anaemia (FA), sickle cell disease, Pyruvate kinase deficiency (PKD), Leukocyte adhesion deficiency (LAD), metachromatic leukodystrophy (MLD), globoid cell leukodystrophy (GLD), $GM_2$ gangliosidosis, thalassemia and cancer.

The invention may also be, for example, useful in the treatment of mucopolysaccharidoses disorders and other lysosomal storage disorders.

In addition, or in the alternative, the invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Kit

In another aspect, the invention provides a kit comprising an inhibitor and/or cell populations of the invention.

The inhibitor and/or cell populations may be provided in suitable containers.

The kit may also include instructions for use.

Method of Treatment

It is to be appreciated that all references herein to treatment include curative, palliative and prophylactic treatment. The treatment of mammals, particularly humans, is preferred. Both human and veterinary treatments are within the scope of the invention.

Administration

Although the agents for use in the invention (in particular, the populations of cells produced by a method of the invention) can be administered alone, they will generally be administered in admixture with a pharmaceutical carrier, excipient or diluent, particularly for human therapy.

Dosage

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

Subject

A "subject" refers to either a human or non-human animal.

Examples of non-human animals include vertebrates, for example mammals, such as non-human primates (particularly higher primates), dogs, rodents (e.g. mice, rats or guinea pigs), pigs and cats. The non-human animal may be a companion animal.

Preferably, the subject is a human.

EXAMPLES

Example 1

Materials and Methods

Viral Vectors

Third generation self-inactivating lentiviral vectors (LVs) and integrase-defective LV (IDLV) expressing GFP under the control of an internal PGK promoter (SINLV-GFP) stocks were prepared, concentrated and titered as described in Follenzi et al. and Lombardo et al. (Follenzi, A. et al. (2000) Nature Genetics 25: 217-222; Lombardo, A. et al. (2007) Nature Biotechnology 25: 1298-1306). Purified LV was obtained as described in Biffi et al. (Biffi, A. et al. (2013) Science 341: 1233158). Retroviral Vectors were prepared and used as described in Montini et al. (Montini, E. et al. (2006) Nature Biotechnology 24: 687-696). Bald vector, an entry-incompetent LV was produced omitting the Env-encoding plasmid during vector production. Empty LV, a genome-less lentiviral vector was produced omitting the SINLV PGK-GFP transfer vector during vector production. To produce the p21 overexpressing LV we replaced the Thymidine Kinase cDNA of a previously described bidirectional LV expression cassette (Amendola, M. et al. (2005) Nature Biotechnology 23: 108-116), with the cDNA of the human p21 gene which is expressed under the control of the human PGK promoter. The GFP is expressed from the minimal CMV promoter in the opposite orientation. Inactivated purified LV were obtaining by heating (1 h at 56° C.) purified LV. AAV6-IL2RG-eGFP was as described in Wang et al. (Wang, J. et al. (2015) Nature Biotechnology 33: 1256-1263) except that instead of the homology arms for CCR5 or AAVS1 locus, it contains the homology arms for the IL2RG locus, as described in Genovese et al. (Genovese et al. (2014) Nature 510: 235-40).

Cell Culture and Transduction

Human CD34+ hematopoietic stem and progenitor cells (HSPC) and CD4+ T cells were isolated through magnetic bead selection according to the manufacturer's instructions (Milteny) from umbilical cord blood (CB) collected upon informed consent from healthy volunteers according to the Institutional Ethical Committee approved protocol (TIGET01). Otherwise, CB and bone marrow (BM)-derived CD34+ were directly purchased from Lonza. Cells were purified and cultured as described in Petrillo et al. (Petrillo, C. et al. (2015) Molecular Therapy 23: 352-362). K562 and Hela cell lines were plated in complete Iscove's modified Dulbecco's medium (Euroclone). HL-60 cells were grown and transduced in complete RPMI. HCT-116 cells were grown and transduced in complete Dulbecco's Modified Eagle Medium (DMEM). Murine Lin– cells were isolated through magnetic bead selection according to the manufacturer's instructions (Miltenyi) from bone marrow of euthanised C57/BL6 mice. For the clinical standard double-hit transduction protocol, cells were washed 16 h after the first vector exposure, left to recover in cytokine-supplemented medium for 10 h and re-exposed to the second hit of vector for another 16 h before transplantation. All animal procedures were performed according to protocols approved by the Animal Care and Use Committee of the Ospedale San Raffaele (IACUC 611) and according to Italian law. All cells were transduced at the indicated multiplicity of infection (MOI) as calculated by titration of vector stocks on 293T cells for Lentiviral and Retroviral vectors. Transductions with the AAV6 vectors were performed at an MOI of 10000 as calculated by titration of the vector preparation expressed in vector genome per mL (vg/mL). All the transductions were performed at $1\times10^6$ cells/mL concentration. In the experiment with anti-retroviral inhibitors, the drugs were added together with the vector. Raltegravir and 3TC were used at 10 µM, and AZT at 25 µM. In the ATM inhibition experiment, single hit of the ATM inhibitor KU55933 (Selleck Chemicals) was added to the cells 2 hours before the transduction at 10 µM concentration. All cells were maintained in a 5% $CO_2$ humidified atmosphere at 37° C.

Colony-Forming Cell (CFC) Assay and Transplantation of Human HSPC in NSG Mice

CFC assay cells were performed as described in Petrillo et al and Gentner et al. (Petrillo, C. et al. (2015) Molecular Therapy 23: 352-362; Gentner, B. et al. (2010) Science Translational Medicine 2: 58ra84). After ten days, colonies were identified as erythroid or myeloid by morphological criteria, counted, plucked and pooled into sets of three to obtain DNA for quantification of vector content. (NSG) mice were purchased from Jackson laboratory. Human CB-derived CD34+ cells were pre-stimulated and transduced as indicated. Eight to ten week old NSG mice were sub-lethally irradiated (radiation dose: 200 cGy for mice weighing 18-25 g and of 220 cGy for mice above 25 g in weight) 24 hours prior to xenotransplantation. $8\times10^4$ human CB-derived CD34+ cells were injected into the tail vein of primary NSG mice 24 hours after transduction. Peripheral blood was sampled at indicated times post-transplant and analysed as described in Petrillo et al. (Petrillo, C. et al. (2015) Molecular Therapy 23: 352-362). At sacrifice, the cells from the spleen and BM isolated from the primary recipients were analysed by flow cytometry and the CD34+ cells were purified from the BM through positive magnetic bead selection on LD and MS columns (Miltenyi) according to the manufacturer's instructions. Purity was verified by FACS prior to pooling by condition and injection into secondary recipients. Between $9\times10^5$ and $1\times10^6$ CD34+ cells isolated from the primary hosts were injected into the tail vein of sub-lethally irradiated secondary NSG mice (8-10 weeks old). Peripheral blood was sampled at indicated times post-transplant and analysed as described above. At 14 weeks of age, all mice were sacrificed by $CO_2$ to analyse the BM and the spleen of the secondary mice as described above.

Limiting Dilution Assay

Limiting dilution assays were performed as previously described (Lechman, E. R. et al. (2012) Cell Stem Cell 11: 799-811; Petrillo, C. et al. (2015) Mol Ther 23: 352-362) by transplanting into irradiated 8-week old NSG mice 4 different doses of CB-CD34+ cells counted prior to transduction (3000, 10000, 30000 or 90000) either for Bald and LV groups. Cells were injected 24 hours after transduction. A mouse was scored as positively engrafted if it had >0.1% engraftment in multiple lineages in the BM at the time of sacrifice (16 weeks). HSC frequency was estimated by linear regression analysis and Poisson statistics using publicly available ELDA (Extreme Limiting Dilution Analysis, http COLON SLASH SLASH bioinf.wehi.edu.au/software/elda/) software (Hu et al. (2009) J Immunol Methods 347: 70-78).

Homing Assay

For homing assays, $5\times10^5$ CB-derived CD34+ cells (pre-treatment dose) were transplanted 24 h after transduction into irradiated 8-week old NSG mice that were sacrificed 16 h post-transplantation for analysis. The whole bone marrow was harvested from the lower leg of the mice. During the FACS analysis cell counts beads (Flow-Count Fluorospheres) by BECKMAN CULTER were added in each sample to estimate the absolute number of human CD34+ cells per sample. Cell counts for all in vivo experiments before and after treatment, prior to transplantation are provided in Table 9.

RNA-Seq Data Generation and Analysis

Total RNA was extracted with the RNeasy Plus Micro kit (Qiagen) according to the manufacturer's instructions. RNA integrity was analysed with the Agilent 2100 Bioanalyzer (Agilent Technologies, Santa Clara, CA). Libraries, prepared from 100 ng of total RNA/sample with the Illumina TruSeq RNA Sample Prep kit v2 procedure, were quantified by the Qubit BR assay (Life Technologies, Illkirch, France) and the Agilent 2100 Bioanalyzer. Sequencing was performed on the Illumina HiSeq 2000 platform using SBS 2×100PE protocol. On average for each sample we obtained 30M reads. Each gene was then characterised by the total number of reads overlapping it. Normalisation and differential gene expression was performed with the Bioconductor of the limma package (Smyth, G. K. (2004) Statistical Applications in Genetics and Molecular Biology 3: Article 3). Pathway analysis was initially performed using EnrichrR platform (Chen, E. Y. et al. (2013) BMC Bioinformatics 14: 128), most of the advanced network modelling was performed using Cytoscape.

FACS and Flow Cytometry

Human HSPC fluorescence associated cell sorting was performed as described in Petrillo et al. (Petrillo, C. et al. (2015) Molecular Therapy 23: 352-362). All cytometric analyses were performed using the FACS Canto III instrument and LSRFortessa instruments (BD Biosciences, San Jose, CA) and analysed with the FACS Express software (De Novo Software, Glendale, CA). GFP expression in transduced cells was measured 5-7 days post-transduction. To exclude dead cells from the analysis, cells were washed and resuspended in PBS containing 10 ng/mL 7-aminoactinomycin D (7-AAD, Sigma-Aldrich). The apoptosis assays were performed with the Annexin V Apoptosis Detection Kit I (BD Pharmigen) according to the manufacturer's instructions and 48 hours after transduction, if not otherwise indicated. The cell proliferation assay was performed with the Cell Proliferation Dye eFluor 670 (eBioscience) according to the manufacturer's instructions. To calibrate the cytometer, rainbow beads (Spherotech) were used to set the dye signal on the different days of the analysis. The cell cycle analysis was performed by Ki67 (BD Pharmigen) and Hoechst (Invitrogen) staining as described in Lechman et al. (Lechman, E. R. et al. (2012) Cell Stem Cell 11: 799-811) 48 hours after the transduction. Antibodies are shown in Table 4.

RNA, DNA and Proteins

Total RNA was extracted with the RNeasy Plus Micro kit or RNeasy Micro Kit (Qiagen) and Reverse transcription was performed using SuperScriptVILO cDNA Synthesis Kit (ThermoFisher Scientific) according to the manufacturers' instructions. Gene expression analysis was performed by Taqman probe (Thermo Fisher, Table 6) as described in Petrillo et al. (Petrillo, C. et al. (2015) Molecular Therapy 23: 352-362), human HPRT1 or murine Hprt were used to normalise the total quantity of human or mouse cDNA input respectively. Table 6 shows the complete list of Taqman Probe reagents.

Vector Copy Number (VCN)

For vector copy number (VCN), total DNA was extracted using a Maxwell 16 instrument (Promega) or Blood & Cell Culture DNA micro kit (Qiagen). Copy number of the integrated lentiviral vector was assessed as described in Lombardo et al., Petrillo et al. and Santoni de Sio et al. (Lombardo, A. et al. (2007) Nature Biotechnology 25: 1298-1306; Petrillo, C. et al. (2015) Molecular Therapy 23: 352-362; Santoni de Sio, F. R. et al. (2008) Stem Cells 26: 2142-2152) or by digital droplet PCR (dd-PCR; BIO-RAD, California, USA) according to the manufacturers' instructions using hTERT gene as a normaliser. Copy number of the total lentiviral DNA (integrated and non-integrated) was analysed as described in Matrai et al. (Matrai, J. et al. (2011) Hepatology 53: 1696-1707) at three days post-transduction. Copy number of the reverse transcribed retroviral vector genome (both integrated and non-integrated) was performed by dd-PCR discriminating it from plasmid carried over from the transient transfection using the following primers: RT-RV; AU3 sense: 5'-CGAGCTCAATAAAAGAGCCCAC-3' (SEQ ID NO: 7), PBS antisense: 5'-GAGTCCTGCGTCG-GAGAGAG-3' (SEQ ID NO: 8). The amount of human DNA loaded in the reaction was quantified with a qPCR or ddPCR designed to amplify the hTERT gene as described in Lombardo et al. (Lombardo, A. et al. (2007) Nature Biotechnology 25: 1298-1306). The 2LTR circle copy number was performed in dd-PCR with primers as described in Petrillo et al. (Petrillo, C. et al. (2015) Molecular Therapy 23: 352-362). Table 7 shows a complete list of primers. Unless otherwise specified, copy numbers are expressed as amplicon copies per cell (diploid genome).

Western Blot

Western Blot was performed as described in Petrillo et al. and Kajaste-Rudnitski et al. (Petrillo, C. et al. (2015) Molecular Therapy 23: 352-362; Kajaste-Rudnitski, A. et al. (2006) The Journal of Biological Chemistry 281: 4624-4637). Samples were subjected to SDS-PAGE on Bolt 4-12% Bis-Tris Plus gels (ThermoFisher, CAT #NW04120BOX) and transferred to PVDF membrane by electroblotting. Table 5 shows a complete list of antibodies.

Statistical Analysis

Data is expressed as mean±standard error of the mean (SEM). Statistical tests were performed as indicated for each experiment. Significance was considered at p<0.05.

Results

Lentiviral Transduction Triggers DNA-Damage Responses in Human HSPCs

Figure 7:
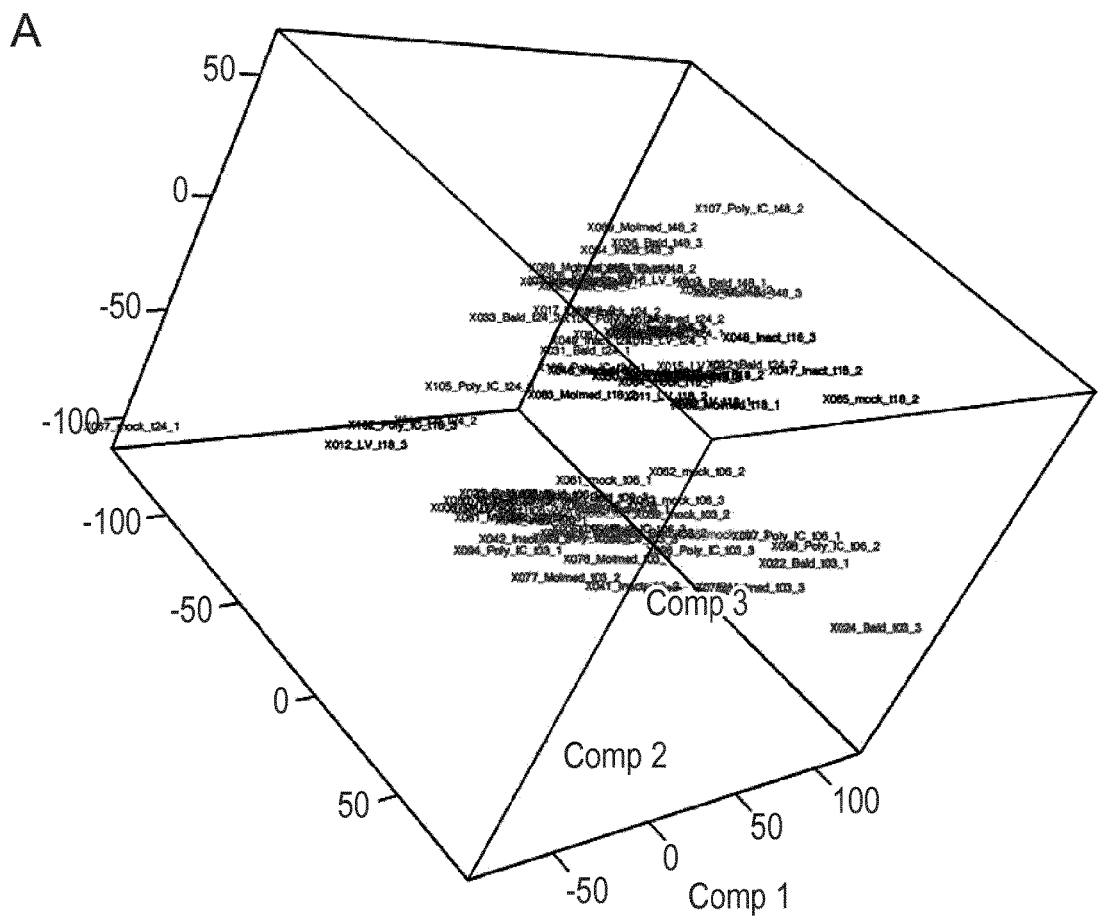
FIG. 7. (A) Principal Component Analysis (PCA) plot. The samples from the RNA-seq experiment are shown in the 3D plane spanned by their first three principal components. The first 3 principal components accounted for the 85% of explained variance among the data set. (B) Bar chart of the pathway enrichment analysis performed with WikiPathways database on the significant (nom p-value 0.05) differentially expressed genes over time (5883) in the untreated condition. The length of the bar represents the significance (p-value Ranking) of that specific pathway. In addition, the brighter the colour, the more significant that term is.
Figure 9:
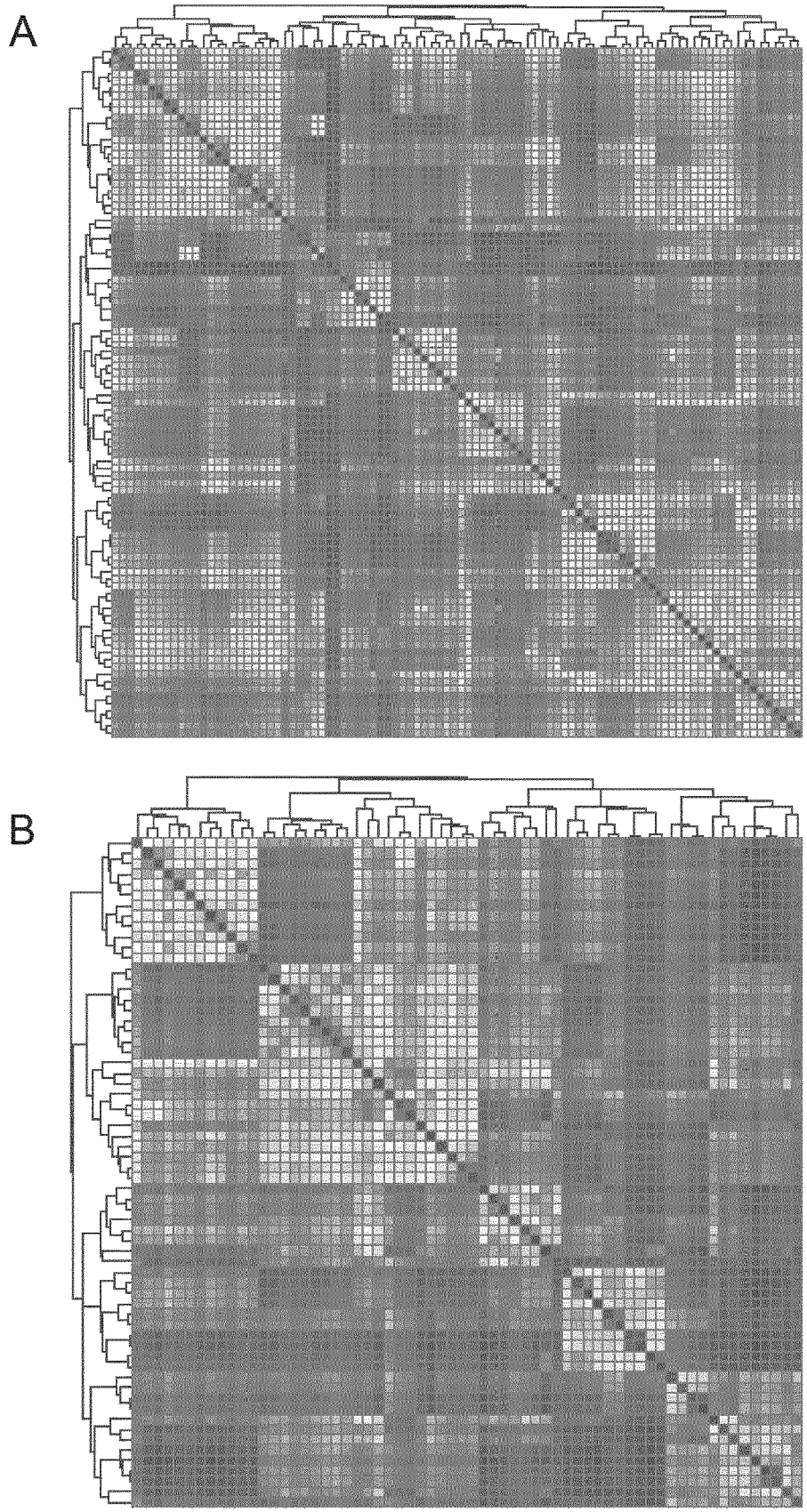
FIG. 9. Heat map of clustered biological terms highlighted by differentially expressed genes in the transduced samples respect to the controls (A) The heat map represents semantic similarity among gene ontology (GO) Biological Process (BP) terms. Rows and columns show the list of enriched GO BP terms derived from term enrichment analysis of the differentially expressed genes over time between the Bald LV and Lab LV conditions. The colours represent the semantic distances calculated using GOSemSim Bioconductor package. Yellow-red clusters identify groups of terms sharing semantic similarity about biological processes. (B) The heat map represents semantic similarity among gene ontology (GO) Biological Process (BP) terms. Rows and columns show the list of enriched GO BP terms derived from term enrichment analysis of the differentially expressed genes over time between the Bald LV and Lab LV conditions. The colours represent the semantic distances calculated using GOSemSim Bioconductor package. Yellow-red clusters identify groups of terms sharing semantic similarity about biological processes.

To extensively address the signalling potentially occurring upon exposure of human HSPCs to LVs, we performed RNA-Seq analysis in time-course on cord-blood (CB)-derived CD34+ cells exposed to either research- or clinical-grade VSV-g pseudotyped (SIN) LV at a high multiplicity of infection, matching current clinical vector dose requirements. As controls, cells were exposed to poly (I:C), non-transducing Env-less (Bald) or heat inactivated control vectors or kept in culture untreated (FIG. 1A). Key pathways significantly modulated in time by the different treatments were assessed by Term Enrichment Analysis considering various annotated pathway databases (KEGG and WikiPathways) and Gene Ontology Biological Processes (GO-BP), further clustered according to their semantical similarities. The greatest transcriptional variance within our dataset was time in culture, as samples clustered in three distinct temporal groups following Principal Component Analysis (PCA), independently of the treatment group (FIG. 7A). The mere culture of HSPCs in the presence of growth-promoting cytokines resulted in the transcriptional modulation of around 6000-9000 genes over time for all treatment categories (Table 1). For untreated HSPCs, the most enriched pathway was the MAPK signalling (FIG. 7B), in accordance with growth factor and cytokine-induced stimulation (Geest, C. R. et al. (2009) J. Leukoc. Biol. 86: 237-250). Poly(I: C)-exposed HSPCs strongly upregulated innate immune responses, significantly mobilising a total of 2691 genes (nominal p-value <0.05) as compared to untreated controls (Table 2). We performed Term Enrichment analysis of the significantly modulated genes to highlight the biological processes affected by Poly (I:C) exposure in HSPCs. Regulation of immune responses, NF-kB signalling, antiviral responses, programmed cell death and antigen processing were among the most represented GO-BP categories (FIG. 8). Instead, LV-exposed HSPCs showed much milder responses, modulating 321 and 281 genes (nominal p-value <0.05) with research- and clinical-grade vectors, respectively (Table 2). The genes altered by LV, whether research- or clinical-grade, converged significantly into DNA-damage responses and in particular the p53 signalling pathway (p-value $6.09 \times 10^{-9}$ for lab-grade LV and $5.1 \times 10^{-3}$ for purified LV) (FIGS. 1B-C; FIGS. 9A and B). No evidence of significant innate immune activation related to TLR-signalling or activation of NF-kB/Interferon Stimulated Gene (ISG) transcription could be detected, even when comparing LV-exposed HSPCs to untreated cells. A closer look into genes primarily involved in innate immune activation did not show significant changes in their patterns of modulation over time (Table 3). Instead, analysis of the differentially expressed genes with a nominal p-value <0.01 in the LV-exposed HSPCs compared to Bald-exposed controls revealed the upregulation, around 18 hours post-transduction, of a cluster of genes mapping to the KEGG p53 signalling pathway (FIGS. 1D and 1E).

Figure 10:
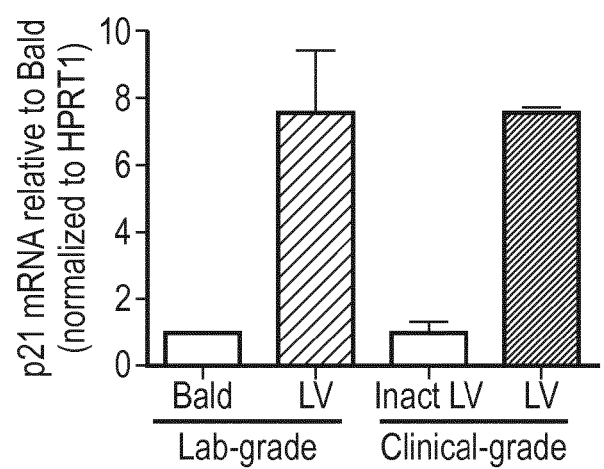
FIG. 10. p21 induction in clinical grade LV (A) p21 mRNA levels were measured after 48 hours from the transduction of CB-CD34+ with an MOI of 100 PGK-GFP SIN LV (LV), MOI of 100 clinical grade LV (Clinical LV), or to p24 equivalent of Env-less (Bald) or inactivated Clinical LV as controls (Inactivated Clinical LV). p21 mRNA was normalised to HPRT1, results are shown respect to Bald set to value 1. Results are shown as mean±SEM of two independent experiments.

Upregulation of some of the most significantly modulated genes involved in p53 signalling was confirmed by Taqman in HSPCs exposed either to LV or the entry-incompetent Bald LV (FIG. 1F). In particular, p21 and PHLDA3, both direct targets of p53 (Kawase, T. et al. (2009) Cell 136: 535-550; Espinosa, J. M. et al. (2001) Molecular Cell 8: 57-69), were highly induced by LV, reaching 10-fold higher expression levels compared to controls at 48 h post-transduction. In agreement with the RNA-Seq results using the purified LV (FIG. 1), a clinical-grade LV expressing the human ARSA used in recent trials to treat MLD (Biffi, A. et al. (2013) Science 341: 1233158) resulted in comparable levels of p21 induction as with the research-grade LV (FIG. 10A). These results suggest that potential contaminants such as plasmid DNA present in research-grade vector preparations (Merten, O. W. et al. (2011) Human Gene Therapy 22: 343-356) are not involved in the observed signalling.

Taken together, these observations indicate that LV transduction of human HSPCs specifically triggers early DNA-damage responses rather than innate immune signalling, despite their capacity to rapidly upregulate these pathways upon poly (I:C) exposure.

Figure 2:
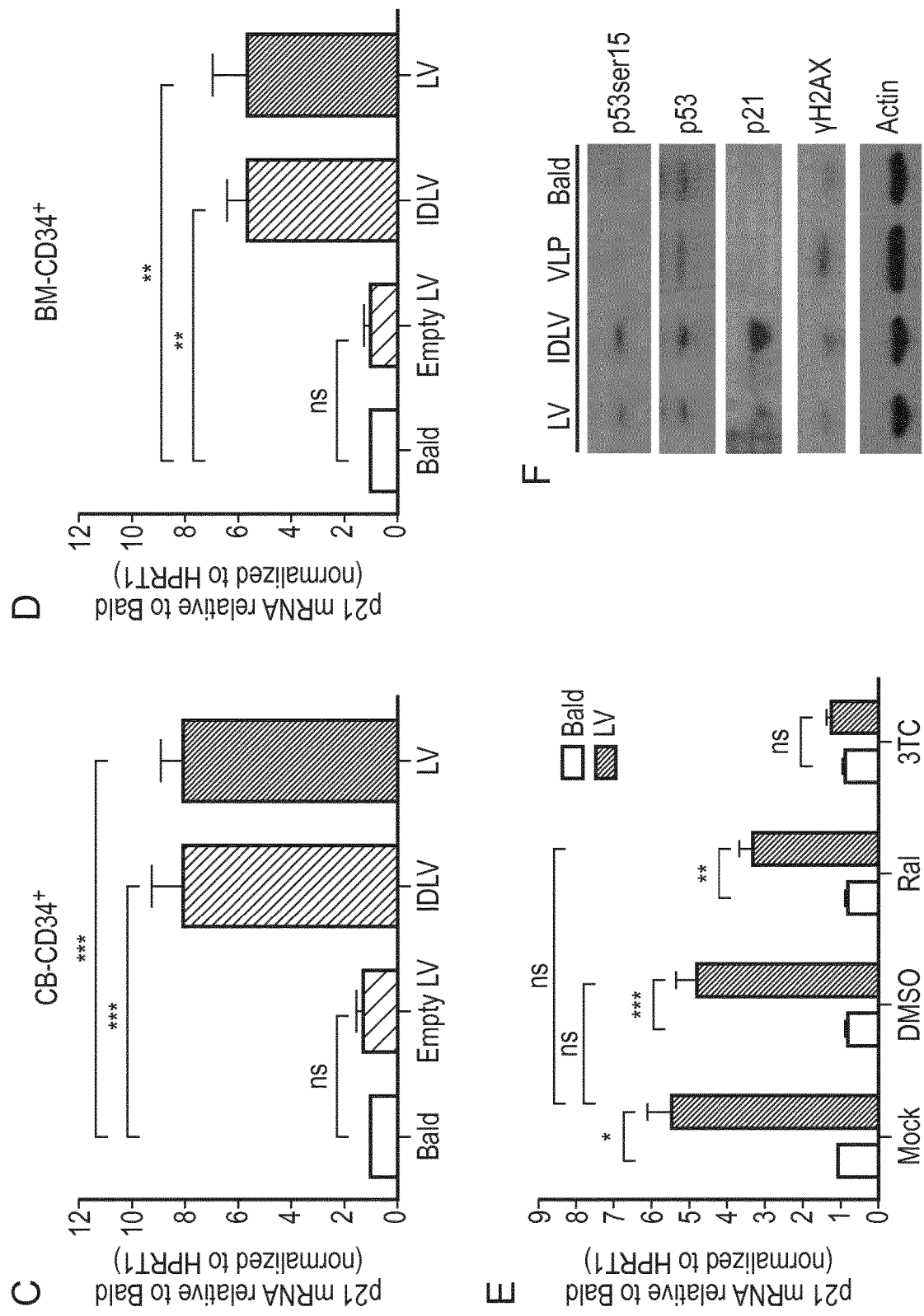
FIG. 2. p53 induction occurs in all CD34+ subpopulations, requires reverse-transcription but is integration independent. (A) Experimental design of the sorting experiment. After 16 hours of cytokine pre-stimulation CB-CD34+ were sorted based on the expression of the CD133 and CD38 surface marker to discriminate the fraction enriched in stem cells (CD133+CD38−) from the more committed progenitors (CD133+CD38int and CD133+CD38hi). Cells were transduced immediately after sorting with an MOI 100 of PGK-GFP SIN LV or exposed to p24 equivalent of Bald as control. p21 mRNA levels were measured in (B) the different sorted CD34+ subpopulations (n=4); (C) total CB-CD34+ (n=6) or (D) bone marrow (BM)-derived CD34+ (BM-CD34+) cells (n=4) exposed to an MOI of 100 PGK-GFP SIN LV (LV), integrase-defective LV (IDLV), or p24 equivalents of genome-less (Empty LV) or Env-less (Bald) vectors; (E) CB-CD34+ transduced in presence of the integrase inhibitor Raltegravir (Ral) or reverse-transcriptase inhibitor Lamivudin (3TC) (n=4). All data is normalised to HPRT1 and shown respect to Bald set to value of 1. Results are the mean±SEM of n independent experiments as indicated, p-values are for Kruskal-Wallis test (* p≤0.05; ** p≤0.01). (F) Western blot was performed on whole CB-CD34+ cells extracts at 24 hours post-transduction. Immunoblots were sequentially probed with phospho- and non phospho-specific antibodies against p53, phospho-specific antibody against γH2AX, nonphospho-specific antibodies against p21, and β-actin (loading controls). One representative out of two gels is shown. (G) Western blot (Left Panel) and quantifications (Right Panel) were performed on whole mPB-CD34+ cell extracts at 24 hours post-transduction. (H) p21 protein upregulation evaluated by FACS 48 hours after transduction.
Figure 2:
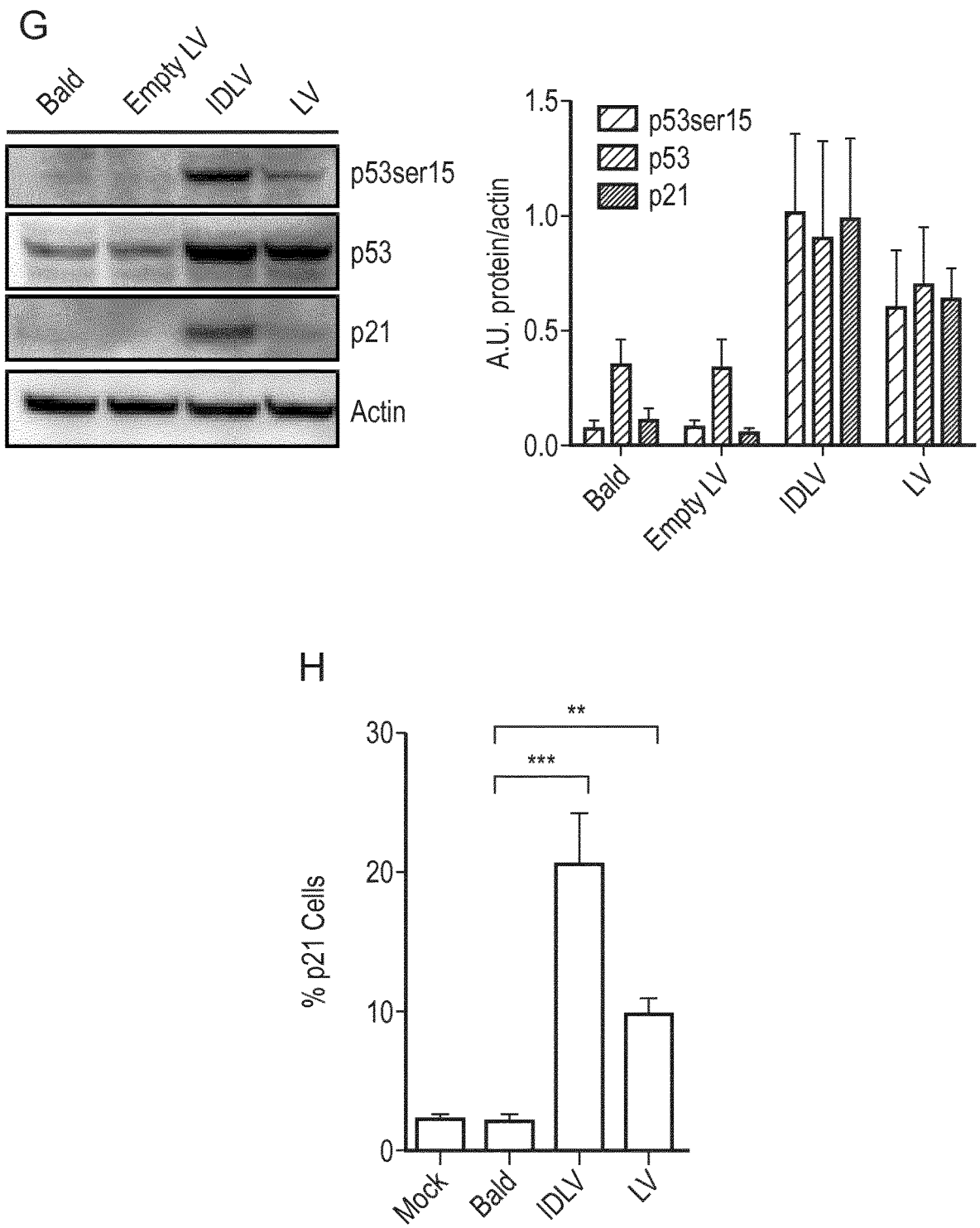

LV-Induced p53 Signalling Requires Reverse Transcription but is Integration-Independent To further investigate how LV induces p53 signalling in HSPCs, we chose to track p21 mRNA induction as a marker of p53 activation, as it was one of the most responsive genes in our transcriptome profiling experiments (FIG. 1). Induction of p21 was dose-dependent (FIG. 11A) and was specific to human HSPCs, as CD4+ T cells, Lin− murine HSPCs and different human cell lines of hematopoietic origin did not up-regulate p21 upon LV exposure (FIG. 11B). We then investigated induction of p21 in the different CD34+ subpopulations (FIG. 2A), as distinct DNA damage responses have been shown to occur between more primitive haematopoietic stem cells (HSCs) and committed progenitors (Milyaysky, M. et al. (2010) Cell Stem Cell 7: 186-197). Overall, LV induced p21 expression to a similar extent in all CD34+ subpopulations, although the most primitive CD34+ CD133+CD38− fraction showed higher levels of induction, correlating with the higher transduction levels reached in this cell fraction (FIGS. 2B and 11C).

The p53 pathway can be triggered by various cellular stress signals such as DNA damage, hypoxia or oncogene activation (Riley, T. et al. (2008) Nature Reviews. Molecular Cell Biology 9: 402-412). HIV-1 infection has been shown to induce p53-dependent apoptosis of CD4+ T cells through activation of the DNA-dependent protein kinase (DNA-PK) during viral integration (Cooper, A. et al. (2013) Nature 498: 376-379). To address whether activation of p53 was dependent on proviral integration also in the context of transduced HSPCs, we exposed cells to equal doses of either integration-competent or -defective LV (IDLV) and measured p21 induction at 48 h post transduction. The two vectors induced p21 to similar extent both in CB as well as in bone marrow (BM)-derived CD34+ HSPCs (FIGS. 2C and 2D) at comparable vector DNA input (FIG. 11D). Of note, triggering was not due to vector stock contaminants, LV particle entry nor exposure of cells to viral cores, as neither the Env-less Bald vector nor the genome-less Empty LV lead to upregulation of p21 (FIGS. 2C and 2D). In agreement with the IDLV-mediated up-regulation, p21 induction still occurred in HSPCs transduced in presence of the integrase inhibitor Raltegravir (FIG. 2E), despite an efficient block in LV integration (FIG. 11E). Integration-independent activation of p53 signalling was confirmed by Western blot, FACS and indirect immunofluorescence (IFI) staining in terms of phosphorylation of p53 at Serine 15, increase in basal p53 levels as well as induction of p21 by both LV and IDLV also in mobilised peripheral blood (mPB)-derived CD34+ HSPCs (FIGS. 2G-H and FIGS. 11G-1). Furthermore, no changes in phosphorylated Histone 2AX (γH2AX) foci were observed, in line with a DNA break-independent induction of p53 (FIG. 11I). Finally, p21 up-regulation was abrogated in the presence of the reverse-transcriptase inhibitor 3TC (FIGS. 2E and 11E), suggesting that lentiviral DNA synthesis is required for p53 signalling to occur in HSPCs.

p53 Induction Requires Active Nuclear Import of Vector DNA

Figure 3:
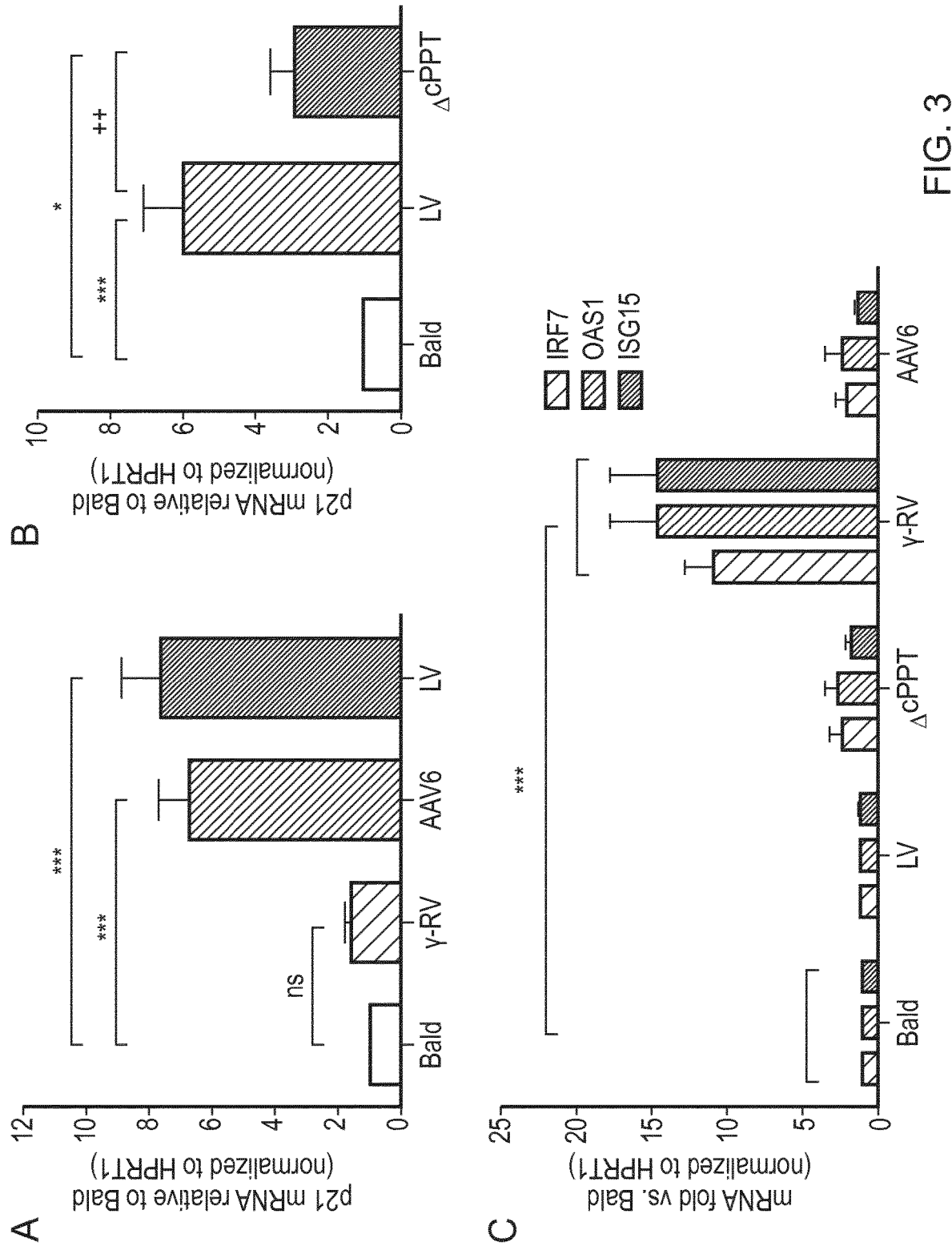
FIG. 3. p53 induction requires active nuclear import. mRNA levels of p21 (A-B) and IFN-stimulated genes (IRF7, OAS1 and ISG15) (C) were measured at 48 hours post-exposure of CB-CD34+ to PGK-GFP SIN LV (LV), PGK-GFP LV lacking the central polypurine tract-deleted (ΔcPPT) or PGK-GFP SIN RV (γ-RV) at MOI 100, p24 equivalent of Env-less (Bald) vector or MOI 10000 of PGK-GFP Adeno-associated Vector (AAV6) as indicated. All data are normalised to HPRT1 and shown respect to Bald set to value of 1. Results are the mean±SEM of 4 independent experiments p-values are for Kruskal-Wallis test (* p≤0.05;  p≤0.01; * p≤0.001); ++ p 0.01 is for Wilcoxon Matched paired test.
Figure 12:
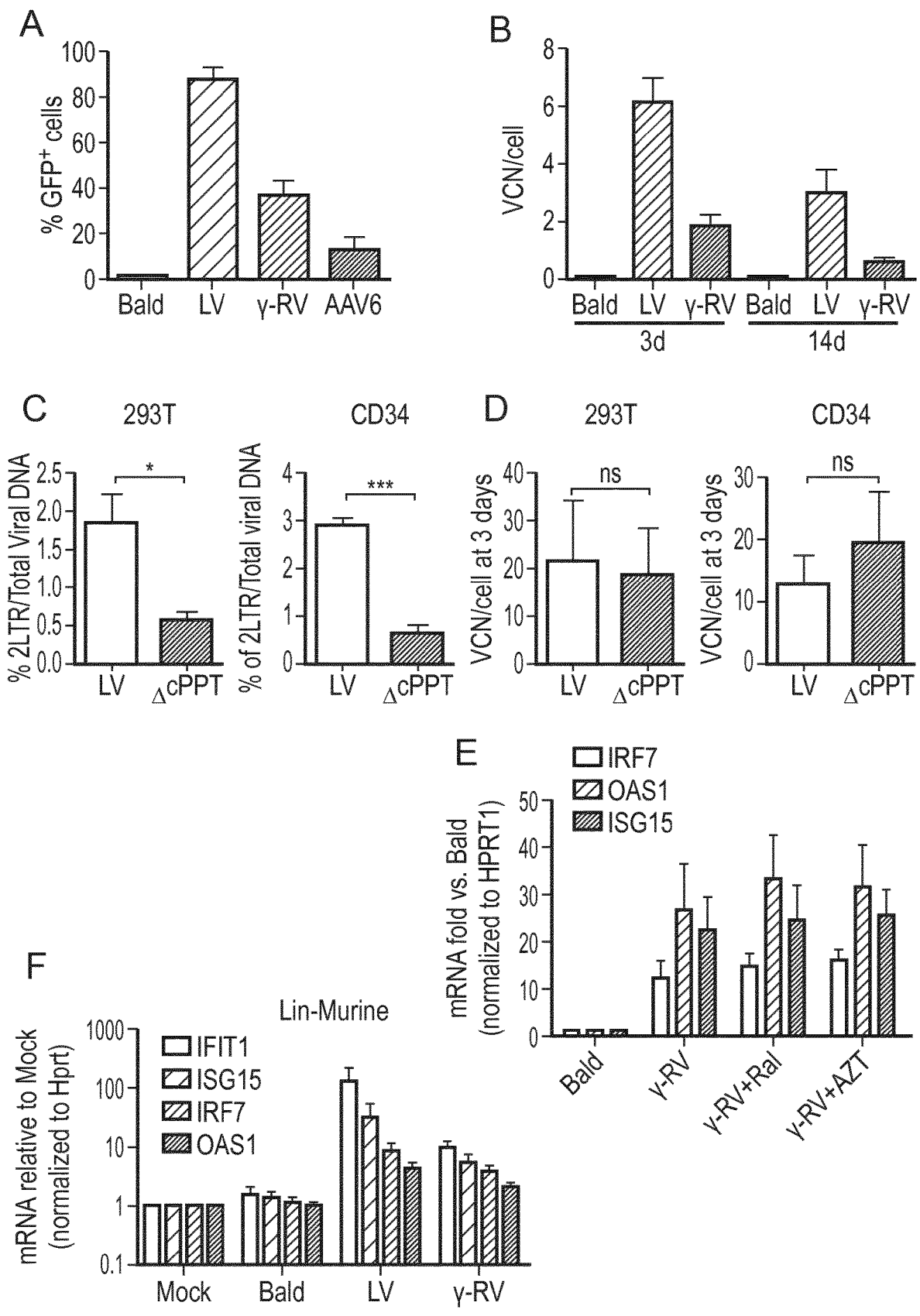
FIG. 12. γ-RV, AAV6 and ΔcPPT (A) Percentage of GFP positive CB-CD34+ transduced with PGK-GFP SIN LV at MOI 100 (LV), or exposed to p24 equivalent of Env-less (Bald) vector as control, cells were also transduced with an MOI 100 of a PGK-GFP SIN RV or to an MOI 10000 of PGK-GFP Adeno-associated Vector (AAV6). GFP expression was assessed at FACS 5 days after transduction for the integrating vector, and 2 days post TD for the AAV6. Results are shown as mean±SEM. (B) Vector copy number results of CB-CD34+ transduced with PGK-GFP SIN LV or PGK-GFP SIN RV (RV) at MOI 100 or exposed to p24 equivalent of Env-less (Bald) vector as control. Copy per cell of total viral DNA was assessed three days after transduction, while VCN on the integrated vectors were performed 14 days after transduction. Values are mean±SEM. (C) Comparison of the nuclear import efficiency and (D) total viral DNA three days after transduction with LV or ΔcPPT. Nuclear import efficiency is reported as the percentage of 2LTR circles on the total reverse transcribed viral DNA. The same analysis was performed in 293T cells (MOI 1) (Left Panel) and in human CBCD34+ cells (MOI 100) (Right Panel). Values are mean±SEM of 6 independent experiments. (E) Interferon stimulated genes results of human CB-CD34+ transduced with an MOI of 100 of PGK-GFP SIN RV (RV), or Env-less (Bald) as control. Transductions were performed in presence of the integrase inhibitor Raltegravir (Ral), or reverse transcriptase inhibitor azidothymidine (AZT). Interferon stimulated genes (IRF7, OAS1, ISG15) were measured 48 hours post-transduction. Expression levels were normalised to HPRT1 and shown respect to Bald set to value of 1. (F) Interferon stimulated genes (IFIT1, IRF7, OAS1, and ISG15) induction of Murine HSPC transduced with an MOI of 100 of PGK-GFP SIN LV (LV), PGK-GFP SIN RV (RV), or to p24 equivalent of Env-less (Bald). Cells were also left untreated as a control in the mock condition. 48 hours post-transduction. Expression levels were normalised to HPRT1 and shown respect to mock set to value of 1.

Other viral vectors used to introduce exogenous genetic material into HSPCs (Naldini, L. (2011) Nature Reviews. Genetics 12: 301-315) will also expose the cells to exogenous DNA. Similarly to LV, gamma-retroviral vectors (γRV) reverse-transcribe their genomic RNA into DNA that will be integrated into the host genome (Coffin, J. M., Hughes, S. H., and Varmus, H. E. (1997). The Interactions of Retroviruses and their Hosts. In Retroviruses. J. M. Coffin, S. H. Hughes, and H. E. Varmus, editors. Cold Spring Harbor (NY)). Different serotypes of adeno-associated virus vectors (AAV) are instead DNA-based non-integrating viral vectors widely used for transient gene expression or as donor DNA during gene editing (Mingozzi, F. et al. (2011) Nat. Rev. Genet. 12: 341-355; Naldini, L. (2015) Nature 526: 351-360). We tested the capacity of both γRV and AAV-6 to induce p21 in HSPCs. AAV-6-exposed HSPC showed robust p21 induction, while γRV very moderately affected p21 expression at clinically relevant vector doses (FIGS. 3A and 12A-B). As opposed to HIV-1-derived LV and AAV-6 that actively import the vector DNA into the nucleus of target cells, γRV relies on cellular mitosis to access the host genome (Bushman, F. et al. (2005) Nature Reviews. Microbiology 3: 848-858; Nonnenmacher, M. et al. (2012) Gene Therapy 19: 649-658). To test if active nuclear import of LV DNA is required to trigger p53 signalling in HSPCs, we generated a vector devoid of the central polypurine tract (cPPT) required for efficient nuclear import of the pre-integration complex (PIC) (Follenzi, A. et al. (2000) Nature Genetics 25: 217-222; Zennou, V. et al. (2000) Cell 101: 173-185). Up to 3-fold lower nuclear import of the ΔcPPT LV compared to unmodified LV was verified in both 293T cells and CD34+ HSPCs, as measured by lower percentages of nuclear 2LTR circles over total viral DNA 3 days post transduction at comparable input viral cDNA (FIGS. 12C-D). In human HSPCs, the ΔcPPT LV induced p21 mRNA 2-fold less compared to WT LV (FIG. 3B), suggesting that efficient nuclear import of vector DNA is required to activate p53 signalling in HSPCs.

As p53 signalling has recently been linked with type I IFN pathways (Yu, Q. et al. (2015) Cell Reports 11: 785-797; Hartlova, A. et al. (2015) Immunity 42: 332-343), we also examined expression of several ISG in human HSPCs after exposure to the different vectors. In agreement with our RNA-Seq dataset, no activation of ISG could be evidenced in human HSPCs upon LV transduction, independently of the presence of the cPPT (FIG. 3C). No type I IFN responses were observed in AAV-6 transduced human HSPCs, while γRV triggered significant up-regulation of all ISG tested (FIG. 3C). As opposed to LV-mediated signalling, innate immune activation upon exposure of human HSPC to γRV was independent of reverse-transcription and integration, as ISG induction occurred also in presence of the reverse-transcriptase inhibitor azidothymidine (AZT) or Raltegravir (FIG. 12E). γRV-mediated ISG induction was inhibited when the type I IFN receptor signalling was blocked, but it does not explain lack of p53 signalling upon γRV exposure, as pre-treatment of HSPCs with type I IFN did not prevent induction of p21 by LV (FIG. 11J). Of note, both LV and γRV readily triggered ISG expression in murine Lin− cells (FIG. 12F), indicating that the capacity of LV to avoid type I IFN activation is specific to human HSPCs.

Figure 4:
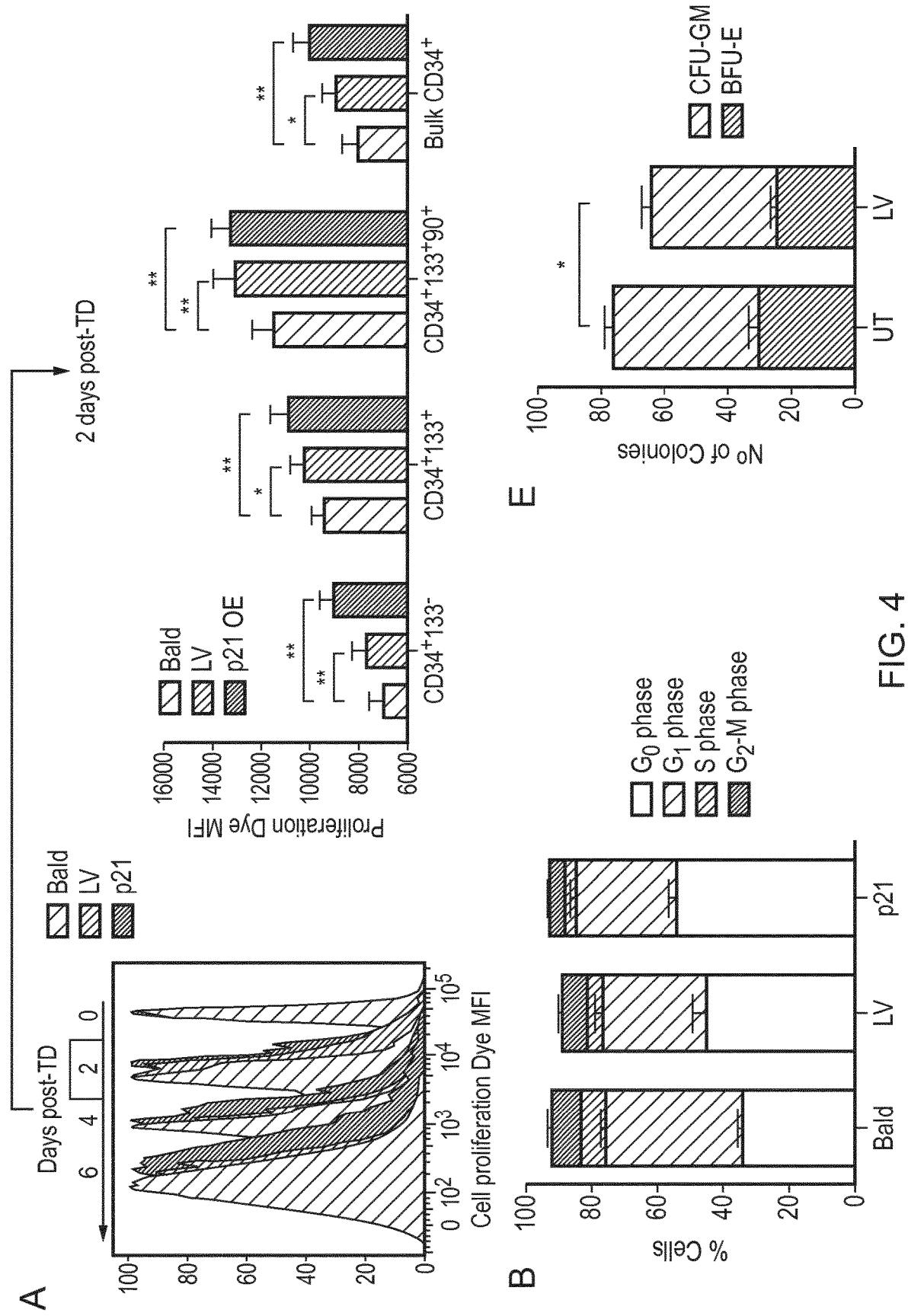
FIG. 4. Functional consequences of LV-mediated signalling in human HSPC in vitro. (A) CB-CD34+ cells were stained with the cell proliferation dye and transduced with MOI 100 of PGK-GFP SIN LV (LV), p21 overexpressing LV (p21) or p24 equivalent of Bald. Cell proliferation was followed over time in terms of dye MFI in the different subpopulations gated as shown in FIG. 13B. Representative histograms (one out of four) of the Cell proliferation dye MFI in the different conditions over time is shown in the top panel. Dye MFI at 2 days after the transduction within each subpopulation is shown in the lower panel. Results are the mean±SEM of 4 independent experiments, p-values are for Wilcoxon Matched paired test (* p≤0.05; ** p≤0.01). (B) Cell cycle analysis was performed with Anti-Ki67 antibody and Hoechst at FACS 2 days after the transduction of CB-CD34+ cells with an MOI 100 of PGK-GFP SIN LV (LV), p21 overexpressing LV (p21) or p24 equivalent of Bald. Annexin staining for apoptotic cells was performed two days after exposure of (C) total or (D) sorted CB-CD34+ to PGK-GFP SIN LV (LV), integrase-defective LV (IDLV) at MOI 100 or p24 equivalents of genome-less (Empty LV) or Env-less (Bald) as indicated. (E) A fraction of non-transduced (UT) (Bald, Empty LV, or untreated) and transduced (PGK-GFP SIN LV MOI 100/150) CB-CD34+ cells were plated in semi-solid culture and the number of White and Red colonies were counted after 2 weeks of differentiation. (F) Impact of integrase (Ral) or reverse-transcriptase (3TC) inhibition on apoptosis was evaluated in total CB-CD43+. (G) CB-CD34+ cells were counted 2, 4 and 6 days after the transduction. Results are the mean±SEM of n≥4 independent experiments, p-values are for Kruskal-Wallis test (*P≤0.05; P≤0.01; *P≤0.001) in (C, D, F) and Wilcoxon Matched paired test, *P≤0.05) in (A and E) and Two-Way ANOVA, P=0.002, with Bonferonni's post-test **P≤0.01 at day 6 in (G).
Figure 4:
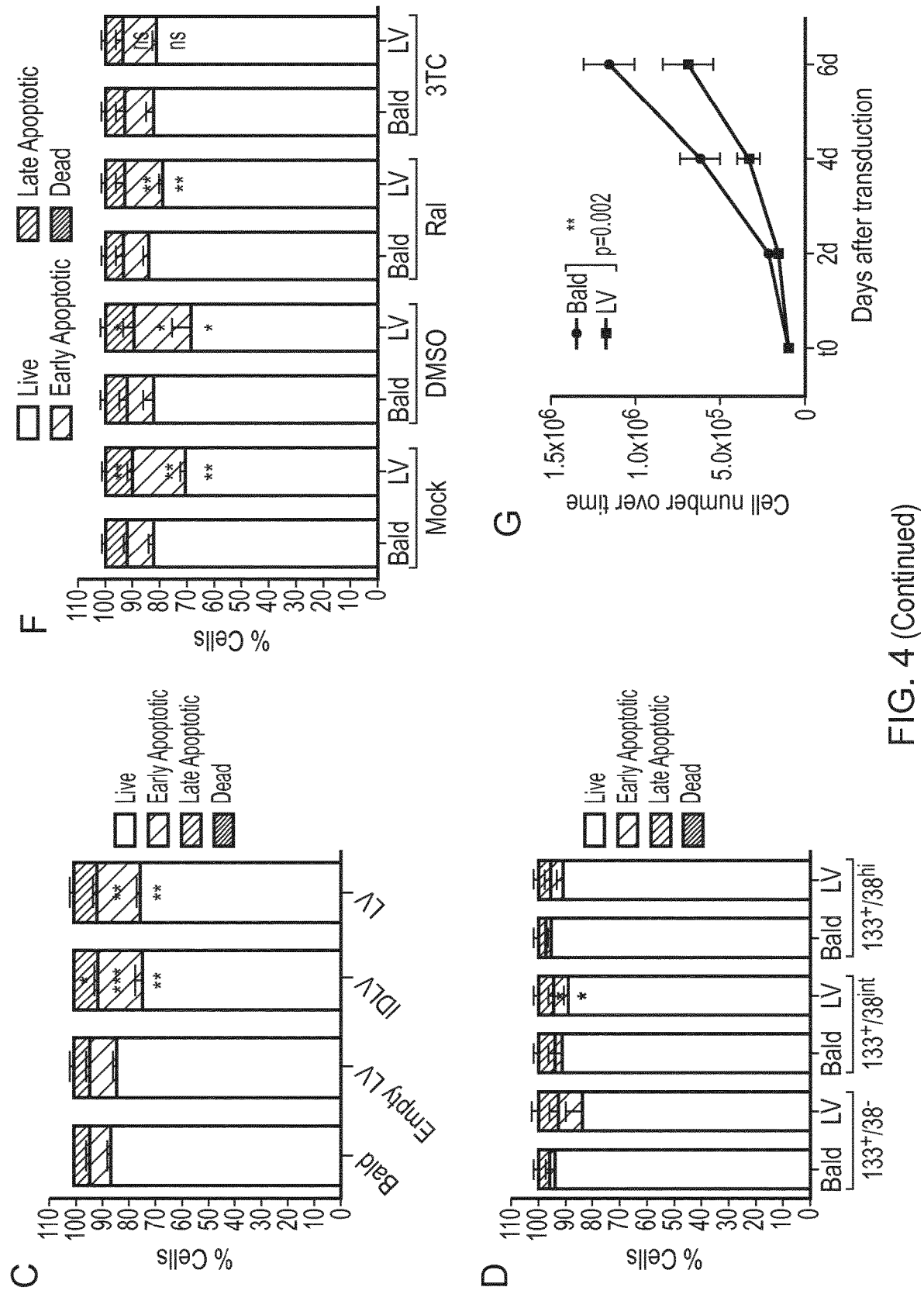
Figure 13:
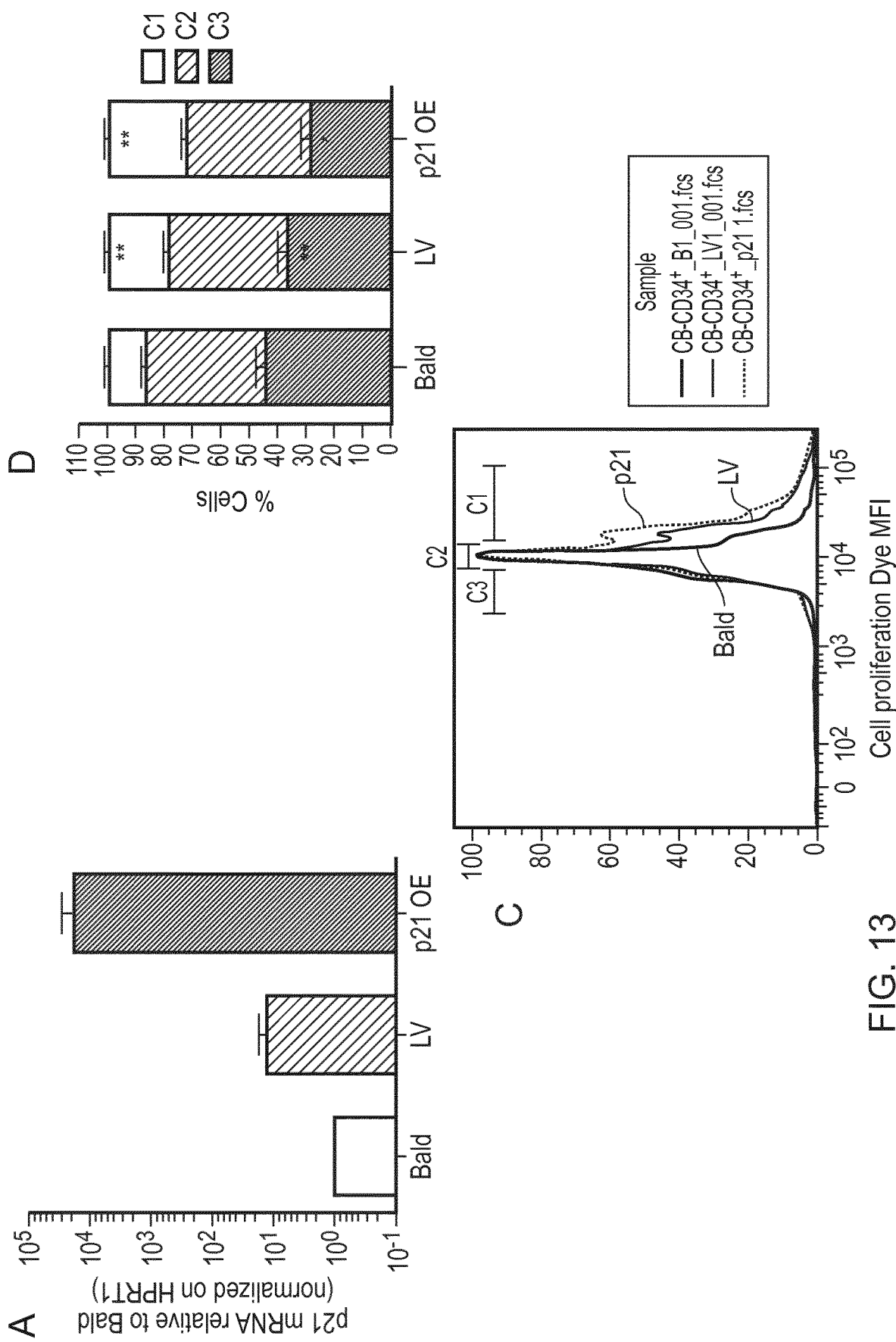
FIG. 13. In vitro impact of LV (A) p21 expression levels 48 hours after the transduction of human CB-CD34+ exposed to an MOI of 100 PGK-GFP SIN LV (LV), p21 overexpressing LV (p21) or p24 equivalent of Bald. p21 mRNA was normalised to HPRT1. Results are mean±SEM of two independent experiments shown respect to Bald set to value 1. (B) Representative gating strategy to analyse the CD34+ cells treated as in FIG. 4A. The upper panel shows the percentage of CD34, CD133 and CD90 at the moment of transduction, the lower panel reports the same markers two days after the transduction. In The left panel the bar graphs show the MFI of the cell proliferation dye at the moment of transduction or 4 and 6 days after the transduction within each subpopulation. Results are shown in mean±SEM of four independent experiments. (C) Representative histograms and (D) bar graphs of cells treated as in FIG. 4A at two days after transduction. The analyses was performed to assess the percentage of CBCD34+ cells that are contained within each gate (C1, C2, C3) for LV, p21 and Bald conditions. The cells within the C1 gate have proliferated less, while the one in the C3 have proliferated more. Results are shown in mean±SEM of four independent experiments. (E) CD34+ HSPCs subpopulation distribution at the moment of transduction or 2, 4 and 6 days after the transduction. (F) After the sorting indicated in FIG. 2A and the transduction, CBCD34+ cells were plated in semisolid, cytokine-containing CFC medium. Colonies were scored after 14 days. Mean±SEM of total colonies per 800 transduced or bald exposed cells per subpopulation (n=4). (G) Annexin V staining for apoptotic cells was performed two days after transduction of human CB-CD34+ exposed to increasing MOI of PGK-GFP SIN LV (LV).
Figure 13:
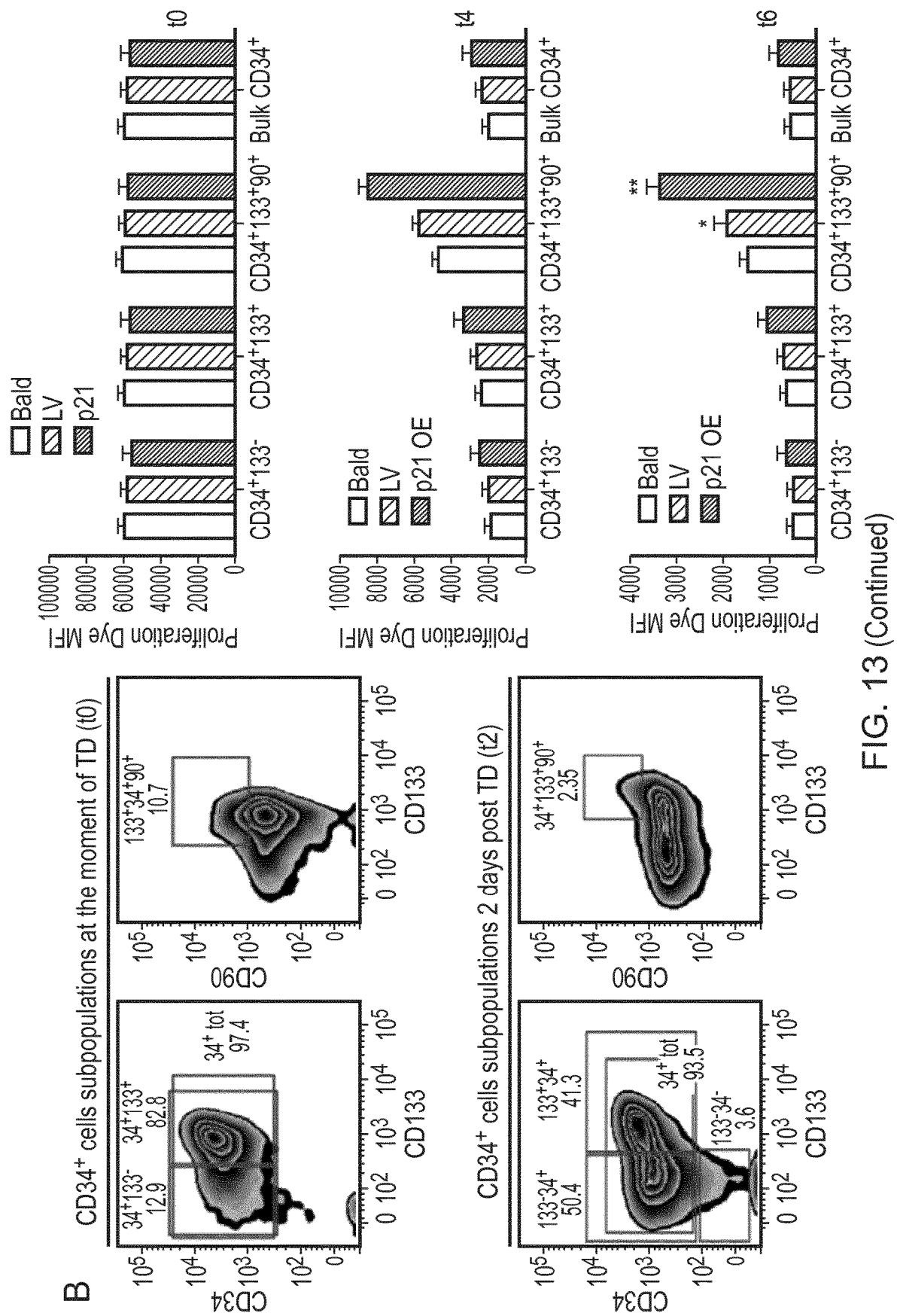
Figure 13:
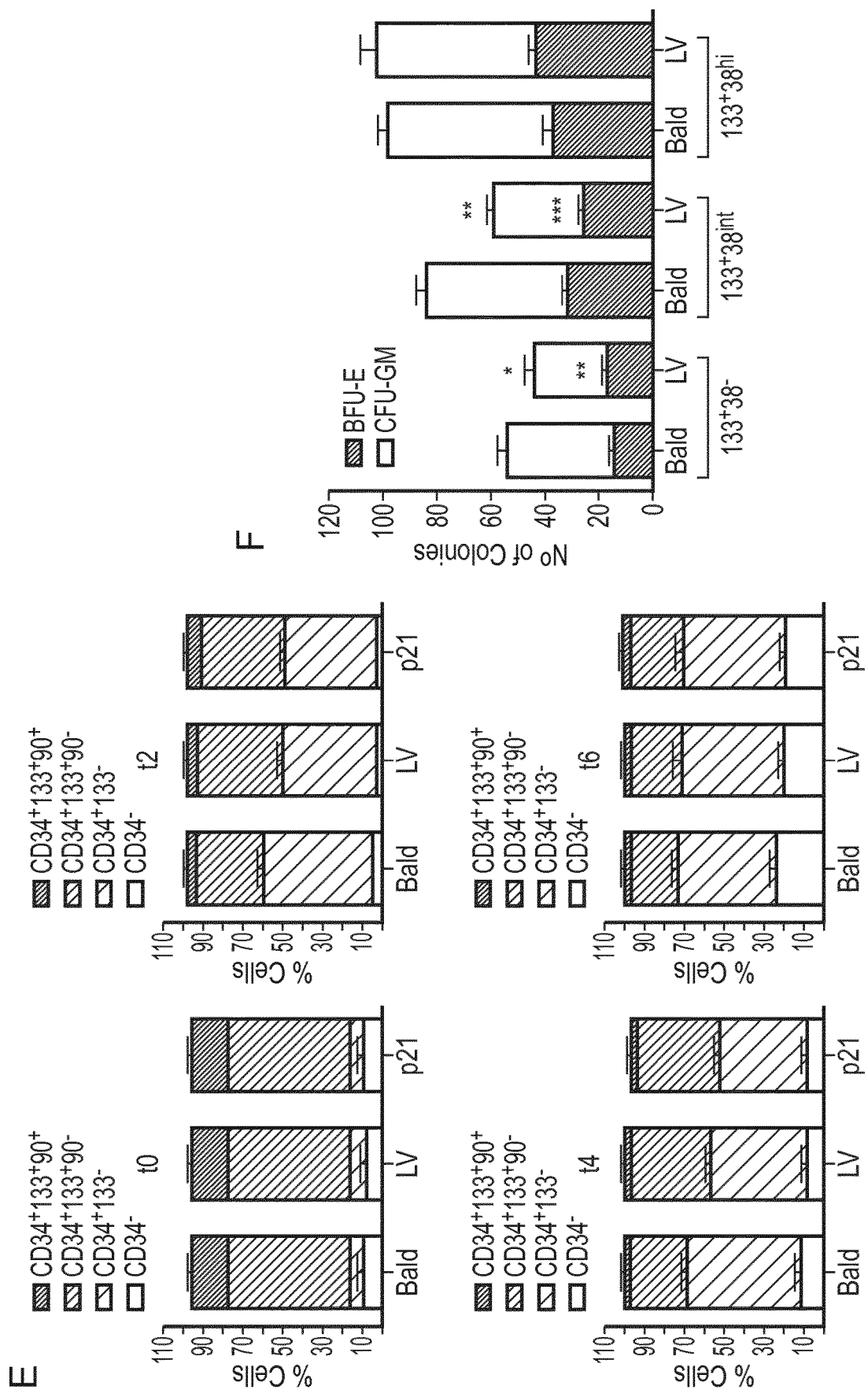

Functional Consequences of L V-Induced Signalling in HSPCs In Vitro p53 has a pivotal role in regulating HSC quiescence and homeostasis during both steady-state haematopoiesis as well as under replicative stress (Liu, Y. et al. (2009) Cell Cycle 8: 3120-3124; Liu, Y. et al. (2009) Cell Stem Cell 4: 37-48; Milyaysky, M. et al. (2010) Cell Stem Cell 7: 186-197; Lane, A. A. et al. (2010) Cell 142: 360-362; Mohrin, M. et al. (2010) Cell Stem Cell 7: 174-185). Depending on the extent of the damage and the transcriptional program activated, cells can undergo several faiths upon p53 activation (Riley, T. et al. (2008) Nature Reviews. Molecular Cell Biology 9: 402-412; Brady, C. A. et al. (2011) Cell 145: 571-583). Although p21 and PHDLA3 were among the most strongly upregulated genes in our RNA-Seq dataset (FIG. 1), no evident skewing towards a particular p53 transcriptional program could be seen. Therefore, we studied several of the possible functional outcomes of LV-induced p53 signalling in HSPCs. The 10-fold p21 induction observed upon LV transduction (FIG. 13A) led to a slight but significant delay in cellular proliferation rates two days after transduction (FIG. 4A). Similar growth arrest was observed in p21 overexpressing HSPC used as a positive control for this assay (FIG. 4A and FIG. 13A). Slower proliferation was seen in particular in the most primitive CD34+CD133+ CD90+ fraction in which this effect seemed to persist up to 6 days post transduction (FIGS. 4A and 13B). In agreement, the portion of cells that had undergone fewer divisions, falling into the population with the highest MFI of cell proliferation dye (C1 group in FIG. 13C), tended to be more represented in the LV-exposed condition as compared to control cells in the bulk CD34+ HSPCs (FIG. 13D). These differences were not due to an increase in the slower proliferating CD34+CD133+CD90+ cells, as no significant difference in the CD34+ subpopulation composition could be observed over time between the different conditions (FIG. 13E). In agreement with slower cell proliferation, transduced HSPCs displayed a higher fraction of cells in the G0 cell cycle phase as compared to controls (FIG. 4B). Furthermore, within the transduced population, a stronger proliferation delay was observed for the GFPhigh fraction, likely harbouring more vector copies, compared to the GFPlow ones (FIG. 13D). In agreement, higher p21 induction was detected by FACS in the more transduced BFPhigh cells (FIG. 11G).

LV-exposed HSPCs showed a slight but significant dose-dependent increase in apoptotic cells (FIGS. 4C and 13G). The combined effects of lower proliferation and apoptosis of LV transduced HSPCs was also reflected in terms of total cell counts over time in culture (FIG. 4G). Apoptosis occurred to a similar extent in all CD34+ subpopulations (FIG. 4D) and lower GM-CFU colony output was observed in LV-exposed total HSPCs (FIG. 4E). Looking at the CFU output capacity of the different CD34+ subpopulations, the LV-exposed CD133+CD38− and CD133+CD38int fractions were the ones to show significantly lower GM-CFU counts as compared to controls (FIG. 13F), correlating with higher p53 activation (FIG. 2B). Increased apoptosis also followed exposure of HSPCs to AAV-6 and clinical-grade LV, but does not necessarily correlate with p53 activation as also γRV-exposed HSPC showed similar percentages of apoptotic cells (FIGS. 14A and B). Inhibition of reverse-transcription, but not of integration, completely inhibited LV-mediated induction of apoptosis in HSPCs, correlating with their impact on p21 induction (FIGS. 4F and 2E).

Taken together, these results indicate that the major in vitro functional consequences of p53 triggering upon LV transduction in human HSPCs are a slight delay in proliferation, a higher fraction of cells in the G0 phase of the cell cycle as well as increased apoptosis and decrease in clonogenic output.

Functional Consequences of LV-Induced Signalling in HSPCs In Vivo

Figure 5:
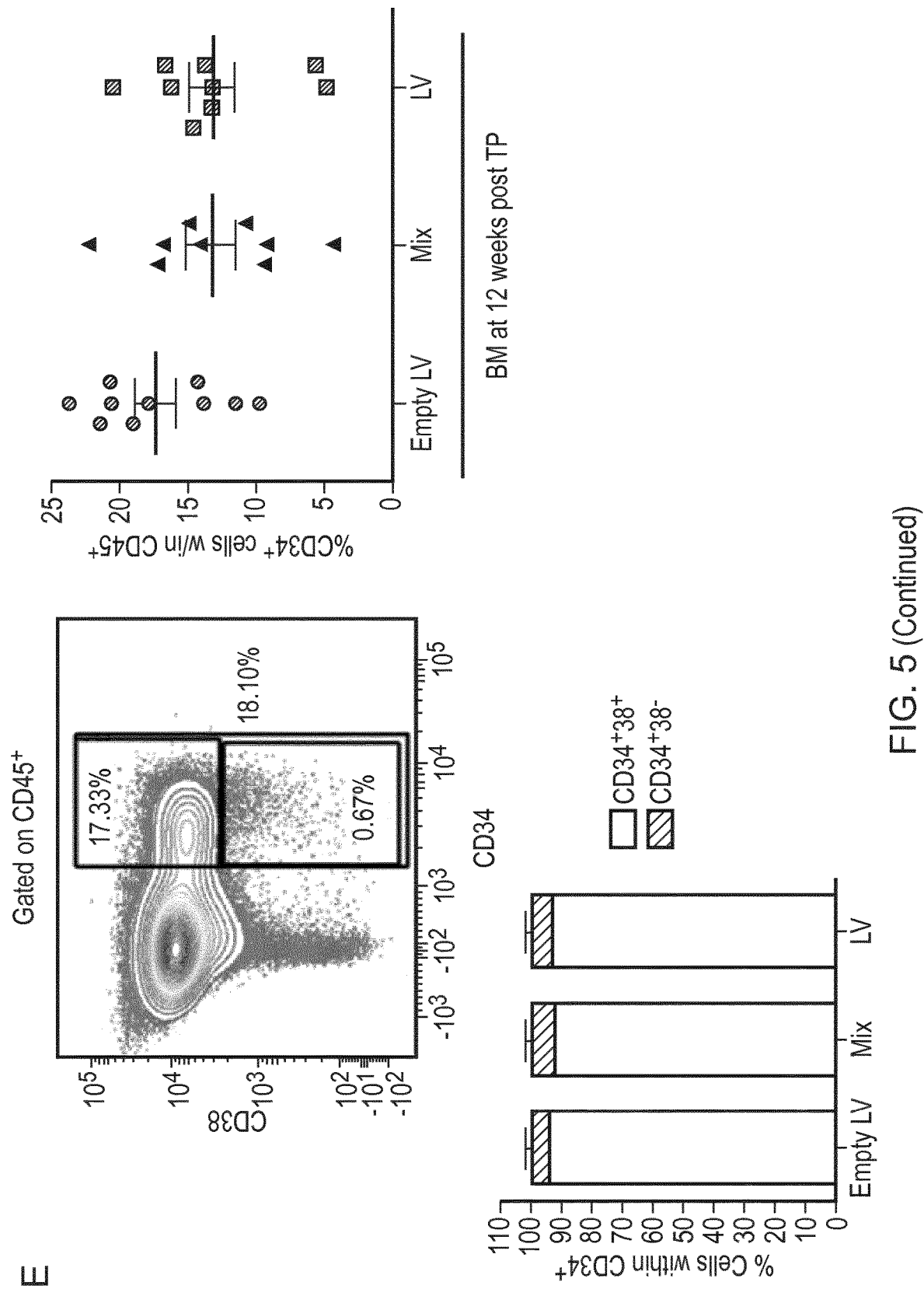
FIG. 5. In vivo impact of LV-mediated signalling. (A) Schematic representation in vivo experimental design. 24 hours after the transduction CB-CD34+ cells were washed and injected either separately (Empty LV (n=10), LV (n=9) or in a mixed condition composed of LV:Empty LV exposed cells in a 30:70 ratio (Mix (n=9)). Secondary recipients received 900.000-1.000.000 of CD34+ cells purified from the bone marrow of primary mice sacrificed at 12 weeks post-transplantation. Percentages of (B) total human CD45+ cells as well as (C) myeloid (CD13+) and lymphoid (CD19+ B, CD3+ T) cells within the human CD45+ cells were monitored in the peripheral blood over time and (D) in the bone marrow at the time of sacrifice. The bone marrow composition at time of sacrifice of primary recipients was evaluated. Representative FACS plot and frequencies of (E) CD34+, CD34+38+ and CD34+CD38− within the human CD45+ cells and of (F) CD45RA-90+(HSC), CD45RA-90− (MPP) and CD45RA+90− (MLP) within the human CD34+ 38− cells are shown. Results are shown as mean±SEM and p-values are for Kruskal-Wallis test (*P≤0.05; P≤0.01, * p≤0.0001). (G) Peripheral blood and (H) frequency of CD34+ cells within the bone marrow at time of sacrifice of the secondary recipients are shown. (I) Schematic representation of the experimental design and percentages of total human CD45+ cells monitored in the peripheral blood over time and in the bone marrow at the end of the experiments. (J) Percentages and absolute numbers of human CD34+ cells retrieved from the bone marrow of NSG mice 16 h post-transplantation. (K) Table and plot of the calculated HSC frequency obtained by LDA for untransduced (Bald) and MOI 100 transduced (LV) CB-CD34+ cells. Results are the mean±SEM of Empty LV (n=10), LV (n=9), and Mix (n=11) secondary recipients per group. HSC=Hematopoietic Stem Cells, MPP=Multi potent Progenitors, MLP=Multi Lymphoid Progenitors.
Figure 5:
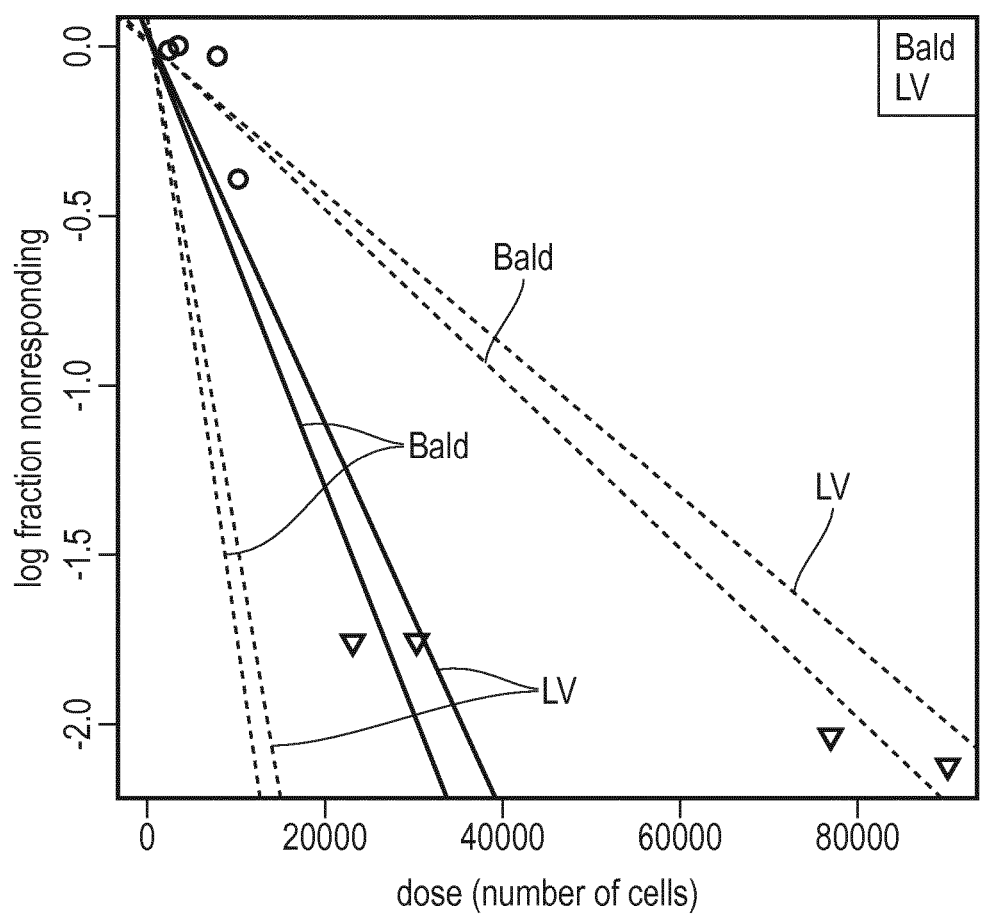
Figure 15:
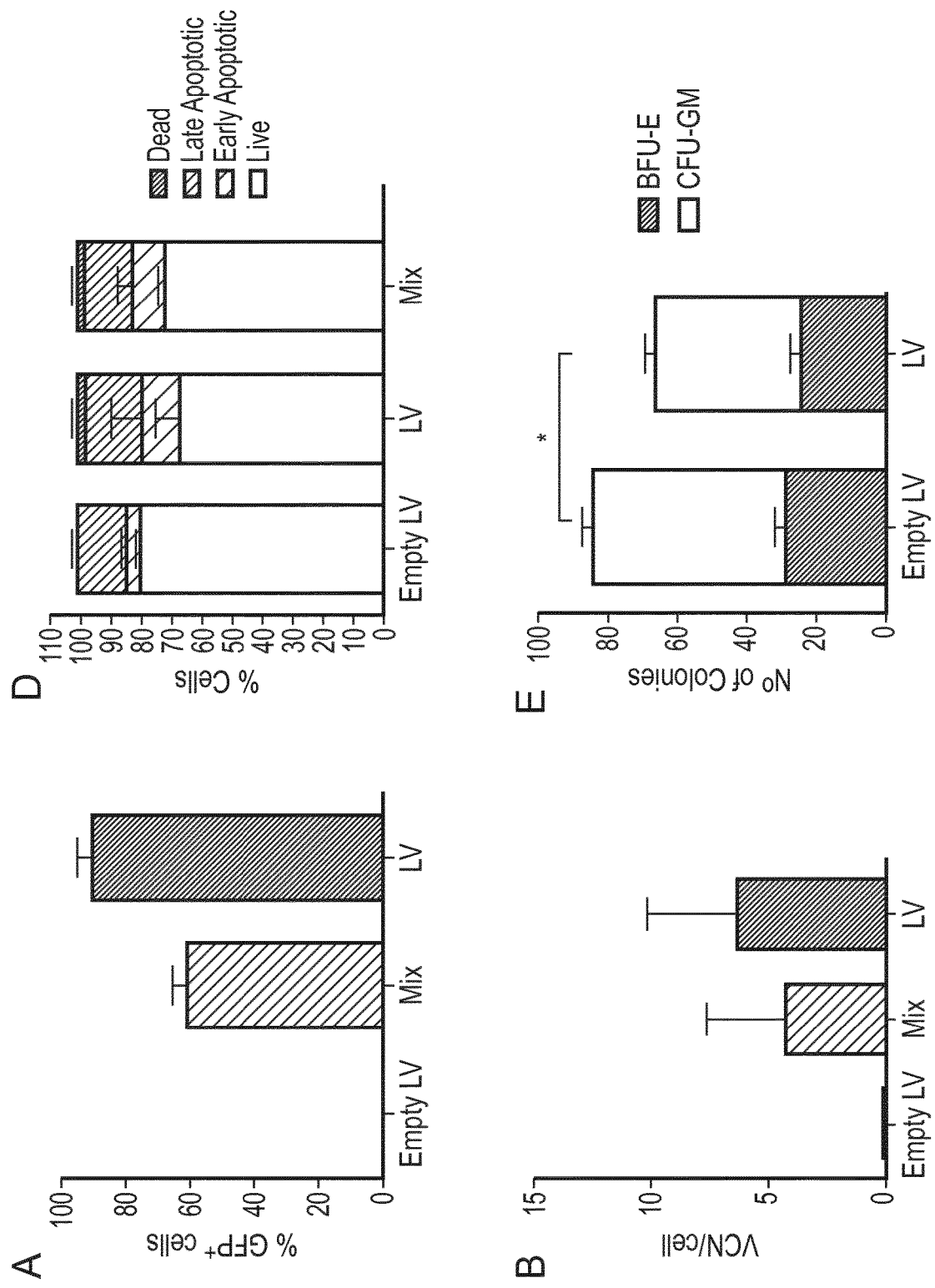
FIG. 15. Liquid culture, CFU and in vivo transduction of primary and secondary transplants. (A) Transduction efficiency at five days, (B) VCN at 14 days after (C) p21 mRNA induction (D) and Annexin V staining at 48 hours after transduction of the cells that were transplanted in NSG Mice (FIG. 5). Results are in mean±SEM of two independent experiments. (E) CB-CD34+ cells were plated in semisolid, cytokine-containing CFC medium. Colonies were scored after 14 days. Mean±SEM of total colonies per 800 transduced or bald exposed cells per subpopulation (n=4). (F) Percentage of the GFP positive cells within the human CD45+ cells in the peripheral blood over time, spleen and BM at the moment of sacrifice of (upper panel) primary or (lower panel) secondary mice. (G) VCN retrieved from the liquid culture of mPB-CD34+ 14 days after transduction with the two-hit clinical standard protocol as described in FIG. 5I. (H) Percentage of the Myeloid (CD13+), lymphoid (CD19+ B, CD3+ T) cells within the human CD45+ cells in the peripheral blood over time, spleen and BM at the end of the experiment of the primary or secondary mice. (1) Frequencies of CD34+38+ and CD34+CD38- within the human CD34+ cells retrieved from the bone marrow of secondary recipients at the end of the experiment. (J) Percentages of human CD45+ cells (Left Panel) detected in the Bone marrow of NSG mice at 16 weeks after the transplant in the Limiting Dilution Assay (LDA) experiment, and (Right Panel) the real number of CB-CD34+ cells injected in the mice for the same experiment. (K) Interferon stimulated genes (Left Panel) mRNA levels in CB-CD34+ 48 hours after the transduction with an MOI 100 of PGK-SIN RV vector in presence of KU55933 ATM inhibitor, (Right Panel) cell proliferation assay in CB CD34+ 2 days after the transduction with MOI 100 of PGK LV in DMSO or KU55933 or MOI 100 of PGK RV or empty RV as control.
Figure 15:
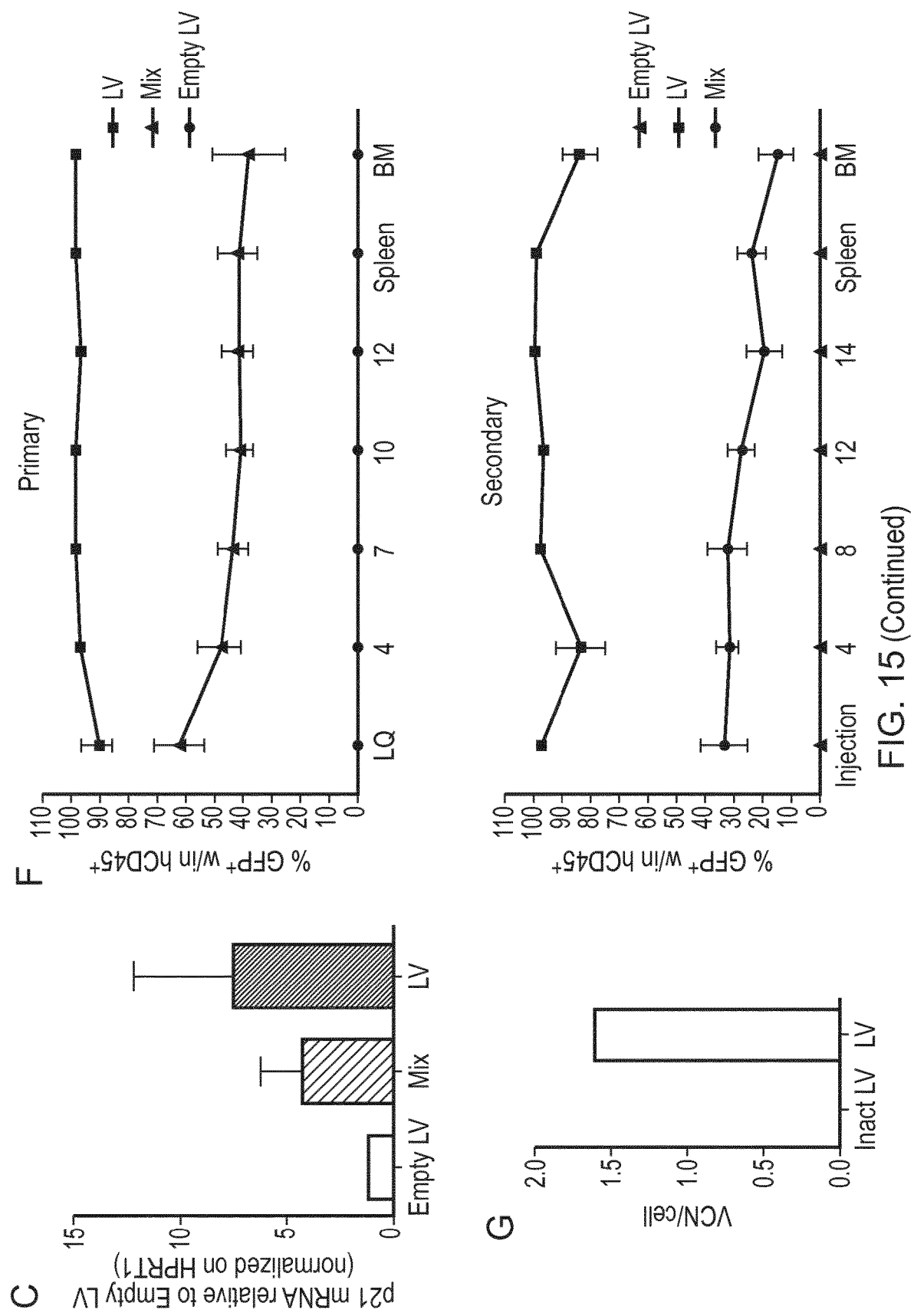
Figure 15:
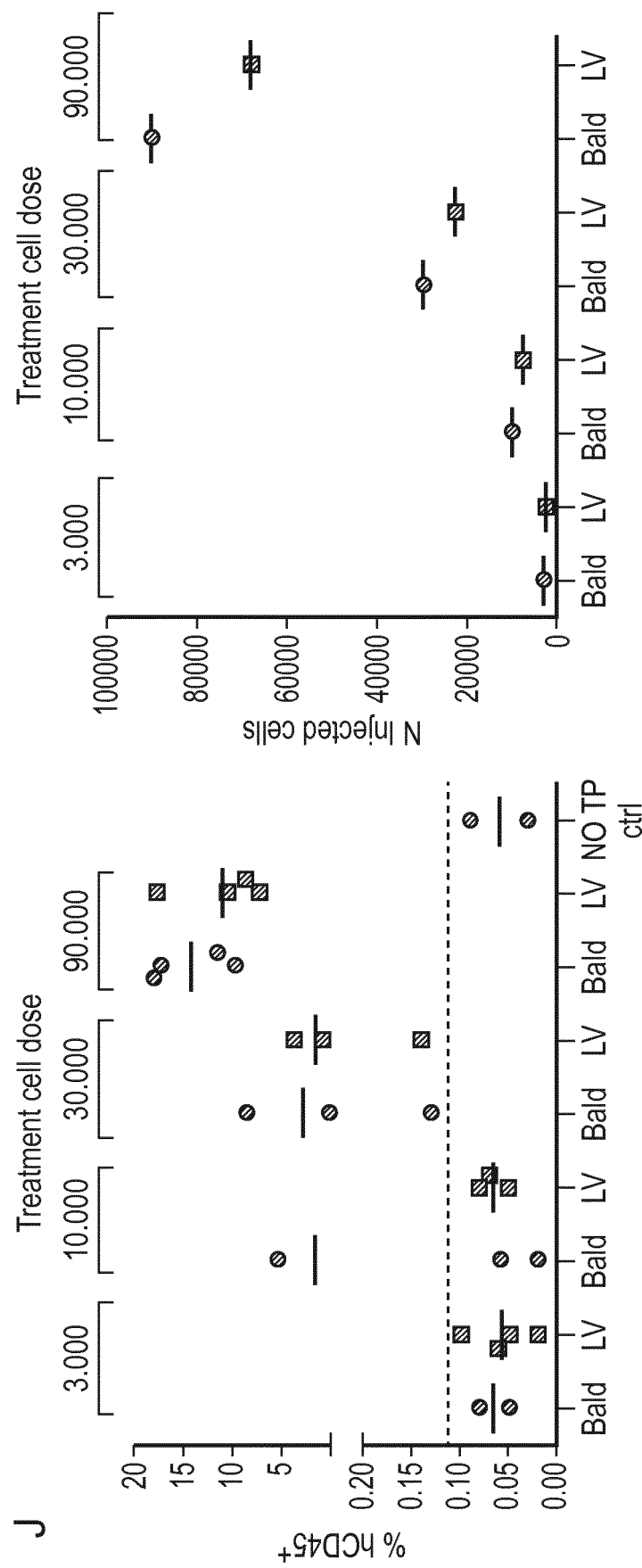
Figure 15:
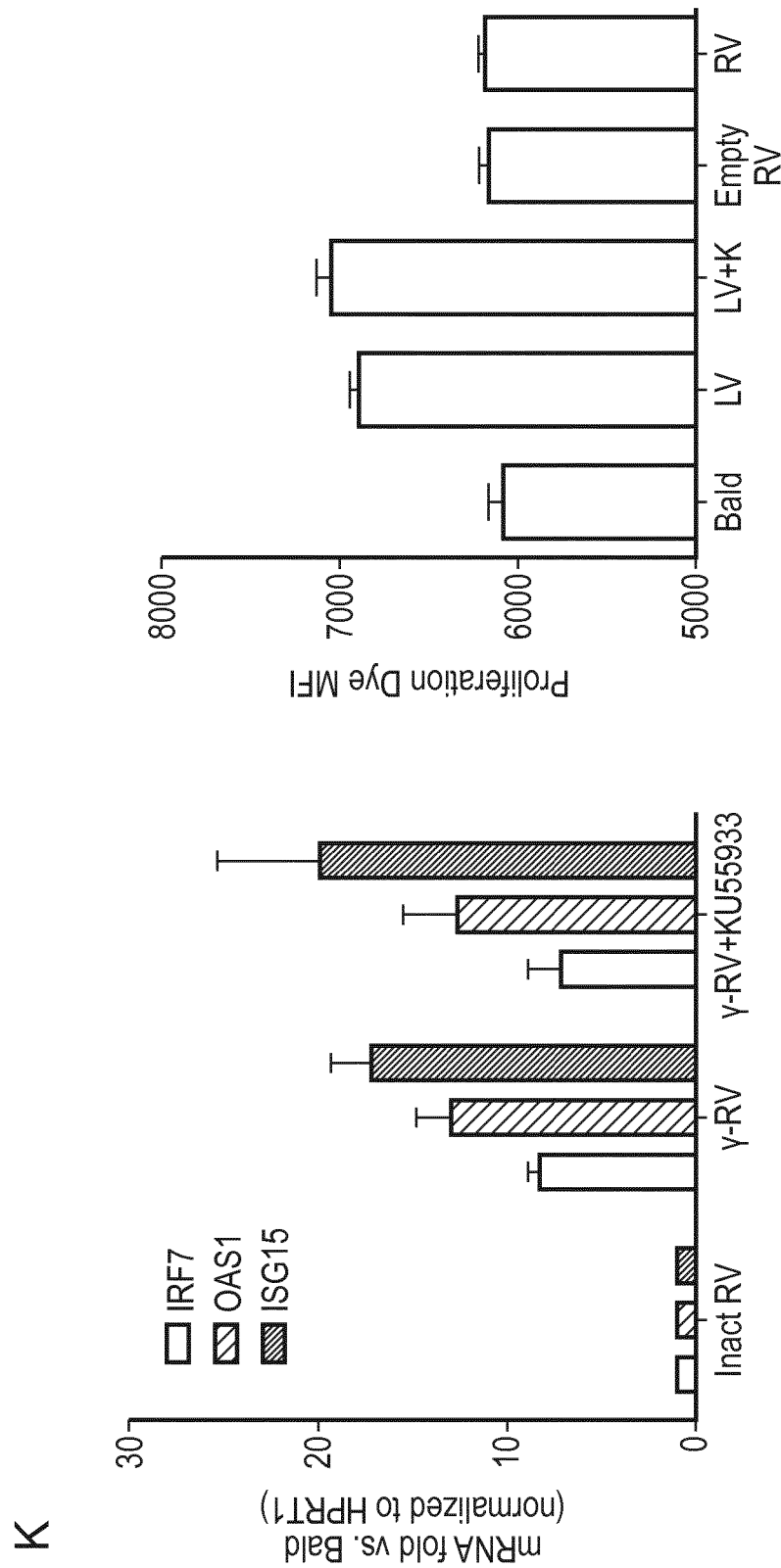

Although our in vitro results suggest a functional impact of LV exposure on HSPCs, including on the more primitive CD34+CD133+CD90+ cells, in vivo repopulation studies remain the gold standard to probe HSC self-renewal and differentiation capacity. To determine how LV transduction would affect human HSC function, we transplanted immunocompromised NSG mice with equal and limiting numbers of CB-derived CD34+ HSPCs exposed to either a transducing LV or a genome-less "Empty LV" control vector. To investigate an eventual selective advantage or disadvantage over time of transduced HSPCs, a group of mice received a mix of LV and Empty LV exposed cells in a 3:1 ratio (FIG. 5A). The level of transduction, p53 activation and consequent impact on cell viability and clonogenicity of transplanted HSPCs was verified in vitro (FIGS. 15A-E). Haematopoietic output in peripheral blood, measured as the percentage of human CD45+ cells, was followed over time up to 12 weeks post-transplantation. Despite equal cellular input, LV-exposed HSPCs showed a significantly lower engraftment at all time points compared to cells exposed to the empty vector (FIG. 5B). Decreased engraftment was also confirmed in mPB-derived HSPCs transduced according to the current clinical standard protocol based on two subsequent rounds of transduction with a VSV-g pseudotyped clinical-grade LV (FIGS. 5I and 15G). Of note, no significant differences in the numbers of CD34+ cells retrieved from the bone marrow of NSG mice 16 h after transplantation could be detected between transduced and control HSPCs (FIG. 5J), suggesting that LV transduction does not alter HSPC homing capacity. Nevertheless, once engrafted, no selective disadvantage of transduced HSPCs over controls could be seen. Mice transplanted with the mix of transduced and control HSPCs yielded stable engraftment levels proportional to the original in vitro ratio and taking into account the lower engraftment observed for the LV-exposed cells alone (FIG. 5B). Accordingly, the percentages of transduced GFP+ cells remained constant over time (FIG. 15F). Furthermore, despite reduced engraftment, LV transduction did not alter the lineage composition of human cells in periphery (FIG. 5C).

To assess the impact of LV-induced signalling on long-term repopulating HSCs, we performed secondary transplantations with the CD34+ cells recovered from the three different groups of primary recipients at 12 weeks post-transplantation (FIG. 5A). The percentages of human CD45+ cells retrieved from the bone marrow of the primary recipients at the time of sacrifice reflect the levels observed in the periphery and confirmed significantly lower engraftment of LV-exposed HSPCs (FIG. 5D). However, upon more detailed examination of the bone marrow stem cell compartment, no significant differences in the percentages of total CD34+ cells could be observed between the different groups and equal frequency of more primitive CD34+CD38− and committed CD34+CD38+ cells was seen (FIG. 5E). Within the more primitive CD34+CD38− fraction, the proportion of HSCs, immature lymphoid progenitors (MLP) and multipotent progenitors (MPP) (Doulatov, S. et al. (2012) Cell Stem Cell 10: 120-136; Notta, F. et al. (2016) Science 351: aab2116) remained conserved between groups (FIG. 5F), and no differences in lineage composition could be observed in the spleen of sacrificed primary recipients. Upon secondary transplantation, all mice were successfully repopulated independently of the treatment group (FIG. 5G).

Although a trend towards lower engraftment of LV-exposed HSPCs was still observed in secondary recipients, the differences compared to the control group were no longer significant. Moreover, no differences were observed between the LV condition and the mice having received a mixed population of transduced and control HSPCs (FIG. 5G). Absence of selective advantage of untransduced control HSPCs was confirmed in this setting as the level of engraftment and percentage of GFP+ cells remained stable over time in the mix condition (FIGS. 5G and 15F). At sacrifice, no major differences in the bone marrow composition were seen in terms of total CD34+ HSPCs and frequency of more primitive CD34+CD38− and committed CD34+CD38+ cells (FIG. 5H). In agreement, a limiting dilution assay (LDA) further confirmed that LV transduction does not significantly alter the long-term repopulating stem cell frequencies (FIG. 5K), although engraftment levels were again slightly lower in the LV-exposed group due to lower numbers of viable cells infused from matched treatment doses (FIG. 15J).

Overall, these results indicate that although exposure to LV negatively impacts HSPC maintenance ex vivo and engraftment in vivo due to acute induction of apoptosis, it does not affect their homing, composition, lineage output or long-term repopulating capacity.

Inhibition of p53 Activation Rescues HSPC Apoptosis and Engraftment

Figure 6:
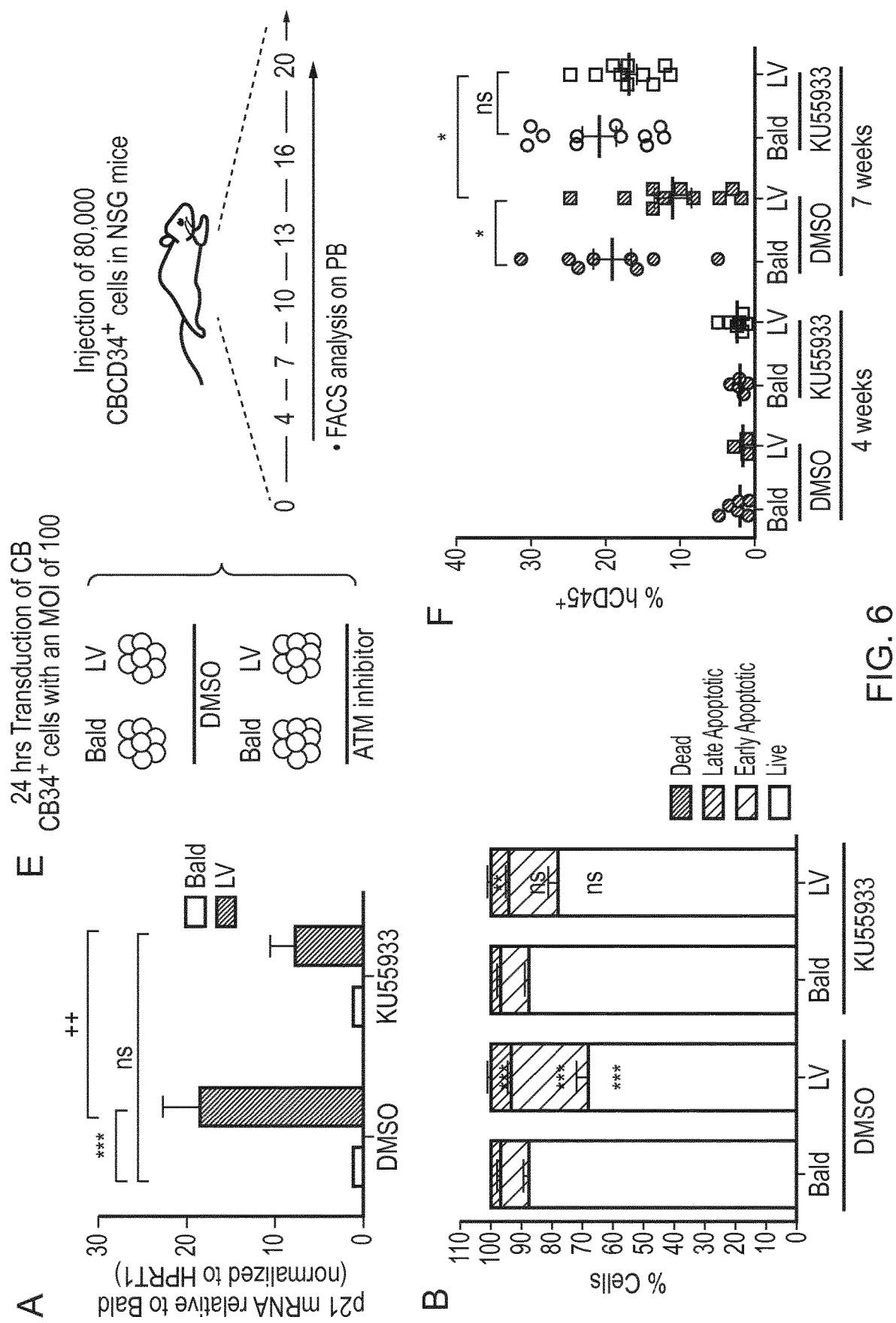
FIG. 6. LV-mediated activation of p53 signalling is ATM-dependent. Human CB-CD34+ cells were transduced with MOI of 100 of PGK-GFP SIN LV (LV), or Env-less (Bald) in presence 10 µM KU55933 and levels of p21 mRNA induction (A), of cellular apoptosis (B) and transduction in terms of GFP expression and integrated vector copy numbers (VCN) (C, one representative FACS plot out of 5 is shown) were monitored 48 hours post-exposure. Impact of ATM inhibition on AAV6-mediated induction of p21 mRNA and apoptosis are shown in (D). Results are the mean±SEM of n≥3 independent experiments, p-values are for Friedman's test (n=6, ***P≤0.001) or for Wilcoxon Matched Paired test (++ for P≤0.01). (E) Schematic representation of the experimental design to test in vivo impact of ATM inhibition is shown. After 16 hours of pre-stimulation cells were transduce with PGK-GFP SIN LV at MOI 100 (LV) or p24 equivalent of bald LV in presence of KU55933 or DMSO as a control. Twenty four hours after the transduction cells were washed and injected into sub-lethally irradiated NSG mice. (F) Percentages of total human CD45+ cells over time in the peripheral blood are shown. Results are the mean±SEM of Bald DMSO (n=8), LV DMSO (n=10), and Bald KU55933 (n=11) and LV KU5933 (n=11) NSG mice. Inhibition of LV signalling rescues HSPC apoptosis and engraftment. (G) p21 levels measured 24 hours after the second hit of transduction and 6 hours after CPT treatment in CB-CD34+ overexpressing a dominant negative form of p53 (GSE56) or GFP as control. (H) Apoptosis was evaluated 48 hours after the second hit of transduction with (Bald, LV or AAV6 vectors) in CB-CD34+ overexpressing GSE56 or GFP as control. (I) Western Blot-(left panel) and p21 FACS staining (right panel) was performed on whole mPB-CD34+ and CB-CD34+ 24 and 48 hours after the transduction, respectively, in the presence of 10 µM KU55933. (J-L) Impact of ATM inhibition on apoptosis, CFC assay and p21 mRNA induction on mPB-CD34+ cells after transduction with two hits at MOI 100 of clinical-grade LV or p21 equivalent of Inactivated Clinical LV (Inact LV) as a control. (M) In vivo impact of ATM inhibition on total human CD45+ cells in the peripheral blood over time. Results are the mean±SEM and of n≥3 independent experiments for in vitro. * p≤0.05;  p≤0.01; * p≤0.001.
Figure 6:
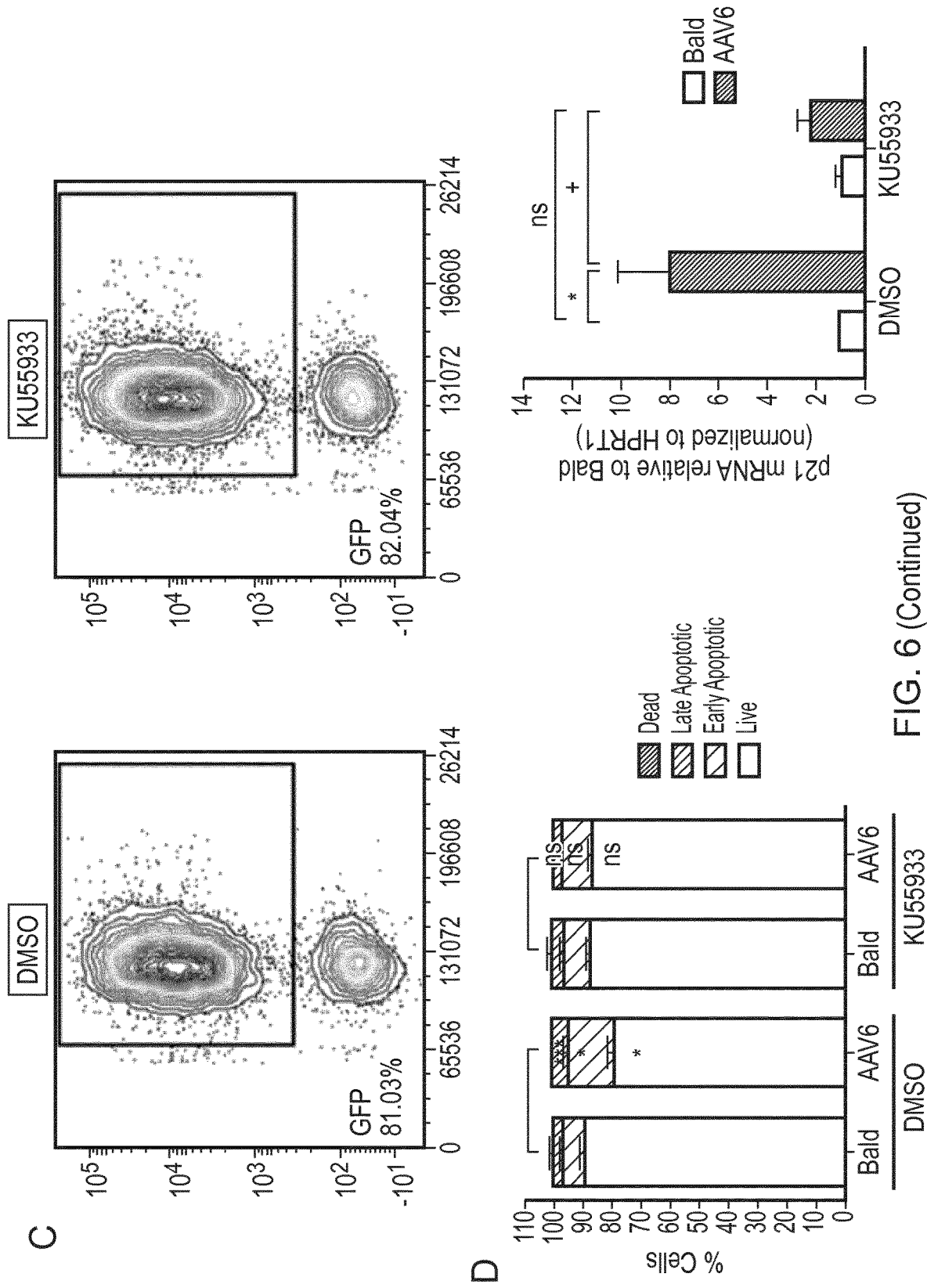
Figure 6:
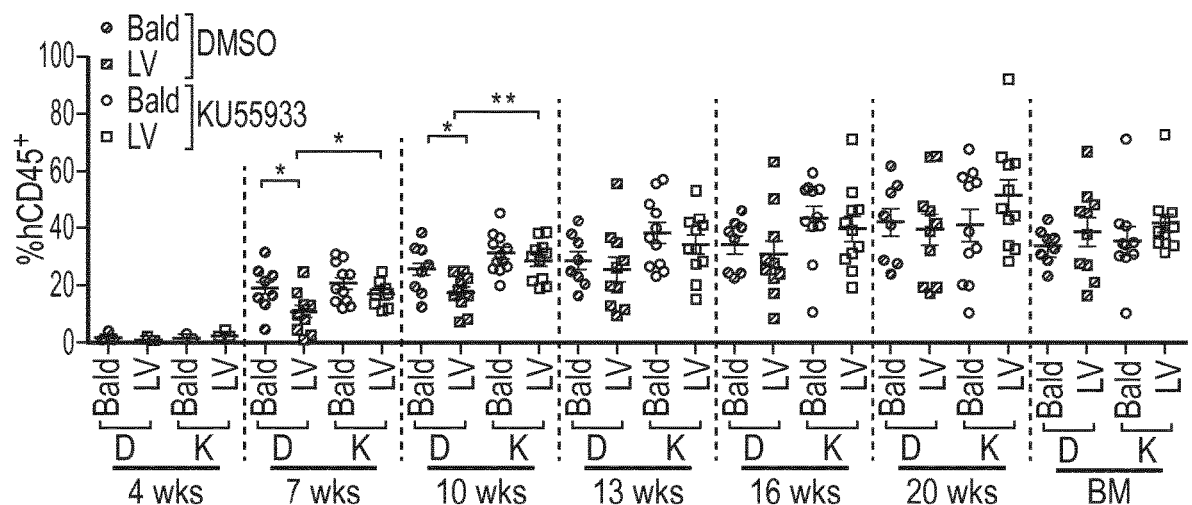

To test whether blocking the p53 signalling during ex vivo HSPC transduction could prevent some of the above described functional consequences, we exposed HSPCs to a control LV or a LV over-expressing a dominant negative form of p53, GSE56 (Milyaysky, M. et al. (2010) Cell Stem Cell 7: 186-197; Nucera, S. et al. (2016) Cancer Cell 29: 905-921), that we verified to efficiently block p53 signalling in HSPCs even upon strong DNA damage by Captothecin (CPT) (FIG. 6E). Activation of the p53 signalling in terms of p21 induction upon a second round of LV or AAV6 transduction was completely prevented in GSE56-expressing cells compared to control transduced counterparts (FIG. 6E). In agreement, reduced apoptosis was observed in GSE56-expressing HSPCs upon a second round of transduction (FIG. 6F).

Upon cellular stress, p53 signalling can be induced by different upstream signal mediators that will activate it through phosphorylation of certain residues or by inhibiting ubiquitinylation by MDM2 (Riley, T. et al. (2008) Nature Reviews. Molecular Cell Biology 9: 402-412). ATM kinase mediated activation leads to phosphorylation of p53 at Serine 15 (Roos, W. P. et al. (2016) Nature Reviews. Cancer 16: 20-33), as we observed to occur in HSPCs upon LV exposure (FIG. 3F). To assess involvement of ATM in LV-mediated activation of p53 in human HSPCs, we transduced the cells in the presence of the ATM inhibitor KU55933 (Hickson, I. et al. (2004) Cancer Research 64: 9152-9159) and tracked p53 signalling. Inhibition of the ATM kinase during LV exposure significantly reduced the levels of p21 mRNA (FIG. 6A) and partially abrogated induction of apoptosis in HSPCs (FIG. 6B). ATM inhibition did not compromise transduction efficiencies either in terms of GFP+ cells as well as of integrated vector copies (FIG. 6C). Positive impact of ATM inhibition on apoptosis, colony output and cell counts in culture together with reduced p21 induction was confirmed also in the more clinically relevant setting of a two-hit transduction protocol in mPB CD34+ cells using a clinical-grade LV (FIGS. 6H-J). Given that AAV-6-mediated gene transfer triggered similar responses as LV in human HSPCs, we tested whether ATM inhibition could also prevent the in vitro consequences in this setting. Both p21 mRNA induction as well as apoptosis were rescued upon ATM inhibition in CB-CD34+ exposed to AAV-6 (FIG. 6D). ATM inhibition had no impact on γRV-mediated induction of ISG (FIG. 15K). Of note, although ATM inhibition improved cell survival of transduced HSPC it did not affect the observed proliferation delay potentially due to residual p21 activity (FIG. 15K). In agreement with lack of p21 induction, no proliferation delay was detected in γRV transduced HSPCs (FIG. 15K).

Figure 16:
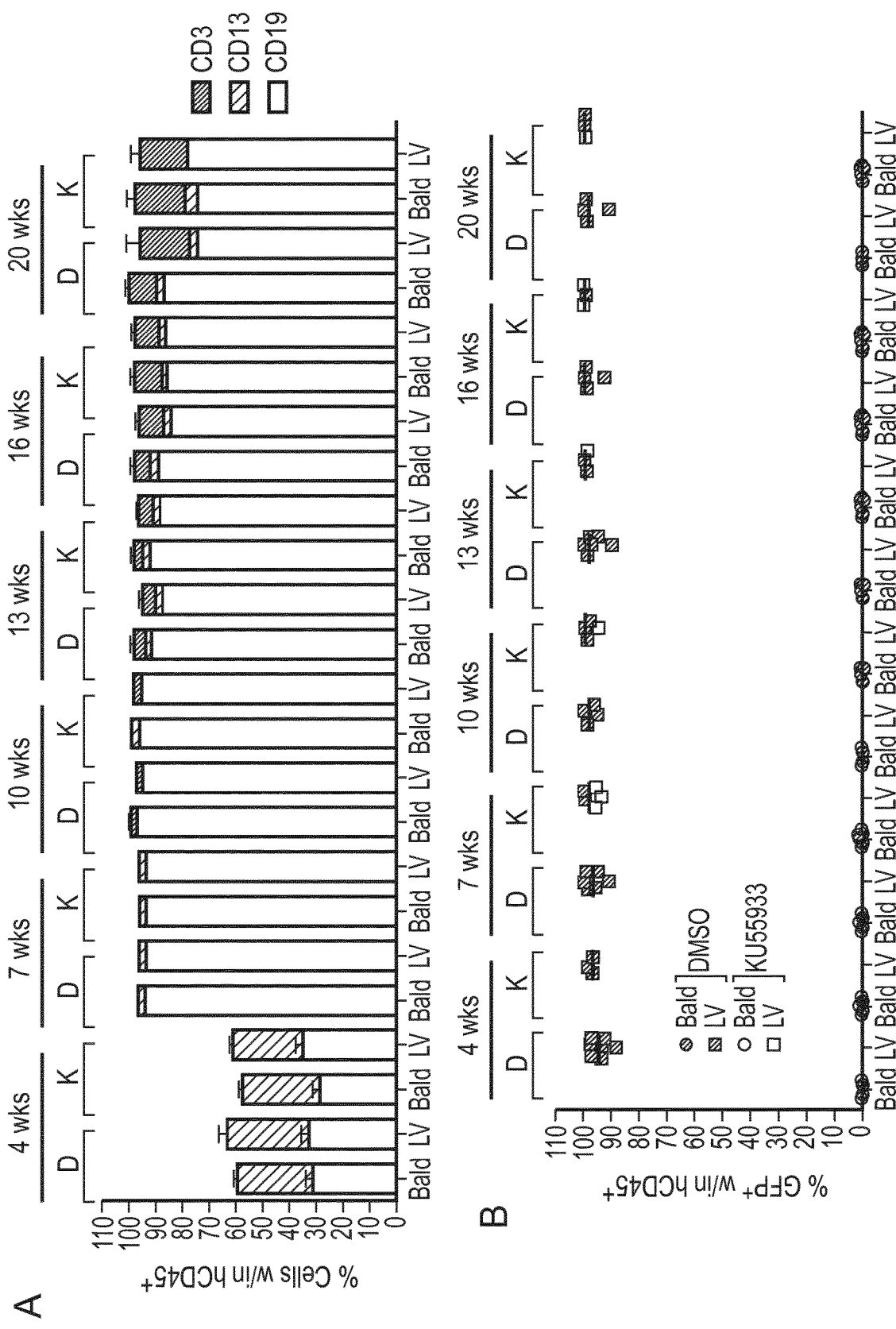
FIG. 16. In vivo of ATM inhibition. (A) Myeloid (CD13+) and lymphoid (CD19+ B, CD3+ T) cells and (B) GFP+ cells within the human CD45+ cells were monitored in the peripheral blood over time (D=DMSO; and K=KU55933). Results are the mean±SEM of Bald DMSO (n=8), LV DMSO (n=10), and Bald KU55933 (n=11) and LV KU5933 (n=11) NSG mice.

To investigate whether transient ATM inhibition during HSPC transduction could rescue their lower engraftment in vivo, cells were exposed to LV or the entry-incompetent Bald vector in presence of KU55933 or the vehicle as control, and transplanted at equal doses into NSG mice (FIG. 6E). Reduced engraftment of LV-exposed HSPCs was confirmed in the control group as compared to Bald-treated cells, both in peripheral blood over time (FIG. 6F). Transient inhibition of p53 signalling during the ex vivo transduction procedure improved LV-exposed HSPC engraftment by around 25% resulting in comparable levels of human CD45+ cells detected in the peripheral blood between transduced and Bald-exposed cells (FIG. 6F). Exposure of HSPCs to the ATM inhibitor did not alter CD34+ nor lineage composition or transduction efficiency in vivo (FIG. 16). Also in this setting long-term human cell engraftment was less affected by LV exposure, further indicating that activation of the p53 signaling upon transduction predominantly impacts short-term HSPC.

Taken together, these results suggest that the in vitro apoptosis and lower in vivo engraftment related to p53 activation in human HSPCs during ex vivo gene transfer can be at least partially prevented by transient inhibition of the upstream mediator ATM without affecting transduction efficiency.

Discussion

HIV-1 mediated signalling has been widely studied in model cell lines and primary targets of the virus (Towers, G. J. et al. (2014) Cell Host & Microbe 16: 10-18) but little information is available in the CD34+ hematopoietic stem cell compartment that remains a debated target for the virus (Josefsson, L. et al. (2012) The Journal of Infectious Diseases 206: 28-34; Carter, C. C. et al. (2010) Nature Medicine 16: 446-451). The poor permissiveness of these cells to lentiviral transduction in the context of gene therapy approaches has however prompted investigation of the potential immune hurdles and cellular responses to LV as they could hamper efficient and safe gene transfer in HSPCs (Kajaste-Rudnitski, A. et al. (2015) Cellular innate immunity and restriction of viral infection—implications for lentiviral gene therapy in human hematopoietic cells, Human Gene Therapy). Here we have addressed the global transcriptional changes LV transduction triggers early on upon gene transfer in human HSPCs and provide substantial mechanistic insight into the nucleic acid-mediated triggering of DNA damage responses, rather than innate immune signalling, in this primitive stem cell compartment.

Our observation that LV transduction triggers DNA damage responses rather than canonical innate immune activation in human HSPCs underscores their particularity as compared to differentiated hematopoietic cells. Although HIV-1 has been shown to activate p53 signalling in primary CD4+ T cells as well as in the U2OS cell line (Cooper, A. et al. (2013) Nature 498: 376-379; Lau, A. et al. (2005) Nat. Cell Biol. 7: 493-500), in both cases induction was strictly dependent on viral integration and thus on the generation of physical breaks within the host genome. Furthermore, p21 may not be the preferential downstream effector of p53 activation in this context as we did not observe significant alterations in its expression levels in CD4+ T cells and several other cell lines tested upon exposure to LVs. Our findings suggest that activation of the p53 signalling in human HSPCs upon LV transduction is related instead to nuclear sensing of exogenous DNA, rather than recognition of genomic DNA breaks, as induction occurs independently of integration for LVs and can also be triggered by non-integrating adenoviral DNA.

Nuclear sensing of the double-stranded vector DNA triggered ATM-dependent activation of p53 in human HSPCs. Phosphorylation of the histone variant H2AX is a key feature of ATM-dependent triggering of a cascade of DDR events (Marechal, A. et al. (2013) DNA damage sensing by the ATM and ATR kinases, Cold Spring Harb. Perspect. Biol. 5), but it is not critical for phosphorylation of ATM substrates such as Chk2 and p53 (Kang, J. et al. (2005) Mol. Cell Biol. 25: 661-670). In agreement with a break-independent activation of p53 through ATM, we could not detect significant levels of phosphorylated H2AX foci upon transduction. These results also suggest that HIV-1 integration per se may not robustly recruit the DNA repair machinery in human HSPCs, potentially due to steric protection by the viral pre-integration complex (Craigie, R. et al. (2012) Cold Spring Harb Perspect Med 2, a006890). Interestingly, mouse embryonic fibroblasts deficient for the cytoplasmic DNA exonuclease Trex1 show defective G1/S transition and chronic ATM-dependent checkpoint activation, even in the absence of any additional exogenous stress, suggesting that aberrant nucleic acid accumulation, in this case in the ER of Trex1-defective cells, can trigger ATM-dependent DDR responses (Yang, Y. G. et al. (2007) Cell 131: 873-886). In the nucleus, ATM has been shown to be activated in the presence of free double-strand (ds) DNA ends in a length-dependent manner (Lee, J. H. et al. (2005) Science 308: 551-554). In human cell extracts, ATM is not only activated by blunt dsDNA ends, but also by dsDNA ends with short single-stranded (ss) DNA overhangs (Shiotani, B. et al. (2009) Molecular Cell 33: 547-558). This type of molecular pattern, including free 3' overhangs and secondary structures, often characterise viral and bacterial genetic material and are usually associated with the triggering of innate immune responses through activation of various cytoplasmic nucleic acid sensors (Roers, A. et al. (2016) Immunity 44: 739-754).

Both HIV-1 and MLV have been shown to trigger IFN responses through activation of the cytosolic nucleic acid sensor cGAS (Gao, D. et al. (2013) Science 341: 903-906). In this context, the retroviral DNA is sensed by cGAS followed by activation of the adaptor protein STING, ultimately leading to synthesis of type I IFN and other pro-inflammatory cytokines. Also the proteins that detect damaged self-DNA in mammalian cells can activate signalling responses that can lead to IFN production, cell cycle regulation and programmed cell death (Jackson, S. P. et al. (2009) Nature 461: 1071-1078). Discoveries like ATM-mediated induction of the NF-kB pathways (Wu, Z. H. et al. (2006) Science 311: 1141-1146) or DDR-induced IFN signalling in MEF and in the U025 cell line (Yu, Q. et al. (2015) Cell Reports 11: 785-797) highlight the emerging concept of cross-talk between innate immune signalling and DDR. Indeed, poly(I:C)-mediated induction of innate immune responses in HSPCs was also accompanied by significant activation of apoptosis-related pathways. Nevertheless, although we carefully searched for signs of IFN and NF-κB signalling in LV transduced HSPCs, we could not find any significant modulations of these pathways. On the other hand, the MLV-based γRV did trigger substantial expression of several ISG, but this type I IFN activation likely depends on cytosolic recognition of viral RNA, rather than DNA, in human HSPCs. In this setting, the retroviral RNA could be sensed by endosomal TLR, RIG-I or the more recently described zinc-finger antiviral protein (ZAP) (Lee, H. et al. (2013) Proceedings of the National Academy of Sciences of the United States of America 110: 12379-12384). Absence of p53 activation is more likely due to the lower transduction efficiencies of γRV in HSPC. The capacity of both LV and AAV to actively enter into the nucleus of non-dividing, quiescent cells (Bushman, F. et al. (2005) Nature Reviews. Microbiology 3: 848-858; Nonnenmacher, M. et al. (2012) Gene Therapy 19: 649-658), such as the HSPCs, could allow them to evade the cytosolic sensors that instead detect the γRV nucleic acids that potentially accumulate in the cytoplasm while waiting for mitosis to occur. Nevertheless, although less efficient nuclear import upon removal of the cPPT from the LV significantly reduced p21 mRNA induction, it was not accompanied by an induction of ISG. The rates of cytoplasmic accumulation of the ΔcPPT vector may not be sufficient to trigger cytosolic innate sensors, although we cannot exclude that differences in reverse-transcription and/or uncoating rates between LV and γRV or other mechanisms of innate immune evasion exploited by HIV-1 could also avoid IFN responses to LV in human HSPCs (Towers, G. J. et al. (2014) Cell Host & Microbe 16: 10-18; Sauter, D. et al. (2016) Curr. Opin. HIV AIDS 11: 173-181).

Increased p53 activity has been shown to promote HSC quiescence (Liu, Y. et al. (2009) Cell Stem Cell 4: 37-48), but has also been recently associated with loss of HSPCs in the context of a mouse knock-out for type II protein arginine methyltransferase (PRMT5) (Liu, F. et al. (2015) The Journal of Clinical Investigation 125: 3532-3544). We observed that in human HSPCs, induction of p53 by LV led to their lower proliferation and a higher fraction of quiescent cells in G0. This, in principle, could preserve the long-term repopulating cells during gene transfer and allow higher engraftment of transduced cells over controls in vivo. The parallel induction of apoptosis seems however to counterbalance these potential benefits, in particular in the fraction containing the short-term repopulating HSPC, as significantly lower percentages of human cells were retrieved from mice having received transduced HSPC. Nevertheless, we did not observe any apparent long-term consequences of the LV-mediated p53 activation in HSPCs, indicating that in the context of ex vivo transduction the transient wave of p53 signalling has only an acute impact on the stem cells.

Although several reports have elegantly addressed the role of DDR and p53 signalling in HSC quiescence and self-renewal, most of these studies have been conducted in the murine context. Quiescent murine HSCs have been shown to resist apoptosis and to repair their DNA by non-homologous end joining (NHEJ), while committed progenitors were more likely to undergo apoptosis or repair their DNA using higher-fidelity homologous recombination (HR) (Mohrin, M. et al. (2010) Cell Stem Cell 7: 174-185). In agreement, increased expression of DDR-related genes has been recently shown to characterise more committed murine progenitors over HSCs (Cabezas-Wallscheid, N. et al. (2014) Cell Stem Cell 15: 507-522). In contrast to the mouse setting, damaged human HSCs have been shown to preferentially undergo apoptosis after low level irradiation (Milyaysky, M. et al. (2010) Cell Stem Cell 7: 186-197). Indeed, we observed that although LV transduction triggered apoptosis in all CD34+ subpopulations, the most affected ones seemed the more primitive CD133+CD38− and CD133+CD38int fractions, also in terms of lower CFU outputs. Nevertheless, we cannot exclude a potential contribution of the higher transduction efficiency observed in the primitive HSC compartment as induction of p53 signalling was vector dose-dependent.

Decreased p53 levels have been shown to rescue human HSCs from irradiation-induced programmed cell death (Milyaysky, M. et al. (2010) Cell Stem Cell 7: 186-197). Inhibition of p53 activation during the LV transduction process also partially rescued ex-vivo apoptosis of human HSPCs leading to higher engraftment compared to controls in vivo. Although ATM inhibition has been shown to dramatically decrease LV transduction efficiency in the context of cell lines (Lau, A. et al. (2005) Nat. Cell Biol. 7: 493-500), we did not observe any negative impact of KU55933 on LV gene transfer in human HSPCs at similar concentrations. This is most likely due to shorter time of exposure of the cells to the drug in our studies, but cell-type dependent sensitivity to ATM blockade cannot be excluded. Transient inhibition of the p53 signalling cascade could be of clinical benefit for LV-based gene therapy approaches. In particular, LV-mediated signalling could have more pronounced functional consequences in the context of diseases characterised by an elevated pro-inflammatory state or by genetic defects impacting the DDR pathways. However, although we observed only a partial and transient inhibition of p53 induction upon pharmacological ATM blockade in HSPCs, careful evaluation of its potential consequences in terms of LV integrations and genomic stability will be required prior to considering it for clinical testing. Conversely, induction of DDR pathways by IDLV or AAV donor vectors could potentially benefit targeted HSPC gene editing, as one of the major challenges in the field remains the low frequency of HR in the most primitive cell fraction (Naldini, L. (2015) Nature 526: 351-360; Genovese, P. et al. (2014) Nature 510: 235-240). Development of strategies to specifically block the apoptosis-inducing arm of the vector signalling while preserving the component of DNA damage responses that potentially promote HR could further improve targeted gene editing efficiency in human HSPCs.

Of note, although ATM inhibition rescued LV-induced apoptosis, it did not impact the reduced HSPC proliferation. These data favour the hypothesis that a window of non-apoptotic quiescence can be reached in these conditions yielding improved HSPC engraftment. In this setting, control cells also seemed to benefit from ATM inhibition suggesting that transplantation per se may activate potentially harmful p53 signalling in HSPCs, as also suggested by experiments in which p53 knock-down HSPCs engrafted more compared to control transduced counterparts even in the absence of irradiation-induced DNA damage (Milyaysky, M. et al. (2010) Cell Stem Cell 7: 186-197).

The transient wave of p53 signalling did not lead to any apparent long-term consequences as engraftment levels tended to normalise over time between untransduced and treated HSPCs and the long-term repopulating stem cell frequencies remained unaffected, in agreement with unaltered telomere length and gene expression profiles observed in LV-transduced rhesus macaque HSPCs long-term in vivo (Sellers, S. E. et al. (2014) Mol Ther 22: 52-58). Our finding that both integrating and non-integrating vectors do not detectably affect the biological properties of long-term HSPCs despite triggering similar molecular responses as observed for the short-term repopulating cells underscores clear biological differences between these two subsets of HSPCs, warranting further investigation in the future. The more persistent proliferation arrest observed in the primitive CD34+CD133+CD90+ fraction could in part account for better preserving the long-term HSC engraftment potential. Furthermore, it is possible that the long-term HSPCs are less sensitive to DDR, as recently reported for quiescent versus activated murine HSPCs (Walter, D. et al. (2015) Nature 520: 549-552).

The negative impact LV-mediated p53 signalling has on short-term hematopoietic stem cell (ST-HSC) engraftment is of significant clinical relevance as rapid engraftment of ST-HSC is critical for a safe and successful clinical outcome. Indeed, neutropenia-related infection is reported as the primary cause of death in 8% of autologous hematopoietic stem cell transplantation (HSCT) patients and 17-20% of allogeneic HSCT recipients (Tomblyn, M. et al. (2009) Biol Blood Marrow Transplant 15: 1143-1238). Moreover, antibiotic and antifungal prophylaxis can also be associated with significant side effects and does not offer complete protection. Therefore, there is a clear need for alternative strategies to prevent infections in the most vulnerable early neutropenic phase after HSCT (Kandalla, P. K. (2016) J Exp Med 213: 2269-2279). Similarly to autologous HSC transplantation, the major cause of treatment related morbidity and mortality in HSC gene therapy can be attributed to prolonged neutropenia due to delayed engraftment. Furthermore, the neutrophil recovery time is longer in the context of gene therapy as compared to normal HSCT, around 4 weeks as compared to 3 weeks for BM-derived HSPC transplantation (Tomblyn, M. et al. (2009) Biol Blood Marrow Transplant 15: 1143-1238) and cannot be overcome by increasing the cell dose, as supported also by a recent follow-up report on the metachromatic leukodystrophy (MLD) gene therapy trial (Sessa, M. et al. (2016) Lancet 388: 476-487). Clonal tracking studies performed in the context of a gene therapy trial to treat the Wiskott-Aldrich syndrome (WAS) demonstrate the critical role of ST-HSC in these first phases of engraftment and hematopoietic reconstitution in humans (Biasco, L. et al. (2016) Cell Stem Cell 19: 107-119). This notion is further consolidated in the murine setting in which the early phase of hematopoietic reconstitution has been shown to be almost exclusively supported by the ST-HSC-enriched CD34+CD38+ fraction of HSPC (Zonari, E. et al. (2017) Stem Cell Reports 8: 977-990). Overall, these observations suggest that loss of ST-HSC and the ensuing neutropenia in transplanted patients may be particularly relevant in settings in which ex vivo manipulation of HSCs is required. Although we cannot exclude a potential contribution of the growth conditions applied to HSPCs during their ex vivo manipulation, our results clearly indicate that gene therapy vectors significantly contribute to their delayed engraftment and provide proof-of-principle that dampening the vector signalling can restore hematopoietic reconstitution. Indeed, even a relatively small improvement, such as the 2-fold rescue of ST-HSC engraftment achieved by transiently blocking vector signalling may turn out highly significant from a clinical perspective.

Overall, our studies shed light on the molecular mechanisms and functional consequences of gene therapy vector sensing in human HSPCs. Better knowledge regarding these vector-host interactions will allow the development of more stealth gene therapy protocols tailored for specific disease settings in which vector signalling might impact both gene transfer efficiency as well as HSPC biology. Furthermore, deeper understanding of the signalling cascades activated by non-integrating vector platforms in HSPCs can contribute to the design of more efficient targeted gene editing strategies in the future.

TABLE 1

Number of genes changing over time under p-value ≤ 0.05.

| Condition | Genes changing over time |
| --- | --- |
| Untreated | 5883 |
| Poly(I:C) | 9496 |
| Bald LV | 7307 |
| Lab LV | 7080 |
| Purified LV | 7248 |
| Inactivated purified LV | 7512 |

TABLE 2

Number of differentially expressed genes over time between the conditions under p-value ≤ 0.05.

| Condition | Genes |
| --- | --- |
| Untreated Vs. Poly (I:C) | 2691 |
| Untreated Vs. Lab LV | 645 |
| Untreated Vs. Purified LV | 397 |
| Bald LV Vs. Lab LV | 321 |
| Inactivated Purified LV vs. Purified LV | 281 |

TABLE 3

Significance of Selected genes from type I IFN signalling cascade retrieved from the comparison between Lab LV and Bald LV

| Gene | p value |
| --- | --- |
| IFI6 | 0.662955 |
| TVP23A | 0.407102 |
| ISG15 | 0.964351 |
| IFI44L | 0.525873 |
| IFI44 | 0.812837 |
| IFI35 | 0.955392 |
| ISG20 | 0.020014 |
| DDX60 | 0.840026 |
| HERC6 | 0.973159 |
| LGALS3BP | 0.753786 |
| HLA-F | 0.935258 |
| MX1 | 0.904987 |
| PARP12 | 0.924286 |
| EPSTI1 | 0.971483 |
| SAT1 | 0.216319 |
| OAS3 | 0.980706 |
| IFITM1 | 0.861568 |
| HCP5 | 0.831475 |
| IRF7 | 0.80476 |
| XAF1 | 0.796685 |
| DHX58 | 0.764003 |
| H19 | 0.217731 |
| ODF3B | 0.569558 |
| IFI27 | 0.456448 |
| TRIM22 | 0.00061 |

TABLE 3-continued

Significance of Selected genes from type I IFN signalling cascade retrieved from the comparison between Lab LV and Bald LV

| Gene | p value |
| --- | --- |
| CSAG3 | 0.369604 |
| USP18 | 0.95428 |
| KLHDC7B | 0.960367 |
| MX2 | 0.948736 |
| OAS1 | 0.983136 |
| HLA-DQA1 | 0.566047 |
| CCL5 | 0.503809 |
| GDF11 | 0.74255 |
| ARG2 | 0.864504 |
| OPTN | 0.953236 |
| OAS2 | 0.971224 |
| GP1BA | 0.714797 |
| USP41 | 0.784604 |
| LAMC2 | 0.256181 |
| STAT1 | 0.586429 |
| PLSCR1 | 0.496799 |
| IFITM3 | 0.441251 |
| HELZ2 | 0.695985 |
| ACO1 | 0.579893 |
| DDX58 | 0.86283 |
| C19orf66 | 0.724447 |
| PARP9 | 0.950643 |
| OASL | 0.832593 |
| CXCL11 | 0.182701 |

TABLE 4

List of anti-human antibodies used for flow cytometry.

| Antibody | Fluorochrome | Dilution | Clone | Company | Code |
| --- | --- | --- | --- | --- | --- |
| hCD235a | APC | 1:25 | GA-R2 | BD Biosciences | 551336 |
| hCD33 | BV421 | 1:25 | WM53 | BD Biosciences | 562854 |
| Anti human FCR Blocking | | 1:50 | | Miltenyi Biotec | 120-000-442 |
| Anti murine FCR Blocking | | 1:100 | 2.4G2 | BD Pharmigen | 553142 |
| hCD45 | APC-Cy7 | 1:33 | HI30 | eBiosciences | 47-0459-42 |
| hCD19 | PE | 1:25 | SJ25C1 | BD Biosciences | 345789 |
| hCD33 | PeCy7 | 1:25 | P67.6 | BD Biosciences | 333952 |
| hCD3 | APC | 1:25 | UCHT1 | BD Biosciences | 555335 |
| hCD13 | BV | 1:25 | WM15 | BD Biosciences | 562596 |
| hCD34 | PeCy7 | 1:25 | 8G12 | BD Biosciences | 348811 |
| hCD38 | V450 | 1:25 | HB7 | BD Biosciences | 646851 |
| hCD90 | APC | 1:25 | 5E10 | BD Biosciences | 559869 |
| hCD45RA | VioBlue | 1:10 | T6D11 | Miltenyi Biotec | 130-095-464 |
| hCD133 | PE | 1:15 | 293C3 | Miltenyi Biotec | 130-090-853 |
| hCD38 | APC | 1:10 | IB6 | Miltenyi Biotec | 130-092-261 |
| Ki-67 | PE | | B56 | BD Bioesciences | 556027 |
| hCD90 | Brillant Violet | 1:29 | | | |
| Annexin V | Pacific Blue | 1:20 | | Biolegend | 640918 |
| Hoechst | | | | Thermo Fisher | H3570 |
| 7-AAD | | | | Sigma-Aldricht | A9400 |

TABLE 5

List of anti-human antibodies used for WB.

| Antibody | Produced in | Dilution | Incubation | Clone | Company | Code |
| --- | --- | --- | --- | --- | --- | --- |
| p53Ser15 | Rabbit | 1:1000 | 5% BSA-TTBS (4° C. O/N) | Polyclonal | Cell signalling Technology | 284S |
| p53 | Mouse | 1:200 | 5% BSA-TTBS (4° C. O/N) | DO-1 | Santa Cruz | Sc126 |
| p21 | Rabbit | 1:1000 | 5% BSA-TTBS (4° C. O/N) | 12D1 | Cell signalling Technology | 2947 |
| γ-H2AX | Rabbit | 1:1000 | 5% BSA-TTBS (4° C. O/N) | 20E3 | Cell signalling Technology | 9718 |

TABLE 5-continued

List of anti-human antibodies used for WB.

| Antibody | Produced in | Dilution | Incubation | Clone | Company | Code |
|---|---|---|---|---|---|---|
| pSer1981ATM | Rabbit | 1:1000 | 5% BSA-TTBS (4° O/N) | D25E5 | Cell signalling Technology | 13050 |
| ATM | Rabbit | 1:1000 | 5% BSA-TTBS (4° O/N) | D2E2 | Cell signalling Technology | 2873 |

TABLE 6

List of primers used for gene expression.

| Primer | Method | Company | Code |
|---|---|---|---|
| hCDKN1A (p21) | RT-PCR | Thermo Fisher | Hs00355782_m1 |
| hHPRT1 | RT-PCR | Thermo Fisher | Hs01003267_m1 |
| hIRF7 | RT-PCR | Thermo Fisher | Hs01014809_g1 |
| hPHLDA3 | RT-PCR | Thermo Fisher | Hs00385313_m1 |
| hISG15 | RT-PCR | Thermo Fisher | Hs01921425_s1 |
| hOAS1 | RT-PCR | Thermo Fisher | Hs00973637_m1 |
| hDDB2 (p48) | RT-PCR | Thermo Fisher | Hs03044953_m1 |
| hBBC3 (PUMA) | RT-PCR | Thermo Fisher | Hs00248075_m1 |
| mIrf7 | RT-PCR | Thermo Fisher | Mm00516788_m1 |
| mOas1 | RT-PCR | Thermo Fisher | Mm00836412_m1 |
| mIfit1 | RT-PCR | Thermo Fisher | Mm00515153_m1 |
| mIsg15 | RT-PCR | Thermo Fisher | Mm01705338_s1 |
| mHprt | RT-PCR | Thermo Fisher | Mm01545399_m1 |
| mCdkn1a | RT-PCR | Thermo Fisher | Mm04207341_m1 |

TABLE 7

List of primers used for VCN.

| Primer | Sequence | Method | Reference |
|---|---|---|---|
| LV-Sense | 5'-TACTGACGCTCTCGCACC-3' (SEQ ID NO: 9) | RT-PCR/ddPCR | (Matrai, J. et al. (2011) Hepatology 53: 1696-1707) |
| LV-Antisense | 5'-TCTCGACGCAGGACTCG-3' (SEQ ID NO: 10) | RT-PCR/ddPCR | |
| LV-Probe | FAM-5'-ATCTCTCTCCTTCCTTCTAGCCTC-3'-MGBNFQ (SEQ ID NO: 11) | | |
| RT-LV (ΔU3 sense) | 5'-TCACTCCCAACGAAGACAAGATC-3' (SEQ ID NO: 12) | RT-PCR/ddPCR | |
| RT-LV (Gag antisense) | 5'-GAGTCCTGCGTCGAGAGAG-3' (SEQ ID NO: 13) | RT-PCR/ddPCR | |
| RT-RV (ΔU3 sense) | 5'-CGAGCTCAATAAAAGAGCCCAC-3' (SEQ ID NO: 14) | ddPCR | |
| RT-RV (PBS antisense) | 5'-ACAGATAGGTTGCTGGCCAG-3' (SEQ ID NO: 15) | ddPCR | |
| hTert fw | 5'-GGCACACGTGGCTTTTCG-3' (SEQ ID NO: 16) | RT-PCR/ddPCR | (Lombardo, A. et al. (2007) Nature Biotechnology 25: 1298-1306) |
| hTert rev | 5'-GGTGAACCTCGTAAGTTTATGCAA-3' (SEQ ID NO: 17) | RT-PCR/ddPCR | |
| hTert Probe | VIC-5'-TCAGGACGTCGAGTGGACACGGTG-3'-TAMRA (SEQ ID NO: 18) | | |
| 2LTR Fw (2Junct) | 5'-CAGTGTGGAAAATCTCTAGCAGTAC-3' (SEQ ID NO: 19) | ddPCR | |
| 2LTR Rev (J2 Rev) | 5'-GCCGTGCGCGCTTCAGCAAGC-3' (SEQ ID NO: 20) | ddPCR | |

TABLE 8

PCR reactions for dd-PCR.

| Cycling step | Temperature °C. | Time | Number of Cycles | |
|---|---|---|---|---|
| Enzyme Activation | 95 | 5 min | 1 | LV ddPCR |
| Denaturation | 95 | 30 sec | 40 | |
| Annealing/Extension | 60 | 1 min | 40 | |
| Signal Stabilisation | 4 | 5 min | 1 | |
| | 90 | 5 min | 1 | |
| Hold (Optional) | 4 | Infinite | 1 | |
| Enzyme Activation | 95 | 5 min | 1 | RT-LV ddPCR |
| Denaturation | 95 | 30 sec | 40 | |
| Annealing/Extension | 60-63 | 1 min | 40 | |
| Signal Stabilisation | 4 | 5 min | 1 | |
| | 90 | 5 min | 1 | |
| Hold (Optional) | 4 | Infinite | 1 | |
| Enzyme Activation | 95 | 5 min | 1 | RT-RV ddPCR |
| Denaturation | 95 | 30 sec | 40 | |
| Annealing/Extension | 63 | 1 min | 40 | |
| Signal Stabilisation | 4 | 5 min | 1 | |
| | 90 | 5 min | 1 | |
| Hold (Optional) | 4 | Infinite | 1 | |
| Enzyme Activation | 95 | 5 min | 1 | hTERT ddPCR |
| Denaturation | 95 | 30 sec | 40 | |
| Annealing/Extension | 60-63 | 1 min | 40 | |
| Signal Stabilisation | 4 | 5 min | 1 | |
| | 90 | 5 min | 1 | |
| Hold (Optional) | 4 | Infinite | 1 | |
| Enzyme Activation | 95 | 5 min | 1 | 2LTR ddPCR |
| Denaturation | 95 | 30 sec | 40 | |
| Annealing/Extension | 63 | 1 min | 40 | |
| Signal Stabilisation | 4 | 5 min | 1 | |
| | 90 | 5 min | 1 | |
| Hold (Optional) | 4 | Infinite | 1 | |

TABLE 9

Cell counts of in vivo experiments.

| | N Cell Counted at TD | N Cell Counted at TP | N Cell Infused | Source |
|---|---|---|---|---|
| Empty LV | 890000 | 816666 | 80000 | CB |
| LV | 1240000 | 1390000 | 80000 | |
| Empty LV | 840000 | 690000 | 80000 | |
| LV | 1160000 | 900000 | 80000 | |
| Bald DMSO | 700000 | 904000 | 80000 | |
| LV DMSO | 700000 | 840000 | 80000 | |
| Bald KU | 800000 | 957000 | 80000 | |
| LV KU | 800000 | 1030000 | 80000 | |
| Bald DMSO | 625000 | 1000000 | 80000 | |
| LV DMSO | 625000 | 600000 | 80000 | |
| Bald KU | 625000 | 800000 | 80000 | |
| LV KU | 625000 | 600000 | 80000 | |
| Inact LV | 1750000 | 3710000 | 514285 | mPB |
| Clinical-grade LV | 1750000 | 3050000 | 422857 | |
| Bald | 800000 | 1744000 | | CB |
| LV | 800000 | 1216000 | | |
| Bald DMSO | 2000000 | 2200000 | 500000 | CB |
| LV DMSO | 2000000 | 2075000 | 500000 | |

All publications mentioned in the above specification are herein incorporated by reference. Various modifications and variations of the described agents, compositions, uses and methods of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A method of haematopoietic stem and/or progenitor cell gene therapy for reducing in vitro or ex vivo apoptosis of human haematopoietic stem and/or progenitor cells transduced by an integration-defective viral vector comprising a therapeutic nucleotide of interest, the method comprising contacting a population of human haematopoietic stem and/or progenitor cells with an inhibitor of p53 activation during in vitro or ex vivo culture, wherein the inhibitor of p53 activation is an ataxia telangiectasia mutated (ATM) kinase inhibitor or a p53 dominant negative peptide, and wherein the inhibition of p53 activation is transient, and wherein the population of cells is contacted with the inhibitor of p53 activation 30 minutes to 4 hours before transducing the population of cells with the integration-defective viral vector.

2. The method of claim 1, wherein the integration-defective viral vector is an integration-defective lentiviral vector (IDLV) or adeno-associated viral (AAV) vector.

3. The method of claim 1, wherein the inhibitor of p53 activation is KU-55933 or a derivative thereof; GSE56; KU-60019, CP-466722, Torin 2, CGK 733, or derivatives thereof; or an siRNA, shRNA, miRNA or antisense DNA/RNA.

4. The method of claim 3, wherein the inhibitor of p53 activation is added to the human haematopoietic stem and/or progenitor cells at a concentration of 1-50 µM.

5. The method of claim 3, wherein the inhibitor of p53 activation is added to the human haematopoietic stem and/or progenitor cells at a concentration of 5-50 µM.

6. The method of claim 1, wherein the integration-defective viral vector is an integration-defective lentiviral vector (IDLV) or adeno-associated viral (AAV) vector.

7. The method of claim 1, wherein the inhibitor of p53 activation is a p53 dominant negative peptide comprising an amino acid sequence having at least 80% identity to SEQ ID NO: 6.

8. The method of claim 1, wherein the inhibitor of p53 activation is KU-55933, GSE56 or KU-60019.

9. The method of claim 1, wherein the population of cells is contacted with the inhibitor of p53 activation 2 hours before transducing the population of cells with the integration-defective viral vector.

10. A method of reducing in vitro or ex vivo apoptosis of human haematopoietic stem and/or progenitor cells transduced by an integration-defective viral vector comprising a therapeutic nucleotide of interest, the method comprising contacting a population of human haematopoietic stem and/or progenitor cells with an inhibitor of p53 activation during in vitro or ex vivo culture, wherein the inhibitor of p53 activation is an ataxia telangiectasia mutated (ATM) kinase inhibitor or a p53 dominant negative peptide, and wherein the inhibition of p53 activation is transient, and wherein the population of cells is contacted with the inhibitor of p53 activation 30 minutes to 4 hours before transducing the population of cells with the integration-defective viral vector.

11. The method of claim 10, wherein the inhibitor of p53 activation is KU-55933 or a derivative thereof; GSE56; KU-60019, CP-466722, Torin 2, CGK 733, or derivatives thereof; or an siRNA, shRNA, miRNA or antisense DNA/RNA.

12. The method of claim 11, wherein the inhibitor of p53 activation is added to the human haematopoietic stem and/or progenitor cells at a concentration of 1-50 µM.

13. The method of claim 11, wherein the inhibitor of p53 activation is added to the human haematopoietic stem and/or progenitor cells at a concentration of 5-50 µM.

14. The method of claim 10, wherein the inhibitor of p53 activation is a p53 dominant negative peptide comprising an amino acid sequence having at least 80% identity to SEQ ID NO: 6.

15. The method of claim 10, wherein the inhibitor of p53 activation is KU-55933, GSE56 or KU-60019.

16. The method of claim 10, wherein the population of cells is contacted with the inhibitor of p53 activation 2 hours before transducing the population of cells with the integration-defective viral vector.

17. A method of transducing a population of human haematopoietic stem and/or progenitor cells with an integration-defective viral vector comprising a therapeutic nucleotide of interest, the method comprising:
(a) contacting the population of cells with an inhibitor of p53 activation during in vitro or ex vivo culture, wherein the inhibitor of p53 activation is an ataxia telangiectasia mutated (ATM) kinase inhibitor or a p53 dominant negative peptide, and wherein the inhibition of p53 activation is transient; and
(b) transducing the population of cells with the integration-defective viral vector during in vitro or ex vivo culture,
wherein the population of cells is contacted with the inhibitor of p53 activation 30 minutes to 4 hours before transducing the population of cells with the integration-defective viral vector.

18. The method of claim 13, wherein the inhibitor of p53 activation is KU-55933 or a derivative thereof; GSE56; KU-60019, CP-466722, Torin 2, CGK 733, or derivatives thereof; or an siRNA, shRNA, miRNA or antisense DNA/RNA.

19. The method of claim 15, wherein the inhibitor of p53 activation is added to the human haematopoietic stem and/or progenitor cells at a concentration of 1-50 µM.

20. The method of claim 18, wherein the inhibitor of p53 activation is added to the human haematopoietic stem and/or progenitor cells at a concentration of 5-50 µM.

21. The method of claim 17, wherein the integration-defective viral vector is a integration-defective lentiviral vector (IDLV) or adeno-associated viral (AAV) vector.

22. The method of claim 17, wherein the population of human haematopoietic stem and/or progenitor cells is obtained from mobilised peripheral blood, bone marrow or umbilical cord blood.

23. The method of claim 17, which includes a further step of enriching the population for haematopoietic stem and/or progenitor cells.

24. The method of claim 17, wherein the inhibitor of p53 activation is a p53 dominant negative peptide comprising an amino acid sequence having at least 80% identity to SEQ ID NO: 6.

25. The method of claim 17, wherein the inhibitor of p53 activation is KU-55933, GSE56 or KU-60019.

26. The method of claim 17, wherein the population of cells is contacted with the inhibitor of p53 activation 2 hours before transducing the population of cells with the integration-defective viral vector.

27. A method of gene therapy comprising the steps:
(a) transducing a population of human haematopoietic stem and/or progenitor cells according to the method of claim 17; and
(b) administering the transduced cells to a subject.

28. The method of claim 27, wherein the transduced cells are administered to a subject as part of an autologous stem cell transplant procedure or an allogeneic stem cell transplant procedure.

* * * * *